US008586006B2

(12) United States Patent
Hood et al.

(10) Patent No.: US 8,586,006 B2
(45) Date of Patent: Nov. 19, 2013

(54) ORGAN-SPECIFIC PROTEINS AND METHODS OF THEIR USE

(75) Inventors: Leroy Hood, Seattle, WA (US); Patricia M. Beckmann, Hansville, WA (US); Richard Johnson, Mercer Island, WA (US); Marcello Marelli, Seattle, WA (US); Xiaojun Li, Bellevue, WA (US)

(73) Assignees: Institute for Systems Biology, Seattle, WA (US); Integrated Diagnostics, Inc., Seattle, WA (US)

( * ) Notice: Subject to any disclaimer, the term of this patent is extended or adjusted under 35 U.S.C. 154(b) by 651 days.

(21) Appl. No.: 12/376,951

(22) PCT Filed: Aug. 9, 2007

(86) PCT No.: PCT/US2007/017868
§ 371 (c)(1),
(2), (4) Date: Jun. 30, 2010

(87) PCT Pub. No.: WO2008/021290
PCT Pub. Date: Feb. 21, 2008

(65) Prior Publication Data
US 2012/0087862 A1    Apr. 12, 2012

Related U.S. Application Data

(60) Provisional application No. 60/836,986, filed on Aug. 9, 2006.

(51) Int. Cl.
*A61K 49/00*    (2006.01)
(52) U.S. Cl.
USPC ............ 424/9.2; 424/1.11; 424/1.65; 424/9.1
(58) Field of Classification Search
USPC ............. 424/1.11, 1.49, 1.65, 1.69, 1.73, 9.1, 424/9.2; 530/300, 350
See application file for complete search history.

(56) References Cited

U.S. PATENT DOCUMENTS

| | | | |
|---|---|---|---|
| 5,346,994 A | | 9/1994 | Chomczynski |
| 6,034,218 A * | | 3/2000 | Reed et al. ............ 530/350 |
| 6,759,211 B1 * | | 7/2004 | Georgiev et al. .......... 435/69.1 |
| 7,883,858 B2 * | | 2/2011 | Hood et al. ............. 435/7.1 |
| 2006/0094064 A1 | | 5/2006 | Sandip et al. |

FOREIGN PATENT DOCUMENTS

| WO | WO-01/40276 | 6/2001 |
|---|---|---|
| WO | WO-03/052119 | 6/2003 |
| WO | WO-2005/114221 | 12/2005 |

OTHER PUBLICATIONS

Caplan et al (Am. J. Clin. Pathol., 2002, vol. 117 (Suppl. 1), pp. S104-S108).*
Colmers et al, Epilepsy Currents , 2003, vol. 3, No. 2, pp. 53-58.*
Robert et al, CMLS, Cell. Mol. Life Sci., 1999, vol. 55, pp. 944-960.*
Lo, The International Journal of Biochemistry & Cell Biology, 2004, vol. 36, pp. 31-34.*
Groves et al, Current Opinion in Chemical Biology, 2000, vol. 4, pp. 687-695.*
Bar-Or et al, Brain, 2003, vol. 126, pp. 2738-2749.*
Seufert et al, The EMBO Journal, 1990, vol. 9, No. 2, pp. 543-550.*
Anderson et al., "The Human Plasma Proteome," Molecular and Cellular Proteomics (2002) 1:845-867.
Barski et al., "High-Resolution Profiling of Histone Methylations in the Human Genome," Cell (2007) 129:823-837.
Casiano et al., "Tumor-Associated Antigen Arrays for the Serological Diagnosis of Cancer," Molecular and Cellular Proteomics (2006) 5:1745-1759.
Chen et al., "Proteomic Analysis of Colonic Myofibroblasts and Effect on Colon Cancer Cell Proliferation," Surgery (2005) 138(2):382-390.
Chomczynski et al., "Single-Step Method of RNA Isolation by Acid Guanidinium Thiocyanate-Phenol-Chloroform Extraction," Analytical Biochemistry (1987) 162:156-159.
Corthals et al., "Prefractionation of Protein Samples Prior to Two-Dimensional Electrophoresis," Electrophoresis (1997) 18:317-323.
Dai et al., "A Cell Proliferation Signature is a Marker of Extremely Poor Outcome in a Subpopulation of Breast Cancer Patients," Cancer Res. (2005) 65:4059-4066.
Deutsch et al., "Human Plasma Peptide Atlas," Proteomics (2005) 5:3497-3500.
Dubbink et al., "The Human Prostate-Specific Transglutaminase Gene (TGM4): Genomic Organization, Tissue-Specific Expression, and Promoter Characterization," Genomics (1998) 51:434-444.
Farooqui et al., "Biochemical Aspects of Neurodegeneration in Human Brain: Involvement of Neural Membrane Phospholipids and Phospholipases $A_2$," Neurochemical Research (2004) 29(11):1961-1977.
Johnson et al., "Genome-Wide Mapping of in Vivo Protein-DNA Interactions," Science (2007) 316(5830):1497-1502.
Jongeneel et al., "An Atlas of Human Gene Expression from Massively Parallel Signature Sequencing (MPSS)," Genome Research (2005) 15:1007-1014.
Kopper et al., "Genomics of Prostate Cancer: Is There Anything to 'Translate'?," Pathology Oncology Research (2005) 11:197-203.
Korkmaz, K.S., "Molecular Cloning and Characterization of STAMP1, A Highly Prostate-Specific Six Transmembrane Protein that is Overexpressed in Prostate Cancer," Journal of Biological Chemistry (2002) 277(39):36689-36696.
Krogh et al., "Predicting Transmembrane Protein Topology with a Hidden Markov Model: Application to Complete Genomes," Journal of Molecular Biology (2001) 305:567-580.
Lee et al., "Biomarker Discovery from the Plasma Proteome using Multidimensional Fractionation Proteomics," Current Opinion in Chemical Biology (2006) 10:42-49.

(Continued)

*Primary Examiner* — D L Jones
(74) *Attorney, Agent, or Firm* — Pabst Patent Group LLP

(57) ABSTRACT

The present invention relates generally to methods for identifying and using organ-specific proteins and transcripts. The present invention further provides compositions comprising organ-specific proteins and transcripts encoding the same, detection reagents for detecting such proteins and transcripts, and diagnostic panels, kits and arrays for measuring organ-specific proteins/transcripts in blood, biological tissue or other biological fluid.

6 Claims, 2 Drawing Sheets

(56) References Cited

OTHER PUBLICATIONS

Figure 1:
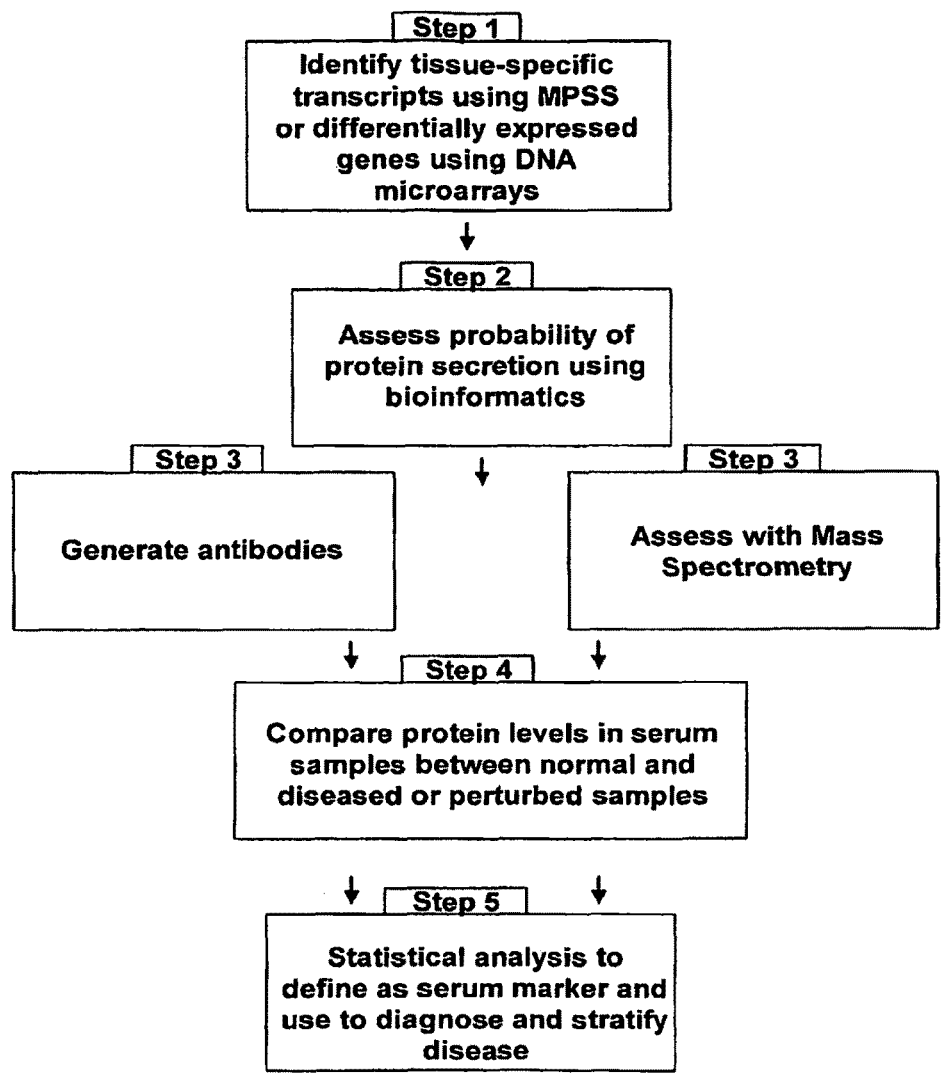

Liu et al., "Human Plasma N-Glycoproteome Analysis by Immunoaffinity Subtraction, Hydrazide Chemistry, and Mass Spectrometry," Journal of Proteome Research (2005) 4(6):2070-2080.
Lopez et al., "Reproducibility of Polypeptide Spot Positions in Two-Dimensional Gels Run Using Carrier Ampholytes in the Isoelectric Focusing Dimension," Electrophoresis (1997) 18:338-343.
Lu et al., "Molecular Analysis of Early Rice Stamen Development Using Organ-Specific Gene Expression Profiling," Plant Molecular Biology (2006) 61:845-861.
Mikkelsen et al., "Genome-Wide Maps of Chromatin State in Pluripotent and Lineage-Committed Cells," Nature (2007) 448(7153):553-560.
Nesvizhskii et al., "A Statistical Model for Identifying Proteins by Tandem Mass Spectrometry," Analytical Chemistry (2003) 75(17):4646-4658.
Omenn et al., Overview of the HUPO Plasma Proteome Project: Results from the Pilot Phase with 35 Collaborating Laboratories and Multiple Analytical Groups, Generating a Core Dataset of 3020 Proteins and a Publicly-Available Database,: Proteomics (2005) 5:3226-3245.
Pilch et al., "Large-Scale and High-Confidence Proteomic Analysis of Human Seminal Plasma," Genome Biology (2006) 7:R40.
Porkka et al., "Cloning and Characterization of a Novel Six-Transmembrane Protein *STEAP2*, Expressed n Normal and Malignant Prostate," Laboratory Investigation (2002) 82(11):1573-1582.
Robertson et al., "Genome-Wide Profiles of STAT1 DNA Association Using Chromatin Immunoprecipitation and Massively Parallel Sequencing," Nature Methods (2007) 4(8):651-657.
Schadt et al., "An Integrative Genomic Approach to Infer Causal Associations Between Gene Expression and Disease," Nature Genetics (2005) 37(7):710-717.
Szmitko et al., "Biomarkers of Vascular Disease Linking Inflammation to Endothelial Activation: Part II," Circulation (2003) 108:2041-2048.
Stolovitzky et al., "Statistical Analysis of MPSS Measurements: Application to the Study of LPS-Activated Macrophage Gene Expression," Publication of the National Academy of Sciences of the USA (2005) 102(5):1402-1407.
Sudhir, K., "Clinical Review: Lipoprotein-Associated Phospholipase $A_2$, a Novel Inflammatory Biomarker and Independent Risk Predictor for Cardiovascular Disease," Journal of Clinical Endocrinology & Metabolism (2005) 90(5):3100-3105.
Sumara et al., "'Jnking' Atherosclerosis," Cellular and Molecular Life Sciences (2005) 62:2487-2494.
Thompson et al. Screening for Prostate Cancer: Opportunities and Challenges,: Surgical Oncology Clinics of North America (2005) 14:747-760.
Triggiani et al., "Secretory Phospholipases $A_2$ in Inflammatory and Allergic Diseases: Not Just Enzymes," Journal of Allergy and Clinical Immunology (2005) 116:1000-1006.
Lin et al., "Evidence for the presence of disease-perturbed networks in prostate cancer cells by genomic and proteomic analyses: A Systems approach to disease", Cancer Research (2005) 65(8):3081-3091.
Lu et al., "Molecular analysis of early rice stamen development using organ-specific gene expression profiling", Plant Molecular Biology (2006) 61(6):845-861.
Partial European Search Report for EP 12174646.5, mailed Sep. 19, 2012.
Ricciarelli et al., "Microarray Analysis in Alzheimer's Disease and Normal Aging", IUBMB Life (2004) 56(6):349-354.
European Search Report for EP 12174646.5, mailed Jan. 11, 2013.

* cited by examiner

ORGAN-SPECIFIC PROTEINS AND METHODS OF THEIR USE

STATEMENT OF GOVERNMENT INTEREST

This invention was made with government support under Grant Nos. P50 CA097186 and P01 CA085859 awarded by the National Cancer Institute. The government may have certain rights in this invention.

SUBMISSION OF SEQUENCE LISTING ON COMPACT DISC

The content of the following submission on compact discs is incorporated herein by reference in its entirety: A computer readable form (CRF) of the Sequence Listing on compact disc (file name: 655652003300Seqlist.txt, date recorded: Nov. 3, 2011, size: 135,150,157 bytes); a duplicate compact disc copy of the Sequence Listing (COPY 1) (file name: 655652003300Seqlist.txt, date recorded: Nov. 3, 2011, size: 135,150,157 bytes); and a duplicate compact disc copy of the Sequence Listing (COPY 2) (file name: 655652003300Seqlist.txt, date recorded: Nov. 3, 2011, size: 135,150,157 bytes).

STATEMENT REGARDING TABLES SUBMITTED ON CD-ROM

Tables 1A-32A, 1B-32B, 36A-45A, 36B-45B, 47A-79A and 47B-79B associated with this application are provided on CD-ROM in lieu of a paper copy, and are hereby incorporated by reference into the specification. Three cd-roms are provided, containing identical copies of the tables, which are designed to be viewed in landscape presentation: CD-ROM no. 1 is labeled "COPY 1—TABLES PART," contains the 150 table files which are 20.15 MB combined and created on Aug. 9, 2007; CD-ROM no. 2 is labeled "COPY 2—TABLES PART," contains the 150 table files which are 20.15 MB combined and created on Aug. 9, 2007; CD-ROM no. 3 is labeled "COPY 3—TABLES PART," contains the 150 table files which are 20.15 MB combined and created on Aug. 9, 2007.

BACKGROUND OF THE INVENTION

1. Field of the Invention

The present invention relates generally to organ-specific proteins and polynucleotides that encode them. In particular the invention relates to diagnostic and prognostic panels, sets, and individual agents comprising reagents or probes to detect organ-specific proteins or polynucleotides and methods of identifying and using organ-specific proteins.

2. Description of the Related Art

The ability to monitor normal health and to detect the onset of disease at a very early and treatable stage is critical to diagnostic medicine. Early detection for most diseases, including diseases of the lung, cardiovascular disease, cancer, hematological disease (including most hematological cancers), inflammatory disorders, metabolic disease and neurological disease may permit treatment at an earlier stage that will produce healthier and typically more successful outcomes for the patient. Accordingly, there is a great need for more sensitive and accurate assays and methods to measure health and detect disease and monitor treatment at earlier stages.

Diagnostic assays are often incapable of identifying truly informative proteins for analyses and, to be useful, often require significant changes in protein composition in for example, blood, at the cellular level to detect the presence of disease or to define a change in health from normal. Current diagnostic assays may not detect disease until it has progressed to a stage where it is too late for effective treatment. For example, most cancers may be cured if diagnosed at the earliest stage. If cancer is diagnosed at later or advanced stages, effective treatment may be difficult or impossible and lead to reduced patient survival. In general, current diagnostic assays have severe limitations that prevent early detection and diagnosis.

In the context of blood protein diagnostics the major impediment to use in the early detection of disease is that most proteins are not disease-specific in that multiple organs synthesize them and different diseases may perturb their expression in different ways. Moreover, the specific proteins that are released in the disease state that are markers of the disease may be difficult to identify or to measure because of the enormous dynamic range of protein expression in the blood and because of the enormous protein complexity in the blood. These proteins must be distinguished from other protein markers found in the blood that are not likely to be disease markers. Other protein markers that are present in the blood that are not typically considered indicators of disease include proteins released due to: cellular damage, normal cellular turnover, stress responses (liver proteins) or other slight protein changes in the plasma. Additionally, 22 proteins constitute about 99% of the total blood protein mass. Indeed, one protein, albumin, comprises about 51% of this total blood protein mass. Most of these abundant blood proteins are not useful diagnostic markers. Useful diagnostic proteins are present in much lower abundance and typically in 1% of the remaining proteins (Lee et al., Curr Opin in Chem Bio (2006) 10:1-8). Many proteins are released into the blood following physiological changes from normal to the disease state and are likely present in plasma as low abundance proteins. Furthermore, blood proteins exhibit large differences in the concentration of the most abundant and least abundant proteins that range over many orders of magnitude. Proteins are expressed in blood across a range of about $10^{10}$ between the numbers of proteins. This means that one protein may be present at one copy in a given volume of blood, whereas another may be present at $10^{10}$ copies (Anderson and Anderson Mol and Cell Proteomics (2002) 1:845). Low abundance proteins may be hidden or dwarfed by the more prevalent high abundance proteins. Additionally, many proteins that are low abundance proteins are not indicative of disease. Distinguishing between the low abundance proteins that indicate disease from the low abundance proteins that are found in the normal cellular state is a major challenge to modern protein diagnostics. A major obstacle in diagnostic protein analysis of the blood is the numerous blood proteins and an inability by current methods to distinguish proteins from one another. Determining which blood proteins are predictive of disease at the earliest stages is very difficult at best, because the diagnostician must distinguish which low abundance protein is a marker of disease within the mass of proteins that are circulating in the blood.

Different approaches for identifying blood proteins are known in the art and have been used with varying and limited degrees of success. In particular, two-dimensional gel electrophoresis (2-DE) has been used for analysis of proteomic patterns in blood, but it is difficult to resolve large numbers of proteins such as are expressed in the average cell (up to 10,000 proteins). Moreover, 2-DE is incapable of identifying low abundance proteins without enrichment techniques.

Another method known in the art for blood protein diagnostics is capillary isoelectric focusing electrophoresis (CGE) although, the lack of reproducibility of protein patterns limits its use (Corthals, G. L., et al. *Electrophoresis*, (1997), 18:317, Lopez, M. F., and W. F. Patton, *Electrophoresis*, (1997), 18:338). Consequently, protein pattern analysis using techniques such as 2-DE, CGE and other similar techniques cannot generally be used for the analysis of blood proteins due to the inability to detect very low abundance proteins, irreproducible gel patterns, and the inability to quantify or identify individual spots (e.g., proteins). Further, the ability to extend these techniques to reproducible, consistent, easy to use and accurate high throughput diagnostic assays has been extremely limited. Thus, current assays that detect proteins do not provide the accuracy to use levels of blood (or other biological fluid or tissue) proteins, polypeptides or nucleic acids to monitor health and disease.

It is evident that a new diagnostic strategy is needed to distinguish between the many proteins that are found in the blood that reflect the normal health of a mammal and the organ-specific proteins that reflect a state of disease.

For the foregoing reasons, there is a need in the art to provide diagnostic and prognostic assays, nucleic acid and protein panels and arrays as well as methods to monitor health and diagnose disease. The present invention provides compositions, methods and assays that fulfill these and other needs.

BRIEF SUMMARY OF THE INVENTION

According to one aspect of the invention, there is provided a diagnostic panel comprising a plurality of detection reagents wherein each detection reagent is specific for one organ-specific protein; wherein the organ-specific proteins detected by the plurality of detection reagents are selected from any one of the organ-specific protein sets provided in the Tables herein; and wherein the plurality of detection reagents is selected such that the level of at least one of the organ-specific proteins detected by the plurality of detection reagents in a blood sample from a subject afflicted with a disease affecting the organ from which the organ-specific proteins are derived is above or below a predetermined normal range.

According to another aspect of the invention, there is provided a diagnostic panel comprising a plurality of detection reagents wherein each detection reagent is specific for one organ-specific protein; wherein the organ-specific proteins detected by the plurality of detection reagents are selected from two or more of the organ-specific protein sets provided in the Tables herein; and wherein the plurality of detection reagents is selected such that the level of at least one of the organ-specific proteins detected by the plurality of detection reagents in a blood sample from a subject afflicted with a disease affecting the organs from which the organ-specific proteins are derived is above or below a predetermined normal range.

According to yet another aspect of the invention, there is provided a method for defining a biological state of a subject comprising (a) measuring the level of at least two organ-specific proteins selected from any one of the organ-specific protein sets provided in the Tables herein in a blood sample from the subject; and (b) comparing the level determined in (a) to a predetermined normal level of the at least two organ-specific proteins; wherein a level of at least one of the two organ-specific proteins that is above or below the predetermined normal level defines the biological state of the subject.

In one embodiment of this aspect of the invention, the level of the at least two organ-specific proteins is measured using an immunoassay, e.g., by an ELISA assay. Alternatively, the level of the at least two organ-specific proteins is measured using mass spectrometry, an aptamer capture assay or any other suitable technique.

In another aspect of the invention, there is provided a method for defining a biological state of a subject comprising (a) measuring the level of at least two organ-specific proteins selected from any two or more of the organ-specific protein sets provided in the Tables herein in a blood sample from the subject; and (b) comparing the level determined in (a) to a predetermined normal level of the at least two organ-specific proteins; wherein a level of at least one of the two organ-specific proteins that is above or below the predetermined normal level defines the biological state of the subject. In one embodiment of this aspect of the invention, the level of the at least two organ-specific proteins is measured using an immunoassay, e.g., by an ELISA assay. Alternatively, the level of the at least two organ-specific proteins is measured using mass spectrometry, an aptamer capture assay or any other suitable technique.

In another aspect of the invention, a method is provided for defining a disease-associated organ-specific blood fingerprint comprising: (a) measuring the level of at least two organ-specific proteins selected from any one of the organ-specific protein sets provided in the Tables herein in a blood sample from a subject determined to have a disease affecting the organ from which the at least two organ-specific proteins are selected; and (b) comparing the level of the at least two organ-specific proteins determined in (a) to a predetermined normal level of the at least two organ-specific proteins; wherein a level of at least one of the at least two organ-specific proteins in the blood sample from the subject determined to have the disease that is below or above the corresponding predetermined normal level defines the disease-associated organ-specific blood fingerprint.

In one illustrative embodiment of this aspect of the invention, step (a) comprises measuring the level of at least three organ-specific proteins selected from any one of the organ-specific protein sets provided in the Tables herein and wherein a level of at least two of the at least three organ-specific proteins in the blood sample from the subject determined to have the disease that is below or above the corresponding predetermined normal level defines the disease-associated organ-specific blood fingerprint.

In another embodiment, step (a) comprises measuring the level of four or more organ-specific proteins selected from any one of the organ-specific protein sets provided in the Tables herein and wherein a level of at least three of the four or more organ-specific proteins in the blood sample from the subject determined to have the disease that is below or above the corresponding predetermined normal level defines the disease-associated organ-specific blood fingerprint.

In yet another embodiment, step (a) comprises measuring the level of four or more organ-specific proteins selected from any one of the organ-specific protein sets provided in the Tables herein and wherein a level of at least four of the four or more organ-specific proteins in the blood sample from the subject determined to have the disease that is below or above the corresponding predetermined normal level defines the disease-associated organ-specific blood fingerprint.

In another embodiment, step (a) comprises measuring the level of five or more organ-specific proteins selected from any one of the organ-specific protein sets provided in the Tables herein and wherein a level of at least five of the five or more organ-specific proteins in the blood sample from the subject determined to have the disease that is below or above the corresponding predetermined normal level defines the disease-associated organ-specific blood fingerprint.

Another aspect of the invention relates to a method for defining a disease-associated organ-specific blood fingerprint comprising; (a) measuring the level of at least two organ-specific proteins selected from two or more of the organ-specific protein sets provided in the Tables herein in a blood sample from a subject determined to have a disease of interest; and (b) comparing the level of the at least two organ-specific proteins determined in (a) to a predetermined normal level of the at least two organ-specific proteins; wherein a level of at least one of the at least two organ-specific proteins in the blood sample from the subject determined to have the disease that is below or above the corresponding predetermined normal level defining the disease-associated organ-specific blood fingerprint.

In one embodiment of this aspect of the invention, step (a) comprises measuring the level of at least three organ-specific proteins selected from two or more of the organ-specific protein sets provided in the Tables herein and wherein a level of at least two of the at least three organ-specific proteins in the blood sample from the subject determined to have the disease that is below or above the corresponding predetermined normal level defining the disease-associated organ-specific blood fingerprint.

In another embodiment, step (a) comprises measuring the level of four or more organ-specific proteins selected from two or more of the organ-specific protein sets provided in the Tables herein and wherein a level of at least three of the four or more organ-specific proteins in the blood sample from the subject determined to have the disease that is below or above the corresponding predetermined normal level defining the disease-associated organ-specific blood fingerprint.

In another embodiment, step (a) comprises measuring the level of four or more organ-specific proteins selected from two or more of the organ-specific protein sets provided in the Tables herein and wherein a level of at least four of the four or more organ-specific proteins in the blood sample from the subject determined to have the disease that is below or above the corresponding predetermined normal level defining the disease-associated organ-specific blood fingerprint.

In yet another embodiment, step (a) comprises measuring the level of five or more organ-specific proteins selected from two or more of the organ-specific protein sets provided in the Tables herein and wherein a level of at least five of the five or more organ-specific proteins in the blood sample from the subject determined to have the disease that is below or above the corresponding predetermined normal level defining the disease-associated organ-specific blood fingerprint.

According to another aspect of the invention, there is provided a method for detecting perturbation of a normal biological state in a subject comprising, (a) contacting a blood sample from the subject with a plurality of detection reagents wherein each detection reagent is specific for one organ-specific protein; wherein the organ-specific proteins detected by the plurality of detection reagents are selected from any one of the organ-specific protein sets provided in the Tables herein; (b) measuring the amount of the organ-specific protein detected in the blood sample by each detection reagent; and (c) comparing the amount of the organ-specific protein detected in the blood sample by each detection reagent to a predetermined normal amount for each respective organ-specific protein; wherein a statistically significant altered level in one or more of the organ-specific proteins indicates a perturbation in the normal biological state.

In another aspect, the invention provides a method for detecting perturbation of a normal biological state in a subject comprising, (a) contacting a blood sample from the subject with a plurality of detection reagents wherein each detection reagent is specific for one organ-specific protein; wherein the organ-specific proteins detected by the plurality of detection reagents are selected from two or more of the organ-specific protein sets provided in the Tables herein; (b) measuring the amount of the organ-specific protein detected in the blood sample by each detection reagent; and (c) comparing the amount of the organ-specific protein detected in the blood sample by each detection reagent to a predetermined normal amount for each respective organ-specific protein; wherein a statistically significant altered level in one or more of the organ-specific proteins indicates a perturbation in the normal biological state.

Another aspect of the invention provides a method for detecting prostate disease in a subject comprising, (a) contacting a blood sample from the subject with a plurality of detection reagents wherein each detection reagent is specific for one prostate-specific protein; wherein the prostate-specific proteins are selected from the organ-specific protein set provided in Table 21; (b) measuring the amount of the organ-specific protein detected in the blood sample by each detection reagent; and (c) comparing the amount of the organ-specific protein detected in the blood sample by each detection reagent to a predetermined normal control amount for each respective organ-specific protein;

wherein a statistically significant altered level in one or more of the organ-specific proteins indicates a perturbation in the normal biological state.

In one embodiment of this aspect of the invention, the prostate-specific proteins are selected from those proteins in Table 21 designated as secreted and with a specificity of 0.9 or greater. In another embodiment, the prostate disease is selected from the group consisting of prostate cancer, prostatitis, and benign prostatic hyperplasia. In another embodiment, the plurality of detection reagents comprises at least 2, at least 3, at least 4, at least 5 or at least 6 detection reagents as described herein.

In another aspect of the invention, there is provided a method for monitoring a response to a therapy in a subject, comprising the steps of: (a) measuring in a blood sample obtained from the subject the level of a plurality of organ-specific proteins, wherein the plurality of organ-specific proteins are selected from any one of the organ-specific protein sets provided in the Tables herein; (b) repeating step (a) using a blood sample obtained from the subject after undergoing therapy; and (c) comparing the level of the plurality of organ-specific proteins detected in step (b) to the amount detected in step (a) and therefrom monitoring the response to the therapy in the patient.

In yet another aspect of the invention, there is provide a method for monitoring a response to a therapy in a subject, comprising the steps of: (a) measuring in a blood sample obtained from the subject the level of a plurality of organ-specific proteins, wherein the plurality of organ-specific proteins are selected from two or more of the organ-specific protein sets provided in the Tables herein; (b) repeating step (a) using a blood sample obtained from the subject after undergoing therapy; and (c) comparing the level of the plurality of organ-specific proteins detected in step (b) to the amount detected in step (a) and therefrom monitoring the response to the therapy in the patient.

In the methods of the present invention, the plurality of detection reagents may be of any suitable or desire number, and will generally be between about two and 100 detection reagents. In one embodiment, the plurality of detection reagents is selected such that the level of at least two, at least three or at least four of the organ-specific proteins detected by the plurality of detection reagents in a blood sample from a subject afflicted with a disease affecting the organ from which the organ-specific proteins are derived is above or below a predetermined normal range.

The organ-specific proteins detected by the plurality of detection reagents may be selected from any one of the organ-specific protein sets provided in the Tables herein, and from among the proteins identified as secreted. In one embodiment, the organ-specific proteins detected by the plurality of detection reagents are selected from any one of the organ-specific protein sets provided in the Tables herein and from among the proteins identified as transmembrane. In another related embodiment, the organ-specific proteins detected by the plurality of detection reagents are selected from any one of the organ-specific protein sets provided in the Tables herein and from among the proteins with a specificity of 0.8 or greater. In one embodiment, the organ-specific proteins detected by the plurality of detection reagents are selected from any one of the organ-specific protein sets provided in Tables 47-79 and from among the proteins identified by MPSS data and SBS data. In this regard, these proteins are identified in Tables 47-79 by an "&".

The detection reagent used in the methods of the invention can be any suitable reagent for detection of the protein or proteins of interest. For example, in one embodiment, the detection reagent comprises an antibody (e.g., monoclonal antibody) or an antigen-binding fragment thereof. In another embodiment, the detection reagent comprises a DNA or RNA aptamer. In yet another embodiment, the detection reagent comprises an isotope labeled peptide.

The disease or diseases evaluated using the methods described herein can include essentially any diseases for which the organ-specific protein sets of the invention provide information of diagnostic or other medical value.

For example, in one embodiment, the disease affects the adrenal gland and the organ-specific proteins detected by the plurality of detection reagents are selected from Table 1.

In another embodiment, the disease affects the bladder and the organ-specific proteins detected by the plurality of detection reagents are selected from Table 2. In another embodiment, the disease is bladder cancer and the at least two organ-specific proteins are selected from Table 2.

In another embodiment, the disease affects the bone marrow and the organ-specific proteins detected by the plurality of detection reagents are selected from Table 3.

In another embodiment, the disease affects the brain amygdala and the organ-specific proteins detected by the plurality of detection reagents are selected from Table 4.

In another embodiment, the disease affects the colon and the organ-specific proteins detected by the plurality of detection reagents are selected from Table 11. In another embodiment, the colon disease is colon cancer and the organ-specific proteins detected by the plurality of detection reagents are selected from Table 11.

In another embodiment, the disease affects the heart and the organ-specific proteins detected by the plurality of detection reagents are selected from Table 12.

In another embodiment, the disease affects the kidney and the organ-specific proteins detected by the plurality of detection reagents are selected from Table 13. In another embodiment, the disease is kidney cancer and the at least two organ-specific proteins are selected from Table 13.

In another embodiment, the disease affects the lung and the organ-specific proteins detected by the plurality of detection reagents are selected from Table 14.

In another embodiment, the disease affects the mammary gland and the organ-specific proteins detected by the plurality of detection reagents are selected from Table 15. In another embodiment, the disease is breast cancer and the at least two organ-specific proteins are selected from Table 15.

In another embodiment, the disease affects the peripheral blood and the organ-specific proteins detected by the plurality of detection reagents are selected from Table 16.

In another embodiment, the disease affects the pancreas and the organ-specific proteins detected by the plurality of detection reagents are selected from Table 17.

In another embodiment, the disease affects the peripheral blood and the organ-specific proteins detected by the plurality of detection reagents are selected from Table 18.

In another embodiment, the disease affects the pituitary gland and the organ-specific proteins detected by the plurality of detection reagents are selected from Table 19.

In another embodiment, the disease affects the prostate and the organ-specific proteins detected by the plurality of detection reagents are selected from Table 21. In another embodiment, the disease is prostate cancer and the at least two organ-specific proteins are selected from Table 21.

In another embodiment, the disease affects the retina and the organ-specific proteins detected by the plurality of detection reagents are selected from Table 22.

In another embodiment, the disease affects the salivary gland and the organ-specific proteins detected by the plurality of detection reagents are selected from Table 23.

In another embodiment, the disease affects the Small intestine and the organ-specific proteins detected by the plurality of detection reagents are selected from Table 24.

In another embodiment, the disease affects the Spinal cord and the organ-specific proteins detected by the plurality of detection reagents are selected from Table 25.

In another embodiment, the disease affects the spleen and the organ-specific proteins detected by the plurality of detection reagents are selected from Table 26.

In another embodiment, the disease affects the stomach and the organ-specific proteins detected by the plurality of detection reagents are selected from Table 27.

In another embodiment, the disease affects the testis and the organ-specific proteins detected by the plurality of detection reagents are selected from Table 28.

In another embodiment, the disease affects the thymus and the organ-specific proteins detected by the plurality of detection reagents are selected from Table 29.

In another embodiment, the disease affects the thyroid and the organ-specific proteins detected by the plurality of detection reagents are selected from Table 30.

In another embodiment, the disease affects the uterus and the organ-specific proteins detected by the plurality of detection reagents are selected from Table 32.

In another embodiment, the disease is Cushing's syndrome.

In another embodiment, the disease is a bladder disease and the organ-specific proteins detected by the plurality of detection reagents are selected from any one or both of Tables 13 and 2.

In another embodiment, the disease is a neurological disease and the organ-specific proteins detected by the plurality of detection reagents are selected from any one or more of Tables 3, 4, 5, 6, 7, 8 and 9.

BRIEF DESCRIPTION OF THE SEVERAL VIEWS OF THE DRAWING(S)

FIG. 1 is a schematic of the instant invention and provides a general overview of the steps involved in one embodiment of the invention.

Figure 2:
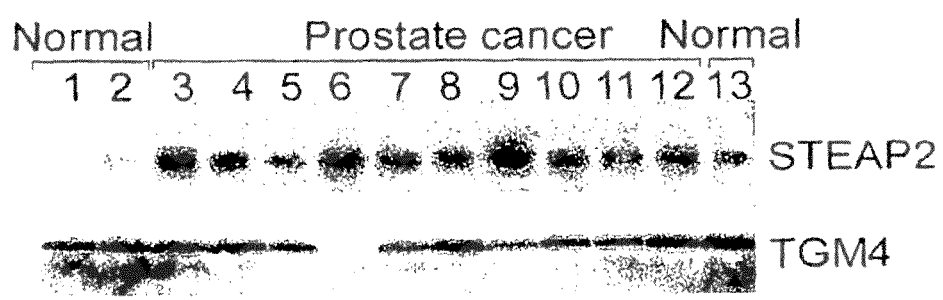

FIG. 2 is a photograph of a Western blot of serum from normal patients, early stage prostate cancer patients and late stage prostate cancer patients identifying differential expression of prostate-specific proteins. Serum samples from normal (1,2,8,13), and from early (3-7) and late (9-12) prostate cancer patients were resolved by SDS-PAGE and visualized by western blotting using antibodies directed against STEAP2 and TGM4. The experiment was conducted as described in Example 4.

BRIEF DESCRIPTION OF THE SEQUENCE IDENTIFIERS

SEQ ID NOs:1-368 correspond to polynucleotides encoding adrenal gland-specific proteins as described in Table 1.

SEQ ID NOs: 369-736 are the amino acid sequences of adrenal gland-specific proteins as described in Table 1.

SEQ ID NOs: 737-1028 are the polynucleotide sequences of the MPSS signature sequences of adrenal gland-specific proteins as described in Table 1.

SEQ ID NOs: 1029-1311 correspond to polynucleotides encoding bladder-specific proteins as described in Table 2.

SEQ ID NOs: 1312-1594 are the amino acid sequences of bladder-specific proteins as described in Table 2.

SEQ ID NOs: 1595-1795 are the polynucleotide sequences of the MPSS signature sequences of bladder-specific proteins as described in Table 2.

SEQ ID NOs: 1796-2094 correspond to polynucleotides encoding bone marrow-specific proteins as described in Table 3.

SEQ ID NOs: 2095-2393 are the amino acid sequences of bone marrow-specific proteins as described in Table 3.

SEQ ID NOs: 2394-2623 are the polynucleotide sequences of the MPSS signature sequences of bone marrow-specific proteins as described in Table 3.

SEQ ID NOs: 2624-2979 correspond to polynucleotides encoding brain amygdala-specific proteins as described in Table 4.

SEQ ID NOs: 2980-3335 are the amino acid sequences of brain amygdala-specific proteins as described in Table 4.

SEQ ID NOs: 3336-3579 are the polynucleotide sequences of the MPSS signature sequences of brain amygdala-specific proteins as described in Table 4.

SEQ ID NOs: 3580-4128 correspond to polynucleotides encoding brain caudate nucleus-specific proteins as described in Table 5.

SEQ ID NOs: 4129-4677 are the amino acid sequences of brain caudate nucleus-specific proteins as described in Table 5.

SEQ ID NOs: 4678-5069 are the polynucleotide sequences of the MPSS signature sequences of brain caudate nucleus-specific proteins as described in Table 5.

SEQ ID NOs: 5070-5903 correspond to polynucleotides encoding brain cerebellum-specific proteins as described in Table 6.

SEQ ID NOs: 5904-6737 are the amino acid sequences of brain cerebellum-specific proteins as described in Table 6.

SEQ ID NOs: 6738-7211 are the polynucleotide sequences of the MPSS signature sequences of brain cerebellum-specific proteins as described in Table 6.

SEQ ID NOs: 7212-7541 correspond to polynucleotides encoding brain corpus callosum-specific proteins as described in Table 7.

SEQ ID NOs: 7542-7871 are the amino acid sequences of brain corpus callosum-specific proteins as described in Table 7.

SEQ ID NOs: 7872-8113 are the polynucleotide sequences of the MPSS signature sequences of brain corpus callosum-specific proteins as described in Table 7.

SEQ ID NOs: 8114-9441 correspond to polynucleotides encoding brain fetal-specific proteins as described in Table 8.

SEQ ID NOs: 9442-10769 are the amino acid sequences of brain fetal-specific proteins as described in Table 8.

SEQ ID NOs: 10770-11903 are the polynucleotide sequences of the MPSS signature sequences of brain fetal-specific proteins as described in Table 8.

SEQ ID NOs: 11904-12159 correspond to polynucleotides encoding brain hypothalamus-specific proteins as described in Table 9.

SEQ ID NOs: 12160-12415 are the amino acid sequences of brain hypothalamus-specific proteins as described in Table 9.

SEQ ID NOs: 12416-12669 are the polynucleotide sequences of the MPSS signature sequences of brain hypothalamus-specific proteins as described in Table 9.

SEQ ID NOs: 12670-12877 correspond to polynucleotides encoding brain thalamus-specific proteins as described in Table 10.

SEQ ID NOs: 12878-13085 are the amino acid sequences of brain thalamus-specific proteins as described in Table 10.

SEQ ID NOs: 13086-13264 are the polynucleotide sequences of the MPSS signature sequences of brain thalamus-specific proteins as described in Table 10.

SEQ ID NOs: 13265-13531 correspond to polynucleotides encoding colon-specific proteins as described in Table 11.

SEQ ID NOs: 13532-13798 are the amino acid sequences of colon-specific proteins as described in Table 11.

SEQ ID NOs: 13799-14035 are the polynucleotide sequences of the MPSS signature sequences of colon-specific proteins as described in Table 11.

SEQ ID NOs: 14036-14449 correspond to polynucleotides encoding heart-specific proteins as described in Table 12.

SEQ ID NOs: 14450-14863 are the amino acid sequences of heart-specific proteins as described in Table 12.

SEQ ID NOs: 14864-15374 are the polynucleotide sequences of the MPSS signature sequences of heart-specific proteins as described in Table 12.

SEQ ID NOs: 15375-15550 correspond to polynucleotides encoding kidney-specific proteins as described in Table 13.

SEQ ID NOs: 15551-15726 are the amino acid sequences of kidney-specific proteins as described in Table 13.

SEQ ID NOs: 15727-15904 are the polynucleotide sequences of the MPSS signature sequences of kidney-specific proteins as described in Table 13.

SEQ ID NOs: 15905-16301 correspond to polynucleotides encoding lung-specific proteins as described in Table 14.

SEQ ID NOs: 16302-16698 are the amino acid sequences of lung-specific proteins as described in Table 14.

SEQ ID NOs: 16669-17022 are the polynucleotide sequences of the MPSS signature sequences of lung-specific proteins as described in Table 14.

SEQ ID NOs: 17023-17182 correspond to polynucleotides encoding mammary gland-specific proteins as described in Table 15.

SEQ ID NOs: 17183-17342 are the amino acid sequences of mammary gland-specific proteins as described in Table 15.

SEQ ID NOs: 17343-17493 are the polynucleotide sequences of the MPSS signature sequences of mammary gland-specific proteins as described in Table 15.

SEQ ID NOs: 17494-17962 correspond to polynucleotides encoding monocyte-specific proteins as described in Table 16.

SEQ ID NOs: 17963-18431 are the amino acid sequences of monocyte-specific proteins as described in Table 16.

SEQ ID NOs: 18432-18843 are the polynucleotide sequences of the MPSS signature sequences of monocyte-specific proteins as described in Table 16.

SEQ ID NOs: 18844-18872 correspond to polynucleotides encoding pancreas-specific proteins as described in Table 17.

SEQ ID NOs: 18873-18901 are the amino acid sequences of pancreas-specific proteins as described in Table 17.

SEQ ID NOs: 18902-18946 are the polynucleotide sequences of the MPSS signature sequences of pancreas-specific proteins as described in Table 17.

SEQ ID NOs: 18947-19350 correspond to polynucleotides encoding peripheral blood lymphocyte-specific proteins as described in Table 18.

SEQ ID NOs: 19351-19754 are the amino acid sequences of peripheral blood lymphocyte-specific proteins as described in Table 18.

SEQ ID NOs: 19755-20134 are the polynucleotide sequences of the MPSS signature sequences of peripheral blood lymphocyte-specific proteins as described in Table 18.

SEQ ID NOs: 20135-20275 correspond to polynucleotides encoding pituitary gland-specific proteins as described in Table 19.

SEQ ID NOs: 20276-20416 are the amino acid sequences of pituitary gland-specific proteins as described in Table 19.

SEQ ID NOs: 20417-20575 are the polynucleotide sequences of the MPSS signature sequences of pituitary gland-specific proteins as described in Table 19.

SEQ ID NOs: 20576-20842 correspond to polynucleotides encoding placenta-specific proteins as described in Table 20.

SEQ ID NOs: 20843-21109 are the amino acid sequences of placenta-specific proteins as described in Table 20.

SEQ ID NOs: 21110-21435 are the polynucleotide sequences of the MPSS signature sequences of placenta-specific proteins as described in Table 20.

SEQ ID NOs: 21436-22022 correspond to polynucleotides encoding prostate-specific proteins as described in Table 21.

SEQ ID NOs: 22023-22609 are the amino acid sequences of prostate-specific proteins as described in Table 21.

SEQ ID NOs: 22610-23274 are the polynucleotide sequences of the MPSS signature sequences of prostate-specific proteins as described in Table 21.

SEQ ID NOs: 23275-23605 correspond to polynucleotides encoding retina-specific proteins as described in Table 22.

SEQ ID NOs: 23606-23936 are the amino acid sequences of retina-specific proteins as described in Table 22.

SEQ ID NOs: 23937-24304 are the polynucleotide sequences of the MPSS signature sequences of retina-specific proteins as described in Table 22.

SEQ ID NOs: 24305-24434 correspond to polynucleotides encoding salivary gland-specific proteins as described in Table 23.

SEQ ID NOs: 24435-24564 are the amino acid sequences of salivary gland-specific proteins as described in Table 23.

SEQ ID NOs: 24565-24713 are the polynucleotide sequences of the MPSS signature sequences of salivary gland-specific proteins as described in Table 23.

SEQ ID NOs: 24714-24916 correspond to polynucleotides encoding small intestine-specific proteins as described in Table 24.

SEQ ID NOs: 24917-2519 are the amino acid sequences of small intestine-specific proteins as described in Table 24.

SEQ ID NOs: 25120-25337 are the polynucleotide sequences of the MPSS signature sequences of small intestine-specific proteins as described in Table 24.

SEQ ID NOs: 25338-25477 correspond to polynucleotides encoding spinal cord-specific proteins as described in Table 25.

SEQ ID NOs: 25478-25617 are the amino acid sequences of spinal cord-specific proteins as described in Table 25.

SEQ ID NOs: 25618-25808 are the polynucleotide sequences of the MPSS signature sequences of spinal cord-specific proteins as described in Table 25.

SEQ ID NOs: 25809-26278 correspond to polynucleotides encoding spleen-specific proteins as described in Table 26.

SEQ ID NOs: 26279-26748 are the amino acid sequences of spleen-specific proteins as described in Table 26.

SEQ ID NOs: 26749-27329 are the polynucleotide sequences of the MPSS signature sequences of spleen-specific proteins as described in Table 26.

SEQ ID NOs: 27330-27359 correspond to polynucleotides encoding stomach-specific proteins as described in Table 27.

SEQ ID NOs: 27360-27389 are the amino acid sequences of stomach-specific proteins as described in Table 27.

SEQ ID NOs: 27390-27422 are the polynucleotide sequences of the MPSS signature sequences of stomach-specific proteins as described in Table 27.

SEQ ID NOs: 27423-28424 correspond to polynucleotides encoding testis-specific proteins as described in Table 28.

SEQ ID NOs: 28425-29426 are the amino acid sequences of testis-specific proteins as described in Table 28.

SEQ ID NOs: 29427-30466 are the polynucleotide sequences of the MPSS signature sequences of testis-specific proteins as described in Table 28.

SEQ ID NOs: 30467-30729 correspond to polynucleotides encoding thymus-specific proteins as described in Table 29.

SEQ ID NOs: 30730-30992 are the amino acid sequences of thymus-specific proteins as described in Table 29.

SEQ ID NOs: 30993-31348 are the polynucleotide sequences of the MPSS signature sequences of thymus-specific proteins as described in Table 29.

SEQ ID NOs: 31349-31510 correspond to polynucleotides encoding thyroid-specific proteins as described in Table 30.

SEQ ID NOs: 31511-31672 are the amino acid sequences of thyroid-specific proteins as described in Table 30.

SEQ ID NOs: 31673-31846 are the polynucleotide sequences of the MPSS signature sequences of thyroid-specific proteins as described in Table 30.

SEQ ID NOs: 31847-31888 correspond to polynucleotides encoding trachea-specific proteins as described in Table 31.

SEQ ID NOs: 31889-31930 are the amino acid sequences of trachea-specific proteins as described in Table 31.

SEQ ID NOs: 31931-32002 are the polynucleotide sequences of the MPSS signature sequences of trachea-specific proteins as described in Table 31.

SEQ ID NOs: 32003-32065 correspond to polynucleotides encoding uterus-specific proteins as described in Table 32.

SEQ ID NOs: 32066-32128 are the amino acid sequences of uterus-specific proteins as described in Table 32.

SEQ ID NOs: 32129-32206 are the polynucleotide sequences of the MPSS signature sequences of uterus-specific proteins as described in Table 32.

SEQ ID NOs: 25362; 5142; 8639; 15453; 15915; 23547; 23548; and 17925 correspond to polynucleotides encoding organ-specific glycosylated proteins identified from a sample of normal human serum as described in Table 34.

SEQ ID NOs: 25502; 5976; 9967; 15629; 16312; 23878; 23879; and 18394 are the amino acid sequences of organ-specific glycosylated proteins identified from a sample of normal human serum as described in Table 34.

The following SEQ ID NOs correspond to the polynucleotides encoding specific to male organ—prostate-specific proteins as described in Table 36A identified using MPSS: 21436; 21437; 15907; 21438; 21439; 21440; 21441; 3582; 3583; 3584; 3585; 21442; 13270; 8131; 21443; 1801; 1032; 8135; 14042; 11908; 11909; 11910; 21444; 21445; 21446; 21447; 8144; 8145; 21448; 21449; 21450; 21451; 21452; 21453; 21454; 32207; 21455; 21456; 21457; 21458; 2633; 2634; 2635; 21459; 21460; 21461; 15; 1040; 16; 5101; 21462; 21463; 21464; 21465; 21466; 21467; 21468; 5102; 1814; 1041; 1042; 1043; 21469; 2638; 2639; 1044; 21470; 21471; 21472; 8187; 21473; 21474; 21475; 21476; 21477; 5110; 5111; 3622; 3623; 21478; 2649; 2650; 8198; 15403; 1820; 5122; 5123; 5124; 5125; 8200; 21479; 5126; 1047; 17520; 21480; 21481; 21482; 7238; 29; 21483; 21484; 8226; 21485; 21486; 21487; 21488; 21489; 21490; 32208; 21491; 21492; 21493; 21494; 21495; 21496; 21497; 21498; 21499; 21500; 21501; 18976; 18977; 21502; 21503; 15937; 21504; 1833; 21505; 21506; 21507; 21508; 5145; 21509; 21510; 11951; 21511; 21512; 21513; 15943; 21514; 18983; 18984; 18985; 18986; 18987; 18988; 18989; 18990; 5156; 5157; 21515; 21516; 21517; 8265; 8266; 21518; 21519; 8271; 3670; 21520; 21521; 19008; 21522; 1074; 20603; 19015; 56; 21523; 21524; 21525; 21526; 8300; 21527; 21528; 21529; 21530; 14100; 14101; 21531; 19017; 19018; 32209; 21532; 21533; 21534; 20605; 21535; 21536; 11967; 21537; 14107; 21538; 21539; 8326; 21540; 1869; 1870; 19043; 19044; 19045; 21541; 21542; 21543; 21544; 21545; 7282; 15423; 16001; 21546; 15428; 21547; 21548; 8356; 17589; 21549; 7283; 21550; 21551; 7285; 21552; 21553; 21554; 90; 8366; 8367; 21555; 21556; 21557; 21558; 21559; 21560; 21561; 21562; 21563; 20618; 20619; 21564; 21565; 21566; 21567; 21568; 8408; 5220; 21569; 21570; 21571; 11982; 2699; 21572; 21573; 21574; 1101; 21575; 21576; 1103; 101; 8422; 8423; 21577; 21578; 21579; 21580; 1104; 1885; 21581; 15441; 2705; 21582; 21583; 8458; 14141; 14142; 21584; 21585; 21586; 20622; 20623; 21587; 21588; 21589; 17065; 17066; 17067; 5242; 5243; 8470; 8471; 8476; 8477; 21590; 21591; 21592; 14147; 21593; 1897; 21594; 21595; 21596; 21597; 21598; 21599; 21600; 21601; 21602; 21603; 21604; 7308; 7309; 8508; 3738; 17620; 21605; 21606; 21607; 21608; 21609; 21610; 21611; 21612; 21613; 21614; 21615; 19078; 21616; 21617; 19082; 1121; 121; 122; 123; 124; 5254; 5256; 5257; 5258; 5259; 5260; 21618; 1122; 1123; 21619; 21620; 21621; 8547; 21622; 17636; 17637; 21623; 21624; 8551; 8552; 1132; 21625; 21626; 2730; 2731; 131; 132; 13364; 21627; 21628; 21629; 21630; 21631; 21632; 21633; 21634; 21635; 21636; 21637; 21638; 21639; 7339; 137; 8596; 8597; 8600; 8602; 21640; 1142; 21641; 21642; 21643; 14188; 21644; 21645; 21646; 21647; 5301; 7346; 21648; 21649; 21650; 156; 21651; 1938; 8641; 8642; 8643; 8644; 1939; 21652; 3796; 3797; 3798; 3799; 3800; 3801; 21653; 21654; 8666; 8667; 21655; 2753; 8674; 3821; 2755; 21656; 15459; 5359; 5360; 5361; 5362; 5363; 5364; 5365; 5366; 5367; 5368; 5369; 5370; 5371; 5372; 5373; 5374; 5375; 21657; 21658; 21659; 8700; 14215; 14216; 14217; 14219; 14220; 14222; 21660; 21661; 21662; 2782; 21663; 21664; 21665; 21666; 21667; 21668; 21669; 21670; 21671; 21672; 21673; 21674; 21675; 21676; 21677; 26010; 26011; 26012; 20698; 21678; 21679; 21680; 2792; 5397; 5398; 8735; 8736; 8737; 8738; 8739; 8740; 8741; 8742; 21681; 21682; 21683; 21684; 21685; 21686; 21687; 21688; 21689; 21690; 21691; 21692; 21693; 21694; 32210; 21695; 21696; 21697; 21698; 3867; 21699; 21700; 21701; 21702; 187; 21703; 21704; 21705; 21706; 21707; 21708; 21709; 21710; 21711; 21712; 21713; 21714; 21715; 21716; 32211; 21717; 21718; 21719; 21720; 21721; 21722; 21723; 21724; 21725; 21726; 21727; 21728; 21729; 21730; 21731; 21732; 21733; 21734; 21735; 21736; 21737; 21738; 21739; 21740; 21741; 32212; 21742; 21743; 21744; 21745; 21746; 21747; 21748; 21749; 21750; 21751; 21752; 17790; 19154; 2810; 21753; 21754; 3894; 16099; 16100; 21755; 21756; 21757; 21758; 21759; 21760; 21761; 2821; 1974; 21762; 21763; 21764; 21765; 21766; 21767; 21768; 21769; 21770; 21771; 8866; 2823; 2824; 2825; 2826; 2827; 2828; 2829; 2830; 21772; 21773; 21774; 2831; 21775; 2832; 8889; 8890; 16108; 5468; 21776; 21777; 8896; 21778; 21779; 21780; 21781; 21782; 21783; 21784; 211; 21785; 20238; 14271; 21786; 21787; 21788; 21789; 21790; 32213; 17117; 21791; 21792; 21793; 21794; 21795; 21796; 21797; 15493; 21798; 21799; 21800; 21801; 21802; 21803; 5477; 3915; 21804; 21805; 21806; 21807; 21808; 21809; 5479; 5480; 5481; 5482; 5483; 5484; 5485; 5486; 5487; 5488; 5489; 5490; 5491; 5492; 5493; 5494; 5495; 5496; 5497; 5498; 5499; 5500; 5501; 5502; 5503; 5504; 5505; 5506; 5507; 5508; 5509; 5510; 5511; 5512; 5513; 5514; 5515; 5516; 5517; 5518; 5519; 5520; 5521; 5522; 5523; 5524; 5525; 5526; 5527; 5528; 5529; 5530; 5531; 5532; 5533; 5534; 5535; 5536; 5537; 5538; 5539; 5540; 5541; 5542; 5543; 5544; 5545; 5546; 5547; 5548; 5549; 5550; 5551; 5552; 5553; 5554; 5555; 5556; 5557; 5558; 5559; 5560; 5561; 5562; 5563; 5564; 5565; 5566; 5567; 5568; 5569; 5570; 5571; 5572; 5573; 5574; 5575; 5576; 5577; 5578; 5579; 5580; 5581; 5582; 5583; 5584; 5585; 5586; 5587; 5588; 5589; 5590; 5591; 5592; 5593; 5594; 5595; 5596; 5597; 5598; 5599; 5600; 5601; 5602; 5603; 5604; 5605; 5606; 5607; 5608; 5609; 5610; 5611; 5612; 5613; 5614; 5615; 16124; 8916; 8917; 21810; 21811; 21812; 21813; 21814; 21815; 25424; 21816; 16133; 21817; 21818; 21819; 21820; 17820; 17821; 14293; 21821; 21822; 21823; 21824; 20745; 20746; 20747; 17123; 21825; 21826; 8959; 2859; 21827; 21828; 21829; 21830; 21831; 21832; 21833; 21834; 21835; 3948; 21836; 21837; 21838; 1201; 1996; 16141; 21839; 21840; 21841; 21842; 17129; 17130; 3952; 21843; 21844; 12815; 32214; 21845; 21846; 32215; 21847; 21848; 21849; 2873; 2874; 2875; 21850; 3964; 21851; 21852; 5682; 5683; 5684; 21853; 21854; 21855; 21856; 21857; 21858; 21859; 3972; 3973; 21860; 21861; 21862; 21863; 5686; 7436; 21864; 21865; 21866; 21867; 21868; 21869; 2881; 2882; 9061; 9062; 9063; 21870; 21871; 21872; 265; 266; 21873; 21874; 14343; 14344; 14345; 3986; 21875; 21876; 21877; 21878; 21879; 21880; 21881; 2891; 16168; 19218; 19219; 21882; 21883; 19220; 19221; 19222; 19223; 21884; 21885; 19224; 19225; 19226; 19227; 21886; 7452; 7453; 7454; 7455; 9097; 21887; 21888; 21889; 16170; 16171; 21890; 21891; 21892; 21893; 21894; 32216; 21895; 21896; 9119; 21897; 21898; 21899; 21900; 21901; 21902; 21903; 9139; 21904; 5739; 21905; 21906; 17888; 19241; 19243; 19244; 19245; 4016; 9156; 9157; 4017; 4018; 7468; 21907; 21908; 4021; 19256; 21909; 21910; 16178; 9166; 9167; 14363; 2039; 19261; 5753; 9179; 9180; 9181; 9182; 9183; 21911; 16188; 21912; 21913; 21914; 21915; 21916; 21917; 9187; 9220; 21918; 21919; 21920; 21921; 14372; 2054; 21922; 21923; 21924; 21925; 19280; 21926; 21927; 4035; 1258; 2911; 2912; 32217; 5777; 21928; 7483; 7484; 7485; 21929; 21930; 1262; 1263; 1264; 1265; 1266; 1267; 9264; 9265; 9266; 9267; 9268; 9269; 9270; 13490; 21931; 21932; 25454; 32218; 21933; 2922; 4051; 4052; 21934; 21935; 21936; 21937; 21938; 21939; 21940; 21941; 1270; 21942; 5789; 4061; 21943; 19299; 1277; 21944; 21945; 21946; 21947; 9308; 20813; 21948;

327; 21949; 21950; 21951; 21952; 21953; 21954; 21955; 21956; 21957; 21958; 21959; 4075; 21960; 16229; 32219; 21961; 21962; 21963; 21964; 21965; 336; 21966; 21967; 21968; 21969; 21970; 21971; 21972; 9326; 14410; 21973; 9329; 21974; 21975; 9332; 21976; 21977; 21978; 21979; 12857; 21980; 21981; 21982; 21983; 13525; 343; 21984; 21985; 20825; 16246; 21986; 15540; 15541; 7521; 21987; 2081; 21988; 12863; 21989; 21990; 21991; 13527; 13528; 21992; 16257; 20830; 21993; 21994; 21995; 19328; 19329; 19330; 21996; 20833; 21997; 21998; 21999; 22000; 32220; 22001; 17955; 17956; 17957; 22002; 22003; 22004; 22005; 22006; 361; 12869; 12870; 22007; 17178; 16290; 22008; 22009; 22010; 22011; 22012; 9416; 9417; 22013; 22014; 22015; 22016; 22017; 22018; 22019; 22020; 22021; 22022.

The following SEQ ID NOs correspond to the amino acid sequences of specific to male organ—prostate-specific proteins as described in Table 36A identified using MPSS: 22023; 22024; 16304; 22025; 22026; 22027; 22028; 4131; 4132; 4133; 4134; 22029; 13537; 9459; 22030; 2100; 1315; 9463; 14456; 12164; 12165; 12166; 22031; 22032; 22033; 22034; 9472; 9473; 22035; 22036; 22037; 22038; 22039; 22040; 22041; 32221; 22042; 22043; 22044; 22045; 2989; 2990; 2991; 22046; 22047; 22048; 383; 1323; 384; 5935; 22049; 22050; 22051; 22052; 22053; 22054; 22055; 5936; 2113; 1324; 1325; 1326; 22056; 2994; 2995; 1327; 22057; 22058; 22059; 9515; 22060; 22061; 22062; 22063; 22064; 5944; 5945; 4171; 4172; 22065; 3005; 3006; 9526; 15579; 2119; 5956; 5957; 5958; 5959; 9528; 22066; 5960; 1330; 17989; 22067; 22068; 22069; 7568; 397; 22070; 22071; 9554; 22072; 22073; 22074; 22075; 22076; 22077; 32222; 22078; 22079; 22080; 22081; 22082; 22083; 22084; 22085; 22086; 22087; 22088; 19380; 19381; 22089; 22090; 16334; 22091; 2132; 22092; 22093; 22094; 22095; 5979; 22096; 22097; 12207; 22098; 22099; 22100; 16340; 22101; 19387; 19388; 19389; 19390; 19391; 19392; 19393; 19394; 5990; 5991; 22102; 22103; 22104; 9593; 9594; 22105; 22106; 9599; 4219; 22107; 22108; 19412; 22109; 1357; 20870; 19419; 424; 22110; 22111; 22112; 22113; 9628; 22114; 22115; 22116; 22117; 14514; 14515; 22118; 19421; 19422; 32223; 22119; 22120; 22121; 20872; 22122; 22123; 12223; 22124; 14521; 22125; 22126; 9654; 22127; 2168; 2169; 19447; 19448; 19449; 22128; 22129; 22130; 22131; 22132; 7612; 15599; 16398; 22133; 15604; 22134; 22135; 9684; 18058; 22136; 7613; 22137; 22138; 7615; 22139; 22140; 22141; 458; 9694; 9695; 22142; 22143; 22144; 22145; 22146; 22147; 22148; 22149; 22150; 20885; 20886; 22151; 22152; 22153; 22154; 22155; 9736; 6054; 22156; 22157; 22158; 12238; 3055; 22159; 22160; 22161; 1384; 22162; 22163; 1386; 469; 9750; 9751; 22164; 22165; 22166; 22167; 1387; 2184; 22168; 15617; 3061; 22169; 22170; 9786; 14555; 14556; 22171; 22172; 22173; 20889; 20890; 22174; 22175; 22176; 17225; 17226; 17227; 6076; 6077; 9798; 9799; 9804; 9805; 22177; 22178; 22179; 14561; 22180; 2196; 22181; 22182; 22183; 22184; 22185; 22186; 22187; 22188; 22189; 22190; 22191; 7638; 7639; 9836; 4287; 18089; 22192; 22193; 22194; 22195; 22196; 22197; 22198; 22199; 22200; 22201; 22202; 19482; 22203; 22204; 19486; 1404; 489; 490; 491; 492; 6088; 6090; 6091; 6092; 6093; 6094; 22205; 1405; 1406; 22206; 22207; 22208; 9875; 22209; 18105; 18106; 22210; 22211; 9879; 9880; 1415; 22212; 22213; 3086; 3087; 499; 500; 13631; 22214; 22215; 22216; 22217; 22218; 22219; 22220; 22221; 22222; 22223; 22224; 22225; 22226; 7669; 505; 9924; 9925; 9928; 9930; 22227; 1425; 22228; 22229; 22230; 14602; 22231; 22232; 22233; 22234; 6135; 7676; 22235; 22236; 22237; 524; 22238; 2237; 9969; 9970; 9971; 9972; 2238; 22239; 4345; 4346; 4347; 4348; 4349; 4350; 22240; 22241; 9994; 9995; 22242; 3109; 10002; 4370; 3111; 22243; 15635; 6193; 6194; 6195; 6196; 6197; 6198; 6199; 6200; 6201; 6202; 6203; 6204; 6205; 6206; 6207; 6208; 6209; 22244; 22245; 22246; 10028; 14629; 14630; 14631; 14633; 14634; 14636; 22247; 22248; 22249; 3138; 22250; 22251; 22252; 22253; 22254; 22255; 22256; 22257; 22258; 22259; 22260; 22261; 22262; 22263; 22264; 26480; 26481; 26482; 20965; 22265; 22266; 22267; 3148; 6231; 6232; 10063; 10064; 10065; 10066; 10067; 10068; 10069; 10070; 22268; 22269; 22270; 22271; 22272; 22273; 22274; 22275; 22276; 22277; 22278; 22279; 22280; 22281; 32224; 22282; 22283; 22284; 22285; 4416; 22286; 22287; 22288; 22289; 555; 22290; 22291; 22292; 22293; 22294; 22295; 22296; 22297; 22298; 22299; 22300; 22301; 22302; 22303; 32225; 22304; 22305; 22306; 22307; 22308; 22309; 22310; 22311; 22312; 22313; 22314; 22315; 22316; 22317; 22318; 22319; 22320; 22321; 22322; 22323; 22324; 22325; 22326; 22327; 22328; 32226; 22329; 22330; 22331; 22332; 22333; 22334; 22335; 22336; 22337; 22338; 22339; 18259; 19558; 3166; 22340; 22341; 4443; 16496; 16497; 22342; 22343; 22344; 22345; 22346; 22347; 22348; 3177; 2273; 22349; 22350; 22351; 22352; 22353; 22354; 22355; 22356; 22357; 22358; 10194; 3179; 3180; 3181; 3182; 3183; 3184; 3185; 3186; 22359; 22360; 22361; 3187; 22362; 3188; 10217; 10218; 16505; 6302; 22363; 22364; 10224; 22365; 22366; 22367; 22368; 22369; 22370; 22371; 579; 22372; 20379; 14685; 22373; 22374; 22375; 22376; 22377; 32227; 17277; 22378; 22379; 22380; 22381; 22382; 22383; 22384; 15669; 22385; 22386; 22387; 22388; 22389; 22390; 6311; 4464; 22391; 22392; 22393; 22394; 22395; 22396; 6313; 6314; 6315; 6316; 6317; 6318; 6319; 6320; 6321; 6322; 6323; 6324; 6325; 6326; 6327; 6328; 6329; 6330; 6331; 6332; 6333; 6334; 6335; 6336; 6337; 6338; 6339; 6340; 6341; 6342; 6343; 6344; 6345; 6346; 6347; 6348; 6349; 6350; 6351; 6352; 6353; 6354; 6355; 6356; 6357; 6358; 6359; 6360; 6361; 6362; 6363; 6364; 6365; 6366; 6367; 6368; 6369; 6370; 6371; 6372; 6373; 6374; 6375; 6376; 6377; 6378; 6379; 6380; 6381; 6382; 6383; 6384; 6385; 6386; 6387; 6388; 6389; 6390; 6391; 6392; 6393; 6394; 6395; 6396; 6397; 6398; 6399; 6400; 6401; 6402; 6403; 6404; 6405; 6406; 6407; 6408; 6409; 6410; 6411; 6412; 6413; 6414; 6415; 6416; 6417; 6418; 6419; 6420; 6421; 6422; 6423; 6424; 6425; 6426; 6427; 6428; 6429; 6430; 6431; 6432; 6433; 6434; 6435; 6436; 6437; 6438; 6439; 6440; 6441; 6442; 6443; 6444; 6445; 6446; 6447; 6448; 6449; 16521; 10244; 10245; 22397; 22398; 22399; 22400; 22401; 22402; 25564; 22403; 16530; 22404; 22405; 22406; 22407; 18289; 18290; 14707; 22408; 22409; 22410; 22411; 21012; 21013; 21014; 17283; 22412; 22413; 10287; 3215; 22414; 22415; 22416; 22417; 22418; 22419; 22420; 22421; 22422; 4497; 22423; 22424; 22425; 1484; 2295; 16538; 22426; 22427; 22428; 22429; 17289; 17290; 4501; 22430; 22431; 13023; 32228; 22432; 22433; 32229; 22434; 22435; 22436; 3229; 3230; 3231; 22437; 4513; 22438; 22439; 6516; 6517; 6518; 22440; 22441; 22442; 22443; 22444; 22445; 22446; 4521; 4522; 22447; 22448; 22449; 22450; 6520; 7766; 22451; 22452; 22453; 22454; 22455; 22456; 3237; 3238; 10389; 10390; 10391; 22457; 22458; 22459; 633; 634; 22460; 22461; 14757; 14758; 14759; 4535; 22462; 22463; 22464; 22465; 22466; 22467; 22468; 3247; 16565; 19622; 19623; 22469; 22470; 19624; 19625; 19626; 19627; 22471; 22472; 19628; 19629; 19630; 19631; 22473; 7782; 7783; 7784; 7785; 10425; 22474; 22475; 22476; 16567; 16568; 22477; 22478; 22479; 22480; 22481; 32230; 22482; 22483; 10447; 22484; 22485; 22486; 22487; 22488; 22489; 22490; 10467; 22491; 6573; 22492; 22493; 18357; 19645; 19647; 19648; 19649; 4565; 10484; 10485; 4566; 4567; 7798; 22494; 22495; 4570; 19660;

22496; 22497; 16575; 10494; 10495; 14777; 2338; 19665; 6587; 10507; 10508; 10509; 10510; 10511; 22498; 16585; 22499; 22500; 22501; 22502; 22503; 22504; 10515; 10548; 22505; 22506; 22507; 22508; 14786; 2353; 22509; 22510; 22511; 22512; 19684; 22513; 22514; 4584; 1541; 3267; 3268; 32231; 6611; 22515; 7813; 7814; 7815; 22516; 22517; 1545; 1546; 1547; 1548; 1549; 1550; 10592; 10593; 10594; 10595; 10596; 10597; 10598; 13757; 22518; 22519; 25594; 32232; 22520; 3278; 4600; 4601; 22521; 22522; 22523; 22524; 22525; 22526; 22527; 22528; 1553; 22529; 6623; 4610; 22530; 19703; 1560; 22531; 22532; 22533; 22534; 10636; 21080; 22535; 695; 22536; 22537; 22538; 22539; 22540; 22541; 22542; 22543; 22544; 22545; 22546; 4624; 22547; 16626; 32233; 22548; 22549; 22550; 22551; 22552; 704; 22553; 22554; 22555; 22556; 22557; 22558; 22559; 10654; 14824; 22560; 10657; 22561; 22562; 10660; 22563; 22564; 22565; 22566; 13065; 22567; 22568; 22569; 22570; 13792; 711; 22571; 22572; 21092; 16643; 22573; 15716; 15717; 7851; 22574; 2380; 22575; 13071; 22576; 22577; 22578; 13794; 13795; 22579; 16654; 21097; 22580; 22581; 22582; 19732; 19733; 19734; 22583; 21100; 22584; 22585; 22586; 22587; 32234; 22588; 18424; 18425; 18426; 22589; 22590; 22591; 22592; 22593; 729; 13077; 13078; 22594; 17338; 16687; 22595; 22596; 22597; 22598; 22599; 10744; 10745; 22600; 22601; 22602; 22603; 22604; 22605; 22606; 22607; 22608; 22609.

The following SEQ ID NOs correspond to the polynucleotides encoding specific to male organ—Testis-specific proteins as described in Table 37A identified using MPSS: 27423; 27424; 14038; 27425; 27426; 21443; 27427; 27428; 27429; 27430; 27431; 32260; 27432; 27433; 5088; 27434; 27435; 27436; 27437; 32261; 27438; 27439; 27440; 27441; 27442; 8160; 15913; 27443; 27444; 21460; 27445; 27446; 27447; 27448; 27449; 27450; 27451; 27452; 27453; 27454; 27455; 27456; 27457; 27458; 27459; 32262; 27460; 12678; 5109; 27461; 27462; 27463; 13276; 27464; 27465; 27466; 27467; 27468; 27469; 27470; 20586; 27471; 27472; 27473; 27474; 27475; 27476; 13277; 13278; 27477; 27478; 27479; 27; 28; 27480; 27481; 27482; 21483; 18967; 27483; 27484; 24735; 2653; 31; 32; 27485; 27486; 8228; 27487; 27488; 27489; 27490; 27491; 27492; 27493; 27494; 27495; 27496; 27497; 27498; 27499; 27500; 27501; 27502; 27503; 27504; 27505; 27506; 27507; 27508; 27509; 27510; 7246; 7247; 7248; 7249; 7250; 7251; 27511; 27512; 27513; 27514; 27515; 27516; 27517; 27518; 27519; 17531; 27520; 12689; 12690; 12691; 12692; 12693; 12694; 12695; 12696; 12697; 12698; 12699; 12700; 27521; 27522; 27523; 27524; 13304; 27525; 27526; 27527; 27528; 3646; 3647; 3648; 3649; 8248; 27529; 27530; 27531; 27532; 27533; 5135; 27534; 27535; 27536; 27537; 27538; 27539; 27540; 27541; 27542; 27543; 27544; 18981; 27545; 27546; 27547; 27548; 27549; 27550; 27551; 27552; 27553; 27554; 27555; 27556; 27557; 24745; 27558; 27559; 27560; 27561; 27562; 27563; 27564; 27565; 27566; 27567; 27568; 27569; 27570; 12709; 12710; 12711; 12712; 27571; 21517; 27572; 27573; 27574; 27575; 27576; 27577; 45; 20160; 27578; 47; 2677; 27579; 27580; 7271; 27581; 27582; 27583; 27584; 27585; 27586; 27587; 27588; 27589; 27590; 27591; 27592; 8275; 3677; 27593; 27594; 20164; 27595; 27596; 27597; 20602; 27598; 27599; 27600; 27601; 1075; 27602; 27603; 27604; 27605; 20603; 27606; 21525; 27607; 23315; 23316; 27608; 27609; 27610; 27611; 23318; 8309; 8310; 8311; 25892; 27612; 27613; 27614; 1081; 27615; 27616; 27617; 14109; 17579; 17580; 27618; 27619; 27620; 27621; 32263; 65; 27622; 27623; 27624; 27625; 27626; 27627; 27628; 27629; 27630; 19049; 19050; 27631; 27632; 27633; 27634; 27635; 27636; 27637; 8353; 27638; 27639; 8356; 27640; 27641; 19052; 23340; 27642; 27643; 27644; 27645; 93; 94; 27646; 11981; 27647; 27648; 27649; 27650; 27651; 27652; 27653; 21557; 21558; 21559; 21560; 21561; 7289; 27654; 27655; 27656; 27657; 27658; 1100; 27659; 13337; 27660; 27661; 27662; 27663; 27664; 27665; 27666; 27667; 27668; 27669; 27670; 27671; 20179; 20180; 20181; 27672; 27673; 27674; 27675; 27676; 27677; 21578; 8426; 27678; 1885; 21581; 27679; 8447; 27680; 27681; 27682; 27683; 8459; 17611; 1891; 27684; 20183; 20184; 27685; 27686; 27687; 27688; 27689; 7299; 27690; 5241; 27691; 27692; 27693; 27694; 27695; 27696; 27697; 27698; 13350; 27699; 27700; 27701; 27702; 27703; 27704; 27705; 27706; 27707; 27708; 27709; 27710; 27711; 23360; 27712; 27713; 27714; 27715; 27716; 27717; 27718; 27719; 27720; 27721; 1119; 8507; 27722; 27723; 25382; 27724; 27725; 27726; 27727; 27728; 27729; 27730; 27731; 27732; 27733; 27734; 27735; 21613; 27736; 27737; 27738; 27739; 27740; 27741; 27742; 27743; 27744; 27745; 27746; 27747; 27748; 27749; 27750; 27751; 27752; 21616; 27753; 27754; 27755; 27756; 27757; 27758; 25947; 25948; 27759; 27760; 27761; 27762; 27763; 27764; 8533; 13354; 27765; 27766; 27767; 27768; 27769; 27770; 19083; 19084; 13355; 27771; 7320; 7321; 27772; 27773; 27774; 27775; 126; 127; 128; 27776; 27777; 27778; 27779; 27780; 27781; 27782; 8559; 27783; 27784; 27785; 27786; 27787; 27788; 27789; 27790; 27791; 25959; 24802; 3765; 27792; 8573; 27793; 27794; 27795; 27796; 27797; 1142; 27798; 3774; 27799; 27800; 27801; 27802; 27803; 27804; 8605; 5292; 17083; 8608; 27805; 27806; 27807; 8613; 8614; 8615; 8616; 27808; 27809; 2743; 27810; 27811; 27812; 27813; 27814; 12009; 12010; 27815; 27816; 14202; 14203; 14204; 14205; 27817; 27818; 27819; 8646; 27820; 3791; 27821; 27822; 27823; 27824; 27825; 27826; 27827; 27828; 27829; 20678; 15458; 8653; 8654; 27830; 8658; 25401; 8661; 27831; 27832; 27833; 23402; 23403; 27834; 27835; 20683; 25402; 27836; 27837; 8677; 27838; 27839; 27840; 27841; 27842; 27843; 27844; 14213; 27845; 27846; 27847; 8693; 8694; 1152; 1153; 19121; 27848; 27849; 32264; 27850; 3827; 3828; 3829; 3830; 3831; 3832; 3833; 3834; 3835; 3836; 3837; 3838; 3839; 3840; 3841; 3842; 3843; 3844; 3845; 3846; 12020; 12021; 27851; 27852; 27853; 27854; 2783; 13385; 27855; 27856; 2784; 27857; 27858; 27859; 5390; 27860; 27861; 27862; 27863; 27864; 27865; 27866; 23411; 23412; 23413; 27867; 27868; 27869; 27870; 2792; 27871; 27872; 27873; 27874; 27875; 27876; 27877; 27878; 27879; 27880; 27881; 27882; 27883; 27884; 27885; 27886; 27887; 27888; 27889; 27890; 32265; 27891; 27892; 27893; 27894; 27895; 27896; 27897; 27898; 27899; 27900; 2794; 2795; 2796; 2797; 2798; 2799; 2800; 2801; 2802; 27901; 27902; 27903; 27904; 27905; 27906; 27907; 27908; 27909; 27910; 27911; 12031; 27912; 27913; 27914; 27915; 27916; 27917; 27918; 27919; 27920; 27921; 27922; 27923; 27924; 27925; 27926; 27927; 27928; 27929; 27930; 27931; 27932; 27933; 27934; 27935; 27936; 21700; 27937; 27938; 27939; 27940; 27941; 27942; 27943; 27944; 27945; 27946; 27947; 27948; 5434; 27949; 27950; 27951; 27952; 27953; 27954; 27955; 27956; 27957; 27958; 27959; 27960; 27961; 27962; 27963; 27964; 27965; 27966; 27967; 27968; 27969; 27970; 27971; 27972; 27973; 27974; 27975; 27976; 27977; 27978; 27979; 27980; 27981; 27982; 27983; 27984; 27985; 27986; 3874; 27987; 3877; 27988; 27989; 27990; 12036; 27991; 27992; 27993; 3880; 27994; 27995; 27996; 27997; 27998; 27999; 28000; 28001; 28002; 28003; 28004; 28005; 28006; 28007; 28008; 32266; 32267; 28009; 28010; 28011; 28012; 28013; 28014; 28015; 28016; 28017; 28018; 28019; 28020; 28021; 28022; 28023; 28024; 28025; 28026; 28027; 28028; 28029; 28030; 28031; 28032; 28033; 21723; 28034; 28035; 21724; 21725; 28036; 28037; 28038; 28039; 28040; 28041; 28042; 28043;

28044; 28045; 28046; 28047; 21726; 21727; 21728; 21729; 21730; 21731; 28048; 28049; 28050; 28051; 28052; 21732; 21733; 21734; 21735; 21736; 21737; 28053; 28054; 28055; 28056; 28057; 28058; 28059; 28060; 28061; 28062; 28063; 28064; 28065; 21742; 28066; 28067; 28068; 32268; 32269; 28069; 1164; 8838; 28070; 28071; 28072; 28073; 8844; 24852; 28074; 28075; 28076; 28077; 28078; 28079; 28080; 28081; 28082; 28083; 2816; 19161; 19162; 28084; 12050; 28085; 23457; 23458; 23459; 8862; 28086; 28087; 28088; 28089; 28090; 28091; 28092; 28093; 28094; 14261; 14262; 28095; 210; 28096; 28097; 12799; 28098; 28099; 26067; 28100; 28101; 28102; 28103; 12800; 28104; 28105; 28106; 8894; 5468; 28107; 21782; 28108; 28109; 28110; 14267; 28111; 28112; 28113; 28114; 28115; 28116; 28117; 25420; 5475; 28118; 32270; 28119; 28120; 17814; 28121; 3918; 217; 218; 219; 16125; 13428; 13429; 28122; 20239; 14289; 26095; 2848; 17820; 17821; 8945; 231; 232; 8951; 8952; 8953; 28123; 8957; 8958; 28124; 28125; 28126; 28127; 28128; 28129; 28130; 28131; 28132; 28133; 3937; 28134; 28135; 28136; 28137; 28138; 28139; 28140; 28141; 28142; 28143; 20749; 28144; 28145; 28146; 28147; 28148; 2861; 8970; 28149; 28150; 28151; 28152; 28153; 3948; 28154; 28155; 28156; 28157; 28158; 28159; 8980; 28160; 28161; 8982; 28161; 8983; 8984; 28162; 8985; 28163; 8986; 28164; 8987; 28165; 28166; 8988; 28167; 8989; 28168; 8990; 28169; 8991; 28170; 8992; 8993; 28171; 8994; 28172; 28173; 8995; 8996; 28174; 8997; 28175; 28176; 28177; 5659; 5660; 9001; 9002; 28178; 28179; 28180; 32271; 14317; 14318; 14319; 14320; 14321; 28181; 28182; 28183; 28184; 28185; 2871; 2872; 9010; 249; 250; 251; 28186; 28187; 28188; 28189; 28190; 28191; 28192; 15507; 28193; 28194; 16147; 28195; 28196; 28197; 21853; 21854; 21855; 21856; 21857; 21858; 21859; 13443; 28198; 28199; 28200; 28201; 28202; 28203; 5687; 13456; 28204; 28205; 28206; 28207; 28208; 28209; 28210; 28211; 28212; 28213; 28214; 28215; 28216; 28217; 28218; 28219; 28220; 28221; 28222; 2885; 28223; 28224; 28225; 28226; 2889; 28227; 28228; 9098; 23511; 23512; 23513; 23514; 23515; 28229; 21889; 271; 28230; 28231; 12100; 3995; 274; 278; 28232; 28233; 28234; 28235; 28236; 28237; 4008; 16175; 28238; 5733; 28239; 28240; 28241; 28242; 28243; 283; 12827; 284; 28244; 28245; 28246; 28247; 23530; 23531; 28248; 26161; 26162; 28249; 28250; 28251; 28252; 28253; 28254; 28255; 28256; 28257; 28258; 28259; 28260; 28261; 28262; 28263; 28264; 28265; 28266; 28267; 9148; 28268; 19250; 19251; 19252; 19255; 28269; 28270; 28271; 28272; 12832; 1241; 28273; 291; 28274; 5753; 28275; 17897; 28276; 28277; 2901; 28278; 28279; 28280; 28281; 28282; 1253; 1254; 28283; 28284; 9236; 28285; 28286; 28287; 21922; 21923; 25453; 28288; 28289; 28290; 28291; 28292; 28293; 28294; 28295; 26197; 1259; 1260; 1261; 7480; 7481; 28296; 28297; 28298; 24898; 16206; 9260; 28299; 28300; 305; 306; 307; 2058; 2059; 28301; 28302; 28303; 28304; 28305; 28306; 28307; 28308; 28309; 308; 309; 28310; 28311; 28312; 28313; 7486; 28314; 28315; 28316; 12129; 28317; 28318; 28319; 28320; 2920; 2921; 24900; 28321; 28322; 28323; 28324; 28325; 14394; 9291; 28326; 4061; 9297; 28327; 28328; 28329; 28330; 5790; 28331; 32272; 32273; 28332; 17921; 21946; 28333; 28334; 28335; 28336; 21957; 21958; 28337; 28338; 28339; 4076; 23571; 9320; 20818; 28340; 28341; 28342; 28343; 12141; 28344; 28345; 28346; 28347; 28348; 28349; 28350; 14409; 28351; 28352; 28353; 28354; 12148; 28355; 28356; 28357; 28358; 28359; 28360; 16238; 28361; 2080; 16245; 28362; 28363; 28364; 12857; 17174; 28365; 28366; 28367; 28368; 5820; 28369; 28370; 28371; 28372; 28373; 28374; 28375; 28376; 28377; 28378; 28379; 28380; 9349; 7521; 28381; 28382; 4100; 28383; 28384; 1299; 28385; 21991; 1300; 28386; 28387; 28388; 28389; 28390; 9365; 9366; 9367; 9368; 4106; 28391; 2963; 2964; 2965; 2966; 12151; 27359; 23595; 9380; 28392; 28393; 28394; 5842; 28395; 355; 5846; 5847; 5848; 22002; 28396; 28397; 28398; 28399; 9396; 9397; 5880; 28400; 28401; 361; 28402; 12155; 4112; 28403; 4120; 1307; 26267; 13529; 28404; 12874; 28405; 28406; 28407; 26273; 26274; 28408; 28409; 28410; 28411; 28412; 28413; 28414; 28415; 28416; 28417; 22021; 28418; 28419; 28420; 28421; 28422; 28423; 12876; 12877; 28424; 7541.

The following SEQ ID NOs correspond to the amino acid sequences of specific to male organ—testis-specific proteins as described in Table 37A identified using MPSS: 28425; 28426; 14452; 28427; 28428; 22030; 28429; 28430; 28431; 28432; 28433; 32274; 28434; 28435; 5922; 28436; 28437; 28438; 28439; 32275; 28440; 28441; 28442; 28443; 28444; 9488; 16310; 28445; 28446; 22047; 28447; 28448; 28449; 28450; 28451; 28452; 28453; 28454; 28455; 28456; 28457; 28458; 28459; 28460; 28461; 32276; 28462; 12886; 5943; 28463; 28464; 28465; 13543; 28466; 28467; 28468; 28469; 28470; 28471; 28472; 20853; 28473; 28474; 28475; 28476; 28477; 28478; 13544; 13545; 28479; 28480; 28481; 395; 396; 28482; 28483; 28484; 22070; 19371; 28485; 28486; 24938; 3009; 399; 400; 28487; 28488; 9556; 28489; 28490; 28491; 28492; 28493; 28494; 28495; 28496; 28497; 28498; 28499; 28500; 28501; 28502; 28503; 28504; 28505; 28506; 28507; 28508; 28509; 28510; 28511; 28512; 7576; 7577; 7578; 7579; 7580; 7581; 28513; 28514; 28515; 28516; 28517; 28518; 28519; 28520; 28521; 18000; 28522; 12897; 12898; 12899; 12900; 12901; 12902; 12903; 12904; 12905; 12906; 12907; 12908; 28523; 28524; 28525; 28526; 13571; 28527; 28528; 28529; 28530; 4195; 4196; 4197; 4198; 9576; 28531; 28532; 28533; 28534; 28535; 5969; 28536; 28537; 28538; 28539; 28540; 28541; 28542; 28543; 28544; 28545; 28546; 19385; 28547; 28548; 28549; 28550; 28551; 28552; 28553; 28554; 28555; 28556; 28557; 28558; 28559; 24948; 28560; 28561; 28562; 28563; 28564; 28565; 28566; 28567; 28568; 28569; 28570; 28571; 28572; 12917; 12918; 12919; 12920; 28573; 22104; 28574; 28575; 28576; 28577; 28578; 28579; 413; 20301; 28580; 415; 3033; 28581; 28582; 7601; 28583; 28584; 28585; 28586; 28587; 28588; 28589; 28590; 28591; 28592; 28593; 28594; 9603; 4226; 28595; 28596; 20305; 28597; 28598; 28599; 20869; 28600; 28601; 28602; 28603; 1358; 28604; 28605; 28606; 28607; 20870; 28608; 22112; 28609; 23646; 23647; 28610; 28611; 28612; 28613; 23649; 9637; 9638; 9639; 26362; 28614; 28615; 28616; 1364; 28617; 28618; 28619; 14523; 18048; 18049; 28620; 28621; 28622; 28623; 32277; 433; 28624; 28625; 28626; 28627; 28628; 28629; 28630; 28631; 28632; 19453; 19454; 28633; 28634; 28635; 28636; 28637; 28638; 28639; 9681; 28640; 28641; 9684; 28642; 28643; 19456; 23671; 28644; 28645; 28646; 28647; 461; 462; 28648; 12237; 28649; 28650; 28651; 28652; 28653; 28654; 28655; 22144; 22145; 22146; 22147; 22148; 7619; 28656; 28657; 28658; 28659; 28660; 1383; 28661; 13604; 28662; 28663; 28664; 28665; 28666; 28667; 28668; 28669; 28670; 28671; 28672; 28673; 20320; 20321; 20322; 28674; 28675; 28676; 28677; 28678; 28679; 22165; 9754; 28680; 2184; 22168; 28681; 9775; 28682; 28683; 28684; 28685; 9787; 18080; 2190; 28686; 20324; 20325; 28687; 28688; 28689; 28690; 28691; 7629; 28692; 6075; 28693; 28694; 28695; 28696; 28697; 28698; 28699; 28700; 13617; 28701; 28702; 28703; 28704; 28705; 28706; 28707; 28708; 28709; 28710; 28711; 28712; 28713; 23691; 28714; 28715; 28716; 28717; 28718; 28719; 28720; 28721; 28722; 28723; 1402; 9835; 28724; 28725; 25522; 28726; 28727; 28728; 28729; 28730; 28731; 28732; 28733; 28734; 28735; 28736; 28737; 22200; 28738; 28739; 28740;

28741; 28742; 28743; 28744; 28745; 28746; 28747; 28748; 28749; 28750; 28751; 28752; 28753; 28754; 22203; 28755; 28756; 28757; 28758; 28759; 28760; 26417; 26418; 28761; 28762; 28763; 28764; 28765; 28766; 9861; 13621; 28767; 28768; 28769; 28770; 28771; 28772; 19487; 19488; 13622; 28773; 7650; 7651; 28774; 28775; 28776; 28777; 494; 495; 496; 28778; 28779; 28780; 28781; 28782; 28783; 28784; 9887; 28785; 28786; 28787; 28788; 28789; 28790; 28791; 28792; 28793; 26429; 25005; 4314; 28794; 9901; 28795; 28796; 28797; 28798; 28799; 1425; 28800; 4323; 28801; 28802; 28803; 28804; 28805; 28806; 9933; 6126; 17243; 9936; 28807; 28808; 28809; 9941; 9942; 9943; 9944; 28810; 28811; 3099; 28812; 28813; 28814; 28815; 28816; 12265; 12266; 28817; 28818; 14616; 14617; 14618; 14619; 28819; 28820; 28821; 9974; 28822; 4340; 28823; 28824; 28825; 28826; 28827; 28828; 28829; 28830; 28831; 20945; 15634; 9981; 9982; 28832; 9986; 25541; 9989; 28833; 28834; 28835; 23733; 23734; 28836; 28837; 20950; 25542; 28838; 28839; 10005; 28840; 28841; 28842; 28843; 28844; 28845; 28846; 14627; 28847; 28848; 28849; 10021; 10022; 1435; 1436; 19525; 28850; 28851; 32278; 28852; 4376; 4377; 4378; 4379; 4380; 4381; 4382; 4383; 4384; 4385; 4386; 4387; 4388; 4389; 4390; 4391; 4392; 4393; 4394; 4395; 12276; 12277; 28853; 28854; 28855; 28856; 3139; 13652; 28857; 28858; 3140; 28859; 28860; 28861; 6224; 28862; 28863; 28864; 28865; 28866; 28867; 28868; 23742; 23743; 23744; 28869; 28870; 28871; 28872; 3148; 28873; 28874; 28875; 28876; 28877; 28878; 28879; 28880; 28881; 28882; 28883; 28884; 28885; 28886; 28887; 28888; 28889; 28890; 28891; 28892; 32279; 28893; 28894; 28895; 28896; 28897; 28898; 28899; 28900; 28901; 28902; 3150; 3151; 3152; 3153; 3154; 3155; 3156; 3157; 3158; 28903; 28904; 28905; 28906; 28907; 28908; 28909; 28910; 28911; 28912; 28913; 12287; 28914; 28915; 28916; 28917; 28918; 28919; 28920; 28921; 28922; 28923; 28924; 28925; 28926; 28927; 28928; 28929; 28930; 28931; 28932; 28933; 28934; 28935; 28936; 28937; 28938; 22287; 28939; 28940; 28941; 28942; 28943; 28944; 28945; 28946; 28947; 28948; 28949; 28950; 6268; 28951; 28952; 28953; 28954; 28955; 28956; 28957; 28958; 28959; 28960; 28961; 28962; 28963; 28964; 28965; 28966; 28967; 28968; 28969; 28970; 28971; 28972; 28973; 28974; 28975; 28976; 28977; 28978; 28979; 28980; 28981; 28982; 28983; 28984; 28985; 28986; 28987; 28988; 4423; 28989; 4426; 28990; 28991; 28992; 12292; 28993; 28994; 28995; 4429; 28996; 28997; 28998; 28999; 29000; 29001; 29002; 29003; 29004; 29005; 29006; 29007; 29008; 29009; 29010; 32280; 32281; 29011; 29012; 29013; 29014; 29015; 29016; 29017; 29018; 29019; 29020; 29021; 29022; 29023; 29024; 29025; 29026; 29027; 29028; 29029; 29030; 29031; 29032; 29033; 29034; 29035; 22310; 29036; 29037; 22311; 22312; 29038; 29039; 29040; 29041; 29042; 29043; 29044; 29045; 29046; 29047; 29048; 29049; 22313; 22314; 22315; 22316; 22317; 22318; 29050; 29051; 29052; 29053; 29054; 22319; 22320; 22321; 22322; 22323; 22324; 29055; 29056; 29057; 29058; 29059; 29060; 29061; 29062; 29063; 29064; 29065; 29066; 29067; 22329; 29068; 29069; 29070; 32282; 32283; 29071; 1447; 10166; 29072; 29073; 29074; 29075; 10172; 25055; 29076; 29077; 29078; 29079; 29080; 29081; 29082; 29083; 29084; 29085; 3172; 19565; 19566; 29086; 12306; 29087; 23788; 23789; 23790; 10190; 29088; 29089; 29090; 29091; 29092; 29093; 29094; 29095; 29096; 14675; 14676; 29097; 578; 29098; 29099; 13007; 29100; 29101; 26537; 29102; 29103; 29104; 29105; 13008; 29106; 29107; 29108; 10222; 6302; 29109; 22369; 29110; 29111; 29112; 14681; 29113; 29114; 29115; 29116; 29117; 29118; 29119; 25560; 6309; 29120; 32284; 29121; 29122; 18283; 29123; 4467; 585; 586; 587; 16522; 13695; 13696; 29124; 20380; 14703; 26565; 3204; 18289; 18290; 10273; 599; 600; 10279; 10280; 10281; 29125; 10285; 10286; 29126; 29127; 29128; 29129; 29130; 29131; 29132; 29133; 29134; 29135; 4486; 29136; 29137; 29138; 29139; 29140; 29141; 29142; 29143; 29144; 29145; 21016; 29146; 29147; 29148; 29149; 29150; 3217; 10298; 29151; 29152; 29153; 29154; 29155; 4497; 29156; 29157; 29158; 29159; 29160; 29161; 10308; 29162; 10309; 10310; 29163; 10311; 10312; 29164; 10313; 29165; 10314; 29166; 10315; 29167; 29168; 10316; 29169; 10317; 29170; 10318; 29171; 10319; 29172; 10320; 10321; 29173; 10322; 29174; 29175; 10323; 10324; 29176; 10325; 29177; 29178; 29179; 6493; 6494; 10329; 10330; 29180; 29181; 29182; 32285; 14731; 14732; 14733; 14734; 14735; 29183; 29184; 29185; 29186; 29187; 3227; 3228; 10338; 617; 618; 619; 29188; 29189; 29190; 29191; 29192; 29193; 29194; 15683; 29195; 29196; 16544; 29197; 29198; 29199; 22440; 22441; 22442; 22443; 22444; 22445; 22446; 13710; 29200; 29201; 29202; 29203; 29204; 29205; 6521; 13723; 29206; 29207; 29208; 29209; 29210; 29211; 29212; 29213; 29214; 29215; 29216; 29217; 29218; 29219; 29220; 29221; 29222; 29223; 29224; 3241; 29225; 29226; 29227; 29228; 3245; 29229; 29230; 10426; 23842; 23843; 23844; 23845; 23846; 29231; 22476; 639; 29232; 29233; 12356; 4544; 642; 646; 29234; 29235; 29236; 29237; 29238; 29239; 4557; 16572; 29240; 6567; 29241; 29242; 29243; 29244; 29245; 651; 13035; 652; 29246; 29247; 29248; 29249; 23861; 23862; 29250; 26631; 26632; 29251; 29252; 29253; 29254; 29255; 29256; 29257; 29258; 29259; 29260; 29261; 29262; 29263; 29264; 29265; 29266; 29267; 29268; 29269; 10476; 29270; 19654; 19655; 19656; 19659; 29271; 29272; 29273; 29274; 13040; 1524; 29275; 659; 29276; 6587; 29277; 18366; 29278; 29279; 3257; 29280; 29281; 29282; 29283; 29284; 1536; 1537; 29285; 29286; 10564; 29287; 29288; 29289; 22509; 22510; 25593; 29290; 29291; 29292; 29293; 29294; 29295; 29296; 29297; 26667; 1542; 1543; 1544; 7810; 7811; 29298; 29299; 29300; 25101; 16603; 10588; 29301; 29302; 673; 674; 675; 2357; 2358; 29303; 29304; 29305; 29306; 29307; 29308; 29309; 29310; 29311; 676; 677; 29312; 29313; 29314; 29315; 7816; 29316; 29317; 29318; 12385; 29319; 29320; 29321; 29322; 3276; 3277; 25103; 29323; 29324; 29325; 29326; 29327; 14808; 10619; 29328; 4610; 10625; 29329; 29330; 29331; 29332; 6624; 29333; 32286; 32287; 29334; 18390; 22533; 29335; 29336; 29337; 29338; 22544; 22545; 29339; 29340; 29341; 4625; 23902; 10648; 21085; 29342; 29343; 29344; 29345; 12397; 29346; 29347; 29348; 29349; 29350; 29351; 29352; 14823; 29353; 29354; 29355; 29356; 12404; 29357; 29358; 29359; 29360; 29361; 29362; 16635; 29363; 2379; 16642; 29364; 29365; 29366; 13065; 17334; 29367; 29368; 29369; 29370; 6654; 29371; 29372; 29373; 29374; 29375; 29376; 29377; 29378; 29379; 29380; 29381; 29382; 10677; 7851; 29383; 29384; 4649; 29385; 29386; 1582; 29387; 22578; 1583; 29388; 29389; 29390; 29391; 29392; 10693; 10694; 10695; 10696; 4655; 29393; 3319; 3320; 3321; 3322; 12407; 27389; 23926; 10708; 29394; 29395; 29396; 6676; 29397; 723; 6680; 6681; 6682; 22589; 29398; 29399; 29400; 29401; 10724; 10725; 6714; 29402; 29403; 729; 29404; 12411; 4661; 29405; 4669; 1590; 26737; 13796; 29406; 13082; 29407; 29408; 29409; 26743; 26744; 29410; 29411; 29412; 29413; 29414; 29415; 29416; 29417; 29418; 29419; 22608; 29420; 29421; 29422; 29423; 29424; 29425; 13084; 13085; 29426; 7871.

The following SEQ ID NOs correspond to the polynucleotides encoding specific to Female Organ—Mammary Gland-specific proteins as described in Table 38A identified using MPSS: 17023; 17024; 17025; 17026; 32311; 8155; 8156; 17027; 17028; 7228; 17029; 17030; 17031; 5101; 17032; 23288; 5107; 5108; 17033; 17034; 17035; 17036;

17037; 17038; 32312; 32313; 32314; 32315; 32316; 32317; 17039; 8210; 8211; 8212; 8213; 17040; 17041; 17042; 17043; 17044; 17045; 17046; 40; 17047; 2669; 17048; 17049; 17050; 17051; 17052; 17053; 17054; 32318; 17055; 17056; 13327; 17057; 17058; 17059; 17060; 2699; 2700; 2701; 2702; 17061; 17062; 17063; 17064; 32319; 8458; 17065; 17066; 17067; 17068; 17069; 17070; 17071; 17072; 17073; 17074; 17075; 17076; 17077; 17078; 17079; 32320; 5254; 5255; 5256; 5257; 5258; 5259; 5260; 32321; 27774; 17080; 17081; 131; 11994; 11995; 27793; 17082; 17083; 17084; 17085; 150; 151; 17086; 17087; 17088; 164; 17089; 17090; 17091; 17092; 17093; 17094; 17095; 17096; 17097; 17098; 17099; 17100; 17101; 17102; 17103; 17104; 17105; 17106; 17107; 17108; 17109; 17110; 24820; 17111; 32322; 32323; 14246; 2814; 2815; 3903; 17112; 17113; 17114; 8888; 17115; 2835; 17116; 17117; 17118; 17119; 17120; 17121; 17122; 17123; 32324; 17124; 28123; 17125; 14298; 17126; 8970; 17127; 17128; 15503; 17129; 17130; 32215; 17131; 17132; 17133; 17134; 17135; 17136; 17137; 17138; 17139; 17140; 32325; 32326; 32327; 32328; 17141; 17142; 17143; 17144; 17145; 17146; 17147; 17148; 17149; 17150; 1236; 13473; 9158; 16177; 9163; 17151; 17152; 17153; 17154; 17155; 17156; 17157; 14365; 2043; 2044; 2045; 2046; 17158; 17159; 16190; 17160; 17161; 4033; 9243; 17162; 5776; 17163; 12843; 16225; 17164; 7509; 17165; 14407; 17166; 17167; 17168; 1281; 17169; 17170; 9327; 17171; 17172; 14421; 17173; 7516; 12857; 17174; 17175; 1299; 12151; 5837; 5838; 17176; 355; 17177; 17178; 16293; 17179; 5892; 5895; 17180; 17181; 17182.

The following SEQ ID NOs correspond to the amino acid sequences of specific to Female Organ—Mammary Gland-specific proteins as described in Table 38A identified using MPSS: 17183; 17184; 17185; 17186; 32329; 9483; 9484; 17187; 17188; 7558; 17189; 17190; 17191; 5935; 17192; 23619; 5941; 5942; 17193; 17194; 17195; 17196; 17197; 17198; 32330; 32331; 32332; 32333; 32334; 32335; 17199; 9538; 9539; 9540; 9541; 17200; 17201; 17202; 17203; 17204; 17205; 17206; 408; 17207; 3025; 17208; 17209; 17210; 17211; 17212; 17213; 17214; 32336; 17215; 17216; 13594; 17217; 17218; 17219; 17220; 3055; 3056; 3057; 3058; 17221; 17222; 17223; 17224; 32337; 9786; 17225; 17226; 17227; 17228; 17229; 17230; 17231; 17232; 17233; 17234; 17235; 17236; 17237; 17238; 17239; 32338; 6088; 6089; 6090; 6091; 6092; 6093; 6094; 32339; 28776; 17240; 17241; 499; 12250; 12251; 28795; 17242; 17243; 17244; 17245; 518; 519; 17246; 17247; 17248; 532; 17249; 17250; 17251; 17252; 17253; 17254; 17255; 17256; 17257; 17258; 17259; 17260; 17261; 17262; 17263; 17264; 17265; 17266; 17267; 17268; 17269; 17270; 25023; 17271; 32340; 32341; 14660; 3170; 3171; 4452; 17272; 17273; 17274; 10216; 17275; 3191; 17276; 17277; 17278; 17279; 17280; 17281; 17282; 17283; 32342; 17284; 29125; 17285; 14712; 17286; 10298; 17287; 17288; 15679; 17289; 17290; 32229; 17291; 17292; 17293; 17294; 17295; 17296; 17297; 17298; 17299; 17300; 32343; 32344; 32345; 32346; 17301; 17302; 17303; 17304; 17305; 17306; 17307; 17308; 17309; 17310; 1519; 13740; 10486; 16574; 10491; 17311; 17312; 17313; 17314; 17315; 17316; 17317; 14779; 2342; 2343; 2344; 2345; 17318; 17319; 16587; 17320; 17321; 4582; 10571; 17322; 6610; 17323; 13051; 16622; 17324; 7839; 17325; 14821; 17326; 17327; 17328; 1564; 17329; 17330; 10655; 17331; 17332; 14835; 17333; 7846; 13065; 17334; 17335; 1582; 12407; 6671; 6672; 17336; 723; 17337; 17338; 16690; 17339; 6726; 6729; 17340; 17341; 17342.

The following SEQ ID NOs correspond to the polynucleotides encoding specific to Female Organ—Uterus-specific proteins as described in Table 39A identified using MPSS: 1031; 32003; 32004; 5091; 32005; 32006; 32007; 32008; 32009; 32010; 32011; 32012; 21481; 20149; 32013; 32014; 13305; 32015; 32016; 8280; 11961; 32017; 32018; 32019; 25906; 32020; 32021; 32022; 32023; 7309; 32024; 32025; 21631; 32026; 8603; 20656; 32027; 32028; 21646; 32029; 32030; 8671; 20682; 32031; 32032; 8715; 8716; 32033; 5400; 32034; 32035; 32036; 32037; 32038; 32039; 32040; 16098; 21755; 21756; 32041; 32042; 32043; 8942; 8943; 8944; 32044; 21828; 32045; 32367; 32046; 32047; 32048; 32049; 32050; 32051; 19202; 1211; 9018; 9019; 32052; 32053; 32054; 32055; 32056; 32057; 23503; 23504; 31459; 31460; 31461; 31462; 31463; 31464; 31465; 31466; 31467; 31468; 32058; 20784; 32059; 23532; 23533; 23534; 23535; 23536; 13473; 19269; 19270; 32060; 32061; 21921; 26197; 2917; 2918; 20813; 32062; 31484; 1285; 1286; 1287; 1288; 1289; 1290; 1291; 27357; 32063; 5898; 366; 9426; 9427; 9432; 9433; 32064; 32065;

The following SEQ ID NOs correspond to the amino acid sequences of specific to Female Organ—Uterus-specific proteins as described in Table 39A identified using MPSS: 1314; 32066; 32067; 5925; 32068; 32069; 32070; 32071; 32072; 32073; 32074; 32075; 22068; 20290; 32076; 32077; 13572; 32078; 32079; 9608; 12217; 32080; 32081; 32082; 26376; 32083; 32084; 32085; 32086; 7639; 32087; 32088; 22218; 32089; 9931; 20923; 32090; 32091; 22233; 32092; 32093; 9999; 20949; 32094; 32095; 10043; 10044; 32096; 6234; 32097; 32098; 32099; 32100; 32101; 32102; 32103; 16495; 22342; 22343; 32104; 32105; 32106; 10270; 10271; 10272; 32107; 22415; 32108; 32368; 32109; 32110; 32111; 32112; 32113; 32114; 19606; 1494; 10346; 10347; 32115; 32116; 32117; 32118; 32119; 32120; 23834; 23835; 31621; 31622; 31623; 31624; 31625; 31626; 31627; 31628; 31629; 31630; 32121; 21051; 32122; 23863; 23864; 23865; 23866; 23867; 13740; 19673; 19674; 32123; 32124; 22508; 26667; 3273; 3274; 21080; 32125; 31646; 1568; 1569; 1570; 1571; 1572; 1573; 1574; 27387; 32126; 6732; 734; 10754; 10755; 10760; 10761; 32127; 32128.

The following SEQ ID NOs correspond to the polynucleotides encoding CL1 prostate cancer cell-specific proteins as described in Table 40A identified using MPSS: 32374; 17023; 32375; 32376; 12; 13; 32377; 32378; 5110; 5111; 32379; 8199; 8203; 8204; 8205; 8206; 32380; 5127; 3629; 32381; 32382; 32383; 32384; 32385; 1826; 32386; 32387; 2663; 2664; 32388; 11950; 7257; 32389; 25869; 20596; 32390; 32391; 32392; 32393; 21522; 32394; 32395; 32396; 32397; 32398; 15416; 32399; 11965; 11966; 32400; 14109; 32401; 25369; 8362; 8363; 32402; 20617; 7290; 32403; 32404; 32405; 101; 32406; 1105; 1106; 32407; 7299; 14145; 32408; 30506; 21592; 2717; 32409; 32410; 32411; 32412; 32413; 1124; 32414; 32415; 13363; 32416; 32417; 32418; 32419; 32420; 32421; 25973; 5301; 7346; 20211; 32422; 32423; 32424; 27831; 30542; 32425; 32426; 19120; 27853; 30551; 23411; 23412; 23413; 7360; 32427; 20220; 13394; 32428; 13397; 32429; 31873; 30603; 30606; 19143; 32430; 5450; 21755; 21756; 8858; 21762; 21763; 21764; 21765; 21766; 21767; 21768; 8869; 28092; 28093; 32431; 1174; 1175; 1176; 1177; 1178; 32432; 32433; 32434; 32435; 1179; 1180; 1181; 1182; 1183; 1184; 32436; 5471; 23463; 32437; 32438; 26079; 26081; 26082; 26084; 26085; 26087; 26088; 26090; 13418; 13419; 32439; 3925; 32440; 26104; 26105; 32441; 32442; 12811; 12812; 21832; 21833; 21834; 32443; 32444; 28177; 32445; 14317; 14318; 14319; 14320; 14321; 32214; 32446; 5667; 32447; 32448; 32449; 32450; 32451; 26134; 26135; 32452; 32453; 13458; 13459; 13460; 13461; 13462; 13463; 2890; 32454; 2038; 32455; 32456; 28274; 19264; 23545; 23546; 32457; 7474; 32458; 32459; 14376; 16200; 32460; 21933; 310; 20801; 32461; 9315; 2073;

32462; 331; 12850; 17930; 32463; 32464; 32465; 4089; 5819; 32466; 1297; 32467; 32468; 32469; 32470; 32471; 32472; 22002; 32473; 32474; 12874; 32475; 32476; 12875; 26277; 32477; 32478; 32479; 32480.

The following SEQ ID NOs correspond to the amino acid sequences of CL1 prostate cancer cell-specific proteins as described in Table 40A identified using MPSS: 32481; 17183; 32482; 32483; 380; 381; 32484; 32485; 5944; 5945; 32486; 9527; 9531; 9532; 9533; 9534; 32487; 5961; 4178; 32488; 32489; 32490; 32491; 32492; 2125; 32493; 32494; 3019; 3020; 32495; 12206; 7587; 32496; 26339; 20863; 32497; 32498; 32499; 32500; 22109; 32501; 32502; 32503; 32504; 32505; 15592; 32506; 12221; 12222; 32507; 14523; 32508; 25509; 9690; 9691; 32509; 20884; 7620; 32510; 32511; 32512; 469; 32513; 1388; 1389; 32514; 7629; 14559; 32515; 30769; 22179; 3073; 32516; 32517; 32518; 32519; 32520; 1407; 32521; 32522; 13630; 32523; 32524; 32525; 32526; 32527; 32528; 26443; 6135; 7676; 20352; 32529; 32530; 32531; 28833; 30805; 32532; 32533; 19524; 28855; 30814; 23742; 23743; 23744; 7690; 32534; 20361; 13661; 32535; 13664; 32536; 31915; 30866; 30869; 19547; 32537; 6284; 22342; 22343; 10186; 22349; 22350; 22351; 22352; 22353; 22354; 22355; 10197; 29094; 29095; 32538; 1457; 1458; 1459; 1460; 1461; 32539; 32540; 32541; 32542; 1462; 1463; 1464; 1465; 1466; 1467; 32543; 6305; 23794; 32544; 32545; 26549; 26551; 26552; 26554; 26555; 26557; 26558; 26560; 13685; 13686; 32546; 4474; 32547; 26574; 26575; 32548; 32549; 13019; 13020; 22419; 22420; 22421; 32550; 32551; 29179; 32552; 14731; 14732; 14733; 14734; 14735; 32228; 32553; 6501; 32554; 32555; 32556; 32557; 32558; 26604; 26605; 32559; 32560; 13725; 13726; 13727; 13728; 13729; 13730; 3246; 32561; 2337; 32562; 32563; 29276; 19668; 23876; 23877; 32564; 7804; 32565; 32566; 14790; 16597; 32567; 22520; 678; 21068; 32568; 10643; 2372; 32569; 699; 13058; 18399; 32570; 32571; 32572; 4638; 6653; 32573; 1580; 32574; 32575; 32576; 32577; 32578; 32579; 22589; 32580; 32581; 13082; 32582; 32583; 13083; 26747; 32584; 32585; 32586; 32587.

The following SEQ ID NOs correspond to the polynucleotides encoding LNCaP prostate cancer cell-specific proteins as described in Table 41A identified using MPSS: 32757; 32758; 32759; 32760; 21467; 32761; 32762; 32763; 32764; 23296; 23297; 23298; 32765; 30482; 32766; 32767; 58; 59; 60; 5196; 32768; 32769; 32770; 32771; 1107; 1108; 5241; 30506; 20629; 8513; 8514; 30522; 27760; 25387; 19096; 131; 32772; 32773; 32774; 32775; 2740; 8602; 32776; 19108; 32777; 8632; 1149; 32778; 32779; 32780; 5358; 5408; 5409; 32781; 32782; 32783; 32784; 32785; 32786; 32787; 32788; 32789; 28085; 8872; 8873; 8874; 8875; 8876; 8877; 8878; 8879; 32790; 32791; 32792; 32793; 32794; 32795; 21829; 23485; 1997; 1998; 32796; 14312; 30648; 14313; 14314; 14315; 32797; 32798; 32799; 32800; 32801; 5662; 1210; 2873; 2874; 2875; 32802; 21860; 32803; 32804; 21870; 14350; 32805; 32806; 32807; 32218; 32808; 21938; 32809; 32810; 32811; 32812; 5887.

The following SEQ ID NOs correspond to the amino acid sequences of LNCaP prostate cancer cell-specific proteins as described in Table 41A identified using MPSS: 32813; 32814; 32815; 32816; 22054; 32817; 32818; 32819; 32820; 23627; 23628; 23629; 32821; 30745; 32822; 32823; 426; 427; 428; 6030; 32824; 32825; 32826; 32827; 1390; 1391; 6075; 30769; 20896; 9841; 9842; 30785; 28762; 25527; 19500; 499; 32828; 32829; 32830; 32831; 3096; 9930; 32832; 19512; 32833; 9960; 1432; 32834; 32835; 32836; 6192; 6242; 6243; 32837; 32838; 32839; 32840; 32841; 32842; 32843; 32844; 32845; 29087; 10200; 10201; 10202; 10203; 10204; 10205; 10206; 10207; 32846; 32847; 32848; 32849; 32850; 32851; 22416; 23816; 2296; 2297; 32852; 14726; 30911; 14727; 14728; 14729; 32853; 32854; 32855; 32856; 32857; 6496; 1493; 3229; 3230; 3231; 32858; 22447; 32859; 32860; 22457; 14764; 32861; 32862; 32863; 32232; 32864; 22525; 32865; 32866; 32867; 32868; 6721.

The following SEQ ID NOs correspond to the polynucleotides encoding male organ, prostate-specific proteins identified using MPSS as described in Table 42A and Example 7: 21436; 21437; 15907; 21438; 21439; 21440; 21441; 3582; 3583; 3584; 3585; 21442; 13270; 8131; 21443; 1801; 1032; 8135; 14042; 11908; 11909; 11910; 21444; 21445; 21446; 21447; 8144; 8145; 21448; 21449; 21450; 21451; 21452; 21453; 21454; 21455; 21456; 21457; 21458; 2633; 2634; 2635; 21459; 21460; 21461; 15; 1040; 16; 5101; 21462; 21463; 21464; 21465; 21466; 21467; 21468; 5102; 1814; 1041; 1042; 1043; 21469; 2638; 2639; 1044; 21470; 21471; 21472; 8187; 21473; 21474; 21475; 21476; 21477; 5110; 5111; 3622; 3623; 21478; 2650; 8198; 15403; 1820; 5122; 5123; 5124; 5125; 8200; 21479; 5126; 1047; 17520; 21480; 21482; 7238; 29; 21483; 21484; 8226; 21485; 21486; 21487; 21488; 21489; 21490; 32208; 21491; 21492; 21493; 21494; 21495; 21496; 21497; 21498; 21499; 21500; 21501; 18976; 18977; 21502; 21503; 15937; 21504; 1833; 21505; 21506; 21507; 21508; 5145; 21509; 21510; 11951; 21511; 21512; 21513; 15943; 21514; 18983; 18984; 18985; 18986; 18987; 18988; 18989; 18990; 5156; 5157; 21515; 21516; 21517; 21518; 3670; 21520; 21521; 19008; 21522; 1074; 20603; 19015; 56; 21523; 21524; 21525; 21526; 8300; 21527; 21528; 21529; 21530; 14100; 14101; 21531; 19017; 19018; 32209; 21532; 21533; 21534; 20605; 21535; 21536; 11967; 21537; 14107; 21538; 21539; 8326; 21540; 1869; 1870; 19043; 19044; 19045; 21541; 21542; 21543; 21544; 7282; 15423; 16001; 21546; 15428; 21547; 21548; 8356; 17589; 21549; 7283; 21550; 21551; 7285; 21553; 21554; 90; 8366; 8367; 21555; 21556; 21557; 21558; 21559; 21560; 21561; 21562; 21563; 20618; 20619; 21564; 21565; 21566; 21567; 21568; 8408; 5220; 21569; 21570; 21571; 11982; 2699; 21572; 21573; 21574; 1101; 21575; 21576; 1103; 101; 8422; 8423; 21577; 21578; 21579; 21580; 1104; 1885; 21581; 15441; 2705; 21582; 21583; 8458; 14141; 14142; 21584; 21585; 21586; 20622; 20623; 21587; 21588; 21589; 17065; 17066; 17067; 5242; 5243; 8470; 8471; 8476; 8477; 21590; 21591; 21592; 14147; 21593; 1897; 21594; 21595; 21596; 21597; 21598; 21599; 21600; 21601; 21602; 21603; 7308; 7309; 8508; 3738; 17620; 21605; 21606; 21607; 21608; 21609; 21610; 21611; 21612; 21613; 21614; 21615; 19078; 21616; 21617; 19082; 121; 122; 123; 124; 5254; 5256; 5257; 5258; 5259; 5260; 21618; 1122; 1123; 21619; 21620; 21621; 8547; 21622; 17636; 17637; 21623; 21624; 8551; 8552; 1132; 21625; 21626; 2730; 2731; 131; 132; 13364; 21627; 21628; 21629; 21630; 21631; 21632; 21633; 21634; 21635; 21636; 21637; 21638; 21639; 7339; 137; 8596; 8597; 8600; 21640; 1142; 21641; 21642; 21643; 14188; 21645; 21646; 21647; 5301; 7346; 21648; 21649; 21650; 156; 21651; 1938; 8641; 8642; 8643; 8644; 1939; 21652; 3796; 3797; 3798; 3799; 3800; 3801; 21653; 21654; 8666; 8667; 21655; 2753; 8674; 3821; 2755; 21656; 15459; 5359; 5360; 5361; 5362; 5363; 5364; 5365; 5366; 5367; 5368; 5369; 5370; 5371; 5372; 5373; 5374; 5375; 21657; 21658; 21659; 8700; 14215; 14216; 14217; 14219; 14220; 14222; 21660; 21661; 21662; 2782; 21663; 21664; 21665; 21666; 21667; 21668; 21669; 21670; 21671; 21672; 21673; 21674; 21675; 21676; 21677; 20698; 21678; 21679; 21680; 2792; 5397; 5398; 8735; 8736; 8737; 8738; 8739; 8740; 8741; 8742; 21681; 21682; 21683; 21684; 21685; 21686; 21687; 21688; 21689; 21690; 21691; 21692; 21693; 21694; 32210; 21695; 21696; 21697; 21698; 3867; 21699; 21700; 21701; 187; 21703; 21704; 21705;

21706; 21707; 21708; 21710; 21711; 21713; 21714; 21715; 21716; 32211; 21717; 21718; 21719; 21721; 21722; 21723; 21724; 21725; 21726; 21727; 21728; 21729; 21730; 21731; 21732; 21733; 21734; 21735; 21736; 21737; 21738; 21739; 21740; 21741; 32212; 21742; 21743; 21744; 21745; 21746; 21747; 21748; 21749; 21750; 21751; 21752; 17790; 19154; 2810; 21753; 21754; 3894; 16099; 16100; 21755; 21756; 21757; 21758; 21759; 21760; 21761; 2821; 1974; 21762; 21763; 21764; 21765; 21766; 21767; 21768; 21769; 21770; 21771; 8866; 2823; 2824; 2825; 2826; 2827; 2828; 2829; 2830; 21772; 21773; 21774; 2831; 21775; 2832; 8889; 8890; 16108; 5468; 21776; 21777; 8896; 21778; 21779; 21780; 21781; 21782; 21783; 21784; 211; 21785; 20238; 14271; 21786; 21787; 21788; 21789; 21790; 17117; 21791; 21792; 21793; 21794; 21795; 21796; 21797; 15493; 21798; 21799; 21800; 21801; 21802; 21803; 5477; 3915; 21804; 21805; 21806; 21807; 21808; 21809; 5479; 5480; 5481; 5482; 5483; 5484; 5485; 5486; 5487; 5488; 5489; 5490; 5491; 5492; 5493; 5494; 5495; 5496; 5497; 5498; 5499; 5500; 5501; 5502; 5503; 5504; 5505; 5506; 5507; 5508; 5509; 5510; 5511; 5512; 5513; 5514; 5515; 5516; 5517; 5518; 5519; 5520; 5521; 5522; 5523; 5524; 5525; 5526; 5527; 5528; 5529; 5530; 5531; 5532; 5533; 5534; 5535; 5536; 5537; 5538; 5539; 5540; 5541; 5542; 5543; 5544; 5545; 5546; 5547; 5548; 5549; 5550; 5551; 5552; 5553; 5554; 5555; 5556; 5557; 5558; 5559; 5560; 5561; 5562; 5563; 5564; 5565; 5566; 5567; 5568; 5569; 5570; 5571; 5572; 5573; 5574; 5575; 5576; 5577; 5578; 5579; 5580; 5581; 5582; 5583; 5584; 5585; 5586; 5587; 5588; 5589; 5590; 5591; 5592; 5593; 5594; 5595; 5596; 5597; 5598; 5599; 5600; 5601; 5602; 5603; 5604; 5605; 5606; 5607; 5608; 5609; 5610; 5611; 5612; 5613; 5614; 5615; 16124; 8916; 8917; 21810; 21811; 21812; 21813; 21814; 21815; 25424; 21816; 16133; 21817; 21818; 21819; 21820; 17820; 17821; 14293; 21821; 21822; 21823; 21824; 20745; 20746; 20747; 17123; 21825; 21826; 8959; 2859; 21827; 21828; 21829; 21830; 21831; 21832; 21833; 21834; 21835; 3948; 21836; 21838; 1201; 1996; 16141; 21839; 21840; 21841; 21842; 17129; 17130; 3952; 21843; 21844; 12815; 32214; 21845; 21846; 32215; 21847; 21848; 21849; 21850; 3964; 21851; 21852; 5682; 5683; 5684; 21853; 21854; 21855; 21856; 21857; 21858; 21859; 3972; 3973; 21861; 21862; 21863; 5686; 7436; 21864; 21865; 21866; 21867; 21868; 21869; 2881; 2882; 9061; 9062; 9063; 21870; 21871; 21872; 265; 266; 21873; 21874; 14343; 14344; 14345; 3986; 21876; 21877; 21878; 21879; 21880; 21881; 2891; 16168; 19218; 19219; 21882; 21883; 19220; 19221; 19222; 19223; 21884; 21885; 19224; 19225; 19226; 19227; 21886; 7452; 7453; 7454; 7455; 9097; 21887; 21889; 16170; 16171; 21890; 21891; 21892; 21893; 21894; 21895; 21896; 9119; 21897; 21898; 21899; 21900; 21901; 21902; 21903; 9139; 21904; 5739; 21905; 17888; 19241; 19243; 19244; 19245; 4016; 4017; 4018; 7468; 21907; 21908; 4021; 19256; 21909; 16178; 9166; 9167; 14363; 2039; 19261; 9179; 9180; 9181; 9182; 9183; 21911; 16188; 21912; 21913; 21914; 21915; 21916; 21917; 9187; 9220; 21918; 21919; 21920; 21921; 14372; 21922; 21923; 21924; 21925; 19280; 21926; 21927; 4035; 1258; 2911; 2912; 32217; 5777; 21928; 7483; 7484; 7485; 21929; 21930; 1262; 1263; 1264; 1265; 1266; 1267; 9264; 9265; 9266; 9267; 9268; 9269; 9270; 13490; 21931; 21932; 25454; 21933; 2922; 4051; 4052; 21934; 21935; 21936; 21937; 21939; 21940; 21941; 1270; 21942; 5789; 4061; 21943; 19299; 1277; 21944; 21945; 9308; 20813; 21948; 327; 21949; 21950; 21951; 21952; 21953; 21954; 21955; 21956; 21957; 21958; 21959; 4075; 21960; 16229; 21961; 21962; 21963; 21964; 21965; 336; 21966; 21967; 21968; 21969; 21970; 21971; 21972; 9326; 14410; 21973; 9329; 21974; 21975; 9332; 21976; 21977; 21978; 21979; 12857; 21980; 21981; 21982; 21983; 13525; 343; 21984; 21985; 20825; 16246; 21986; 15540; 15541; 7521; 21987; 21988; 12863; 21989; 21991; 13527; 13528; 21992; 16257; 20830; 21993; 21994; 19328; 19329; 19330; 21996; 20833; 21997; 21998; 21999; 22000; 32220; 22001; 17955; 17956; 17957; 22002; 22003; 22004; 22005; 22006; 361; 12869; 12870; 22007; 17178; 16290; 22008; 22009; 22010; 22011; 22012; 9416; 9417; 22013; 22014; 22015; 22016; 22017; 22018; 22019; 22020; 22021; 22022

The following SEQ ID NOs correspond to the amino acid sequences of male organ, prostate-specific proteins identified using MPSS as described in Table 42A and Example 7: 22023; 22024; 16304; 22025; 22026; 22027; 22028; 4131; 4132; 4133; 4134; 22029; 13537; 9459; 22030; 2100; 1315; 9463; 14456; 12164; 12165; 12166; 22031; 22032; 22033; 22034; 9472; 9473; 22035; 22036; 22037; 22038; 22039; 22040; 22041; 22042; 22043; 22044; 22045; 2989; 2990; 2991; 22046; 22047; 22048; 383; 1323; 384; 5935; 22049; 22050; 22051; 22052; 22053; 22054; 22055; 5936; 2113; 1324; 1325; 1326; 22056; 2994; 2995; 1327; 22057; 22058; 22059; 9515; 22060; 22061; 22062; 22063; 22064; 5944; 5945; 4171; 4172; 22065; 3006; 9526; 15579; 2119; 5956; 5957; 5958; 5959; 9528; 22066; 5960; 1330; 17989; 22067; 22069; 7568; 397; 22070; 22071; 9554; 22072; 22073; 22074; 22075; 22076; 22077; 32222; 22078; 22079; 22080; 22081; 22082; 22083; 22084; 22085; 22086; 22087; 22088; 19380; 19381; 22089; 22090; 16334; 22091; 2132; 22092; 22093; 22094; 22095; 5979; 22096; 22097; 12207; 22098; 22099; 22100; 16340; 22101; 19387; 19388; 19389; 19390; 19391; 19392; 19393; 19394; 5990; 5991; 22102; 22103; 22104; 22105; 4219; 22107; 22108; 19412; 22109; 1357; 20870; 19419; 424; 22110; 22111; 22112; 22113; 9628; 22114; 22115; 22116; 22117; 14514; 14515; 22118; 19421; 19422; 32223; 22119; 22120; 22121; 20872; 22122; 22123; 12223; 22124; 14521; 22125; 22126; 9654; 22127; 2168; 2169; 19447; 19448; 19449; 22128; 22129; 22130; 22131; 7612; 15599; 16398; 22133; 15604; 22134; 22135; 9684; 18058; 22136; 7613; 22137; 22138; 7615; 22140; 22141; 458; 9694; 9695; 22142; 22143; 22144; 22145; 22146; 22147; 22148; 22149; 22150; 20885; 20886; 22151; 22152; 22153; 22154; 22155; 9736; 6054; 22156; 22157; 22158; 12238; 3055; 22159; 22160; 22161; 1384; 22162; 22163; 1386; 469; 9750; 9751; 22164; 22165; 22166; 22167; 1387; 2184; 22168; 15617; 3061; 22169; 22170; 9786; 14555; 14556; 22171; 22172; 22173; 20889; 20890; 22174; 22175; 22176; 17225; 17226; 17227; 6076; 6077; 9798; 9799; 9804; 9805; 22177; 22178; 22179; 14561; 22180; 2196; 22181; 22182; 22183; 22184; 22185; 22186; 22187; 22188; 22189; 22190; 7638; 7639; 9836; 4287; 18089; 22192; 22193; 22194; 22195; 22196; 22197; 22198; 22199; 22200; 22201; 22202; 19482; 22203; 22204; 19486; 489; 490; 491; 492; 6088; 6090; 6091; 6092; 6093; 6094; 22205; 1405; 1406; 22206; 22207; 22208; 9875; 22209; 18105; 18106; 22210; 22211; 9879; 9880; 1415; 22212; 22213; 3086; 3087; 499; 500; 13631; 22214; 22215; 22216; 22217; 22218; 22219; 22220; 22221; 22222; 22223; 22224; 22225; 22226; 7669; 505; 9924; 9925; 9928; 22227; 1425; 22228; 22229; 22230; 14602; 22232; 22233; 22234; 6135; 7676; 22235; 22236; 22237; 524; 22238; 2237; 9969; 9970; 9971; 9972; 2238; 22239; 4345; 4346; 4347; 4348; 4349; 4350; 22240; 22241; 9994; 9995; 22242; 3109; 10002; 4370; 3111; 22243; 15635; 6193; 6194; 6195; 6196; 6197; 6198; 6199; 6200; 6201; 6202; 6203; 6204; 6205; 6207; 6208; 6209; 22244; 22245; 22246; 10028; 14629; 14630; 14631; 14633; 14634; 14636; 22247; 22248; 22249; 3138; 22250; 22251; 22252; 22253; 22254; 22255; 22256; 22257; 22258; 22259; 22260;

22261; 22262; 22263; 22264; 20965; 22265; 22266; 22267; 3148; 6231; 6232; 10063; 10064; 10065; 10066; 10067; 10068; 10069; 10070; 22268; 22269; 22270; 22271; 22272; 22273; 22274; 22275; 22276; 22277; 22278; 22279; 22280; 22281; 32224; 22282; 22283; 22284; 22285; 4416; 22286; 22287; 22288; 555; 22290; 22291; 22292; 22293; 22294; 22295; 22297; 22298; 22300; 22301; 22302; 22303; 32225; 22304; 22305; 22306; 22308; 22309; 22310; 22311; 22312; 22313; 22314; 22315; 22316; 22317; 22318; 22319; 22320; 22321; 22322; 22323; 22324; 22325; 22326; 22327; 22328; 32226; 22329; 22330; 22331; 22332; 22333; 22334; 22335; 22336; 22337; 22338; 22339; 18259; 19558; 3166; 22340; 22341; 4443; 16496; 16497; 22342; 22343; 22344; 22345; 22346; 22347; 22348; 3177; 2273; 22349; 22350; 22351; 22352; 22353; 22354; 22355; 22356; 22357; 22358; 10194; 3179; 3180; 3181; 3182; 3183; 3184; 3185; 3186; 22359; 22360; 22361; 3187; 22362; 3188; 10217; 10218; 16505; 6302; 22363; 22364; 10224; 22365; 22366; 22367; 22368; 22369; 22370; 22371; 579; 22372; 20379; 14685; 22373; 22374; 22375; 22376; 22377; 17277; 22378; 22379; 22380; 22381; 22382; 22383; 22384; 15669; 22385; 22386; 22387; 22388; 22389; 22390; 6311; 4464; 22391; 22392; 22393; 22394; 22395; 22396; 6313; 6314; 6315; 6316; 6317; 6318; 6319; 6320; 6321; 6322; 6323; 6324; 6325; 6326; 6327; 6328; 6329; 6330; 6331; 6332; 6333; 6334; 6335; 6336; 6337; 6338; 6339; 6340; 6341; 6342; 6343; 6344; 6345; 6346; 6347; 6348; 6349; 6350; 6351; 6352; 6353; 6354; 6355; 6356; 6357; 6358; 6359; 6360; 6361; 6362; 6363; 6364; 6365; 6366; 6367; 6368; 6369; 6370; 6371; 6372; 6373; 6374; 6375; 6376; 6377; 6378; 6379; 6380; 6381; 6382; 6383; 6384; 6385; 6386; 6387; 6388; 6389; 6390; 6391; 6392; 6393; 6394; 6395; 6396; 6397; 6398; 6399; 6400; 6401; 6402; 6403; 6404; 6405; 6406; 6407; 6408; 6409; 6410; 6411; 6412; 6413; 6414; 6415; 6416; 6417; 6418; 6419; 6420; 6421; 6422; 6423; 6424; 6425; 6426; 6427; 6428; 6429; 6430; 6431; 6432; 6433; 6434; 6435; 6436; 6437; 6438; 6439; 6440; 6441; 6442; 6443; 6444; 6445; 6446; 6447; 6448; 6449; 16521; 10244; 10245; 22397; 22398; 22399; 22400; 22401; 22402; 25564; 22403; 16530; 22404; 22405; 22406; 22407; 18289; 18290; 14707; 22408; 22409; 22410; 22411; 21012; 21013; 21014; 17283; 22412; 22413; 10287; 3215; 22414; 22415; 22416; 22417; 22418; 22419; 22420; 22421; 22422; 4497; 22423; 22425; 1484; 2295; 16538; 22426; 22427; 22428; 22429; 17289; 17290; 4501; 22430; 22431; 13023; 32228; 22432; 22433; 32229; 22434; 22435; 22436; 22437; 4513; 22438; 22439; 6516; 6517; 6518; 22440; 22441; 22442; 22443; 22444; 22445; 22446; 4521; 4522; 22448; 22449; 22450; 6520; 7766; 22451; 22452; 22453; 22454; 22455; 22456; 3237; 3238; 10389; 10390; 10391; 22457; 22458; 22459; 633; 634; 22460; 22461; 14757; 14758; 14759; 4535; 22463; 22464; 22465; 22466; 22467; 22468; 3247; 16565; 19622; 19623; 22469; 22470; 19624; 19625; 19626; 19627; 22471; 22472; 19628; 19629; 19630; 19631; 22473; 7782; 7783; 7784; 7785; 10425; 22474; 22476; 16567; 16568; 22477; 22478; 22479; 22480; 22481; 22482; 22483; 10447; 22484; 22485; 22486; 22487; 22488; 22489; 22490; 10467; 22491; 6573; 22492; 18357; 19645; 19647; 19648; 19649; 4565; 4566; 4567; 7798; 22494; 22495; 4570; 19660; 22496; 16575; 10494; 10495; 14777; 2338; 19665; 10507; 10508; 10509; 10510; 10511; 22498; 16585; 22499; 22500; 22501; 22502; 22503; 22504; 10515; 10548; 22505; 22506; 22507; 22508; 14786; 22509; 22510; 22511; 22512; 19684; 22513; 22514; 4584; 1541; 3267; 3268; 32231; 6611; 22515; 7813; 7814; 7815; 22516; 22517; 1545; 1546; 1547; 1548; 1549; 1550; 10592; 10593; 10594; 10595; 10596; 10597; 10598; 13757; 22518; 22519; 25594; 22520; 3278; 4600; 4601; 22521; 22522; 22523; 22524; 22526; 22527; 22528; 1553; 22529; 6623; 4610; 22530; 19703; 1560; 22531; 22532; 10636; 21080; 22535; 695; 22536; 22537; 22538; 22539; 22540; 22541; 22542; 22543; 22544; 22545; 22546; 4624; 22547; 16626; 22548; 22549; 22550; 22551; 22552; 704; 22553; 22554; 22555; 22556; 22557; 22558; 22559; 10654; 14824; 22560; 10657; 22561; 22562; 10660; 22563; 22564; 22565; 22566; 13065; 22567; 22568; 22569; 22570; 13792; 711; 22571; 22572; 21092; 16643; 22573; 15716; 15717; 7851; 22574; 22575; 13071; 22576; 22578; 13794; 13795; 22579; 16654; 21097; 22580; 22581; 19732; 19733; 19734; 22583; 21100; 22584; 22585; 22586; 22587; 32234; 22588; 18424; 18425; 18426; 22589; 22590; 22591; 22592; 22593; 729; 13077; 13078; 22594; 17338; 16687; 22595; 22596; 22597; 22598; 22599; 10744; 10745; 22600; 22601; 22602; 22603; 22604; 22605; 22606; 22607; 22608; 22609.

The following SEQ ID NOs correspond to the amino acid sequences of adrenal gland-specific proteins identified using MPSS and that have been identified by mass spectrometry as described in Table 43A: 370; 371; 373; 374; 375; 380; 381; 383; 384; 386; 387; 388; 392; 393; 394; 397; 398; 399; 400; 401; 404; 406; 407; 408; 409; 410; 411; 412; 421; 423; 424; 426; 427; 428; 429; 430; 431; 432; 440; 441; 442; 443; 444; 449; 450; 451; 454; 456; 459; 460; 466; 467; 468; 469; 470; 471; 479; 480; 485; 488; 497; 499; 500; 503; 507; 511; 516; 517; 518; 519; 522; 523; 524; 525; 526; 527; 528; 532; 538; 541; 543; 544; 546; 547; 553; 556; 559; 563; 564; 565; 566; 567; 568; 569; 570; 572; 574; 576; 577; 590; 598; 608; 609; 611; 612; 613; 614; 615; 623; 624; 625; 628; 629; 630; 636; 637; 638; 639; 641; 642; 643; 644; 645; 648; 649; 653; 656; 659; 660; 661; 662; 663; 668; 670; 673; 674; 675; 676; 678; 686; 687; 688; 689; 699; 707; 708; 709; 710; 712; 713; 714; 715; 716; 717; 723; 724; 725; 730; 731.

The following SEQ ID NOs correspond to the amino acid sequences of bladder-specific proteins identified using MPSS and that have been identified by mass spectrometry as described in Table 43A: 1313; 1316; 1317; 1318; 1319; 1322; 1323; 1324; 1325; 1326; 1327; 1330; 1333; 1341; 1344; 1346; 1347; 1348; 1349; 1350; 1351; 1353; 1354; 1355; 1357; 1358; 1359; 1364; 1369; 1372; 1373; 1374; 1378; 1379; 1380; 1382; 1383; 1384; 1385; 1386; 1388; 1389; 1390; 1392; 1393; 1394; 1397; 1400; 1401; 1402; 1404; 1415; 1417; 1418; 499; 1419; 1420; 1425; 1428; 517; 1430; 1432; 1433; 1434; 1442; 1443; 1447; 1453; 1454; 1469; 1470; 1471; 1473; 1474; 1475; 1476; 1477; 1481; 1482; 1484; 1485; 1487; 1488; 1490; 1491; 1495; 1499; 1500; 1502; 1505; 1506; 1507; 1511; 1516; 1518; 1519; 1520; 1526; 1527; 1529; 1530; 1531; 1532; 1536; 1537; 1540; 1555; 1556; 1557; 1561; 1564; 1565; 1568; 1569; 1570; 1571; 1572; 1574; 1575; 1576; 1577; 1578; 1581; 1582; 1583; 1585; 1588; 1590; 1591; 1592; 1594.

The following SEQ ID NOs correspond to the amino acid sequences of bone marrow-specific proteins identified using MPSS and that have been identified by mass spectrometry as described in Table 43A: 2095; 2096; 2097; 2098; 2099; 2100; 2104; 2108; 2109; 2110; 2111; 2112; 2113; 2118; 2119; 2120; 2125; 2136; 2138; 2143; 2144; 2145; 2148; 2149; 2151; 2152; 2153; 2155; 2160; 2167; 2171; 2172; 2176; 2177; 2178; 2179; 470; 2183; 2184; 2185; 2191; 2192; 2195; 2218; 2219; 2220; 2222; 2224; 2227; 2228; 2230; 2231; 2232; 2233; 2234; 2235; 2242; 2243; 2244; 2245; 2246; 2250; 2252; 2253; 2256; 2257; 2258; 2259; 2260; 2261; 2262; 2263; 2265; 2266; 2267; 2268; 2269; 2271; 2274; 2283; 2290; 2292; 2293; 1484; 2296; 2297; 2306; 2308; 2309; 2310; 2311; 2312; 2316; 2317; 2318; 2319; 2320; 2321; 2322; 1511; 2326; 2328; 2330; 2336; 2337; 2338; 2339; 2340; 2341; 2342; 2343; 2344; 2345; 2346; 2347;

2348; 2349; 2350; 2353; 2354; 2356; 2357; 2358; 2363; 2372; 2373; 2375; 2380; 2381; 2382; 2385; 2386; 2387; 2388; 2389; 2393.

The following SEQ ID NOs correspond to the amino acid sequences of brain amygdala-specific proteins identified using MPSS and that have been identified by mass spectrometry as described in Table 43A: 2980; 2098; 2099; 2982; 2983; 2984; 2985; 2986; 2987; 2988; 2989; 2993; 2998; 3001; 3003; 3004; 3005; 3006; 3007; 1333; 3017; 3019; 3020; 408; 3023; 3024; 3025; 3026; 3033; 3035; 3036; 1358; 3037; 3040; 3041; 3042; 3043; 440; 441; 442; 443; 444; 3050; 3051; 3052; 3055; 3056; 3057; 3058; 3059; 3060; 3071; 3079; 3080; 3082; 3083; 2219; 2222; 3091; 3092; 3093; 3095; 3097; 3098; 3099; 522; 3101; 3110; 3112; 3139; 3141; 3142; 3143; 3148; 3164; 3166; 3167; 3169; 3171; 3172; 3177; 3187; 3189; 3190; 3191; 1470; 1471; 3198; 3199; 1481; 3200; 3201; 3202; 3203; 3204; 3218; 612; 613; 3220; 3221; 3222; 3223; 3227; 3228; 3229; 3230; 3231; 3232; 3233; 628; 3234; 3235; 3237; 3238; 3239; 3240; 3241; 3242; 3245; 3247; 3248; 3255; 1520; 3256; 3257; 3258; 3259; 3261; 3262; 3263; 3267; 3268; 3270; 3272; 3273; 3275; 3276; 3277; 3278; 3279; 3280; 3282; 3283; 3284; 3285; 3292; 3294; 3295; 3297; 3299; 3301; 3307; 3308; 3309; 3310; 3311; 3312; 714; 3314; 3315; 3316; 3317; 3324; 2386; 3327; 3328; 2393.

The following SEQ ID NOs correspond to the amino acid sequences of Brain Caudate Nucleus-specific proteins identified using MPSS and that have been identified by mass spectrometry as described in Table 43A: 4135; 4138; 2983; 2984; 2985; 4139; 4141; 4142; 4143; 4147; 4148; 4151; 4152; 4153; 388; 4158; 4163; 4165; 4168; 4171; 4172; 1330; 4177; 4178; 4179; 4190; 4194; 4205; 4206; 4207; 4208; 3026; 410; 4211; 4213; 4215; 4217; 4218; 4219; 4220; 4221; 4223; 4224; 4226; 4227; 4229; 426; 427; 428; 4238; 1364; 4239; 4240; 4244; 4251; 4252; 4253; 4254; 4255; 4258; 4263; 4264; 4266; 4269; 4270; 1386; 4274; 4278; 4280; 4281; 4282; 4283; 4284; 4288; 4290; 4295; 4296; 4297; 4304; 4305; 4312; 4313; 4314; 4316; 4319; 4323; 4324; 4329; 4333; 4336; 4339; 4341; 4344; 4345; 4346; 4347; 4348; 4349; 4350; 4356; 4371; 3112; 4372; 4374; 4375; 4407; 4408; 4409; 4410; 4425; 4432; 4437; 4439; 4444; 4445; 4446; 4455; 4459; 4462; 4463; 4466; 4467; 4468; 4469; 4470; 4471; 4475; 4478; 4479; 4481; 4483; 4484; 4487; 4496; 4498; 612; 613; 4500; 4503; 4504; 4506; 4510; 4511; 4512; 4513; 4517; 4518; 4521; 4525; 4526; 4535; 4541; 4542; 4544; 4552; 4553; 4554; 4559; 4560; 3255; 4563; 4564; 4565; 4566; 4567; 4570; 4572; 4574; 4576; 4577; 3259; 4580; 4586; 4587; 4588; 4590; 673; 674; 675; 4594; 4595; 4596; 4597; 4598; 4599; 4604; 4605; 4608; 4609; 4611; 4612; 4617; 3284; 3285; 4628; 4630; 4632; 4635; 1568; 1569; 1570; 1571; 1572; 1574; 4638; 4640; 4641; 4642; 4643; 4644; 4645; 4649; 4654; 4655; 4660; 4674; 4677; 2393.

The following SEQ ID NOs correspond to the amino acid sequences of Brain Cerebellum-specific proteins identified using MPSS and that have been identified by mass spectrometry as described in Table 43A: 5904; 2095; 2096; 2097; 5906; 5907; 5908; 5909; 5910; 5911; 5912; 2098; 2099; 5913; 5914; 5915; 5916; 5917; 5918; 5919; 5920; 5921; 5922; 5923; 5924; 5925; 5930; 5931; 5932; 5933; 5935; 2998; 5939; 5940; 5941; 5942; 5943; 5944; 5946; 3006; 5961; 5974; 5976; 5982; 5983; 5987; 5988; 5989; 410; 2138; 5997; 6000; 6001; 6011; 6012; 426; 427; 428; 6015; 6019; 6021; 6024; 6025; 6026; 6029; 6030; 4251; 456; 6037; 6038; 6042; 4255; 6049; 6052; 6054; 6056; 6057; 6058; 6059; 6060; 6061; 6064; 6065; 6066; 469; 6071; 6074; 6076; 6079; 6080; 6088; 6090; 6091; 6092; 6093; 6094; 3082; 3083; 6101; 6102; 2219; 6104; 6108; 6109; 6110; 6111; 6112; 6113; 6114; 6116; 6117; 6118; 6120; 6121; 6126; 6128; 6129; 6130; 6131; 6132; 4329; 6134; 6135; 6136; 6137; 6138; 6142; 1434; 6156; 6157; 4371; 6171; 6173; 6174; 6180; 6181; 6182; 6183; 6189; 6190; 6191; 6210; 6211; 6212; 6224; 6225; 6226; 6231; 6233; 6273; 6284; 6292; 6293; 6296; 6297; 6298; 6303; 6306; 6307; 1473; 1474; 1475; 1476; 1477; 6311; 4466; 6450; 6451; 6453; 6454; 6455; 6456; 6457; 6458; 6459; 6460; 3200; 6461; 6462; 6465; 3204; 6466; 6467; 6470; 6472; 6473; 6475; 6476; 1485; 6478; 6479; 6480; 6482; 6483; 6484; 6485; 6487; 6488; 6489; 6490; 6492; 6493; 6494; 6496; 6500; 1495; 6501; 6506; 4510; 6508; 3229; 3230; 3231; 6512; 6514; 3232; 6515; 1499; 6519; 6524; 6528; 6532; 6533; 6538; 6541; 6542; 6544; 6545; 6546; 6547; 6548; 6549; 6550; 6551; 6552; 6556; 6557; 6558; 6559; 6563; 6564; 6579; 6581; 6585; 6588; 6589; 6593; 1532; 1536; 1537; 6599; 6610; 6611; 6613; 3273; 3275; 6619; 6620; 4605; 6622; 6623; 6624; 6626; 6628; 6631; 6633; 6636; 6638; 4628; 6639; 6643; 6644; 3308; 3309; 3310; 3311; 3312; 1577; 6658; 3314; 3315; 6663; 6665; 6666; 6668; 6672; 6674; 6675; 2387; 2388; 2389; 6725; 6732; 6735; 4677; 2393.

The following SEQ ID NOs correspond to the amino acid sequences of Brain Corpus Callosum-specific proteins identified using MPSS and that have been identified by mass spectrometry as described in Table 43A: 7543; 7544; 7545; 7547; 7548; 7552; 7553; 2989; 7558; 2113; 7560; 7561; 7562; 7563; 7568; 4178; 7572; 7591; 7592; 7593; 7598; 7599; 7601; 4229; 7603; 7604; 7605; 3042; 3043; 7611; 7613; 7614; 7615; 7617; 7618; 3055; 3056; 3057; 3058; 6056; 6057; 6058; 6059; 6060; 6061; 7624; 7625; 7627; 7628; 7648; 4295; 4296; 7658; 7662; 7663; 7664; 7666; 7667; 3091; 3092; 7668; 7669; 7671; 7672; 6126; 2234; 2235; 7674; 7675; 6135; 7676; 7677; 7678; 7679; 7680; 7681; 7686; 7690; 7691; 7697; 7714; 7716; 559; 4446; 3177; 7726; 7729; 7733; 7734; 4475; 7736; 7737; 7742; 4487; 7756; 7757; 7760; 7761; 7762; 7763; 7767; 7768; 7770; 7776; 7777; 7778; 7779; 7780; 7782; 7783; 7784; 7785; 7786; 7791; 7792; 7793; 7795; 7796; 7797; 7798; 7801; 7802; 7803; 7804; 7805; 7813; 7814; 7836; 7838; 7840; 7841; 7844; 7846; 7847; 7851; 7852; 7853; 7861; 7863; 3327; 3328; 7867; 7869; 7871.

The following SEQ ID NOs correspond to the amino acid sequences of Brain Fetal-specific proteins identified using MPSS and that have been identified by mass spectrometry as described in Table 43A: 5904; 2095; 2096; 2097; 9442; 9443; 9446; 9449; 9450; 9451; 9452; 9453; 9454; 9455; 9456; 9457; 9458; 9459; 2100; 9460; 9463; 9464; 9465; 9466; 9467; 9468; 9469; 9472; 9473; 9477; 2983; 2984; 2985; 9485; 9489; 2989; 9490; 9495; 9497; 5935; 4147; 9500; 9503; 2112; 9512; 2998; 9515; 3001; 7561; 7562; 9516; 9517; 5944; 9519; 9520; 9521; 9522; 9523; 4171; 4172; 3006; 9526; 9527; 9528; 9529; 9530; 9536; 9545; 9546; 9550; 9551; 4178; 7572; 9561; 9562; 9563; 9565; 9569; 9574; 3019; 3020; 9581; 4206; 9585; 9589; 1346; 1347; 1348; 1349; 1350; 410; 4217; 4218; 412; 9602; 9603; 9608; 9609; 9611; 9613; 9618; 421; 9623; 9624; 3037; 3040; 9632; 9633; 9634; 9637; 9640; 6015; 9643; 9644; 9647; 9648; 9651; 6021; 9659; 9660; 9661; 9662; 9665; 440; 441; 442; 443; 444; 9667; 9679; 9680; 9682; 9686; 9687; 9689; 4254; 9692; 9694; 9695; 9696; 9699; 9702; 9703; 3050; 3051; 3052; 9705; 9707; 9708; 9711; 9712; 9713; 9714; 9715; 9716; 9717; 9732; 9734; 9735; 9736; 6056; 6057; 6058; 6059; 6060; 6061; 9740; 9741; 9742; 9744; 9746; 9747; 469; 9750; 9751; 9753; 9754; 9755; 9762; 9763; 9769; 9770; 2184; 9771; 9772; 9773; 3060; 9776; 9777; 9778; 9779; 9780; 9781; 9784; 1388; 1389; 9785; 9786; 9787; 9788;

9789; 9790; 9791; 1392; 9795; 4280; 4281; 4282; 9797; 9798; 9801; 4283; 9804; 9808; 9809; 9823; 9824; 9828; 9833; 9844; 9845; 9853; 9864; 9868; 9870; 4295; 4296; 9875; 9876; 3080; 9877; 9883; 497; 9885; 9886; 499; 9888; 9889; 9890; 4312; 4313; 9893; 9894; 9896; 9897; 9898; 9899; 9908; 9909; 9910; 9911; 9914; 9915; 9916; 9917; 9919; 2224; 7669; 9923; 9924; 9925; 9929; 9931; 6120; 9935; 9938; 9939; 9940; 9941; 9942; 9943; 9944; 9945; 9946; 4329; 9947; 9952; 9954; 9955; 9959; 9961; 9962; 9967; 9968; 9976; 9977; 6142; 9980; 9981; 9982; 9984; 9985; 532; 9991; 9992; 9999; 10003; 10004; 10005; 10008; 10009; 10019; 10020; 543; 10027; 10029; 10030; 10031; 10032; 10034; 10035; 10036; 10039; 10042; 10044; 10046; 10051; 7690; 10055; 10056; 4407; 4408; 10082; 10161; 10162; 10164; 10167; 10170; 10173; 10174; 4444; 4445; 563; 564; 565; 566; 567; 568; 569; 570; 10176; 10178; 3172; 10186; 3177; 10196; 10199; 10200; 10201; 10204; 10205; 10213; 10219; 10220; 10224; 10225; 4459; 3190; 10237; 10238; 6311; 10239; 10240; 10244; 10245; 3200; 10248; 6462; 4475; 10254; 10255; 10256; 10258; 10259; 10260; 10261; 10264; 10267; 10268; 10269; 10273; 6470; 6472; 6473; 10277; 10278; 10279; 10280; 10281; 10285; 10286; 10287; 10289; 10290; 10294; 4487; 10295; 10296; 10298; 10299; 10301; 10316; 10324; 10327; 10331; 10333; 10336; 6500; 3227; 3228; 10338; 1495; 10347; 10348; 10349; 10350; 10351; 10352; 10353; 10354; 10355; 6514; 10358; 10360; 10362; 10364; 10366; 10371; 10372; 10373; 10375; 10376; 10383; 10384; 10385; 10386; 6528; 10388; 10389; 10390; 10391; 10392; 10393; 10394; 10398; 3242; 10399; 10400; 10401; 10403; 10404; 10407; 10408; 10409; 10410; 10411; 10413; 10414; 10415; 10416; 10423; 10424; 10425; 10426; 4541; 10437; 1511; 643; 10441; 10444; 2326; 10445; 10447; 2328; 10450; 10457; 10458; 10459; 10460; 10461; 10462; 10463; 10464; 10465; 10467; 3255; 10476; 1519; 10477; 10478; 10479; 10481; 10482; 7795; 10484; 10485; 10486; 10487; 10488; 6579; 10489; 10490; 10491; 10492; 10496; 10497; 10498; 10499; 4574; 10501; 10502; 10506; 10508; 10509; 10511; 10512; 10513; 10514; 4576; 7803; 10515; 10517; 10519; 3257; 10549; 10552; 10553; 7804; 10554; 3259; 10558; 10559; 10560; 10564; 10565; 10570; 10578; 10582; 6611; 10583; 10584; 10590; 10591; 10595; 10596; 10598; 673; 674; 675; 10599; 676; 10600; 10603; 10604; 10605; 10606; 10607; 10608; 10610; 10611; 3275; 10614; 3276; 3277; 10615; 7836; 10616; 3279; 4608; 4609; 10620; 10626; 3283; 10628; 10636; 10639; 10640; 2372; 10644; 10645; 10646; 10647; 10649; 2375; 10652; 10656; 10657; 1568; 1569; 1570; 1571; 1572; 1574; 10660; 10670; 10671; 713; 4641; 10672; 10673; 10676; 10677; 10681; 2380; 10682; 10698; 10699; 10700; 10701; 10702; 10704; 10706; 10710; 10719; 10723; 10724; 10725; 2387; 2388; 2389; 10735; 10744; 10745; 7867.

The following SEQ ID NOs correspond to the amino acid sequences of Brain Hypothalamus-specific proteins identified using MPSS and that have been identified by mass spectrometry as described in Table 43A: 2980; 12162; 373; 374; 5911; 5912; 9472; 9473; 9489; 12175; 12176; 5935; 1324; 1325; 1326; 12177; 12183; 12184; 12187; 12188; 12189; 12190; 12191; 12192; 12193; 12195; 12198; 12202; 12212; 12218; 12220; 9632; 9633; 1359; 12221; 12222; 12223; 12227; 12230; 12232; 12233; 9736; 467; 6065; 6066; 12243; 12244; 12245; 7662; 12249; 7664; 7666; 7667; 7668; 12250; 12251; 12253; 12254; 12258; 12263; 12264; 6134; 522; 12267; 12268; 10004; 10019; 10020; 12276; 12277; 12279; 12280; 12281; 12282; 7691; 546; 4409; 12303; 2271; 12306; 10213; 10220; 3190; 3191; 6311; 2283; 12315; 12316; 6450; 6451; 12317; 12318; 12320; 12321; 12322; 10268; 6471; 12323; 6470; 12324; 12325; 12330; 10298; 12332; 12334; 12335; 4500; 12338; 12339; 6496; 6508; 10348; 10349; 10350; 10351; 10352; 10353; 10354; 10355; 6514; 12342; 12345; 12350; 12356; 6563; 6564; 12357; 12362; 12363; 10506; 12365; 12370; 12376; 12383; 12386; 4609; 12387; 12390; 7838; 12395; 12397; 12399; 12403; 12405; 12406; 7863; 12411; 731.

The following SEQ ID NOs correspond to the amino acid sequences of Brain Thalamus-specific proteins identified using MPSS and that have been identified by mass spectrometry as described in Table 43A: 12878; 12879; 12880; 12890; 4177; 12891; 12893; 12895; 12896; 12897; 12898; 12902; 12903; 12904; 12908; 12914; 12915; 12916; 412; 12921; 12922; 12923; 12927; 12931; 12938; 12939; 4278; 12244; 12245; 12946; 12948; 9875; 12951; 12952; 9908; 7671; 7672; 4329; 12957; 12958; 12959; 1432; 12960; 12964; 6212; 12969; 10161; 13004; 13005; 13007; 13013; 13014; 13015; 6472; 6473; 13016; 13017; 13019; 13020; 10383; 10384; 10385; 13031; 7785; 13033; 13034; 4542; 6550; 6551; 13038; 13039; 13047; 13048; 13049; 676; 3275; 13051; 6622; 10639; 13053; 13054; 13055; 6644; 13062; 13063; 13064; 13065; 13069; 13071; 13073; 13076; 10735; 6725.

The following SEQ ID NOs correspond to the amino acid sequences of Colon-specific proteins identified using MPSS and that have been identified by mass spectrometry as described in Table 43A: 13533; 13534; 13535; 13536; 13537; 9459; 13540; 13541; 13543; 12890; 13544; 13545; 404; 2136; 13577; 13580; 13583; 13584; 13588; 9609; 2151; 2152; 13591; 13592; 13593; 13596; 13599; 13601; 13605; 469; 471; 9786; 13608; 13609; 13611; 13612; 13622; 4295; 4296; 13624; 13625; 13628; 13629; 13630; 13631; 13641; 9938; 6135; 7676; 13643; 9967; 13646; 13647; 13648; 13649; 13653; 12280; 13654; 13655; 13679; 10219; 13681; 13682; 13685; 13686; 13691; 13692; 13693; 13694; 13695; 13696; 13709; 623; 13717; 10383; 10384; 10385; 13736; 10477; 13739; 13740; 4566; 4567; 6585; 13741; 13742; 13743; 13744; 13747; 10565; 13750; 3262; 4588; 4590; 13754; 13755; 4594; 4595; 4596; 4597; 4598; 4599; 13762; 13763; 13051; 13764; 13765; 13766; 13767; 13768; 13769; 13770; 686; 13774; 13775; 13776; 13779; 13780; 13781; 13062; 13063; 13064; 13782; 13783; 13784; 13785; 13786; 13787; 7847; 13791; 13792; 13793; 13794; 13795; 730.

The following SEQ ID NOs correspond to the amino acid sequences of heart-specific proteins identified using MPSS and that have been identified by mass spectrometry as described in Table 43A: 5904; 14450; 14453; 1313; 14454; 9460; 14455; 14458; 14459; 14460; 14461; 14466; 383; 14469; 14470; 14471; 9497; 4163; 4165; 14474; 14475; 14478; 14479; 14480; 14481; 12193; 14488; 14489; 1344; 14492; 14494; 14495; 14496; 14500; 14501; 14502; 14503; 14504; 14505; 14508; 14511; 14512; 12927; 14516; 14517; 14523; 14524; 2178; 459; 14534; 14540; 14541; 7617; 14542; 14543; 7618; 9712; 9735; 466; 9750; 9751; 14549; 14552; 7624; 7625; 14555; 14556; 9798; 14561; 14566; 14567; 14568; 14569; 3079; 9877; 14582; 14583; 4324; 14603; 14604; 14605; 14606; 14607; 14608; 14609; 14610; 14611; 14612; 14613; 14615; 14616; 14617; 6136; 6137; 14619; 13646; 13647; 13648; 13649; 14620; 14621; 14622; 9991; 14624; 14625; 14626; 14627; 14628; 14638; 14640; 7691; 14644; 10162; 14664; 4444; 4445; 14665; 14668; 14669; 14670; 14671; 14672; 14673; 14674; 10200; 10201; 10204; 10205; 6306; 14681; 14684; 14685; 3190; 14691; 14693; 6311; 13692; 3198; 3199; 14698; 14699; 14700; 3200; 14702; 4475; 14704; 4478; 14707; 14709; 14710; 14714; 4487; 14715; 14717; 14718; 14721; 14722; 14723; 14724; 14725; 2296; 2297; 10327; 14730; 14735; 14736; 14737; 14739; 14742; 14744; 14745; 12345; 14747; 14756;

14757; 14758; 10410; 14762; 14764; 14770; 14772; 14777; 10499; 14778; 14780; 14782; 14783; 14784; 10564; 14787; 2353; 14790; 14791; 14793; 14795; 14796; 12383; 10595; 10596; 10598; 14801; 14804; 14805; 14807; 14809; 1557; 6626; 6628; 14819; 14820; 14821; 10657; 14831; 1568; 1569; 1570; 1571; 1572; 1574; 14835; 13065; 14843; 3308; 3309; 3310; 3311; 3312; 14844; 2381; 13073; 4655; 10704; 6665; 6666; 14852; 14855; 14856; 14862.

The following SEQ ID NOs correspond to the amino acid sequences of kidney-specific proteins identified using MPSS and that have been identified by mass spectrometry as described in Table 43A: 15552; 1319; 15561; 15562; 15563; 15564; 2983; 2984; 15568; 15569; 15571; 15572; 15577; 15578; 15579; 4179; 15586; 15587; 4207; 15593; 15597; 15598; 15604; 15605; 2176; 15607; 15612; 15613; 15614; 15616; 3059; 15617; 15620; 1415; 15627; 15628; 15629; 15630; 15631; 15634; 15635; 15645; 15657; 14674; 15658; 15659; 7742; 15674; 15675; 15676; 15677; 15678; 15681; 15683; 15690; 15691; 15692; 15693; 15695; 2337; 10477; 4577; 10549; 15696; 3263; 14793; 15707; 15708; 15709; 12390; 3292; 15711; 15712; 15713; 15714; 15718; 15719; 15720; 15721; 15726.

The following SEQ ID NOs correspond to the amino acid sequences of lung-specific proteins identified using MPSS and that have been identified by mass spectrometry as described in Table 43A: 16302; 16303; 16304; 5911; 5912; 1318; 16305; 16306; 2986; 2987; 2988; 16310; 16311; 16312; 16313; 16314; 5940; 3001; 3006; 16318; 9527; 16319; 16320; 16321; 5961; 16322; 16324; 16327; 16333; 409; 1346; 1347; 1348; 1349; 1350; 12914; 16341; 16342; 16343; 16344; 16345; 16346; 16347; 16348; 16349; 16350; 16351; 16352; 16353; 16354; 16355; 16356; 16357; 16358; 2143; 16378; 16379; 16382; 16383; 9623; 15593; 16384; 16385; 16389; 16390; 16391; 16392; 16395; 16399; 16401; 3055; 3056; 3057; 3058; 16403; 1386; 14549; 16405; 1394; 16412; 16413; 14566; 14567; 14568; 14569; 16428; 16429; 16431; 9883; 9899; 6111; 6112; 6113; 6114; 16437; 16440; 14610; 511; 16442; 16443; 16444; 16445; 16446; 16447; 522; 12267; 6136; 6137; 16448; 16451; 16452; 527; 9981; 9982; 4345; 4346; 4347; 4348; 4349; 4350; 16455; 6225; 6226; 16458; 16459; 2246; 16464; 16495; 16498; 16500; 16504; 16505; 16507; 16508; 16511; 16512; 2283; 16522; 16530; 16532; 16533; 16535; 16536; 1484; 16540; 16541; 4517; 16548; 16549; 16558; 16559; 16560; 16561; 16563; 16564; 16565; 16567; 16568; 4552; 4553; 4554; 16571; 10484; 10485; 16574; 16578; 16580; 16581; 16582; 16583; 1527; 16585; 16586; 1529; 2342; 2343; 2344; 2345; 16587; 16593; 16597; 16602; 16603; 16604; 16605; 16610; 16620; 14819; 16621; 16622; 10639; 15711; 16626; 16627; 3299; 16631; 16634; 1569; 1571; 1572; 1574; 16644; 16645; 2381; 16646; 16647; 16650; 16651; 16655; 16658; 16659; 16662; 16664; 6663; 16665; 16697.

The following SEQ ID NOs correspond to the amino acid sequences of mammary gland-specific proteins identified using MPSS and that have been identified by mass spectrometry as described in Table 43A: 17184; 17185; 17186; 17187; 17188; 7558; 17189; 17190; 17191; 5935; 5941; 5942; 17196; 17197; 17198; 17200; 17201; 408; 3025; 17209; 17210; 17211; 17212; 17213; 17214; 17218; 17219; 17220; 3055; 3056; 3057; 3058; 9786; 17228; 6088; 6090; 6091; 6092; 6093; 6094; 499; 12250; 12251; 17243; 518; 519; 17246; 532; 17258; 17259; 17261; 17262; 17263; 3171; 17275; 3191; 17281; 17283; 17284; 10298; 17288; 17292; 17293; 17298; 17301; 17302; 17303; 17305; 17306; 17307; 1519; 13740; 10486; 16574; 17312; 17313; 17314; 17315; 2342; 2343; 2344; 2345; 16587; 6610; 13051; 16622; 14821; 17326; 1564; 17329; 17332; 14835; 17333; 7846; 13065; 17335; 1582; 6672; 17336; 723.

The following SEQ ID NOs correspond to the amino acid sequences of monocyte-specific proteins identified using MPSS and that have been identified by mass spectrometry as described in Table 43A: 9459; 2983; 2984; 2985; 17975; 17976; 17977; 17978; 12175; 12176; 17979; 17980; 17981; 1327; 12177; 17983; 17986; 392; 393; 17994; 17995; 17996; 17998; 18001; 18007; 14495; 14496; 18020; 18026; 18027; 1354; 1355; 14500; 14501; 14502; 14503; 14504; 18032; 9624; 3040; 16384; 16385; 18050; 9659; 9660; 18051; 18052; 18053; 18054; 440; 441; 442; 443; 444; 18058; 18059; 7614; 15607; 9699; 18063; 18064; 18065; 18066; 16401; 9735; 3055; 3056; 3057; 3058; 18071; 18072; 18073; 18074; 18075; 18076; 18077; 18078; 18079; 9787; 18081; 18083; 4280; 4281; 4282; 12244; 12245; 18088; 18092; 18093; 18094; 6088; 6090; 6091; 6092; 6093; 6094; 18102; 18105; 18106; 18111; 497; 1417; 18114; 500; 18115; 18119; 18121; 18122; 18123; 18126; 18127; 18129; 18130; 18132; 18133; 18134; 18136; 511; 14616; 14617; 18146; 18147; 18148; 18149; 18150; 18151; 18153; 18154; 18155; 18156; 18157; 6156; 15635; 18166; 2246; 18175; 6231; 18258; 18262; 18264; 13007; 18267; 3191; 18281; 3198; 3199; 18284; 18286; 18287; 14704; 10258; 18289; 18291; 18292; 18293; 18297; 18309; 18310; 18311; 10327; 18314; 16540; 1490; 1491; 18317; 18318; 18319; 18322; 2306; 18327; 18328; 18329; 18330; 3235; 4525; 4526; 6532; 18332; 18333; 2316; 16565; 18335; 18336; 18337; 10441; 18342; 18345; 2328; 18354; 18355; 18358; 10491; 10498; 1526; 18364; 18366; 2342; 2343; 2344; 2345; 18371; 18373; 18374; 10583; 18377; 18378; 3276; 3277; 10616; 18392; 18393; 18394; 10649; 18396; 18401; 18403; 18404; 18405; 18406; 14844; 10681; 18410; 3316; 3317; 18424; 18425.

The following SEQ ID NOs correspond to the amino acid sequences of pancreas-specific proteins identified using MPSS and that have been identified by mass spectrometry as described in Table 43A: 18873; 18874; 18875; 18876; 17978; 18881; 18895; 18901.

The following SEQ ID NOs correspond to the amino acid sequences of PBL-specific proteins identified using MPSS and that have been identified by mass spectrometry as described in Table 43A: 19351; 16302; 19353; 14455; 19357; 4138; 4139; 4141; 4142; 9485; 19358; 2993; 9497; 19360; 4148; 19362; 19363; 9528; 4177; 19369; 19371; 19373; 19374; 19375; 19376; 19377; 4178; 19379; 19380; 19381; 1344; 410; 19397; 19398; 14500; 14501; 14502; 14503; 14504; 4224; 19415; 19418; 19419; 19423; 19433; 19435; 19438; 19439; 19440; 19441; 19442; 19443; 19444; 19445; 19452; 19453; 19454; 1369; 19455; 6026; 6030; 1378; 19458; 19460; 18073; 18074; 18075; 18076; 18077; 18078; 18079; 6101; 19495; 9883; 19500; 7664; 7666; 7667; 3091; 3092; 1419; 1420; 18119; 15627; 19509; 19510; 7671; 7672; 16444; 19512; 18146; 19516; 6142; 13646; 13647; 13648; 13649; 12958; 12959; 9981; 9982; 19518; 19522; 19523; 19524; 19533; 7690; 19535; 18175; 19565; 19566; 12306; 19570; 19571; 10237; 1470; 1471; 19572; 19575; 18287; 590; 18291; 19578; 19579; 19588; 19589; 19590; 19591; 19592; 19593; 19594; 19595; 19596; 19601; 19603; 19604; 19605; 19606; 19608; 10338; 10360; 19611; 19612; 18330; 13031; 636; 637; 19618; 19620; 19633; 19634; 19635; 19636; 16567; 16568; 644; 645; 2337; 19644; 19645; 13740; 19646; 19647; 19648; 19649; 19650; 19651; 10487; 10488; 19653; 19654; 19655; 19656; 19657; 19658; 16574; 19659; 19660; 19661; 19663; 19664; 19665; 19668; 1527; 19673; 19674; 2341; 19675; 19676; 1530; 19678; 19682; 12370; 19683; 19684; 6611; 19688; 19692; 10616; 19695; 3279;

19702; 19707; 10645; 10646; 13776; 19710; 4635; 19719; 19720; 1582; 2380; 10704; 19730; 19736; 19738; 19740; 19742; 19745.

The following SEQ ID NOs correspond to the amino acid sequences of pituitary gland-specific proteins identified using MPSS and that have been identified by mass spectrometry as described in Table 43A: 5906; 5907; 5908; 5909; 5910; 5911; 5912; 20276; 20280; 20281; 20282; 20283; 7561; 7562; 20293; 6000; 6001; 20306; 20307; 20308; 20309; 6011; 20311; 20312; 20314; 20315; 20319; 20320; 20321; 20322; 1386; 20323; 13608; 13609; 20327; 20333; 1418; 20350; 499; 6134; 20353; 20354; 20356; 20362; 20371; 576; 20374; 12332; 14721; 14722; 14723; 14724; 20386; 18327; 10375; 10389; 10390; 10391; 10414; 10415; 10416; 14762; 20392; 12363; 20394; 16582; 16583; 20395; 20396; 13747; 20402; 20404; 20405; 6644; 20410; 20416.

The following SEQ ID NOs correspond to the amino acid sequences of placenta-specific proteins identified using MPSS and that have been identified by mass spectrometry as described in Table 43A: 20843; 375; 20844; 1318; 20849; 20850; 20851; 5925; 20852; 2112; 1330; 20858; 20859; 20860; 20861; 4219; 20865; 20866; 20867; 20868; 20869; 20871; 20872; 20873; 20874; 4239; 4240; 20876; 9680; 9699; 20885; 20886; 20887; 15613; 15614; 15616; 9754; 20890; 20892; 20893; 20894; 20895; 20905; 20906; 488; 20909; 20910; 20911; 20912; 20913; 20914; 20920; 7669; 19509; 20922; 20934; 20938; 18151; 20940; 20945; 20946; 14622; 20947; 9999; 20949; 20951; 10003; 20952; 20953; 20955; 20956; 20958; 20959; 20960; 20962; 20963; 20964; 4409; 20969; 20970; 20971; 20988; 10186; 20991; 20999; 21000; 2283; 21008; 13692; 18284; 4475; 21012; 21014; 21015; 4487; 21019; 21022; 21023; 21024; 3220; 3221; 18319; 21032; 3229; 3230; 3231; 625; 21041; 21042; 21043; 21045; 21046; 21049; 6548; 6549; 6556; 7798; 21053; 19673; 19674; 4577; 14782; 21057; 6599; 21058; 21059; 21060; 21061; 21068; 21069; 21073; 21074; 21078; 21080; 21082; 21083; 21084; 18394; 13776; 16626; 21086; 21087; 21088; 21090; 21091; 19730; 6672; 10706; 21101; 6732; 21107; 21109.

The following SEQ ID NOs correspond to the amino acid sequences of prostate-specific proteins identified using MPSS and that have been identified by mass spectrometry as described in Table 43A: 16304; 22026; 22027; 13537; 9459; 2100; 9463; 22031; 22032; 22033; 22034; 9472; 9473; 22037; 22038; 22039; 22040; 2989; 22047; 1323; 384; 5935; 22050; 22051; 22052; 22053; 22054; 22055; 2113; 1324; 1325; 1326; 22056; 1327; 22058; 9515; 22064; 5944; 4171; 4172; 3005; 3006; 9526; 15579; 2119; 9528; 22066; 1330; 7568; 397; 22071; 22074; 22085; 22086; 22087; 22088; 19380; 19381; 22089; 22094; 22101; 22102; 22104; 22106; 4219; 1357; 19419; 424; 22113; 22114; 22115; 22116; 22117; 22119; 22120; 20872; 22123; 12223; 22124; 22125; 22126; 22127; 22128; 22132; 15604; 22135; 18058; 22136; 7613; 22137; 22138; 7615; 22140; 9694; 9695; 22144; 22146; 22147; 20885; 20886; 22151; 22152; 22153; 22154; 9736; 6054; 3055; 22159; 1384; 22162; 22163; 1386; 469; 9750; 9751; 22164; 22167; 2184; 22168; 15617; 9786; 14555; 14556; 22171; 22172; 22173; 20890; 22174; 22175; 22176; 6076; 9798; 9804; 22177; 22179; 22180; 22191; 22193; 6088; 6090; 6091; 6092; 6093; 6094; 9875; 22209; 18105; 18106; 1415; 22212; 499; 500; 13631; 22218; 22221; 22222; 7669; 9924; 9925; 1425; 22228; 6135; 7676; 524; 22239; 4345; 4346; 4347; 4348; 4349; 4350; 22240; 15635; 22244; 22247; 22252; 22253; 22254; 22255; 22257; 22259; 22263; 22264; 3148; 6231; 22269; 22287; 22293; 22313; 22318; 22319; 22320; 22324; 22329; 3166; 22342; 3177; 22351; 22357; 22358; 3187; 16505; 22363; 10224; 22365; 22366; 22367; 22368; 22371; 14685; 22373; 22378; 22384; 22387; 22388; 22389; 22390; 6311; 10244; 10245; 22400; 22401; 16530; 14707; 21012; 21014; 17283; 22412; 10287; 22417; 22418; 22419; 22420; 22421; 22422; 22424; 1484; 22430; 22431; 22432; 22433; 22434; 22435; 22436; 3229; 3230; 3231; 22437; 4513; 4521; 22448; 22449; 22450; 22452; 22455; 3237; 3238; 10389; 10390; 10391; 22458; 22459; 22460; 22461; 14757; 14758; 4535; 22464; 22465; 22466; 22467; 22468; 3247; 16565; 7782; 7783; 7784; 7785; 10425; 22474; 22475; 22476; 16567; 16568; 22479; 22480; 10447; 22484; 10467; 22491; 19645; 19647; 19648; 19649; 4565; 10484; 10485; 4566; 4567; 7798; 22494; 4570; 19660; 22496; 14777; 2338; 19665; 10508; 10509; 10511; 16585; 22499; 22500; 22501; 22502; 22503; 10515; 22507; 2353; 22509; 22510; 19684; 3267; 3268; 6611; 22515; 7813; 7814; 10595; 10596; 10598; 22519; 3278; 22526; 22527; 6623; 22530; 22531; 22532; 22533; 22534; 21080; 22547; 16626; 22549; 22551; 22552; 22554; 22559; 22560; 10657; 22562; 10660; 22564; 13065; 22569; 13792; 22571; 22572; 7851; 2380; 22575; 13071; 13794; 13795; 22579; 22581; 22584; 22585; 18424; 18425; 22589; 22590; 22592; 22593; 22594; 22598; 10744; 10745.

The following SEQ ID NOs correspond to the amino acid sequences of retina-specific proteins identified using MPSS and that have been identified by mass spectrometry as described in Table 43A: 16302; 23606; 23613; 23614; 23615; 23616; 5935; 23617; 4168; 23620; 5961; 12891; 4194; 23630; 23631; 23632; 409; 12914; 12915; 12916; 23637; 23639; 23640; 23641; 23643; 23646; 23647; 23652; 23654; 22125; 2167; 23658; 23663; 9659; 9660; 23664; 22132; 23667; 7614; 23674; 23676; 23677; 23678; 23679; 23680; 23681; 23682; 23683; 23684; 23685; 471; 23688; 23696; 23700; 1417; 22221; 22222; 23712; 23713; 23714; 3095; 23715; 9923; 23721; 14613; 15630; 23724; 18157; 23728; 23729; 23730; 20947; 541; 23738; 23739; 23741; 3148; 23782; 23784; 6296; 23787; 23791; 10199; 1473; 1474; 1475; 1476; 1477; 3198; 3199; 4467; 23799; 23800; 23801; 16522; 6453; 6454; 6455; 6456; 6457; 6458; 6459; 6460; 4478; 23810; 23813; 23814; 23815; 23817; 21022; 23820; 1490; 1491; 23825; 3227; 3228; 23828; 23829; 6515; 15690; 15691; 10383; 10384; 10385; 14756; 12350; 636; 637; 23836; 23837; 23838; 10424; 23839; 23840; 23841; 6546; 23851; 23855; 22484; 23861; 23862; 23863; 23864; 23865; 23866; 23867; 10512; 23878; 23879; 23881; 23884; 14783; 14784; 4587; 23894; 23895; 23899; 19702; 23904; 18405; 23909; 23912; 23913; 23915; 23916; 23919; 2380; 23922; 23924; 19730; 23928; 21109; 2393.

The following SEQ ID NOs correspond to the amino acid sequences of salivary gland-specific proteins identified using MPSS and that have been identified by mass spectrometry as described in Table 43A: 22031; 22032; 24435; 22056; 24437; 15579; 19371; 24447; 24448; 24450; 16341; 16342; 16343; 16344; 19423; 24456; 24458; 440; 441; 442; 443; 444; 7613; 24463; 470; 24466; 14561; 24499; 24500; 532; 24515; 24516; 4375; 22247; 24519; 24530; 24531; 16507; 6453; 6454; 6455; 6456; 6457; 6458; 6459; 6460; 24533; 24534; 24535; 24536; 24537; 24539; 24540; 24545; 24547; 24548; 10399; 10400; 24550; 24552; 6546; 661; 662; 663; 3257; 13754; 13755; 10595; 10596; 10598; 21069; 21073; 21074; 21078; 18406; 24563; 24564.

The following SEQ ID NOs correspond to the amino acid sequences of small intestine-specific proteins identified using MPSS and that have been identified by mass spectrometry as described in Table 43A: 5906; 5907; 5908; 5909; 5910; 24919; 24920; 24921; 9485; 2986; 2987; 2988; 16310; 4147; 24928; 2119; 13544; 13545; 24932; 9536; 24933; 24935; 24942; 9574; 24946; 18007; 24963; 24964; 24967; 24968;

9651; 440; 441; 442; 443; 444; 24978; 24979; 24980; 15604; 24985; 22135; 24986; 24987; 9699; 9787; 1394; 24997; 6101; 25001; 9935; 25008; 516; 25009; 14619; 14620; 20946; 14622; 22240; 25011; 19524; 25015; 13653; 25017; 25018; 25024; 25025; 25026; 25027; 25028; 25030; 25031; 25036; 25038; 25043; 25044; 25045; 25046; 25047; 25048; 25049; 25050; 15657; 25055; 6298; 6303; 25064; 13693; 12330; 25068; 25069; 25070; 22437; 6550; 6551; 25076; 25080; 25081; 25086; 25087; 10487; 10488; 19661; 4574; 10502; 25089; 25090; 25092; 25094; 12370; 14791; 16597; 25096; 25104; 25105; 10645; 10646; 25106; 13781; 1568; 1569; 1570; 1571; 1572; 1574; 25112; 25113; 25114; 10699; 10700; 25117; 10735.

The following SEQ ID NOs correspond to the amino acid sequences of spinal cord-specific proteins identified using MPSS and that have been identified by mass spectrometry as described in Table 43A: 9449; 22031; 22032; 13540; 4139; 4141; 4142; 17978; 2113; 12184; 9550; 9551; 9562; 25488; 25491; 9585; 17209; 17210; 14500; 14501; 14502; 14503; 14504; 25498; 25499; 25500; 424; 3037; 25501; 25502; 25503; 25504; 25505; 22124; 25506; 14523; 4244; 25507; 25508; 1369; 9692; 9746; 9747; 25518; 18072; 18073; 18074; 18075; 18076; 18077; 18078; 18079; 1388; 1389; 25520; 22177; 25521; 18092; 18093; 18094; 25526; 25527; 25528; 19500; 25529; 25531; 25532; 25533; 25534; 18121; 18122; 18123; 18126; 18127; 18129; 18130; 18132; 25535; 25536; 19512; 522; 20354; 25538; 527; 25540; 13653; 4409; 25548; 10161; 25551; 25552; 6297; 25554; 10200; 10201; 10204; 10205; 22365; 22366; 22367; 22368; 25558; 25561; 25562; 25563; 4470; 10248; 13013; 25566; 7742; 14715; 21023; 21024; 25572; 3232; 10375; 10398; 3242; 25577; 25578; 25579; 25581; 25582; 19660; 10512; 25588; 25589; 25593; 25594; 3276; 3277; 25597; 25598; 25602; 25603; 723.

The following SEQ ID NOs correspond to the amino acid sequences of spleen-specific proteins identified using MPSS and that have been identified by mass spectrometry as described in Table 43A: 26279; 26280; 26281; 26282; 26290; 4135; 26293; 2983; 2984; 2985; 9489; 26296; 9497; 4148; 26299; 26300; 26301; 26304; 5944; 13543; 9522; 9523; 26305; 26306; 26308; 26309; 12890; 26310; 13544; 13545; 26311; 1333; 5961; 26319; 26321; 26322; 26324; 26325; 26329; 26335; 3024; 26339; 26341; 2138; 4219; 9602; 26350; 26351; 9613; 16383; 26355; 26356; 7604; 26357; 26358; 9637; 26362; 16391; 16392; 26363; 26364; 2167; 26365; 19452; 26366; 26370; 26371; 12233; 16401; 26375; 9736; 26380; 22162; 469; 22168; 26381; 9773; 23684; 23685; 3060; 13608; 13609; 1390; 22174; 26383; 26384; 26386; 26390; 26391; 18083; 4280; 4281; 4282; 26400; 26401; 26402; 26409; 14566; 14567; 14568; 14569; 26411; 26420; 13622; 25528; 1417; 26426; 26427; 500; 24499; 7669; 25535; 25536; 26431; 511; 26432; 9939; 26442; 12267; 26444; 26445; 18147; 18148; 18149; 26447; 17246; 26448; 26450; 26451; 26453; 1432; 14620; 532; 26457; 2243; 26463; 14627; 6173; 6174; 6180; 6181; 6182; 6183; 6189; 6190; 10036; 26473; 26474; 26476; 26477; 26478; 20964; 2246; 18175; 2252; 2253; 556; 26503; 2256; 26504; 26505; 20988; 26527; 3167; 10176; 26530; 10186; 26531; 26534; 26538; 26541; 26542; 4455; 26544; 13681; 13682; 26547; 4462; 26561; 3198; 3199; 16522; 4471; 26563; 26564; 26573; 10273; 26574; 26575; 26578; 12332; 4496; 26584; 26585; 26586; 14725; 4498; 1484; 26590; 10327; 3220; 3221; 18318; 14736; 18319; 26598; 26599; 2306; 26603; 6519; 6528; 2312; 26610; 21041; 21042; 21043; 21045; 21046; 26611; 10399; 10400; 26612; 26613; 26614; 26615; 24552; 10410; 19618; 19620; 10413; 26619; 26621; 7782; 7783; 7784; 7785; 12356; 4544; 20392; 4552; 4553; 4554; 23863; 23864; 23865; 23866; 23867; 10489; 7798; 656; 26647; 26649; 23878; 23879; 26650; 10554; 14783; 14784; 1532; 13747; 26657; 26659; 6610; 14793; 26667; 10599; 26673; 26674; 26675; 686; 26680; 18392; 21083; 12397; 3299; 707; 708; 709; 26695; 18404; 26699; 26702; 3308; 3309; 3311; 3312; 26704; 4642; 4643; 10677; 26705; 1583; 16655; 16658; 16659; 16662; 23922; 4655; 26723; 26724; 26725; 26726; 26729; 22589; 26731; 26732; 26739; 6725; 26745; 26746; 26748.

The following SEQ ID NOs correspond to the amino acid sequences of stomach-specific proteins identified using MPSS and that have been identified by mass spectrometry as described in Table 43A: 13580; 12223; 18058; 27369; 27382; 27383; 27384; 3261; 27385; 1582; 27388; 2386.

The following SEQ ID NOs correspond to the amino acid sequences of testis-specific proteins identified using MPSS and that have been identified by mass spectrometry as described in Table 43A: 28427; 28433; 5922; 28437; 28438; 28439; 28442; 16310; 22047; 28447; 28452; 28453; 28458; 28459; 28461; 5943; 28465; 13543; 28466; 28467; 28468; 28469; 13544; 13545; 28480; 28483; 28484; 19371; 399; 400; 28495; 28496; 28497; 28501; 28504; 28513; 28520; 12897; 12898; 12902; 12903; 12904; 12908; 28534; 28541; 28542; 28548; 28564; 28566; 28568; 28569; 28570; 28573; 22104; 28576; 28577; 28580; 3033; 28581; 9603; 4226; 28595; 20869; 28602; 1358; 28608; 23646; 23647; 9637; 26362; 28614; 28615; 14523; 28622; 28625; 28626; 28627; 19453; 19454; 28634; 28635; 28636; 28637; 28640; 28642; 28646; 28651; 22144; 22146; 22147; 28656; 28659; 28660; 1383; 20320; 20321; 20322; 28675; 28676; 9754; 2184; 22168; 28681; 28682; 9787; 28699; 28702; 28703; 28707; 28710; 1402; 28729; 28738; 28748; 28751; 28752; 28755; 28756; 28757; 28759; 28771; 28777; 28781; 28784; 28787; 4314; 28794; 1425; 28800; 4323; 6126; 17243; 9941; 9942; 9943; 9944; 28810; 28811; 3099; 28816; 28817; 28818; 14616; 14617; 14619; 28819; 28820; 28821; 20945; 15634; 9981; 9982; 28832; 28833; 10005; 28845; 28846; 14627; 12276; 12277; 28853; 28854; 28856; 3139; 28858; 28859; 6224; 28867; 28870; 28871; 3148; 28876; 28878; 28879; 28894; 28921; 28931; 28934; 22287; 28939; 28940; 28941; 28942; 28943; 28959; 28960; 28961; 28974; 28999; 29002; 29036; 29037; 22313; 22318; 22319; 22320; 22324; 29055; 29057; 29058; 29059; 29060; 29061; 29062; 29063; 29064; 29065; 22329; 1447; 29074; 29075; 25055; 29077; 29078; 29085; 3172; 19565; 19566; 29086; 12306; 29088; 29089; 29092; 13007; 29101; 29109; 14681; 29121; 4467; 16522; 13695; 13696; 3204; 18289; 10273; 10279; 10280; 10281; 29125; 10285; 10286; 29126; 29128; 29129; 29130; 29131; 29132; 29141; 10298; 29159; 10316; 10324; 6493; 6494; 29182; 14735; 29185; 3227; 3228; 10338; 15683; 29195; 29207; 29210; 29217; 3241; 29225; 29226; 29227; 3245; 10426; 29231; 22476; 639; 12356; 4544; 642; 29239; 23861; 23862; 29257; 29258; 29261; 29262; 29263; 10476; 19654; 19655; 19656; 19659; 659; 18366; 3257; 1536; 1537; 29286; 10564; 22509; 22510; 25593; 29290; 26667; 29298; 29299; 16603; 29301; 29302; 673; 674; 675; 2357; 2358; 676; 29314; 29319; 3276; 3277; 29324; 29328; 6624; 29333; 22533; 29344; 12397; 29354; 29355; 29363; 29364; 29365; 13065; 29368; 29376; 10677; 7851; 4649; 1582; 29387; 1583; 29388; 29391; 4655; 29394; 29395; 723; 22589; 12411; 1590; 29413; 29417; 29419; 29423; 29424; 29425; 7871.

The following SEQ ID NOs correspond to the amino acid sequences of thymus-specific proteins identified using MPSS and that have been identified by mass spectrometry as described in Table 43A: 19351; 14455; 22031; 22032; 30730; 1324; 1325; 1326; 22056; 30734; 13543; 9528; 30736;

30737; 4177; 1333; 30738; 12895; 30742; 28580; 30746; 30747; 30748; 30749; 30753; 4226; 28602; 23643; 30757; 23658; 6019; 30759; 30760; 30761; 30762; 6026; 16401; 470; 23684; 23685; 9786; 9787; 30770; 30771; 20905; 30779; 30783; 30784; 488; 6088; 6090; 6091; 6092; 6093; 6094; 9883; 26426; 26427; 30790; 500; 30793; 30795; 4323; 30796; 30797; 30798; 9952; 522; 26444; 26445; 9981; 9982; 30803; 30809; 28845; 28846; 14627; 6191; 30813; 30816; 6225; 6226; 30817; 30818; 30822; 30823; 30824; 30825; 30826; 30887; 30888; 30889; 30890; 26530; 30892; 30893; 3187; 20999; 7729; 4455; 26544; 30898; 30899; 25561; 19572; 30902; 26561; 12315; 12316; 3198; 3199; 4471; 26564; 30903; 16535; 30904; 7742; 30905; 30906; 30907; 30908; 30911; 30914; 30915; 30916; 7767; 29210; 30920; 30921; 30922; 19618; 19620; 23841; 30928; 30929; 6548; 6549; 22479; 18342; 23863; 23864; 23865; 23866; 23867; 29257; 3255; 30935; 30936; 30937; 19663; 19664; 30938; 6585; 30939; 30940; 30943; 30944; 30946; 4588; 4590; 14793; 30954; 30955; 30956; 27385; 30959; 30960; 3276; 3277; 30961; 10639; 30962; 16627; 30968; 30969; 10660; 18404; 13065; 3308; 3309; 3311; 3312; 30974; 30975; 30976; 30977; 30978; 13794; 13795; 30981; 10701; 30982; 30983; 30984; 30985; 30992.

The following SEQ ID NOs correspond to the amino acid sequences of thyroid-specific proteins identified using MPSS and that have been identified by mass spectrometry as described in Table 43A: 31511; 31515; 31516; 31517; 31518; 3001; 31520; 31529; 31530; 31531; 16341; 16342; 16343; 16344; 24963; 9611; 14517; 31537; 23679; 9744; 31544; 9786; 7627; 7628; 9797; 31546; 1400; 1401; 31547; 18111; 31564; 31565; 31566; 2242; 31572; 19523; 31576; 16458; 31582; 31583; 20969; 31584; 22269; 1453; 1454; 31589; 31590; 31593; 31596; 31597; 31598; 31599; 31601; 31602; 14699; 14715; 31612; 31613; 31614; 31615; 31616; 10327; 18314; 23825; 1495; 18319; 6506; 4510; 10347; 31620; 31632; 2342; 2343; 2344; 2345; 10560; 31638; 31642; 6626; 6628; 31646; 14835; 31652; 31654; 717; 31658; 31670; 31671; 31672.

The following SEQ ID NOs correspond to the amino acid sequences of trachea-specific proteins identified using MPSS and that have been identified by mass spectrometry as described in Table 43A: 31889; 17979; 17980; 17981; 31891; 3025; 9602; 7613; 31897; 31898; 9795; 3071; 31902; 16458; 2269; 2271; 31920; 4475; 4487; 22418; 19618; 19620; 31925; 31926; 31927; 31928; 25096; 6619; 6620; 4605; 12395.

The following SEQ ID NOs correspond to the amino acid sequences of uterus-specific proteins identified using MPSS and that have been identified by mass spectrometry as described in Table 43A: 32066; 32067; 32068; 32069; 32075; 32079; 9608; 32081; 32082; 32083; 32084; 22218; 9931; 32090; 32092; 32093; 9999; 20949; 10044; 32096; 16495; 22342; 32107; 32108; 32111; 32112; 32114; 19606; 10347; 32115; 32116; 32121; 32122; 23863; 23864; 23865; 23866; 23867; 13740; 19673; 19674; 26667; 3273; 31646; 1568; 1569; 1570; 1571; 1572; 1574; 6732.

The following SEQ ID NOs correspond to the amino acid sequences of prostate-specific proteins identified using MPSS and that have been identified by mass spectrometry as described in Table 44A: 16304; 22026; 22027; 13537; 9459; 2100; 9463; 22031; 22032; 22033; 22034; 9472; 9473; 22037; 22038; 22039; 22040; 32221; 2989; 22047; 383; 1323; 384; 5935; 22050; 22051; 22052; 22053; 22054; 22055; 2113; 1324; 1325; 1326; 22056; 1327; 22058; 9515; 22064; 5944; 4171; 4172; 3005; 3006; 9526; 15579; 2119; 9528; 22066; 1330; 7568; 397; 22071; 22074; 22085; 22086; 22087; 22088; 19380; 19381; 22089; 22094; 22101; 22102; 22104; 22106; 4219; 1357; 19419; 424; 22113; 22114; 22115; 22116; 22117; 22119; 22120; 20872; 22123; 12223; 22124; 22125; 22126; 22127; 22128; 22132; 15604; 22135; 18058; 22136; 7613; 22137; 22138; 7615; 22140; 9694; 9695; 22144; 22146; 22147; 20885; 20886; 22151; 22152; 22153; 22154; 9736; 6054; 3055; 22159; 1384; 22162; 22163; 1386; 469; 9750; 9751; 22164; 22167; 2184; 22168; 15617; 9786; 14555; 14556; 22171; 22172; 22173; 20890; 22174; 22175; 22176; 6076; 9798; 9804; 22177; 22179; 14561; 22180; 22191; 22193; 1404; 6088; 6090; 6091; 6092; 6093; 6094; 9875; 22209; 18105; 18106; 1415; 22212; 499; 500; 13631; 22218; 22221; 22222; 7669; 9924; 9925; 1425; 22228; 6135; 7676; 524; 22239; 4345; 4346; 4347; 4348; 4349; 4350; 22240; 15635; 22244; 22247; 22252; 22253; 22254; 22255; 22257; 22259; 22263; 22264; 3148; 6231; 22269; 22287; 22293; 22313; 22318; 22319; 22320; 22324; 22329; 3166; 22342; 3177; 22351; 22357; 22358; 3187; 16505; 22363; 10224; 22365; 22366; 22367; 22368; 22371; 14685; 22373; 32227; 22378; 22384; 22387; 22388; 22389; 22390; 6311; 10244; 10245; 22400; 22401; 16530; 18289; 14707; 21012; 21014; 17283; 22412; 10287; 22417; 22418; 22419; 22420; 22421; 22422; 22424; 1484; 22430; 22431; 32228; 22432; 22433; 22229; 22434; 22435; 22436; 3229; 3230; 3231; 22437; 4513; 4521; 22448; 22449; 22450; 22452; 22455; 3237; 3238; 10389; 10390; 10391; 22458; 22459; 22460; 22461; 14757; 14758; 4535; 22464; 22465; 22466; 22467; 22468; 3247; 16565; 7782; 7783; 7784; 7785; 10425; 22474; 22475; 22476; 16567; 16568; 22479; 22480; 10447; 22484; 10467; 22491; 19645; 19647; 19648; 19649; 4565; 10484; 10485; 4566; 4567; 7798; 22494; 4570; 19660; 22496; 14777; 2338; 19665; 10508; 10509; 10511; 16585; 22499; 22500; 22501; 22502; 22503; 10515; 22507; 2353; 22509; 22510; 19684; 3267; 3268; 6611; 22515; 7813; 7814; 10595; 10596; 10598; 22519; 25594; 3278; 22526; 22527; 6623; 22530; 22531; 22532; 22533; 22534; 10636; 21080; 22547; 16626; 22549; 22551; 22552; 22554; 22559; 22560; 10657; 22562; 10660; 22564; 13065; 22569; 13792; 22571; 22572; 7851; 2380; 22575; 13071; 13794; 13795; 22579; 22581; 22584; 22585; 18424; 18425; 22589; 22590; 22592; 22593; 22594; 22598; 10744; 10745.

The following SEQ ID NOs correspond to the amino acid sequences of testis-specific proteins identified using MPSS and that have also been identified by mass spectrometry as described in Table 44A: 28427; 28433; 32274; 5922; 28437; 28438; 28439; 28442; 16310; 22047; 28447; 28452; 28453; 28458; 28459; 28461; 5943; 28465; 13543; 28466; 28467; 28468; 28469; 13544; 13545; 28480; 28483; 28484; 19371; 399; 400; 28495; 28496; 28497; 28501; 28504; 28513; 28520; 12897; 12898; 12902; 12903; 12904; 12908; 28534; 28541; 28542; 28548; 28564; 28566; 28568; 28569; 28570; 28573; 22104; 28576; 28577; 28580; 3033; 28581; 7601; 9603; 4226; 28595; 20869; 28602; 1358; 28608; 23646; 23647; 9637; 26362; 28614; 28615; 1364; 14523; 28622; 32277; 28625; 28626; 28627; 19453; 19454; 28634; 28635; 28636; 28637; 28640; 28642; 28646; 28651; 22144; 22146; 22147; 28656; 28659; 28660; 1383; 20320; 20321; 20322; 28675; 28676; 9754; 2184; 22168; 28681; 28682; 9787; 28699; 28702; 28703; 28707; 28710; 1402; 28729; 28738; 28748; 28751; 28752; 28755; 28756; 28757; 28759; 28771; 13622; 28777; 28781; 28784; 28787; 4314; 28794; 1425; 28800; 4323; 6126; 17243; 9941; 9942; 9943; 9944; 28810; 28811; 3099; 28816; 28817; 28818; 14616; 14617; 14619; 28819; 28820; 28821; 20945; 15634; 9981; 9982; 28832; 28833; 10005; 28845; 28846; 14627; 32278; 12276; 12277; 28853; 28854; 28856; 3139; 28858; 28859; 6224; 28867; 28870; 28871; 3148; 28876; 28878; 28879; 28894; 28921; 28931; 28934; 22287; 28939; 28940; 28941; 28942; 28943;

28959; 28960; 28961; 28974; 28999; 29002; 29036; 29037; 22313; 22318; 22319; 22320; 22324; 29055; 29057; 29058; 29059; 29060; 29061; 29062; 29063; 29064; 29065; 22329; 32283; 1447; 29074; 29075; 25055; 29077; 29078; 29085; 3172; 19565; 19566; 29086; 12306; 29088; 29089; 29092; 13007; 29101; 29109; 14681; 32284; 29121; 4467; 16522; 13695; 13696; 3204; 18289; 10273; 10279; 10280; 10281; 29125; 10285; 10286; 29126; 29128; 29129; 29130; 29131; 29132; 29141; 10298; 29159; 10316; 10324; 6493; 6494; 29182; 14735; 29185; 3227; 3228; 10338; 15683; 29195; 29207; 29210; 29217; 3241; 29225; 29226; 29227; 3245; 10426; 29231; 22476; 639; 12356; 4544; 642; 29239; 23861; 23862; 29257; 29258; 29261; 29262; 29263; 10476; 19654; 19655; 19656; 19659; 659; 18366; 3257; 1536; 1537; 29286; 10564; 22509; 22510; 25593; 29290; 26667; 29298; 29299; 16603; 29301; 29302; 673; 674; 675; 2357; 2358; 676; 29314; 29319; 3276; 3277; 29324; 29328; 6624; 29333; 32286; 32287; 22533; 29344; 12397; 29354; 29355; 29363; 29364; 29365; 13065; 29368; 29376; 10677; 7851; 4649; 1582; 29387; 1583; 29388; 29391; 4655; 29394; 29395; 723; 22589; 10724; 10725; 12411; 1590; 29413; 29417; 29419; 29423; 29424; 29425; 7871.

The following SEQ ID NOs correspond to the amino acid sequences of mammary gland-specific proteins identified using MPSS and that have been identified by mass spectrometry as described in Table 44A: 17184; 17185; 17186; 17187; 17188; 7558; 17189; 17190; 17191; 5935; 5941; 5942; 17196; 17197; 17198; 32330; 32332; 32333; 32334; 32335; 17200; 17201; 408; 3025; 17209; 17210; 17211; 17212; 17213; 17214; 17218; 17219; 17220; 3055; 3056; 3057; 3058; 9786; 17228; 6088; 6090; 6091; 6092; 6093; 6094; 32339; 499; 12250; 12251; 17243; 518; 519; 17246; 532; 17258; 17259; 17261; 17262; 17263; 3171; 17275; 3191; 17281; 17283; 17284; 29125; 10298; 17288; 32229; 17292; 17293; 17298; 17301; 17302; 17303; 17305; 17306; 17307; 1519; 13740; 10486; 16574; 10491; 17312; 17313; 17314; 17315; 2342; 2343; 2344; 2345; 16587; 6610; 13051; 16622; 14821; 17326; 1564; 17329; 17332; 14835; 17333; 7846; 13065; 17335; 1582; 6672; 17336; 723.

The following SEQ ID NOs correspond to the amino acid sequences of uterus-specific proteins identified using MPSS and that have been identified by mass spectrometry as described in Table 44A: 32066; 32067; 5925; 32068; 32069; 32075; 32079; 9608; 32081; 32082; 32083; 32084; 22218; 9931; 32090; 32092; 32093; 9999; 20949; 10044; 32096; 16495; 22342; 32107; 32108; 32111; 32112; 32114; 19606; 10347; 32115; 32116; 32121; 32122; 23863; 23864; 23865; 23866; 23867; 13740; 19673; 19674; 26667; 3273; 21080; 31646; 1568; 1569; 1570; 1571; 1572; 1574; 6732.

The following SEQ ID NOs correspond to the amino acid sequences of CL1 (late-stage prostate cancer cell line)-specific proteins identified by MPSS that have also been identified by mass spectrometry as described in Table 45A: 32481; 32482; 32483; 380; 381; 5944; 32486; 9527; 5961; 4178; 32490; 32491; 2125; 3019; 3020; 32495; 32496; 26339; 32503; 32506; 12221; 12222; 14523; 32511; 32512; 469; 32513; 1388; 1389; 32514; 22179; 32517; 13630; 32523; 32524; 6135; 7676; 32529; 32530; 28833; 19524; 7690; 6284; 22342; 10186; 22351; 32539; 32540; 32541; 32543; 13685; 13686; 32547; 26574; 26575; 13019; 13020; 22419; 22420; 22421; 32550; 14735; 32228; 6501; 32554; 32555; 32556; 32557; 32560; 32561; 2337; 32563; 19668; 7804; 32565; 14790; 16597; 678; 21068; 32568; 2372; 699; 4638; 32574; 32575; 32576; 32577; 22589; 32580; 32581.

The following SEQ ID NOs correspond to the amino acid sequences of LNCaP (early-stage prostate cancer cell line)-specific proteins identified by MPSS that have also been identified by mass spectrometry as described in Table 45A: 22054; 32817; 32818; 32823; 426; 427; 428; 6030; 1390; 25527; 19500; 499; 32828; 32829; 32830; 32831; 32832; 19512; 1432; 32834; 32835; 32836; 32841; 10200; 10201; 10204; 10205; 32848; 2296; 2297; 32852; 30911; 6496; 3229; 3230; 3231; 32859; 14764; 32866.

The following SEQ ID NOs correspond to the amino acid sequences of normal prostate-specific proteins identified by MPSS that have also been identified by mass spectrometry as described in Table 45A: 16304; 22026; 22027; 13537; 9459; 2100; 9463; 22031; 22032; 22033; 22034; 9472; 9473; 22037; 22038; 22039; 22040; 2989; 22047; 383; 1323; 384; 5935; 22050; 22051; 22052; 22053; 22054; 22055; 2113; 1324; 1325; 1326; 22056; 1327; 22058; 9515; 22064; 5944; 4171; 4172; 3006; 9526; 15579; 2119; 9528; 22066; 1330; 7568; 397; 22071; 22074; 22085; 22086; 22087; 22088; 19380; 19381; 22089; 22094; 22101; 22102; 22104; 4219; 1357; 19419; 424; 22113; 22114; 22115; 22116; 22117; 22119; 22120; 20872; 22123; 12223; 22124; 22125; 22126; 22127; 22128; 15604; 22135; 18058; 22136; 7613; 22137; 22138; 7615; 22140; 9694; 9695; 22144; 22146; 22147; 20885; 20886; 22151; 22152; 22153; 22154; 9736; 6054; 3055; 22159; 1384; 22162; 22163; 1386; 469; 9750; 9751; 22164; 22167; 2184; 22168; 15617; 9786; 14555; 14556; 22171; 22172; 22173; 20890; 22174; 22175; 22176; 6076; 9798; 9804; 22177; 22179; 14561; 22180; 22193; 6088; 6090; 6091; 6092; 6093; 6094; 9875; 22209; 18105; 18106; 1415; 22212; 499; 500; 13631; 22218; 22221; 22222; 7669; 9924; 9925; 1425; 22228; 6135; 7676; 524; 22239; 4345; 4346; 4347; 4348; 4349; 4350; 22240; 15635; 22244; 22247; 22252; 22253; 22254; 22255; 22257; 22259; 22263; 22264; 3148; 6231; 22269; 22287; 22293; 22313; 22318; 22319; 22320; 22324; 22329; 3166; 22342; 3177; 22351; 22357; 22358; 3187; 16505; 22363; 10224; 22365; 22366; 22367; 22368; 22371; 14685; 22373; 22378; 22384; 22387; 22388; 22389; 22390; 6311; 10244; 10245; 22400; 22401; 16530; 18289; 14707; 21012; 21014; 17283; 22412; 10287; 22417; 22418; 22419; 22420; 22421; 22422; 1484; 22430; 22431; 32228; 22432; 22433; 32229; 22434; 22435; 22436; 22437; 4513; 4521; 22448; 22449; 22450; 22452; 22455; 3237; 3238; 10389; 10390; 10391; 22458; 22459; 22460; 22461; 14757; 14758; 4535; 22464; 22465; 22466; 22467; 22468; 3247; 16565; 7782; 7783; 7784; 7785; 10425; 22474; 22476; 16567; 16568; 22479; 22480; 10447; 22484; 10467; 22491; 19645; 19647; 19648; 19649; 4565; 4566; 4567; 7798; 22494; 4570; 19660; 22496; 14777; 2338; 19665; 10508; 10509; 10511; 16585; 22499; 22500; 22501; 22502; 22503; 10515; 22507; 22509; 22510; 19684; 3267; 3268; 6611; 22515; 7813; 7814; 10595; 10596; 10598; 22519; 25594; 3278; 22526; 22527; 6623; 22530; 22531; 22532; 10636; 21080; 22547; 16626; 22549; 22551; 22552; 22554; 22559; 22560; 10657; 22562; 10660; 22564; 13065; 22569; 13792; 22571; 22572; 7851; 22575; 13071; 13794; 13795; 22579; 22581; 22584; 22585; 18424; 18425; 22589; 22590; 22592; 22593; 22594; 22598; 10744; 10745.

The following SEQ ID NOs correspond to the polynucleotides encoding adrenal gland-specific proteins as described in Table 47A identified using SBS: 52865; 20; 52866; 27630; 77; 78; 79; 80; 81; 52867; 91; 20175; 20176; 52868; 111; 112; 152; 153; 30543; 30544; 30545; 173; 52869; 52870; 52871; 52872; 52873; 206; 207; 52874; 235; 280; 281; 52875; 52876; 312; 313; 52877; 52878; 52879.

The following SEQ ID NOs correspond to the amino acid sequences of adrenal gland-specific proteins as described in Table 47A identified using SBS: 52880; 388; 52881; 28632; 445; 446; 447; 448; 449; 52882; 459; 20316; 20317; 52883; 479; 480; 520; 521; 30806; 30807; 30808; 541; 52884;

52885; 52886; 52887; 52888; 574; 575; 52889; 603; 649; 648; 52890; 52891; 680; 681; 52892; 52893; 52894.

The following SEQ ID NO corresponds to the polynucleotide encoding an artery-specific protein as described in Table 48A identified using SBS: 24329.

The following SEQ ID NO correspond to the amino acid sequence of an artery-specific protein as described in Table 48A identified using SBS: 24459.

The following SEQ ID NOs correspond to the polynucleotides encoding bladder-specific proteins as described in Table 49A identified using SBS: 1032; 52986; 52987; 52988; 52989; 52990; 21541; 52991; 52992; 52993; 52994; 1187; 1188; 52995; 52996; 52997; 52998; 1259; 1260; 1261; 52999; 53000; 1301; 4105.

The following SEQ ID NOs correspond to the amino acid sequences of bladder-specific proteins as described in Table 49A identified using SBS: 1315; 53001; 53002; 53003; 53004; 53005; 22128; 53006; 53007; 53008; 53009; 1470; 1471; 53010; 53011; 53012; 53013; 1542; 1543; 1544; 53014; 53015; 1584; 4654.

The following SEQ ID NOs correspond to the polynucleotides encoding brain-specific proteins as described in Table 50A identified using SBS: 1796; 1797; 1798; 53036; 53037; 53038; 53039; 53040; 53041; 53042; 53043; 8142; 53044; 53045; 53046; 53047; 11914; 11915; 53048; 53049; 53050; 5100; 12673; 12674; 12675; 12676; 12677; 53051; 53052; 53053; 53054; 11919; 11920; 25344; 25345; 53055; 53056; 23286; 53057; 3605; 3606; 3607; 15916; 3608; 53058; 2643; 53059; 8191; 3620; 3621; 5112; 5113; 2646; 2647; 5115; 5116; 53060; 53061; 7236; 7237; 53062; 53063; 8201; 53064; 2651; 53065; 17519; 53066; 2652; 53067; 5128; 1051; 53068; 53069; 53070; 53071; 53072; 53073; 53074; 53075; 25349; 53076; 53077; 53078; 53079; 2667; 53080; 53081; 53082; 53083; 8262; 3659; 53084; 5153; 5154; 5155; 5158; 53085; 53086; 53087; 3660; 3661; 3662; 3663; 3664; 3665; 3666; 3667; 53088; 21515; 53089; 53090; 53091; 53092; 19012; 53093; 53094; 53095; 53096; 53097; 3681; 2682; 2683; 53098; 53099; 53100; 53101; 7275; 53102; 32018; 53103; 8312; 25364; 53104; 8318; 19032; 19033; 53105; 2691; 53106; 53107; 53108; 8334; 53109; 8337; 7282; 53110; 53111; 53112; 53113; 8354; 53114; 53115; 53116; 8378; 8381; 8382; 53117; 20178; 53118; 53119; 53120; 53121; 3711; 53122; 53123; 53124; 32769; 32770; 32771; 3712; 53125; 53126; 53127; 5223; 5226; 5227; 5229; 5230; 53128; 53129; 53130; 53131; 8455; 53132; 1107; 1108; 2714; 53133; 53134; 53135; 53136; 25926; 14146; 8481; 8482; 11985; 31386; 31387; 31388; 31389; 31390; 31391; 31392; 31394; 31395; 53137; 25382; 53138; 53139; 53140; 7316; 7317; 53141; 53142; 53143; 8524; 53144; 53145; 53146; 8536; 8540; 53147; 53148; 53149; 53150; 53151; 53152; 53153; 8549; 8550; 53154; 53155; 3752; 3753; 3754; 3755; 2725; 53156; 53157; 8556; 7332; 24800; 2730; 2731; 53158; 53159; 53160; 53161; 53162; 53163; 21627; 21628; 21629; 21630; 53164; 7338; 2737; 3768; 5272; 53165; 8579; 8580; 8581; 8582; 8583; 53166; 53167; 53168; 8586; 53169; 53170; 8587; 8588; 53171; 53172; 53173; 53174; 53175; 53176; 53177; 3787; 53178; 53179; 27818; 27819; 53180; 53181; 53182; 53183; 12014; 2749; 3804; 3805; 3806; 8668; 8669; 53184; 53185; 5311; 5312; 5313; 5314; 5315; 5316; 53186; 53187; 53188; 53189; 8670; 8671; 53190; 53191; 53192; 53193; 53194; 2752; 53195; 53196; 19119; 27845; 27846; 53197; 53198; 8691; 8692; 53199; 53200; 53201; 53202; 53203; 53204; 2784; 53205; 53206; 5379; 5380; 5381; 5382; 5383; 5384; 5385; 5386; 5387; 5388; 5389; 2785; 2789; 53207; 53208; 21681; 53209; 53210; 53211; 53212; 53213; 53214; 53215; 53216; 53217; 53218; 53219; 53220; 53221; 53222; 53223; 53224; 30591; 53225; 53226; 5434; 53227; 53228; 53229; 53230; 53231; 53232; 53233; 53234; 53235; 53236; 53237; 5435; 53238; 53239; 53240; 53241; 53242; 53243; 53244; 53245; 53246; 53247; 28013; 53248; 53249; 53250; 53251; 53252; 53253; 53254; 30618; 53255; 53256; 53257; 53258; 53259; 3892; 53260; 23449; 53261; 53262; 28072; 53263; 53264; 53265; 53266; 53267; 53268; 53269; 53270; 3899; 12796; 12797; 53271; 53272; 53273; 53274; 53275; 14253; 53276; 3902; 53277; 53278; 53279; 7391; 7392; 7393; 7394; 53280; 53281; 53282; 53283; 53284; 53285; 53286; 53287; 53288; 53289; 53290; 53291; 53292; 12053; 8884; 8885; 53293; 53294; 53295; 53296; 53297; 3907; 3908; 3909; 53298; 53299; 53300; 53301; 2836; 8912; 53302; 8914; 3917; 12061; 53303; 53304; 53305; 53306; 53307; 32795; 53308; 53309; 53310; 53311; 8934; 8935; 20742; 20743; 53312; 7408; 1199; 53313; 53314; 53315; 2849; 12806; 53316; 12807; 3933; 5636; 5637; 25426; 12068; 8949; 53317; 53318; 8950; 53319; 3936; 2860; 5640; 53320; 53321; 3938; 23483; 23484; 3941; 3942; 53322; 53323; 53324; 53325; 53326; 53327; 53328; 53329; 53330; 53331; 53332; 53333; 53334; 17128; 53335; 53336; 244; 245; 20245; 53337; 53338; 3954; 28182; 53339; 14324; 12820; 7428; 7429; 12088; 53340; 53341; 53342; 53343; 3974; 3975; 16154; 16155; 16156; 16157; 16158; 16159; 5691; 5692; 2878; 53344; 53345; 53346; 53347; 53348; 2887; 2888; 3987; 53349; 53350; 23506; 53351; 53352; 12099; 53353; 53354; 53355; 53356; 53357; 53358; 3994; 53359; 23525; 23526; 23527; 16175; 53360; 5739; 53361; 53362; 53363; 53364; 53365; 20252; 28267; 53366; 53367; 23542; 53368; 53369; 53370; 9166; 9167; 53371; 12107; 5752; 53372; 53373; 53374; 53375; 53376; 53377; 53378; 53379; 53380; 53381; 53382; 53383; 53384; 53385; 53386; 53387; 53388; 53389; 28284; 12836; 53390; 300; 53391; 53392; 53393; 23559; 4035; 12839; 5774; 53394; 53395; 53396; 53397; 53398; 20258; 20259; 2914; 53399; 53400; 53401; 53402; 28300; 53403; 5781; 25454; 53404; 9291; 14396; 53405; 53406; 4059; 4060; 4061; 53407; 53408; 53409; 53410; 53411; 53412; 53413; 53414; 53415; 53416; 53417; 5795; 53418; 2927; 4066; 5796; 9301; 53419; 53420; 53421; 53422; 4069; 4070; 4071; 53423; 7509; 53424; 53425; 53426; 19306; 7515; 2941; 12142; 53427; 4081; 53428; 53429; 2951; 53430; 5812; 5813; 5814; 5815; 5816; 5817; 5818; 5819; 53431; 53432; 1294; 4092; 53433; 21988; 53434; 5825; 2958; 5826; 2959; 5827; 53435; 53436; 53437; 53438; 53439; 5884; 53440; 2973.

The following SEQ ID NOs correspond to the amino acid sequences of brain-specific proteins as described in Table 50A identified using SBS: 2095; 2096; 2097; 53441; 53442; 53443; 53444; 53445; 53446; 53447; 53448; 9470; 53449; 53450; 53451; 53452; 12170; 12171; 53453; 53454; 53455; 5934; 12881; 12882; 12883; 12884; 12885; 53456; 53457; 53458; 53459; 12175; 12176; 25484; 25485; 53460; 53461; 23617; 53462; 4154; 4157; 4156; 16313; 4155; 53463; 2999; 53464; 9519; 4169; 4170; 5946; 5947; 3002; 3003; 5949; 5950; 53465; 53466; 7566; 7567; 53467; 53468; 9529; 53469; 3007; 53470; 17988; 53471; 3008; 53472; 5962; 1334; 53473; 53474; 53475; 53476; 53477; 53478; 53479; 53480; 25489; 53481; 53482; 53483; 53484; 3023; 53485; 53486; 53487; 53488; 9590; 4208; 53489; 5987; 5988; 5989; 5992; 53490; 53491; 53492; 4209; 4210; 4211; 4212; 4213; 4214; 4215; 4216; 53493; 22102; 53494; 53495; 53496; 53497; 19416; 53498; 53499; 53500; 53501; 53502; 4230; 3039; 3038; 53503; 53504; 53505; 53506; 7605; 53507; 32081; 53508; 9640; 25504; 53509; 9646; 19437; 19436; 53510; 3047; 53511; 53512; 53513; 9662; 53514; 9665; 7612; 53515; 53516; 53517; 53518; 9682; 53519; 53520; 53521; 9706; 9709; 9710; 53522; 20319; 53523; 53524;

53525; 53526; 4260; 53527; 53528; 53529; 32825; 32826; 32827; 4261; 53530; 53531; 53532; 6057; 6060; 6061; 6063; 6064; 53533; 53534; 53535; 53536; 9783; 53537; 1390; 1391; 3070; 53538; 53539; 53540; 53541; 26396; 14560; 9809; 9810; 12241; 31548; 31549; 31550; 31551; 31552; 31553; 31554; 31556; 31557; 53542; 25522; 53543; 53544; 53545; 7646; 7647; 53546; 53547; 53548; 9852; 53549; 53550; 53551; 9864; 9868; 53552; 53553; 53554; 53555; 53556; 53557; 53558; 9877; 9878; 53559; 53560; 4301; 4302; 4303; 4304; 3081; 53561; 53562; 9884; 7662; 25003; 3086; 3087; 53563; 53564; 53565; 53566; 53567; 53568; 22214; 22215; 22216; 22217; 53569; 7668; 3093; 4317; 6106; 53570; 9907; 9908; 9909; 9910; 9911; 53571; 53572; 53573; 9914; 53574; 53575; 9915; 9916; 53576; 53577; 53578; 53579; 53580; 53581; 53582; 4336; 53583; 53584; 28820; 28821; 53585; 53586; 53587; 53588; 12270; 3105; 4353; 4354; 4355; 9996; 9997; 53589; 53590; 6145; 6149; 6147; 6148; 6146; 6150; 53591; 53592; 53593; 53594; 9998; 9999; 53595; 53596; 53597; 53598; 53599; 3108; 53600; 53601; 19523; 28848; 28847; 53602; 53603; 10019; 10020; 53604; 53605; 53606; 53607; 53608; 53609; 3140; 53610; 53611; 6213; 6214; 6215; 6216; 6221; 6218; 6219; 6220; 6217; 6222; 6223; 3141; 3145; 53612; 53613; 22268; 53614; 53615; 53616; 53617; 53618; 53619; 53620; 53621; 53622; 53623; 53624; 53625; 53626; 53627; 53628; 53629; 30854; 53630; 53631; 6268; 6269; 53632; 53633; 53634; 53635; 53636; 53637; 53638; 53639; 53640; 53641; 53642; 53643; 53644; 53645; 53646; 53647; 53648; 53649; 53650; 53651; 53652; 29015; 53653; 53654; 53655; 53656; 53657; 53658; 53659; 30881; 53660; 53661; 53662; 53663; 53664; 4441; 53665; 23780; 53666; 53667; 29074; 53668; 53669; 53670; 53671; 53672; 53673; 53674; 53675; 4448; 13004; 13005; 53676; 53677; 53678; 53679; 53680; 14667; 53681; 4451; 53682; 53683; 53684; 7721; 7722; 7723; 7724; 53685; 53686; 53687; 53688; 53689; 53690; 53691; 53692; 53693; 53694; 53695; 53696; 53697; 12309; 10212; 10213; 53698; 53699; 53700; 53701; 53702; 4456; 4457; 4458; 53703; 53704; 53705; 53706; 3192; 10240; 53707; 10242; 4466; 12317; 53708; 53709; 53710; 53711; 53712; 32851; 53713; 53714; 53715; 53716; 10262; 10263; 21009; 21010; 53717; 7738; 1482; 53718; 53719; 53720; 3205; 13014; 53721; 13015; 4482; 6470; 6471; 25566; 12324; 10277; 53722; 53723; 10278; 53724; 4485; 3216; 6474; 53725; 53726; 4487; 23814; 23815; 4490; 4491; 53727; 53728; 53729; 53730; 53731; 53732; 53733; 53734; 53735; 53736; 53737; 53738; 53739; 17288; 53740; 53741; 612; 613; 20386; 53742; 53743; 4503; 29184; 53744; 14738; 13028; 7758; 7759; 12344; 53745; 53746; 53747; 53748; 4523; 4524; 16552; 16553; 16551; 16554; 16555; 16556; 6525; 6526; 3234; 53749; 53750; 53751; 53752; 53753; 3244; 3243; 4536; 53754; 53755; 23837; 53756; 53757; 12355; 53758; 53759; 53760; 53761; 53762; 53763; 4543; 53764; 23856; 23857; 23858; 16572; 53765; 6573; 53766; 53767; 53768; 53769; 53770; 20393; 29269; 53771; 53772; 23873; 53773; 53774; 53775; 10494; 10495; 53776; 12363; 6586; 53777; 53778; 53779; 53780; 53781; 53782; 53783; 53784; 53785; 53786; 53787; 53788; 53789; 53790; 53791; 53792; 53793; 53794; 29286; 13044; 53795; 668; 53796; 53797; 53798; 23890; 4584; 13047; 6608; 53799; 53800; 53801; 53802; 53803; 20399; 20400; 3270; 53804; 53805; 53806; 53807; 29302; 53808; 6615; 25594; 53809; 10619; 14810; 53810; 53811; 4608; 4609; 4610; 53812; 53813; 53814; 53815; 53816; 53817; 53818; 53819; 53820; 53821; 53822; 6629; 53823; 3283; 4615; 6630; 10629; 53824; 53825; 53826; 53827; 4618; 4619; 4620; 53828; 7839; 53829; 53830; 53831; 19710; 7845; 3297; 12398; 53832; 4630; 53833; 53834; 3307; 53835; 6646; 6647; 6648; 6649; 6650; 6651; 6652; 6653; 53836; 53837; 1577; 4641; 53838; 22575; 53839; 6659; 3314; 6661; 3315; 6660; 53840; 53841; 53842; 53843; 53844; 6718; 53845; 3329.

The following SEQ ID NOs correspond to the polynucleotides encoding breast-specific proteins as described in Table 51A identified using SBS: 17025; 14099; 8321; 54808; 54809; 17063; 17064; 17080; 54810; 54811; 54812; 54813; 54814; 54815; 54816; 54817; 54818; 54819; 54820; 54821; 17132; 54822; 17152; 17153; 24429; 17171; 17172.

The following SEQ ID NOs correspond to the amino acid sequences of breast-specific proteins as described in Table 51A identified using SBS: 17185; 14513; 9649; 54823; 54824; 17223; 17224; 17240; 54825; 54826; 54827; 54828; 54829; 54830; 54831; 54832; 54833; 54834; 54835; 54836; 17292; 54837; 17312; 17313; 24559; 17331; 17332.

The following SEQ ID NOs correspond to the polynucleotides encoding cervix-specific proteins as described in Table 52A identified using SBS: 14134; 32022; 54868; 14256; 54869; 54870; 54871; 54872; 54873; 54874.

The following SEQ ID NOs correspond to the amino acid sequences of cervix-specific proteins as described in Table 52A identified using SBS: 14548; 32085; 54875; 14670; 54876; 54877; 54878; 54879; 54880; 54881.

The following SEQ ID NOs correspond to the polynucleotides encoding heart-specific proteins as described in Table 53A identified using SBS: 1030; 14040; 8132; 31350; 54896; 14053; 54897; 54898; 14076; 3660; 3661; 3662; 3663; 3664; 3665; 3666; 3667; 14083; 14098; 54899; 14103; 14107; 20608; 14117; 54900; 54901; 14144; 14159; 14160; 27769; 54902; 54903; 14200; 54904; 54905; 54906; 54907; 3808; 3809; 3810; 3811; 3812; 3813; 3814; 14227; 14241; 14244; 14247; 54908; 14254; 14273; 14274; 14275; 14277; 14278; 54909; 54910; 14280; 14282; 14287; 14288; 14292; 14293; 14294; 14295; 14296; 54911; 54912; 54913; 54914; 14332; 54915; 54916; 54917; 54918; 54919; 54920; 54921; 14347; 54922; 14363; 54923; 54924; 14373; 14378; 54925; 14383; 14388; 54926; 54927; 54928; 54929; 14400; 20263; 14411; 14412; 14413; 14414; 14415; 14416; 1285; 1286; 1287; 1288; 1289; 1290; 1291; 14423; 14424; 14425; 14426; 54930; 2952; 2953; 2955; 2956; 14433; 14434.

The following SEQ ID NOs correspond to the amino acid sequences of heart-specific proteins as described in Table 53A identified using SBS: 1313; 14454; 9460; 31512; 54931; 14467; 54932; 54933; 14490; 4209; 4210; 4211; 4212; 4213; 4214; 4215; 4216; 14497; 14512; 54934; 14517; 14521; 20875; 14531; 54935; 54936; 14558; 14573; 14574; 28771; 54937; 54938; 14614; 54939; 54940; 54941; 54942; 4357; 4358; 4359; 4360; 4361; 4362; 4363; 14641; 14658; 14655; 14661; 54943; 14668; 14687; 14688; 14689; 14691; 14692; 54944; 54945; 14694; 14696; 14701; 14702; 14706; 14707; 14708; 14709; 14710; 54946; 54947; 54948; 54949; 14746; 54950; 54951; 54952; 54953; 54954; 54955; 54956; 14761; 54957; 14777; 54958; 54959; 14787; 14792; 54960; 14797; 14802; 54961; 54962; 54963; 54964; 14814; 20404; 14825; 14826; 14827; 14828; 14829; 14830; 1568; 1569; 1570; 1571; 1572; 1573; 1574; 14837; 14838; 14839; 14840; 54965; 3308; 3309; 3311; 3312; 14847; 14848.

The following SEQ ID NOs correspond to the polynucleotides encoding kidney-specific proteins as described in Table 54A identified using SBS: 12671; 12672; 55189; 32757; 32758; 15394; 55190; 32378; 55191; 55192; 55193; 55194; 55195; 55196; 8207; 55197; 55198; 55199; 55200; 15932; 5158; 25869; 30482; 15412; 55201; 55202; 15413; 23310; 8294; 14094; 55203; 55204; 55205; 55206; 55207; 55208; 55209; 55210; 25369; 11972; 20614; 31380; 55211; 5216; 5217; 8403; 55212; 55213; 55214; 55215; 3742; 55216; 55217; 55218; 24367; 24368; 15448; 55219; 55220;

55221; 55222; 55223; 55224; 55225; 55226; 55227; 1943; 55228; 55229; 55230; 55231; 55232; 55233; 55234; 55235; 55236; 55237; 55238; 55239; 55240; 32778; 32779; 27857; 17098; 17099; 17100; 17101; 24815; 55241; 55242; 20695; 55243; 55244; 55245; 55246; 15474; 15473; 15475; 55247; 55248; 55249; 55250; 55251; 55252; 55253; 55254; 55255; 55256; 55257; 55258; 55259; 55260; 55261; 55262; 55263; 55264; 55265; 55266; 55267; 55268; 55269; 55270; 55271; 55272; 55273; 55274; 55275; 55276; 55277; 55278; 55279; 55280; 15479; 55281; 55282; 55283; 55284; 55285; 55286; 55287; 55288; 55289; 55290; 55291; 3898; 5465; 55292; 8893; 32436; 55293; 8908; 55294; 15494; 55295; 55296; 55297; 55298; 8963; 8964; 15498; 15499; 15500; 15501; 15502; 31450; 31451; 31452; 31453; 31454; 23486; 15504; 15507; 55299; 55300; 55301; 55302; 55303; 16183; 16184; 55304; 55305; 55306; 55307; 15522; 15523; 15524; 55308; 15525; 15526; 5766; 5767; 5770; 55309; 55310; 55311; 55312; 15529; 2915; 55313; 55314; 12844; 2936; 55315; 55316; 20816; 2073; 55317; 55318; 55319; 55320; 30707; 30708; 55321; 15547; 15548; 55322; 55323; 55324; 28424.

The following SEQ ID NOs correspond to the amino acid sequences of kidney-specific proteins as described in Table 54A identified using SBS: 12879; 12880; 55325; 32813; 32814; 15570; 55326; 32485; 55327; 55328; 55329; 55330; 55331; 55332; 9535; 55333; 55334; 55335; 55336; 16329; 5992; 26339; 30745; 15588; 55337; 55338; 15589; 23641; 9622; 14508; 55339; 55340; 55341; 55342; 55343; 55344; 55345; 55346; 25509; 12228; 20881; 31542; 55347; 6050; 6051; 9731; 55348; 55349; 55350; 55351; 4291; 55352; 55353; 55354; 24497; 24498; 15624; 55355; 55356; 55357; 55358; 55359; 55360; 55361; 55362; 55363; 2242; 55364; 55365; 55366; 55367; 55368; 55369; 55370; 55371; 55372; 55373; 55374; 55375; 55376; 32834; 32835; 28859; 17261; 17259; 17260; 17258; 25018; 55377; 55378; 20962; 55379; 55380; 55381; 55382; 15649; 15650; 15651; 55383; 55384; 55385; 55386; 55387; 55388; 55389; 55390; 55391; 55392; 55393; 55394; 55395; 55396; 55397; 55398; 55399; 55400; 55401; 55402; 55403; 55404; 55405; 55406; 55407; 55408; 55409; 55410; 55411; 55412; 55413; 55414; 55415; 55416; 15655; 55417; 55418; 55419; 55420; 55421; 55422; 55423; 55424; 55425; 55426; 55427; 4447; 6299; 55428; 10221; 32543; 55429; 10236; 55430; 15670; 55431; 55432; 55433; 55434; 10291; 10292; 15674; 15675; 15676; 15677; 15678; 31612; 31613; 31614; 31615; 31616; 23817; 15680; 15683; 55435; 55436; 55437; 55438; 55439; 16580; 16581; 55440; 55441; 55442; 55443; 15698; 15699; 15700; 55444; 15701; 15702; 6600; 6601; 6604; 55445; 55446; 55447; 55448; 15705; 3271; 55449; 55450; 13052; 3292; 55451; 55452; 21083; 2372; 55453; 55454; 55455; 55456; 30970; 30971; 55457; 15724; 15723; 55458; 55459; 55460; 29426.

The following SEQ ID NOs correspond to the polynucleotides encoding liver-specific proteins as described in Table 55A identified using SBS: 55676; 55677; 55678; 55679; 55680; 55681; 55682; 55683; 24715; 11906; 55684; 55685; 55686; 55687; 15375; 55688; 15377; 55689; 55690; 55691; 55692; 5088; 1036; 55693; 55694; 55695; 15383; 55696; 20139; 17507; 17508; 55697; 32311; 8157; 23281; 15389; 15390; 15391; 55698; 55699; 55700; 15393; 17; 20585; 55701; 55702; 55703; 3598; 18; 55704; 8172; 55705; 55706; 55707; 1814; 55708; 55709; 55710; 55711; 55712; 23; 55713; 55714; 55715; 55716; 55717; 55718; 55719; 5142; 55720; 55721; 55722; 55723; 55724; 55725; 55726; 55727; 55728; 55729; 55730; 55731; 55732; 31367; 31368; 55733; 55734; 55735; 55736; 55737; 19014; 55738; 55; 55739; 55740; 55741; 23315; 23316; 55742; 55743; 19016; 55744; 55745; 55746; 55747; 55748; 55749; 55750; 23326; 55751; 55752; 24330; 24331; 15425; 15426; 55753; 55754; 55755; 55756; 55757; 55758; 55759; 55760; 55761; 55762; 55763; 55764; 24774; 55765; 55766; 3698; 55767; 24775; 24776; 24777; 24778; 55768; 15427; 16001; 24779; 24780; 55769; 55770; 1878; 55771; 55772; 55773; 55774; 55775; 55776; 25375; 20620; 1886; 55777; 13344; 55778; 55779; 55780; 55781; 25380; 23357; 55782; 13345; 55783; 55784; 55785; 55786; 55787; 55788; 55789; 55790; 55791; 55792; 55793; 55794; 55795; 55796; 55797; 55798; 55799; 55800; 55801; 15446; 15447; 55802; 55803; 55804; 14167; 55805; 55806; 55807; 55808; 55809; 55810; 15450; 55811; 13365; 55812; 55813; 55814; 55815; 55816; 55817; 11999; 12000; 55818; 55819; 19105; 14184; 14185; 14186; 14187; 55820; 55821; 55822; 55823; 55824; 55825; 55826; 55827; 14198; 55828; 55829; 15453; 55830; 55831; 55832; 55833; 55834; 55835; 55836; 55837; 55838; 20675; 55839; 55840; 55841; 55842; 55843; 55844; 55845; 55846; 15469; 55847; 55848; 3851; 55849; 55850; 8732; 15472; 55851; 55852; 55853; 55854; 27910; 27909; 55855; 55856; 55857; 55858; 55859; 55860; 55861; 55862; 55863; 55864; 55865; 55866; 55867; 55868; 55869; 55870; 55871; 55872; 55873; 55874; 55875; 55876; 17111; 55877; 55878; 55879; 55880; 55881; 55882; 55883; 55884; 55885; 55886; 55887; 55888; 55889; 55890; 55891; 55892; 55893; 55894; 55895; 55896; 55897; 55898; 55899; 55900; 55901; 55902; 55903; 55904; 14255; 55905; 55906; 55907; 55908; 7396; 55909; 1975; 1978; 1979; 1980; 55910; 55911; 55912; 55913; 55914; 55915; 26100; 26101; 26102; 55916; 12806; 12807; 55917; 55918; 26108; 55919; 55920; 55921; 55922; 55923; 15503; 20763; 55924; 55925; 15506; 55926; 55927; 55928; 55929; 55930; 55931; 55932; 55933; 55934; 55935; 15516; 55936; 55937; 55938; 55939; 55940; 55941; 55942; 55943; 55944; 55945; 55946; 55947; 55948; 2030; 55949; 55950; 17152; 17153; 55951; 55952; 55953; 13475; 13476; 13477; 55954; 55955; 55956; 55957; 55958; 55959; 55960; 55961; 55962; 55963; 9189; 55964; 55965; 55966; 55967; 55968; 55969; 55970; 55971; 55972; 55973; 55974; 55975; 55976; 21924; 15527; 7478; 21926; 14377; 55977; 32460; 55978; 55979; 319; 17164; 55980; 7514; 2072; 55981; 55982; 55983; 55984; 12863; 55985; 55986; 55987; 55988; 55989; 55990; 55991; 55992; 55993; 55994; 15545; 55995; 27358; 13526; 55996; 14431; 15546; 26236; 15549; 55997; 28388.

The following SEQ ID NOs correspond to the amino acid sequences of liver-specific proteins as described in Table 55A identified using SBS: 55998; 55999; 56000; 56001; 56002; 56003; 56004; 56005; 24918; 12162; 56006; 56007; 56008; 56009; 15551; 56010; 15553; 56011; 56012; 56013; 56014; 5922; 1319; 56015; 56016; 56017; 15559; 56018; 20280; 17976; 17977; 56019; 32329; 9485; 23612; 15565; 15566; 15567; 56020; 56021; 56022; 15569; 385; 20852; 56023; 56024; 56025; 4147; 386; 56026; 9500; 56027; 56028; 56029; 2113; 56030; 56031; 56032; 56033; 56034; 391; 56035; 56036; 56037; 56038; 56039; 56040; 56041; 5976; 56042; 56043; 56044; 56045; 56046; 56047; 56048; 56049; 56050; 56051; 56052; 56053; 56054; 31530; 31529; 56055; 56056; 56057; 56058; 56059; 19418; 56060; 423; 56061; 56062; 56063; 23646; 23647; 56064; 56065; 19420; 56066; 56067; 56068; 56069; 56070; 56071; 56072; 23657; 56073; 56074; 24460; 24461; 15601; 15602; 56075; 56076; 56077; 56078; 56079; 56080; 56081; 56082; 56083; 56084; 56085; 56086; 24977; 56087; 56088; 4247; 56089; 24978; 24979; 24980; 24981; 56090; 15603; 16398; 24982; 24983; 56091; 56092; 2177; 56093; 56094; 56095; 56096; 56097; 56098; 25515; 20887; 2185; 56099; 13611; 56100; 56101; 56102; 56103; 25520; 23688; 56104; 13612; 56105; 56106; 56107; 56108; 56109; 56110; 56111; 56112; 56113; 56114; 56115; 56116; 56117; 56118; 56119; 56120; 56121; 56122; 56123; 15622; 15623; 56124; 56125; 56126; 14581; 56127; 56128;

56129; 56130; 56131; 56132; 15626; 56133; 13632; 56134; 56135; 56136; 56137; 56138; 56139; 12256; 12255; 56140; 56141; 19509; 14598; 14599; 14600; 14601; 56142; 56143; 56144; 56145; 56146; 56147; 56148; 56149; 14612; 56150; 56151; 15629; 56152; 56153; 56154; 56155; 56156; 56157; 56158; 56159; 56160; 20942; 56161; 56162; 56163; 56164; 56165; 56166; 56167; 56168; 15645; 56169; 56170; 4400; 56171; 56172; 10060; 15648; 56173; 56174; 56175; 56176; 28911; 28912; 56177; 56178; 56179; 56180; 56181; 56182; 56183; 56184; 56185; 56186; 56187; 56188; 56189; 56190; 56191; 56192; 56193; 56194; 56195; 56196; 56197; 56198; 17271; 56199; 56200; 56201; 56202; 56203; 56204; 56205; 56206; 56207; 56208; 56209; 56210; 56211; 56212; 56213; 56214; 56215; 56216; 56217; 56218; 56219; 56220; 56221; 56222; 56223; 56224; 56225; 56226; 14669; 56227; 56228; 56229; 56230; 7726; 56231; 2274; 2277; 2278; 2279; 56232; 56233; 56234; 56235; 56236; 56237; 26570; 26571; 26572; 56238; 13014; 13015; 56239; 56240; 26578; 56241; 56242; 56243; 56244; 56245; 15679; 21030; 56246; 56247; 15682; 56248; 56249; 56250; 56251; 56252; 56253; 56254; 56255; 56256; 56257; 15692; 56258; 56259; 56260; 56261; 56262; 56263; 56264; 56265; 56266; 56267; 56268; 56269; 56270; 2329; 56271; 56272; 17312; 17313; 56273; 56274; 56275; 13743; 13744; 13742; 56276; 56277; 56278; 56279; 56280; 56281; 56282; 56283; 56284; 56285; 10517; 56286; 56287; 56288; 56289; 56290; 56291; 56292; 56293; 56294; 56295; 56296; 56297; 56298; 22511; 15703; 7808; 22513; 14791; 56299; 32567; 56300; 56301; 687; 17324; 56302; 7844; 2371; 56303; 56304; 56305; 56306; 13071; 56307; 56308; 56309; 56310; 56311; 56312; 56313; 56314; 56315; 56316; 15721; 56317; 27388; 13793; 56318; 14845; 15722; 26706; 15725; 56319; 29390.

The following SEQ ID NOs correspond to the polynucleotides encoding lung-specific proteins as described in Table 56A identified using SBS: 57163; 57164; 8146; 8147; 57165; 25344; 25345; 8190; 57166; 57167; 57168; 57169; 57170; 30481; 57171; 13324; 15987; 15988; 57172; 16015; 16016; 57173; 57174; 57175; 57176; 57177; 57178; 57179; 57180; 57181; 57182; 57183; 57184; 57185; 57186; 57187; 57188; 21631; 16039; 7343; 13373; 57189; 1940; 1941; 16054; 57190; 16062; 57191; 57192; 57193; 57194; 57195; 57196; 57197; 57198; 57199; 57200; 57201; 57202; 57203; 57204; 16079; 16080; 16081; 16082; 16083; 16084; 57205; 57206; 57207; 57208; 57209; 57210; 57211; 57212; 16089; 16090; 16091; 16092; 16093; 16094; 16095; 57213; 31429; 57214; 16121; 57215; 57216; 1996; 16147; 57217; 57218; 57219; 57220; 26177; 57221; 16187; 57222; 16191; 57223; 16192; 16193; 16194; 16195; 57224; 13506; 2928; 2929; 57225; 57226; 20835, The following SEQ ID NOs correspond to the amino acid sequences of lung-specific proteins as described in Table 56A identified using SBS: 57227; 57228; 9474; 9475; 57229; 25484; 25485; 9518; 57230; 57231; 57232; 57233; 57234; 30744; 57235; 13591; 16384; 16385; 57236; 16412; 16413; 57237; 57238; 57239; 57240; 57241; 57242; 57243; 57244; 57245; 57246; 57247; 57248; 57249; 57250; 57251; 57252; 22218; 16436; 7673; 13640; 57253; 2239; 2240; 16451; 57254; 16459; 57255; 57256; 57257; 57258; 57259; 57260; 57261; 57262; 57263; 57264; 57265; 57266; 57267; 57268; 16480; 16479; 16477; 16478; 16476; 16481; 57269; 57270; 57271; 57272; 57273; 57274; 57275; 57276; 16486; 16487; 16488; 57277; 16489; 16491; 16492; 57278; 31591; 57279; 16518; 57280; 57281; 2295; 16544; 57282; 57283; 57284; 57285; 26647; 57286; 16584; 16490; 16588; 57287; 16589; 16590; 16591; 16592; 57288; 13773; 3284; 3285; 57289; 57290; 21102.

The following SEQ ID NOs correspond to the polynucleotides encoding lymph node-specific proteins as described in Table 57A identified using SBS: 57417; 57418; 57419; 30488; 57420; 57421; 57422; 57423; 57424; 57425; 57426; 25893; 25894; 57427; 57428; 57429; 57430; 57431; 25403; 57432; 57433; 1951; 1956; 57434; 26033; 1957; 1959; 26034; 1961; 57435; 26035; 57436; 57437; 57438; 1963; 1967; 1968; 57439; 57440; 57441; 57442; 26132; 57443; 57444; 57445; 57446; 57447; 19327.

The following SEQ ID NOs correspond to the amino acid sequences of lymph node-specific proteins as described in Table 57A identified using SBS: 57448; 57449; 57450; 30751; 57451; 57452; 57453; 57454; 57455; 57456; 57457; 26363; 26364; 57458; 57459; 57460; 57461; 57462; 25543; 57463; 57464; 2250; 2255; 57465; 26503; 2256; 2258; 26504; 2260; 57466; 26505; 57467; 57468; 57469; 2262; 2266; 2267; 57470; 57471; 57472; 57473; 26602; 57474; 57475; 57476; 57477; 57478; 19731.

The following SEQ ID NOs correspond to the polynucleotides encoding lymphocyte-specific proteins as described in Table 58A identified using SBS: 57517; 8200; 24728; 30473; 30474; 8214; 57518; 24733; 25844; 25845; 57519; 57520; 57521; 57522; 57523; 57524; 22389; 57525; 57526; 19007; 11956; 57527; 57528; 30488; 57420; 57529; 57530; 57531; 57532; 25881; 25882; 57533; 57534; 57535; 57536; 57537; 57538; 57539; 57540; 57541; 57542; 57543; 57544; 1874; 1875; 57545; 57546; 57547; 57548; 57549; 57550; 57551; 25935; 25936; 57552; 57553; 57554; 57555; 57556; 25949; 57557; 19098; 19099; 57558; 24371; 57559; 19102; 19103; 57560; 57561; 57562; 57563; 57564; 57565; 57566; 57567; 25978; 57568; 16056; 8656; 30541; 57569; 8715; 57570; 57571; 57572; 57573; 57574; 57575; 57576; 57577; 57578; 57579; 57580; 57581; 19127; 27865; 25407; 57582; 57583; 57584; 57585; 57586; 57587; 57588; 57589; 8803; 57590; 57591; 8793; 57592; 57593; 57594; 57595; 57596; 57597; 57598; 57599; 57600; 57601; 57602; 57603; 57604; 57605; 57606; 57607; 26075; 26076; 57608; 57609; 57610; 57611; 57612; 26112; 26113; 19197; 57613; 57614; 7419; 57615; 5707; 5708; 5709; 5710; 5711; 30668; 57616; 57617; 57618; 57619; 57620; 30685; 30686; 5783; 57621; 57622; 57623; 57624; 2941; 57625; 57626; 57627; 57628; 57629; 57630; 57631; 57632; 57633; 57634; 30728; 7540.

The following SEQ ID NOs correspond to the amino acid sequences of lymphocyte-specific proteins as described in Table 58A identified using SBS: 57635; 9528; 24931; 30736; 30737; 9542; 57636; 24936; 26314; 26315; 57637; 57638; 57639; 57640; 57641; 57642; 32496; 57643; 57644; 19411; 12212; 57645; 57646; 30751; 57451; 57647; 57648; 57649; 57650; 26351; 26352; 57651; 57652; 57653; 57654; 57655; 57656; 57657; 57658; 57659; 57660; 57661; 57662; 2173; 2174; 57663; 57664; 57665; 57666; 57667; 57668; 57669; 26405; 26406; 57670; 57671; 57672; 57673; 57674; 26419; 57675; 19502; 19503; 57676; 24501; 57677; 19506; 19507; 57678; 57679; 57680; 57681; 57682; 57683; 57684; 57685; 26448; 57686; 16453; 9984; 30804; 57687; 10043; 57688; 57689; 57690; 57691; 57692; 57693; 57694; 57695; 57696; 57697; 57698; 57699; 19531; 28867; 25547; 57700; 57701; 57702; 57703; 57704; 57705; 57706; 57707; 10131; 57708; 57709; 10121; 57710; 57711; 57712; 57713; 57714; 57715; 57716; 57717; 57718; 57719; 57720; 57721; 57722; 57723; 57724; 57725; 26546; 26545; 57726; 57727; 57728; 57729; 57730; 26583; 26582; 19601; 57731; 57732; 7749; 57733; 6541; 6542; 6543; 6544; 6545; 30931; 57734; 57735; 57736; 57737; 57738; 30948; 30949; 6617; 57739; 57740; 57741; 57742; 3297; 57743; 57744; 57745; 57746; 57747; 57748; 57749; 57750; 57751; 57752; 30991; 7870.

The following SEQ ID NOs correspond to the polynucleotides encoding monocyte-specific proteins as described in Table 59A identified using SBS: 57886; 57887; 57888; 18969; 18970; 18971; 18972; 18973; 57889; 57890; 17536; 17548; 57891; 57892; 57893; 57894; 57533; 25886; 57895; 57896; 1857; 57897; 17569; 17570; 17571; 17572; 57898; 1086; 57899; 17613; 1900; 1901; 1902; 1903; 1904; 1905; 57900; 1906; 114; 21617; 54868; 57901; 17675; 17676; 17683; 14207; 8661; 30547; 19131; 57902; 17706; 57903; 57904; 57905; 57906; 57907; 57908; 57909; 57910; 57911; 57912; 57913; 57914; 57915; 57916; 57917; 57918; 57919; 57920; 57921; 57922; 57923; 1972; 17792; 17799; 17800; 17801; 17802; 17803; 17804; 23466; 57924; 8966; 16140; 16144; 19204; 7426; 7427; 2007; 19208; 57925; 57926; 57927; 57928; 57929; 20253; 9231; 57930; 57931; 26224; 19316; 57932.

The following SEQ ID NOs correspond to the amino acid sequences of monocyte-specific proteins as described in Table 59A identified using SBS: 57933; 57934; 57935; 19373; 19374; 19375; 19376; 19377; 57936; 57937; 18005; 18017; 57938; 57939; 57940; 57941; 57651; 26356; 57942; 57943; 2156; 57944; 18038; 18039; 18040; 18041; 57945; 1369; 57946; 18082; 2199; 2200; 2201; 2202; 2203; 2204; 57947; 2205; 482; 22204; 54875; 57948; 18144; 18145; 18152; 14621; 9989; 30810; 19535; 57949; 18175; 57950; 57951; 57952; 57953; 57954; 57955; 57956; 57957; 57958; 57959; 57960; 57961; 57962; 57963; 57964; 57965; 57966; 57967; 57968; 57969; 57970; 2271; 18261; 18270; 18269; 18272; 18271; 18273; 18268; 23797; 57971; 10294; 16537; 16541; 19608; 7756; 7757; 2306; 19612; 57972; 57973; 57974; 57975; 57976; 20394; 10559; 57977; 57978; 26694; 19720; 57979.

The following SEQ ID NOs correspond to the polynucleotides encoding muscle-specific proteins as described in Table 60A identified using SBS: 1796; 1797; 1798; 1030; 8132; 31350; 27432; 27433; 58069; 58070; 58071; 58072; 58073; 58074; 58075; 14044; 14045; 14046; 14047; 14048; 14049; 14050; 14051; 58076; 58077; 58078; 3615; 3617; 8192; 8193; 8194; 8195; 3633; 58079; 58080; 58081; 58082; 58083; 58084; 58085; 21514; 58086; 58087; 58088; 58089; 58090; 58091; 58092; 58093; 58094; 14084; 14085; 27605; 58095; 58096; 14097; 58097; 14102; 14103; 14108; 58098; 53114; 58099; 58100; 58101; 27664; 27665; 27666; 27667; 27668; 27669; 3719; 58102; 1105; 1106; 14141; 14142; 58103; 58104; 58105; 125; 58106; 14184; 14185; 14186; 14187; 58107; 58108; 25984; 58109; 58110; 58111; 58112; 14227; 14230; 58113; 58114; 58115; 58116; 58117; 58118; 58119; 14233; 58120; 58121; 58122; 58123; 58124; 58125; 14235; 58126; 58127; 58128; 58129; 58130; 58131; 58132; 58133; 58134; 58135; 58136; 58137; 58138; 14245; 58139; 58140; 58141; 58142; 58143; 58144; 58145; 14248; 58146; 58147; 58148; 14257; 14258; 14259; 8871; 21800; 21801; 21802; 21803; 58149; 58150; 58151; 31436; 8910; 31437; 31438; 31439; 14275; 31440; 58152; 58153; 58154; 1983; 14279; 58155; 58156; 14281; 58157; 58158; 14283; 2844; 14295; 14296; 58159; 58160; 58161; 58162; 58163; 58164; 58165; 14312; 14314; 14315; 58166; 14317; 14318; 14319; 14320; 14321; 17847; 58167; 52997; 58168; 58169; 32802; 14337; 58170; 58171; 2018; 58172; 2895; 58173; 14358; 58174; 58175; 58176; 58177; 58178; 58179; 1250; 1251; 58180; 2907; 58181; 58182; 58183; 14383; 58184; 9278; 54926; 54927; 54928; 54929; 58185; 58186; 58187; 58188; 58189; 2070; 58190; 58191; 14410; 58192; 58193; 58194; 58195; 58196; 1292; 1293; 17933; 17934; 14421; 58197; 58198; 2952; 2953; 2954; 2955; 2956; 58199; 58200; 1307.

The following SEQ ID NOs correspond to the amino acid sequences of muscle-specific proteins as described in Table 60A identified using SBS: 2095; 2096; 2097; 1313; 9460; 31512; 28434; 28435; 58201; 58202; 58203; 58204; 58205; 58206; 58207; 14458; 14459; 14460; 14461; 14462; 14463; 14464; 14465; 58208; 58209; 58210; 4164; 4166; 9520; 9521; 9522; 9523; 4182; 58211; 58212; 58213; 58214; 58215; 58216; 58217; 22101; 58218; 58219; 58220; 58221; 58222; 58223; 58224; 58225; 58226; 14499; 14498; 28607; 58227; 58228; 14511; 58229; 14516; 14517; 14522; 58230; 53519; 58231; 58232; 58233; 28666; 28667; 28668; 28669; 28670; 28671; 4268; 58234; 1388; 1389; 14556; 14555; 58235; 58236; 58237; 493; 58238; 14598; 14599; 14600; 14601; 58239; 58240; 26454; 58241; 58242; 58243; 58244; 14641; 14644; 58245; 58246; 58247; 58248; 58249; 58250; 58251; 14647; 58252; 58253; 58254; 58255; 58256; 58257; 58258; 14649; 58259; 58260; 58261; 58262; 58263; 58264; 58265; 58266; 58267; 58268; 58269; 58270; 14659; 58271; 58272; 58273; 58274; 58275; 58276; 58277; 14662; 58278; 58279; 58280; 14673; 14671; 14672; 10199; 22387; 22388; 22389; 22390; 58281; 58282; 58283; 31598; 10238; 31599; 31600; 31601; 14689; 31602; 58284; 58285; 58286; 2282; 14693; 58287; 58288; 14695; 58289; 58290; 14697; 3200; 14709; 14710; 58291; 58292; 58293; 58294; 58295; 58296; 58297; 14726; 14728; 14729; 58298; 14731; 14732; 14733; 14734; 14735; 18316; 58299; 53012; 58300; 58301; 32858; 14751; 58302; 58303; 2317; 58304; 3251; 58305; 14772; 58306; 58307; 58308; 58309; 58310; 58311; 1533; 1534; 58312; 3263; 58313; 58314; 58315; 14797; 58316; 10606; 54961; 54962; 54963; 54964; 58317; 58318; 58319; 58320; 58321; 2369; 58322; 58323; 14824; 58324; 58325; 58326; 58327; 58328; 1575; 1576; 18402; 18403; 14835; 58329; 58330; 3308; 3309; 3310; 3311; 3312; 58331; 58332; 1590.

The following SEQ ID NOs correspond to the polynucleotides encoding ovary-specific proteins as described in Table 61A identified using SBS: 58733; 58734; 58735; 58736; 58737; 58738; 58739; 58740; 58741; 58742; 32270; 28222; 58743; 58744; 58745; 58746.

The following SEQ ID NOs correspond to the amino acid sequences of ovary-specific proteins as described in Table 61A identified using SBS: 58747; 58748; 58749; 58750; 58751; 58752; 58753; 58754; 58755; 58756; 32284; 29224; 58757; 58758; 58759; 58760.

The following SEQ ID NOs correspond to the polynucleotides encoding pancreas-specific proteins as described in Table 62A identified using SBS: 5071; 58778; 18844; 18845; 18846; 18847; 18848; 17509; 13275; 58779; 58780; 58781; 58782; 58783; 58784; 58785; 58786; 58787; 58788; 5177; 58789; 58790; 18850; 18851; 18852; 18853; 18854; 8338; 18855; 58791; 21555; 58792; 18856; 58793; 18857; 58794; 105; 58795; 25929; 58796; 58797; 8530; 58798; 2725; 8554; 58799; 58800; 58801; 58802; 58803; 23389; 58804; 58805; 58806; 58807; 58808; 58809; 58810; 58811; 58812; 13387; 58813; 58814; 58815; 58816; 58817; 58818; 58819; 58820; 58821; 55265; 55267; 18858; 18859; 58822; 58823; 18860; 58824; 58825; 58826; 58827; 58828; 58829; 58830; 58831; 58832; 58833; 58834; 5629; 58835; 24865; 8978; 8979; 58836; 20245; 58837; 18862; 58838; 58839; 18863; 18864; 18865; 13444; 13445; 13446; 13447; 13448; 13449; 13450; 58840; 18866; 18867; 58841; 58842; 18869; 18870; 18871; 24874; 24875; 24876; 24877; 24878; 58843; 20254; 58844; 58845; 58846; 18872; 58847; 58848; 58849; 58850; 23559; 1257; 58851; 58852; 5811; 58853; 58854; 58855; 58856; 58857; 58858; 7540.

The following SEQ ID NOs correspond to the amino acid sequences of pancreas-specific proteins as described in Table 62A identified using SBS: 5905; 58859; 18875; 18874; 18876; 18873; 18877; 17978; 13542; 58860; 58861; 58862; 58863; 58864; 58865; 58866; 58867; 58868; 58869; 6011;

58870; 58871; 18879; 18880; 18881; 18882; 18883; 9666; 18884; 58872; 22142; 58873; 18885; 58874; 18886; 58875; 473; 58876; 26399; 58877; 58878; 9858; 58879; 3081; 9882; 58880; 58881; 58882; 58883; 58884; 23720; 58885; 58886; 58887; 58888; 58889; 58890; 58891; 58892; 58893; 13654; 58894; 58895; 58896; 58897; 58898; 58899; 58900; 58901; 58902; 55401; 55403; 18887; 18888; 58903; 58904; 18889; 58905; 58906; 58907; 58908; 58909; 58910; 58911; 58912; 58913; 58914; 58915; 6463; 58916; 25068; 10306; 10307; 58917; 20386; 58918; 18891; 58919; 58920; 18892; 18893; 18894; 13711; 13712; 13713; 13714; 13715; 13716; 13717; 58921; 18895; 18896; 58922; 58923; 18898; 18899; 18900; 25078; 25077; 25079; 25081; 25080; 58924; 20395; 58925; 58926; 58927; 18901; 58928; 58929; 58930; 58931; 23890; 1540; 58932; 58933; 6645; 58934; 58935; 58936; 58937; 58938; 58939; 7870.

The following SEQ ID NOs correspond to the polynucleotides encoding prostate-specific proteins as described in Table 63A identified using SBS: 13270; 21443; 3588; 21444; 21445; 17027; 21460; 59267; 3616; 3618; 8196; 15403; 59268; 21492; 21493; 21494; 21495; 21496; 59269; 59270; 53089; 1847; 1848; 59271; 59272; 59273; 20170; 8343; 59274; 21557; 21558; 21559; 21560; 21561; 20617; 59275; 23359; 59276; 21618; 16037; 59277; 59278; 59279; 59280; 20661; 59281; 21645; 59282; 59283; 8668; 59284; 8669; 55235; 55236; 55237; 59285; 21665; 21666; 21667; 21668; 21669; 21670; 21672; 59286; 1159; 1160; 5391; 17103; 5392; 59287; 59288; 59289; 59290; 59291; 59292; 59293; 20702; 59294; 24389; 59295; 59296; 59297; 59298; 59299; 59300; 21715; 21717; 59301; 59302; 59303; 21723; 21724; 21725; 21726; 21727; 21728; 21729; 21730; 21731; 21732; 21733; 21734; 21735; 21736; 21737; 59304; 59305; 59306; 59307; 21742; 59308; 59309; 59310; 21786; 21787; 59311; 59312; 59313; 21800; 21801; 21802; 21803; 59314; 59315; 21821; 59316; 21829; 20751; 21838; 59317; 59318; 59319; 59320; 59321; 59322; 21853; 21854; 21855; 21856; 21857; 21858; 21859; 32804; 267; 32325; 32326; 59323; 59324; 59325; 32216; 59326; 59327; 32455; 30675; 59328; 21912; 21913; 59329; 59330; 59331; 59332; 12121; 59333; 21932; 9273; 57623; 57624; 21960; 59334; 21961; 21972; 59335; 21980; 59336; 32063; 59337; 59338; 59339; 22001; 59340.

The following SEQ ID NOs correspond to the amino acid sequences of prostate-specific proteins as described in Table 63A identified using SBS: 13537; 22030; 4137; 22031; 22032; 17187; 22047; 59341; 4165; 4167; 9524; 15579; 59342; 22079; 22080; 22082; 22081; 22083; 59343; 59344; 53494; 2147; 2146; 59345; 59346; 59347; 20311; 9671; 59348; 22144; 22145; 22146; 22147; 22148; 20884; 59349; 23690; 59350; 22205; 16434; 59351; 59352; 59353; 59354; 20928; 59355; 22232; 59356; 59357; 9996; 59358; 9997; 55371; 55372; 55373; 59359; 22252; 22253; 22254; 22255; 22256; 22257; 22259; 59360; 1442; 1443; 6225; 17263; 6226; 59361; 59362; 59363; 59364; 59365; 59366; 59367; 20969; 59368; 24519; 59369; 59370; 59371; 59372; 59373; 59374; 22302; 22304; 59375; 59376; 59377; 22310; 22311; 22312; 22313; 22314; 22316; 22315; 22317; 22318; 22319; 22320; 22322; 22321; 22323; 22324; 59378; 59379; 59380; 59381; 22329; 59382; 59383; 59384; 22373; 22374; 59385; 59386; 59387; 22387; 22388; 22389; 22390; 59388; 59389; 22408; 59390; 22416; 21018; 22425; 59391; 59392; 59393; 59394; 59395; 59396; 22440; 22441; 22442; 22443; 22444; 22445; 22446; 32860; 635; 32343; 32344; 59397; 59398; 59399; 32230; 59400; 59401; 32562; 30938; 59402; 22499; 22500; 59403; 59404; 59405; 59406; 12377; 59407; 22519; 10601; 57741; 57742; 22547; 59408; 22548; 22559; 59409; 22567; 59410; 32126; 59411; 59412; 59413; 22588; 59414.

The following SEQ ID NOs correspond to the polynucleotides encoding skin-specific proteins as described in Table 64A identified using SBS: 59601; 59602; 59603; 59604; 59605; 59606; 59607; 59608; 59609; 59610; 32384; 32383; 32385; 59611; 59612; 24318; 24320; 21516; 30483; 59613; 59614; 59615; 59616; 59272; 59617; 59273; 59618; 59619; 59620; 59621; 59622; 59623; 59624; 19055; 59625; 59626; 59627; 59628; 59629; 59630; 97; 98; 2699; 2700; 2701; 2702; 59631; 17615; 59632; 59633; 59634; 59635; 32414; 32415; 59636; 59637; 27794; 27795; 27796; 59638; 59639; 59640; 59641; 59642; 59643; 59644; 59645; 59646; 59647; 59648; 59649; 59283; 59650; 59651; 59652; 59653; 59654; 59655; 59656; 59657; 59658; 59659; 59660; 59661; 59662; 59663; 59664; 59665; 59666; 59667; 59668; 59669; 59670; 59671; 59672; 59673; 59674; 17102; 59675; 59676; 59677; 59678; 59679; 59680; 59681; 59682; 5391; 17103; 5392; 59683; 59684; 59685; 59686; 59687; 59688; 20694; 59689; 59690; 59691; 59692; 59693; 5393; 59694; 59695; 59696; 59697; 59698; 59699; 59700; 30554; 59701; 20696; 59288; 59289; 59290; 59291; 59702; 59703; 59704; 59705; 59706; 59707; 59708; 59709; 59710; 59711; 59712; 59713; 59714; 59715; 59716; 59717; 59718; 59719; 59720; 59721; 59722; 59723; 59724; 59725; 59726; 59727; 59728; 59729; 59730; 59731; 59732; 59733; 59734; 59735; 59736; 59737; 59738; 59739; 59740; 59741; 59742; 59743; 59744; 59745; 59746; 59747; 59748; 59749; 59750; 59751; 59752; 23448; 59753; 59754; 59755; 59756; 59757; 59758; 24398; 23462; 59759; 59760; 59761; 59762; 59763; 59764; 24410; 59765; 59766; 59767; 59768; 59769; 59770; 9046; 24412; 24413; 24414; 24415; 59771; 20775; 59772; 2893; 23522; 59773; 59774; 59775; 30675; 59776; 59777; 59778; 17156; 59779; 17157; 59780; 59781; 17158; 59329; 59782; 59331; 28279; 28280; 23555; 59783; 59784; 59785; 59786; 30697; 59787; 59788; 59789; 59790; 59791; 25457; 25458; 59792; 59793; 23569; 23570; 59794; 59795; 59796; 59797; 1283; 59798; 59799; 59800; 59801; 23585; 23586; 59802; 59803; 59804; 59805; 59806; 59807; 59808; 59809; 59810; 59811; 59812; 59813.

The following SEQ ID NOs correspond to the amino acid sequences of skin-specific proteins as described in Table 64A identified using SBS: 59814; 59815; 59816; 59817; 59818; 59819; 59820; 59821; 59822; 59823; 32491; 32490; 32492; 59824; 59825; 24448; 24450; 22103; 30746; 59826; 59827; 59828; 59829; 59346; 59830; 59347; 59831; 59832; 59833; 59834; 59835; 59836; 59837; 19459; 59838; 59839; 59840; 59841; 59842; 59843; 465; 466; 3055; 3056; 3057; 3058; 59844; 18084; 59845; 59846; 59847; 59848; 32521; 32522; 59849; 59850; 28796; 28797; 28798; 59851; 59852; 59853; 59854; 59855; 59856; 59857; 59858; 59859; 59860; 59861; 59862; 59357; 59863; 59864; 59865; 59866; 59867; 59868; 59869; 59870; 59871; 59872; 59873; 59874; 59875; 59876; 59877; 59878; 59879; 59880; 59881; 59882; 59883; 59884; 59885; 59886; 59887; 17262; 59888; 59889; 59890; 59891; 59892; 59893; 59894; 59895; 6225; 17263; 6226; 59896; 59897; 59898; 59899; 59900; 59901; 20961; 59902; 59903; 59904; 59905; 59906; 6227; 59907; 59908; 59909; 59910; 59911; 59912; 59913; 30817; 59914; 20963; 59362; 59363; 59364; 59365; 59915; 59916; 59917; 59918; 59919; 59920; 59921; 59922; 59923; 59924; 59925; 59926; 59927; 59928; 59929; 59930; 59931; 59932; 59933; 59934; 59935; 59936; 59937; 59938; 59939; 59940; 59941; 59942; 59943; 59944; 59945; 59946; 59947; 59948; 59949; 59950; 59951; 59952; 59953; 59954; 59955; 59956; 59957; 59958; 59959; 59960; 59961; 59962; 59963; 59964; 59965; 23779; 59966; 59967; 59968; 59969; 59970; 59971; 24528; 23793; 59972; 59973; 59974; 59975; 59976; 59977; 24540; 59978; 59979; 59980; 59981; 59982; 59983; 10374; 24542; 24543; 24544; 24545; 59984; 21042; 59985; 3249; 23853; 59986; 59987; 59988;

30938; 59989; 59990; 59991; 17316; 59992; 17317; 59993; 59994; 17318; 59403; 59995; 59405; 29281; 29282; 23886; 59996; 59997; 59998; 59999; 30960; 60000; 60001; 60002; 60003; 60004; 25597; 25598; 60005; 60006; 23900; 23901; 60007; 60008; 60009; 60010; 1566; 60011; 60012; 60013; 60014; 23916; 23917; 60015; 60016; 60017; 60018; 60019; 60020; 60021; 60022; 60023; 60024; 60025; 60026.

The following SEQ ID NOs correspond to the polynucleotides encoding small intestine-specific proteins as described in Table 65A identified using SBS: 12670; 60377; 60378; 60379; 24715; 60380; 20576; 60381; 60382; 60383; 60384; 25339; 25340; 25341; 60385; 24717; 60386; 20139; 60387; 15392; 24719; 60388; 60389; 24721; 24722; 60390; 3598; 60391; 60392; 60393; 60394; 60395; 60396; 24727; 60397; 24736; 24737; 15926; 60398; 8231; 24740; 60399; 60400; 60401; 60402; 60403; 60404; 60405; 60406; 60407; 60408; 60409; 60410; 60411; 18981; 31364; 60412; 24760; 60413; 13322; 13323; 60414; 60415; 60416; 3684; 13328; 15420; 60417; 24770; 60418; 1088; 55761; 2693; 60419; 24785; 13336; 24787; 24788; 24789; 60420; 60421; 60422; 5221; 60423; 60424; 60425; 60426; 60427; 60428; 13346; 60429; 60430; 60431; 25386; 25387; 13360; 24799; 24801; 60432; 60433; 8594; 13371; 60434; 13373; 60435; 60436; 152; 24807; 7353; 60437; 60438; 60439; 60440; 15470; 13388; 60441; 15476; 15477; 60442; 60443; 60444; 13395; 13399; 60445; 60446; 60447; 60448; 24848; 60449; 60450; 60451; 60452; 60453; 1958; 24850; 60454; 57436; 60455; 60456; 1969; 60457; 60458; 60459; 55887; 55888; 60460; 60461; 60462; 60463; 60464; 60465; 15480; 60466; 60467; 60468; 60469; 60470; 60471; 13412; 60472; 15483; 60473; 60474; 212; 60475; 60476; 60477; 60478; 13417; 24860; 60479; 60480; 60481; 60482; 60483; 60484; 60485; 24861; 60486; 60487; 60488; 224; 60489; 24865; 13435; 60490; 32444; 60491; 24409; 60492; 13442; 13457; 60493; 60494; 60495; 60496; 13467; 24873; 24879; 60497; 60498; 60499; 60500; 60501; 9172; 24889; 60502; 60503; 60504; 60505; 60506; 60507; 60508; 60509; 13483; 60510; 60511; 60512; 60513; 12120; 17906; 60514; 60515; 60516; 60517; 16201; 60518; 60519; 60520; 16224; 60521; 60522; 24907; 60523; 60524; 13511; 60525; 24908; 13512; 60526; 60527; 60528; 4087; 7517; 13525; 60529; 7527; 21989; 27358; 13526; 7529; 7530; 24912; 24913; 60530; 13530; 60531.

The following SEQ ID NOs correspond to the amino acid sequences of small intestine-specific proteins as described in Table 65A identified using SBS: 12878; 60532; 60533; 60534; 24918; 60535; 20843; 60536; 60537; 60538; 60539; 25479; 25480; 25481; 60540; 24920; 60541; 20280; 60542; 15568; 24922; 60543; 60544; 24924; 24925; 60545; 4147; 60546; 60547; 60548; 60549; 60550; 60551; 24930; 60552; 24939; 24940; 60553; 60554; 9559; 24943; 60555; 60556; 60557; 60558; 60559; 60560; 60561; 60562; 60563; 60564; 60565; 60566; 60567; 19385; 31526; 60568; 24963; 60569; 13589; 13590; 60570; 60571; 60572; 4233; 13595; 15596; 60573; 24973; 60574; 1371; 56083; 3049; 60575; 24988; 13603; 24990; 24991; 24992; 60576; 60577; 60578; 6055; 60579; 60580; 60581; 60582; 60583; 60584; 13613; 60585; 60586; 60587; 25526; 25527; 13627; 25002; 25004; 60588; 60589; 9922; 13638; 60590; 13640; 60591; 60592; 520; 25010; 7683; 60593; 60594; 60595; 60596; 15646; 13655; 60597; 15653; 15652; 60598; 60599; 60600; 13662; 13666; 60601; 60602; 60603; 60604; 25051; 60605; 60606; 60607; 60608; 60609; 2257; 25053; 60610; 57467; 60611; 60612; 2268; 60613; 60614; 16323; 56209; 56210; 60615; 60616; 60617; 60618; 60619; 60620; 15656; 60621; 60622; 60623; 60624; 60625; 60626; 13679; 60627; 15659; 60628; 60629; 580; 60630; 60631; 60632; 60633; 13684; 25063; 60634; 60635; 60636; 60637; 60638; 60639; 60640; 25064; 60641; 60642; 60643; 592; 60644; 25068; 13702; 60645; 32551; 60646; 24539; 60647; 13709; 13724; 60648; 60649; 60650; 60651; 13734; 25076; 25082; 60652; 60653; 60654; 60655; 60656; 10500; 25092; 60657; 60658; 60659; 60660; 60661; 60662; 60663; 60664; 13750; 60665; 60666; 60667; 60668; 12376; 18375; 60669; 60670; 60671; 60672; 16598; 60673; 60674; 60675; 16621; 60676; 60677; 25110; 60678; 60679; 13778; 60680; 25111; 13779; 60681; 60682; 60683; 4636; 7847; 13792; 60684; 7857; 22576; 27388; 13793; 7859; 7860; 25115; 25116; 60685; 13797; 60686.

The following SEQ ID NOs correspond to the polynucleotides encoding spleen-specific proteins as described in Table 66A identified using SBS: 61104; 61105; 61106; 61107; 61108; 61109; 1837; 25880; 61110; 1878; 55771; 61111; 25904; 25927; 61112; 61113; 61114; 25955; 1927; 1928; 1929; 61115; 1937; 25979; 61116; 61117; 61118; 1954; 1953; 61119; 61120; 61121; 61122; 61123; 1960; 1962; 61124; 55891; 23450; 61125; 61126; 61127; 17798; 61128; 61129; 61130; 61131; 61132; 12067; 223; 229; 1995; 61133; 2003; 2032; 61134; 26203; 61135; 61136; 31485; 31486; 31487; 31488; 31489; 61137.

The following SEQ ID NOs correspond to the amino acid sequences of spleen-specific proteins as described in Table 66A identified using SBS: 61138; 61139; 61140; 61141; 61142; 61143; 2136; 26350; 61144; 2177; 56093; 61145; 26374; 26397; 61146; 61147; 61148; 26425; 2226; 2227; 2228; 61149; 2236; 26449; 61150; 61151; 61152; 2252; 2253; 61153; 61154; 61155; 61156; 61157; 2259; 2261; 61158; 56213; 23781; 61159; 61160; 61161; 18267; 61162; 61163; 61164; 61165; 61166; 12323; 591; 597; 2294; 61167; 2302; 2331; 61168; 26673; 61169; 61170; 31647; 31648; 31649; 31650; 31651; 61171.

The following SEQ ID NOs correspond to the polynucleotides encoding stomach-specific proteins as described in Table 67A identified using SBS: 32377; 61246; 61247; 61248; 61249; 61250; 61251; 13311; 13312; 61252; 61253; 61254; 15987; 15988; 27332; 27333; 27334; 61255; 61256; 61257; 61258; 27335; 27336; 61259; 61260; 61261; 61262; 61263; 61264; 61265; 61266; 61267; 61268; 61269; 61270; 61271; 61272; 61273; 61274; 61275; 61276; 27340; 27341; 27342; 27343; 27344; 27345; 27346; 27347; 61277; 61278; 61279; 61280; 61281; 61282; 61283; 61284; 61285; 61286; 61287; 61288; 61289; 61290; 61291; 61292; 61293; 61294; 61295; 5479; 5480; 5481; 5482; 5483; 5485; 5487; 5500; 5510; 5536; 5537; 5539; 5541; 5542; 5543; 5545; 5547; 5550; 5553; 5554; 5555; 5556; 5557; 5558; 5559; 5560; 5561; 5562; 5563; 5564; 5565; 5566; 5567; 5568; 5569; 5570; 5571; 5572; 5573; 61296; 61297; 61298; 5575; 5576; 5577; 5578; 5579; 5580; 5582; 5583; 5591; 5594; 5595; 5596; 5597; 5598; 5599; 5600; 5601; 5602; 5603; 5604; 5605; 5606; 5607; 5608; 5609; 5610; 5611; 5612; 5613; 5614; 5615; 58837; 61299; 27351; 27352; 61300; 61301; 27356; 61302; 27359; 61303.

The following SEQ ID NOs correspond to the amino acid sequences of stomach-specific proteins as described in Table 67A identified using SBS: 32484; 61304; 61305; 61306; 61307; 61308; 61309; 13578; 13579; 61310; 61311; 61312; 16384; 16385; 27362; 27363; 27365; 61313; 61314; 61315; 61316; 27364; 27366; 61317; 61318; 61319; 61320; 61321; 61322; 61323; 61324; 61325; 61326; 61327; 61328; 61329; 61330; 61331; 61332; 61333; 61334; 27370; 27371; 27376; 27377; 27374; 27375; 27372; 27373; 61335; 61336; 61337; 61338; 61339; 61340; 61341; 61342; 61343; 61344; 61345; 61346; 61347; 61348; 61349; 61350; 61351; 61352; 61353; 6313; 6314; 6404; 6316; 6317; 6319; 6388; 6334; 6344; 6370; 6371; 6373; 6375; 6376; 6377; 6379; 6381; 6384; 6387; 6389; 6321; 6390; 6391; 6392; 6393; 6394; 6395;

6397; 6396; 6398; 6399; 6400; 6401; 6402; 6403; 6315; 6405; 6406; 6407; 61354; 61355; 61356; 6409; 6446; 6445; 6444; 6416; 6425; 6433; 6429; 6414; 6417; 6428; 6438; 6431; 6432; 6413; 6434; 6436; 6435; 6412; 6430; 6439; 6440; 6441; 6442; 6443; 6437; 6411; 6410; 6447; 6448; 6449; 58918; 61357; 27381; 27382; 61358; 61359; 27386; 61360; 27389; 61361.

The following SEQ ID NOs correspond to the polynucleotides encoding testes-specific proteins as described in Table 68A identified using SBS: 61484; 61485; 61486; 61487; 61488; 61489; 61490; 27425; 61491; 8122; 8123; 8124; 8125; 8126; 8127; 8128; 8129; 8130; 27426; 61492; 61493; 27427; 61494; 61495; 27428; 27429; 61496; 27430; 61497; 20136; 20137; 5088; 5090; 17502; 61498; 61499; 61500; 61501; 61502; 27435; 27436; 27437; 27438; 27439; 61503; 61504; 25824; 27441; 27442; 53048; 61505; 61506; 27447; 27448; 8167; 61507; 27449; 27450; 61508; 61509; 61510; 61511; 27452; 1813; 27453; 30470; 61512; 21469; 2638; 2639; 61513; 61514; 61515; 27457; 61516; 27458; 27460; 61517; 12678; 2645; 27462; 27463; 12680; 12681; 5118; 61518; 61519; 27468; 27469; 27470; 27472; 27473; 27474; 27475; 27476; 13277; 13278; 27477; 5126; 61520; 8218; 27481; 27482; 61521; 61522; 61523; 18967; 27483; 27484; 24735; 27485; 27486; 27487; 27490; 27489; 61524; 61525; 61526; 61527; 61528; 61529; 61530; 61531; 27492; 27493; 61532; 61533; 61534; 61535; 24739; 61536; 61537; 61538; 27497; 27498; 61539; 61540; 61541; 61542; 27499; 61543; 61544; 61545; 21488; 21489; 27501; 27502; 61546; 61547; 27503; 61548; 61549; 61550; 61551; 27505; 61552; 8243; 61553; 27507; 27508; 61554; 61555; 5131; 27509; 61556; 61557; 27510; 27511; 61558; 27513; 61559; 61560; 61561; 61562; 61563; 61564; 61565; 61566; 61567; 27516; 61568; 61569; 27517; 12688; 61570; 61571; 2662; 27518; 61572; 27519; 61573; 61574; 17531; 8246; 27521; 61575; 27523; 27524; 61576; 61577; 13304; 61578; 27525; 61579; 61580; 61581; 27527; 61582; 27528; 61583; 61584; 61585; 27530; 27531; 27533; 61586; 5135; 61587; 27535; 61588; 61589; 61590; 27537; 27538; 27539; 61591; 27540; 27541; 27542; 27544; 61592; 61593; 61594; 61595; 61596; 61597; 61598; 61599; 61600; 61601; 61602; 61603; 61604; 61605; 27546; 3657; 27548; 27549; 27550; 27551; 27552; 27553; 27554; 61606; 24744; 61607; 24745; 61608; 61609; 27559; 61610; 27560; 61611; 61612; 61613; 61614; 61615; 27561; 20591; 27562; 27563; 27564; 27565; 27566; 27567; 27568; 27569; 27570; 61616; 61617; 27574; 27575; 27576; 61618; 5162; 20160; 61619; 61620; 2677; 27579; 61621; 27581; 27582; 27583; 27584; 27585; 27586; 27587; 27588; 27589; 27590; 61622; 27591; 27592; 61623; 8278; 53095; 27595; 61624; 27597; 20602; 1075; 15986; 27602; 27604; 27605; 3681; 21525; 61625; 27607; 61626; 61627; 27609; 27610; 27611; 61628; 61629; 61630; 61631; 61632; 61633; 61634; 61635; 61636; 61637; 61638; 61639; 61640; 61641; 15991; 14104; 61642; 23323; 23324; 61643; 27617; 61644; 8317; 17579; 17580; 61645; 27618; 61646; 57536; 61647; 61648; 57537; 57538; 57539; 57540; 61649; 61650; 61651; 61652; 61653; 61654; 61655; 57541; 57542; 57543; 57544; 61656; 27620; 61657; 61658; 27622; 27623; 27624; 27625; 61659; 27629; 30499; 61660; 61661; 61662; 61663; 61664; 61665; 61666; 27632; 21546; 27636; 27637; 8353; 8356; 27641; 13333; 19052; 61667; 61668; 61669; 61670; 61671; 61672; 61673; 31377; 31378; 31379; 61674; 27646; 61675; 61676; 61677; 11981; 21556; 27647; 27648; 61678; 61679; 27649; 27650; 27651; 27653; 61680; 21558; 61681; 31381; 61682; 61683; 27655; 27656; 61684; 27658; 3708; 61685; 61686; 61687; 61688; 61689; 61690; 27661; 27663; 59629; 61691; 61692; 61693; 27670; 27671; 61694; 27672; 27673; 27674; 27675; 61695; 27677; 27676; 61696; 8426; 27678; 61697; 61698; 5237; 27681; 27682; 1105; 1106; 61699; 17611; 27684; 61700; 61701; 61702; 61703; 27690; 61704; 61705; 3731; 3732; 3733; 7300; 27693; 27694; 61706; 61707; 61708; 27695; 14146; 1893; 61709; 61710; 61711; 13347; 61712; 61713; 27696; 61714; 61715; 61716; 27698; 61717; 13350; 61718; 61719; 27699; 61720; 61721; 61722; 8500; 61723; 27708; 27709; 61724; 27712; 61725; 27713; 27715; 61726; 27717; 61727; 27718; 27720; 8507; 27722; 27723; 25382; 61728; 61729; 61730; 27727; 61731; 61732; 25383; 27728; 27729; 27731; 61733; 61734; 27733; 27734; 61735; 61736; 61737; 61738; 27735; 21613; 17625; 17624; 17623; 27737; 27738; 27739; 61739; 27740; 27741; 61740; 27742; 61741; 61742; 61743; 61744; 61745; 27745; 27746; 27747; 61746; 27748; 2721; 27751; 27753; 19080; 61747; 27754; 27755; 27756; 61748; 27757; 27758; 25947; 25948; 27759; 61749; 27763; 27764; 8533; 8535; 8534; 13354; 61750; 61751; 61752; 61753; 61754; 61755; 61756; 27768; 61757; 27770; 61758; 61759; 61760; 61761; 61762; 27771; 5263; 21620; 27773; 61763; 27775; 61764; 61765; 61766; 61767; 61768; 61769; 61770; 61771; 61772; 27777; 27778; 61773; 19091; 61774; 61775; 61776; 27781; 27782; 61777; 61778; 27783; 61779; 61780; 27789; 27790; 27791; 61781; 61782; 27793; 61783; 61784; 61785; 61786; 61787; 61788; 27797; 61789; 61790; 27802; 27803; 27804; 5292; 20662; 61791; 61792; 27805; 27806; 61793; 61794; 27807; 2743; 27810; 61795; 27811; 27812; 61796; 61797; 27814; 61798; 12009; 12010; 61799; 27815; 61800; 16051; 32422; 32423; 27818; 27819; 61801; 61802; 61803; 8650; 61804; 61805; 61806; 27821; 61807; 61808; 27822; 27823; 27824; 27825; 27826; 27827; 27828; 27829; 15458; 61809; 61810; 8657; 8658; 27832; 23402; 23403; 8672; 23404; 167; 27836; 27837; 7357; 61811; 61812; 24810; 2779; 2780; 2781; 61813; 14213; 27847; 8693; 8694; 5359; 26000; 21657; 27849; 61814; 27850; 27854; 8715; 8717; 13385; 27855; 27856; 5379; 5380; 5381; 5382; 5383; 5384; 5385; 5386; 5387; 5388; 5389; 61815; 61816; 61817; 61818; 27859; 61819; 55846; 27861; 27862; 27863; 27864; 23411; 61820; 61821; 27867; 27868; 61822; 61823; 61824; 27870; 61825; 2792; 61826; 61827; 27872; 61828; 27874; 27875; 27878; 61829; 27880; 27881; 27883; 27882; 61830; 61831; 27884; 27885; 27886; 27887; 61832; 27888; 61833; 5404; 61834; 27889; 61835; 61836; 61837; 27890; 61838; 61839; 61840; 61841; 61842; 61843; 61844; 61845; 61846; 27896; 27895; 61847; 27897; 27898; 61848; 27899; 61849; 27900; 61850; 2801; 2802; 61851; 61852; 61853; 27901; 27902; 61854; 61855; 27905; 27906; 27903; 27904; 14232; 61856; 61857; 54818; 54819; 27907; 61858; 61859; 61860; 27908; 61861; 61862; 27911; 12031; 61863; 27912; 61864; 61865; 27914; 27913; 61866; 61867; 27915; 27916; 27917; 61868; 61869; 61870; 61871; 61872; 61873; 61874; 61875; 27918; 27919; 27920; 27921; 27922; 61876; 61877; 61878; 61879; 23419; 61880; 61881; 61882; 8752; 61883; 61884; 61885; 61886; 1948; 61887; 61888; 21697; 61889; 27932; 27933; 61890; 61891; 61892; 61893; 61894; 61895; 61896; 61897; 61898; 61899; 26016; 61900; 27938; 27958; 61901; 27942; 27943; 27946; 27947; 27944; 27945; 61902; 27948; 61903; 61904; 61905; 27950; 61906; 27953; 27954; 61907; 27955; 27956; 27941; 61908; 61909; 61910; 61911; 27964; 61912; 61913; 61914; 61915; 27965; 61916; 61917; 61918; 61919; 61920; 61921; 61922; 61923; 61924; 61925; 61926; 61927; 61928; 61929; 61930; 61931; 61932; 61933; 27969; 61934; 61935; 61936; 61937; 61938; 61939; 61940; 61941; 61942; 61943; 61944; 61945; 61946; 61947; 8774; 61948; 21706; 61949; 61950; 61951; 61952; 61953; 61954; 61955; 61956; 61957; 61958; 61959; 61960; 61961; 61962; 61963; 61964; 61965; 61966; 61967; 61968; 28016; 61969; 61970; 27983; 27984; 27985; 27986; 61971; 27987; 61972; 8809; 61973; 61974; 61975; 3877;

61976; 61977; 61978; 61979; 27988; 27989; 61980; 27990; 61981; 12036; 61982; 61983; 61984; 61985; 61986; 61987; 61988; 61989; 61990; 61991; 61992; 61993; 61994; 61995; 61996; 61997; 61998; 61999; 62000; 3880; 62001; 62002; 62003; 62004; 62005; 27994; 62006; 62007; 62008; 62009; 27995; 28020; 62010; 61282; 61283; 62011; 27998; 62012; 62013; 62014; 62015; 14237; 62016; 62017; 62018; 62019; 62020; 62021; 62022; 62023; 62024; 62025; 62026; 28024; 62027; 62028; 62029; 62030; 62031; 62032; 62033; 62034; 62035; 62036; 62037; 62038; 62039; 62040; 62041; 62042; 62043; 62044; 62045; 62046; 62047; 62048; 62049; 62050; 62051; 62052; 62053; 62054; 62055; 62056; 62057; 62058; 62059; 28001; 62060; 62061; 62062; 62063; 62064; 62065; 62066; 62067; 28002; 62068; 62069; 59300; 62070; 62071; 7376; 62072; 62073; 62074; 28004; 62075; 62076; 62077; 62078; 62079; 62080; 62081; 62082; 28005; 28006; 62083; 62084; 62085; 32266; 32267; 62086; 62087; 62088; 8782; 62089; 62090; 62091; 62092; 62093; 62094; 28009; 62095; 62096; 28012; 62097; 62098; 62099; 62100; 62101; 28014; 28015; 62102; 62103; 27982; 62104; 62105; 62106; 28017; 62107; 62108; 62109; 62110; 28018; 62111; 28019; 62112; 62113; 62114; 62115; 27996; 62116; 62117; 62118; 28022; 62119; 62120; 62121; 62122; 62123; 62124; 62125; 62126; 62127; 62128; 8806; 62129; 62130; 62131; 62132; 62133; 62134; 62135; 27999; 62136; 62137; 62138; 62139; 62140; 62141; 62142; 62143; 62144; 7383; 28027; 28028; 62145; 62146; 28029; 28030; 8780; 28031; 28032; 62147; 62148; 62149; 62150; 62151; 62152; 62153; 62154; 28033; 62155; 62156; 62157; 62158; 62159; 62160; 62161; 62162; 62163; 28036; 28037; 28038; 28039; 28040; 28041; 28042; 62164; 62165; 62166; 62167; 62168; 62169; 62170; 62171; 62172; 28043; 28044; 28045; 62173; 62174; 8812; 28046; 28047; 57212; 62175; 62176; 62177; 62178; 62179; 62180; 62181; 62182; 62183; 62184; 62185; 62186; 62187; 62188; 62189; 28048; 28049; 28050; 28051; 28052; 62190; 62191; 62192; 62193; 62194; 62195; 62196; 62197; 62198; 62199; 62200; 62201; 62202; 62203; 62204; 62205; 62206; 62207; 62208; 62209; 62210; 62211; 62212; 62213; 28063; 62214; 62215; 62216; 62217; 62218; 62219; 62220; 62221; 62222; 62223; 62224; 62225; 28068; 62226; 62227; 62228; 62229; 62230; 62231; 28066; 28067; 28065; 62232; 62233; 32268; 32269; 62234; 62235; 1164; 62236; 62237; 62238; 31425; 19154; 8840; 20720; 62239; 32782; 53265; 28075; 26057; 28076; 62240; 62241; 28077; 28078; 62242; 62243; 62244; 62245; 62246; 62247; 62248; 62079; 28080; 28081; 62249; 62250; 62251; 62252; 28082; 28083; 62253; 62254; 23457; 23458; 23459; 62255; 62256; 62257; 30628; 62258; 15482; 28090; 62259; 62260; 32041; 62261; 62262; 62263; 28095; 62264; 62265; 28097; 28098; 28099; 28100; 62266; 62267; 28101; 8887; 62268; 62269; 28103; 62270; 62271; 62272; 62273; 28104; 26068; 28105; 62274; 62275; 62276; 28106; 8894; 62277; 28107; 62278; 62279; 28109; 62280; 62281; 28115; 17117; 14272; 28118; 62282; 62283; 28119; 28120; 62284; 62285; 28121; 8913; 5554; 5555; 217; 218; 219; 13428; 13429; 28122; 62286; 2846; 2847; 20239; 3926; 8922; 8923; 8924; 8925; 62287; 62288; 62289; 8929; 62290; 62291; 62292; 62293; 5635; 5638; 231; 232; 8957; 8958; 28125; 28126; 1991; 1993; 62294; 62295; 62296; 62297; 62298; 28131; 62299; 28132; 28133; 12810; 62300; 3937; 62301; 62302; 28134; 28135; 28136; 62303; 62304; 62305; 62306; 28140; 236; 62307; 20749; 28144; 62308; 28145; 28149; 62309; 28150; 62310; 62311; 62312; 3948; 28154; 28155; 28156; 28157; 28158; 28159; 62313; 1202; 9000; 62314; 28179; 23490; 62315; 62316; 53337; 62317; 9007; 28318; 28183; 62319; 62320; 9010; 9011; 9012; 62321; 250; 251; 28189; 28191; 28192; 62322; 62323; 28193; 16147; 62324; 62325; 62326; 13443; 28198; 28199; 28200; 28201; 28202; 26135; 62327; 53343; 16151; 16152; 16153; 7437; 62328; 62329; 62330; 62331; 28207; 28209; 28210; 28211; 28212; 28213; 62332; 28215; 28216; 28217; 28218; 62333; 62334; 28221; 62335; 62336; 62337; 62338; 62339; 265; 266; 28223; 28224; 28225; 14343; 14344; 14345; 28226; 62340; 62341; 9098; 62342; 21887; 23511; 23512; 23513; 23514; 23515; 14349; 271; 62343; 274; 17877; 17878; 17879; 17880; 17881; 62344; 62345; 9115; 9116; 2894; 62346; 62347; 62348; 62349; 62350; 4008; 28238; 4010; 62351; 28241; 28242; 28243; 62352; 62353; 62354; 284; 28244; 62355; 28246; 62356; 28248; 26161; 26162; 28249; 28250; 28251; 28252; 28253; 28254; 62357; 28256; 62358; 28257; 62359; 62360; 62361; 62362; 62363; 28258; 28259; 62364; 62365; 62366; 28260; 28261; 28262; 62367; 17888; 62368; 62369; 28265; 62370; 28266; 62371; 28268; 62372; 62373; 62374; 1241; 5749; 1243; 9177; 28275; 62375; 24887; 62376; 52875; 17902; 62377; 62378; 62379; 25450; 28281; 62380; 21920; 62381; 62382; 28286; 28287; 21922; 21923; 62383; 62384; 55311; 28290; 28292; 28294; 62385; 28295; 62386; 24898; 21930; 62387; 62388; 62389; 305; 306; 307; 2058; 2059; 28301; 62390; 62391; 62392; 62393; 28309; 62394; 62395; 308; 309; 62396; 28310; 62397; 62398; 62399; 28311; 28312; 62400; 28313; 62401; 62402; 62403; 7486; 62404; 28314; 62405; 62406; 62407; 28315; 28316; 12129; 28317; 28318; 28319; 28320; 62408; 62409; 62410; 2920; 2921; 26202; 62411; 62412; 24900; 62413; 62414; 62415; 62416; 62417; 62418; 62419; 28324; 28325; 14394; 4061; 28327; 28328; 28329; 62420; 62421; 28330; 5790; 1275; 62422; 4072; 4073; 62423; 28333; 62424; 62425; 62426; 28335; 28336; 62427; 62428; 62429; 17923; 28337; 62430; 62431; 62432; 28338; 28339; 62433; 4076; 62434; 62435; 20818; 28340; 28341; 28343; 62436; 28344; 12848; 28345; 62437; 28346; 62438; 28348; 28350; 62439; 9327; 28351; 28352; 62440; 62441; 62442; 62443; 28355; 28356; 28357; 28358; 28359; 28360; 62444; 62445; 62446; 62447; 62448; 62449; 62450; 62451; 62452; 28362; 62453; 12857; 62454; 62455; 62456; 62457; 62458; 17174; 28365; 62459; 28367; 28368; 5820; 62460; 62461; 28369; 62462; 28370; 28371; 62463; 62464; 62465; 62466; 28372; 62467; 345; 28374; 62468; 28375; 28378; 28379; 4100; 28384; 28385; 62469; 62470; 62471; 62472; 62473; 62474; 62475; 62476; 62477; 62478; 5825; 2958; 5826; 2959; 5827; 28386; 28387; 62479; 28389; 24912; 28390; 62480; 4106; 62481; 62482; 28391; 62483; 62484; 62485; 62486; 12152; 62487; 62488; 62489; 62490; 62491; 25473; 62492; 62493; 62494; 62495; 62496; 20835; 62497; 28396; 28398; 361; 62498; 28403; 12871; 62499; 28404; 62500; 62501; 62502; 62503; 28405; 17180; 17181; 26273; 26274; 62504; 62505; 62506; 62507; 62508; 62509; 28418; 62510; 28419; 62511; 28420; 28421; 28422; 28423; 62512.

The following SEQ ID NOs correspond to the amino acid sequences of testes-specific proteins as described in Table 68A identified using SBS: 62513; 62514; 62515; 62516; 62517; 62518; 62519; 28427; 62520; 9450; 9451; 9452; 9453; 9454; 9455; 9456; 9457; 9458; 28428; 62521; 62522; 28429; 62523; 62524; 28430; 28431; 62525; 28432; 62526; 20277; 20278; 5922; 5924; 17971; 62527; 62528; 62529; 62530; 62531; 28437; 28438; 28439; 28440; 28441; 62532; 62533; 26294; 28443; 28444; 53453; 62534; 62535; 28450; 28449; 9495; 62536; 28451; 28452; 62537; 62538; 62539; 62540; 28454; 2112; 28455; 30733; 62541; 22056; 2994; 2995; 62542; 62543; 62544; 28459; 62545; 28460; 62462; 62546; 12886; 3001; 28464; 28465; 12888; 12889; 5952; 62547; 62548; 28470; 28471; 62472; 62475; 62474; 62476; 28477; 28478; 13544; 13545; 28479; 5960; 62549; 9546; 28483; 28484; 62550; 62551; 62552; 19371; 28486; 28485; 24938; 28488; 28487; 28489; 28492; 28491; 62553; 62554;

62555; 62556; 62557; 62558; 62559; 62560; 28494; 28495; 62561; 62562; 62563; 62564; 24942; 62565; 62566; 62567; 28499; 28500; 62568; 62569; 62570; 62571; 28501; 62572; 62573; 62574; 22076; 22075; 28503; 28504; 62575; 62576; 28505; 62577; 62578; 62579; 62580; 28507; 62581; 9571; 62582; 28509; 28510; 62583; 62584; 5965; 28511; 62585; 62586; 28512; 28513; 62587; 28515; 62588; 62589; 62590; 62591; 62592; 62593; 62594; 62595; 62596; 28518; 62597; 62598; 28519; 12896; 62599; 62600; 3018; 28520; 62601; 28521; 62602; 62603; 18000; 9574; 28523; 62604; 28525; 28526; 62605; 62606; 13571; 62607; 28527; 62608; 62609; 62610; 28529; 62611; 28530; 62612; 62613; 62614; 28532; 28533; 28535; 62615; 5969; 62616; 28537; 62617; 62618; 62619; 28539; 28540; 28541; 62620; 28542; 28543; 28544; 28546; 62621; 62622; 62623; 62624; 62625; 62626; 62627; 62628; 62629; 62630; 62631; 62632; 62633; 62634; 28548; 4206; 28550; 28551; 28552; 28553; 28554; 28555; 28556; 62635; 24948; 62636; 24947; 62637; 62638; 28561; 62639; 28562; 62640; 62641; 62642; 62643; 62644; 28563; 20858; 28564; 28565; 28568; 28567; 28566; 28569; 28570; 28571; 28572; 62645; 62646; 28576; 28577; 28578; 62647; 5996; 20301; 62648; 62649; 3033; 28581; 62650; 28583; 28584; 28585; 28586; 28587; 28588; 28589; 28590; 28591; 28592; 62651; 28593; 28594; 62652; 9606; 53500; 28597; 62653; 28599; 20869; 1358; 16383; 28604; 28606; 28607; 4230; 22112; 62654; 28609; 62655; 62656; 28611; 28612; 28613; 62657; 62658; 62659; 62660; 62661; 62662; 62663; 62664; 62665; 62666; 62667; 62668; 62669; 62670; 16388; 14518; 62671; 23654; 23655; 62672; 28619; 62673; 9645; 18048; 18049; 62674; 28620; 62675; 57654; 62676; 62677; 57655; 57656; 57657; 57658; 62678; 62679; 62680; 62681; 62682; 62683; 62684; 57659; 57660; 57661; 57662; 62685; 28622; 62686; 62687; 28624; 28625; 28627; 29262; 62688; 28631; 30762; 62689; 62690; 62691; 62692; 62693; 62694; 62695; 28634; 22133; 28638; 28639; 9681; 9684; 28643; 13600; 19456; 62696; 62697; 62698; 62699; 62700; 62701; 62702; 31539; 31540; 31541; 62703; 28648; 62704; 62705; 62706; 12237; 22143; 28649; 28650; 62707; 62708; 28651; 28652; 28653; 28655; 62709; 22145; 62710; 31543; 62711; 62712; 28657; 28658; 62713; 28660; 4257; 62714; 62715; 62716; 62717; 62718; 62719; 28663; 28665; 59842; 62720; 62721; 62722; 28672; 28673; 62723; 28674; 28675; 28676; 28677; 62724; 28679; 28678; 62725; 9754; 28680; 62726; 62727; 6071; 28683; 28684; 1388; 1389; 62728; 18080; 28686; 62729; 62730; 62731; 62732; 28692; 62733; 62734; 4281; 4280; 4282; 7630; 28695; 28696; 62735; 62736; 62737; 28697; 14560; 2192; 62738; 62739; 62740; 13614; 62741; 62742; 28698; 62743; 62744; 62745; 28700; 62746; 13617; 62747; 62748; 28701; 62749; 62750; 62751; 9828; 62752; 28710; 28711; 62753; 28714; 62754; 28715; 28722; 62755; 28719; 62756; 28720; 28717; 9835; 28724; 28725; 25522; 62757; 62758; 62759; 28729; 62760; 62761; 25523; 28730; 28731; 28733; 62762; 62763; 28735; 28736; 62764; 62765; 62766; 62767; 28737; 22200; 18094; 18092; 18093; 28739; 29047; 29048; 62768; 28743; 28742; 62769; 28744; 62770; 62771; 62772; 62773; 62774; 28747; 28748; 28749; 62775; 62750; 3077; 28753; 28755; 19484; 62776; 28756; 28757; 28758; 62777; 28759; 62760; 26417; 26418; 28761; 62778; 28765; 62779; 9861; 9863; 9862; 13621; 62780; 62781; 62782; 62783; 62784; 62785; 62786; 28770; 62787; 28772; 62788; 62789; 62790; 62791; 62792; 28773; 6097; 22207; 28775; 62793; 28777; 62794; 62795; 62796; 62797; 62798; 62799; 62800; 62801; 62802; 28779; 28780; 62803; 19495; 62804; 62805; 62806; 28783; 28784; 62807; 62808; 28785; 62809; 62810; 28791; 62792; 28793; 62811; 62812; 28795; 62813; 62814; 62815; 62816; 62817; 62818; 28799; 62819; 62820; 28804; 28805; 28806; 6126; 20929; 62821; 62822; 28807; 28808; 62823; 62824; 28809; 3099; 28812; 62825; 28813; 28814; 28815; 62826; 28816; 62827; 12265; 12266; 62828; 28817; 62829; 16448; 32529; 32530; 28820; 28821; 62830; 62831; 62832; 9978; 62833; 62834; 62835; 28823; 62836; 62837; 28824; 28825; 28826; 28830; 28828; 28829; 28827; 28831; 15634; 62838; 62839; 9985; 9986; 28834; 23733; 23734; 10000; 23735; 535; 28838; 28839; 7687; 62840; 62841; 25013; 3135; 3136; 3137; 62842; 14627; 28849; 10021; 10022; 6207; 62843; 22244; 28851; 62844; 28852; 28856; 10043; 10045; 13652; 28857; 28858; 6213; 6214; 6215; 6216; 6221; 6218; 6219; 6220; 6217; 6222; 6223; 62845; 62846; 62847; 62848; 28861; 62849; 56168; 28863; 28864; 28865; 28866; 23742; 62850; 62851; 28869; 28870; 62852; 62853; 62854; 28872; 62855; 3148; 62856; 62857; 28874; 62858; 28876; 28877; 28880; 62859; 28882; 28883; 28885; 28884; 62860; 62861; 28886; 28888; 28887; 28889; 62862; 28890; 62863; 6238; 62864; 28891; 62865; 62866; 62867; 28892; 62868; 62869; 62870; 62871; 62872; 62873; 62874; 62875; 62876; 28898; 28897; 62877; 28900; 28899; 62878; 28901; 62879; 28902; 62880; 3150; 3158; 62881; 62882; 62883; 28904; 28903; 62884; 62885; 28907; 28908; 28905; 28906; 14646; 62886; 62887; 54833; 54834; 28909; 62888; 62889; 62890; 28910; 62891; 62892; 28913; 12287; 62893; 62894; 28914; 62895; 28915; 28916; 62896; 62897; 28918; 28919; 28917; 62898; 62899; 62900; 62901; 62902; 62903; 62904; 62905; 28920; 28921; 28922; 28923; 28924; 62906; 62907; 62908; 62909; 23750; 10080; 62910; 62911; 62912; 62913; 62914; 62915; 62916; 2247; 62917; 62918; 22284; 62919; 28934; 28935; 62920; 62921; 62922; 62923; 62924; 62925; 62926; 62927; 62928; 62929; 26486; 62930; 28940; 28959; 62931; 28944; 62932; 28948; 28946; 62933; 28947; 62934; 28950; 62935; 62936; 62937; 28952; 62938; 28956; 28955; 62939; 28957; 28958; 28961; 62940; 62941; 62942; 62943; 28966; 62944; 62945; 62946; 62947; 28967; 62948; 62949; 62950; 62951; 62952; 62953; 62954; 62955; 62956; 62957; 62958; 62959; 62960; 62961; 62962; 62963; 62964; 62965; 28971; 62966; 62967; 62968; 62969; 62970; 62971; 62972; 62973; 62974; 62975; 62976; 62977; 62978; 62979; 10102; 62980; 22293; 62981; 62982; 62983; 62984; 62985; 62986; 62987; 62988; 62989; 62990; 62991; 62992; 62993; 62994; 62995; 62996; 62997; 62998; 62999; 63000; 28984; 63001; 63002; 28985; 29049; 28987; 28740; 63003; 29019; 63004; 10108; 63005; 63006; 63007; 4429; 63008; 63009; 63010; 63011; 28991; 28990; 63012; 29035; 63013; 12292; 63014; 63015; 63016; 63017; 63018; 63019; 63020; 63021; 63022; 63023; 63024; 63025; 63026; 63027; 63028; 63029; 63030; 63031; 63032; 4426; 63033; 63034; 63035; 63036; 63037; 28996; 63038; 63039; 63040; 63041; 28997; 28998; 63042; 61340; 61341; 63043; 29000; 63044; 63045; 63046; 63047; 14651; 63048; 63049; 63050; 63051; 63052; 63053; 63054; 63055; 63056; 63057; 63058; 29026; 63059; 63060; 63061; 63062; 63063; 63064; 63065; 63066; 63067; 63068; 63069; 63070; 63071; 63072; 63073; 63074; 63075; 63076; 63077; 63078; 63079; 63080; 63081; 63082; 63083; 63084; 63085; 63086; 63087; 63088; 63089; 63090; 63091; 29003; 63092; 63093; 63094; 63095; 63096; 63097; 63098; 63099; 29011; 63100; 63101; 59374; 63102; 63103; 7706; 63104; 63105; 63106; 29006; 63107; 63108; 63109; 63110; 63111; 63112; 63113; 63114; 29007; 29016; 63115; 63116; 63117; 32280; 32281; 63118; 63119; 63120; 10110; 63121; 63122; 63123; 63124; 63125; 28766; 29004; 63126; 63127; 29014; 63128; 63129; 63130; 63131; 63132; 29008; 29017; 63133; 63134; 29018; 63135; 63136; 63137; 28989; 63138; 63139; 63140; 63141; 29020; 63142; 29021; 63143; 63144; 63145; 63146; 29022; 63147; 63148; 63149; 29024; 63150; 63151; 63152; 63153; 63154; 63155; 63156; 63157; 63158; 63159; 10134; 63160; 63161; 63162; 63163; 63164;

63165; 63166; 29001; 63167; 26470; 63168; 63169; 63170; 63171; 63172; 63173; 63174; 7713; 29029; 29030; 63175; 63176; 29031; 29032; 10137; 29033; 29034; 63177; 63178; 63179; 63180; 63181; 63182; 63183; 63184; 28992; 63185; 63186; 63187; 63188; 63189; 63190; 63191; 63192; 63193; 29038; 29039; 29040; 29041; 29042; 29043; 29044; 63194; 63195; 63196; 63197; 63198; 63199; 63200; 63201; 63202; 29045; 29046; 28986; 19552; 19550; 10140; 28741; 28988; 57276; 63203; 63204; 63205; 63206; 63207; 63208; 63209; 63210; 63211; 63212; 63213; 63214; 63215; 63216; 63217; 29050; 29051; 29052; 29053; 29054; 63218; 63219; 63220; 63221; 63222; 63223; 63224; 63225; 63226; 63227; 63228; 63229; 63230; 63231; 63232; 63233; 63234; 63235; 63236; 63237; 63238; 63239; 63240; 63241; 29065; 63242; 63243; 63244; 63245; 63246; 63247; 63248; 63249; 63250; 63251; 63252; 63253; 29070; 63254; 63255; 63256; 63257; 63258; 63259; 29068; 29069; 29067; 63260; 63261; 32282; 32283; 63262; 63263; 1447; 63264; 63265; 63266; 31587; 19558; 10168; 20987; 63267; 32838; 53670; 29077; 26527; 29078; 63268; 63269; 29079; 29080; 63270; 63271; 63272; 63273; 63274; 63275; 63276; 29083; 29082; 29081; 63277; 63278; 63279; 63280; 29084; 29085; 63281; 63282; 23788; 23789; 23790; 63283; 63284; 63285; 30891; 63286; 15658; 29092; 63287; 63288; 32104; 63289; 63290; 63291; 29097; 63292; 63293; 29099; 29100; 29101; 29102; 63294; 63295; 29103; 10215; 63296; 63297; 29105; 63298; 63299; 63300; 63301; 29106; 26538; 29107; 63302; 63303; 63304; 29108; 10222; 63305; 29109; 63306; 63307; 29111; 63308; 63309; 29117; 17277; 14686; 29120; 63310; 63311; 29121; 29122; 63312; 63313; 29123; 10241; 6389; 6321; 586; 587; 585; 13695; 13696; 29124; 63314; 3202; 3203; 20380; 4475; 10250; 10251; 10252; 10253; 63315; 63316; 63317; 10257; 63318; 63319; 63320; 63321; 6469; 6472; 599; 600; 10285; 10286; 29127; 29128; 2290; 2292; 63322; 63323; 63324; 63325; 63326; 29133; 63327; 29134; 29135; 13018; 63328; 4486; 63329; 63330; 29136; 29137; 29138; 63331; 63332; 63333; 63334; 29142; 604; 63335; 21016; 29146; 63336; 29147; 29151; 63337; 29152; 63338; 63339; 63340; 4497; 29156; 29157; 29158; 29159; 29160; 29161; 63341; 1485; 10328; 63342; 29181; 23821; 63343; 63344; 53742; 63345; 10335; 63346; 29185; 63347; 63348; 10338; 10339; 10340; 63349; 618; 619; 29191; 29193; 29194; 63350; 63351; 29195; 16544; 63352; 63353; 63354; 13710; 29200; 29201; 29202; 29203; 29204; 26605; 63355; 53748; 16548; 16549; 16550; 7767; 63356; 63357; 63358; 63359; 29209; 29213; 29214; 29211; 29212; 29215; 63360; 29217; 29218; 29219; 29220; 63361; 63362; 29223; 63363; 63364; 63365; 63366; 63367; 633; 634; 29225; 29226; 29227; 14757; 14758; 14759; 29228; 63368; 63369; 10426; 63370; 22474; 23842; 23843; 23844; 23845; 23846; 14763; 639; 63371; 642; 18346; 18347; 18348; 18349; 18350; 63372; 63373; 10443; 10444; 3250; 63374; 63375; 63376; 63377; 63378; 4557; 29240; 4559; 63379; 29243; 29244; 29245; 63380; 63381; 63382; 652; 29246; 63383; 29248; 63384; 29250; 26631; 26632; 29251; 29254; 29253; 29252; 29255; 29256; 63385; 29258; 63386; 29259; 63387; 63388; 63389; 63390; 63391; 29260; 29261; 63392; 63393; 63394; 28626; 29263; 29264; 63395; 18357; 63396; 63397; 29267; 63398; 29268; 63399; 29270; 63400; 63401; 63402; 1524; 6583; 1526; 10505; 29277; 63403; 25090; 63404; 52890; 18371; 63405; 63406; 63407; 25590; 29283; 63408; 22507; 63409; 63410; 29288; 29289; 22509; 22510; 63411; 63412; 55447; 29292; 29294; 29296; 63413; 29297; 63414; 25101; 22517; 63415; 63416; 63417; 673; 674; 675; 2357; 2358; 29303; 63418; 63419; 63420; 63421; 29311; 63422; 63423; 676; 677; 63424; 29312; 63425; 63426; 63427; 29313; 29314; 63428; 29315; 63429; 63430; 63431; 7816; 63432; 29316; 63433; 63434; 63435; 29317; 29318; 12385; 29319; 29320; 29321; 29322; 63436; 63437; 63438; 3276; 3277; 26672; 63439; 63440; 25103; 63441; 63442; 63443; 63444; 63445; 63446; 63447; 29326; 29327; 14808; 4610; 29329; 29330; 29331; 63448; 63449; 29332; 6624; 1558; 63450; 4621; 4622; 63451; 29335; 63452; 63453; 63454; 29337; 29338; 63455; 63456; 63457; 18392; 29339; 63458; 63459; 63460; 29340; 29341; 63461; 4625; 63462; 63463; 21085; 29342; 29343; 29345; 63464; 29346; 13056; 29347; 63465; 29348; 63466; 29350; 29352; 63467; 10655; 29353; 29354; 63468; 63469; 63470; 63471; 29357; 29358; 29359; 29360; 29361; 29362; 63472; 63473; 63474; 63475; 63476; 63477; 63478; 63479; 63480; 29364; 63481; 13065; 63482; 63483; 63484; 63485; 63486; 17334; 29367; 63487; 29369; 29370; 6654; 63488; 63489; 29371; 63490; 29372; 29373; 63491; 63492; 63493; 63494; 29374; 63495; 713; 29376; 63496; 29377; 29380; 29381; 4649; 29386; 29387; 63497; 63498; 63499; 63500; 63501; 63502; 63503; 63504; 63505; 63506; 6659; 3314; 6661; 3315; 6660; 29388; 29389; 63507; 29391; 25115; 29392; 63508; 4655; 63509; 63510; 29393; 63511; 63512; 63513; 63514; 12408; 63515; 63516; 63517; 63518; 63519; 25613; 63520; 63521; 63522; 63523; 63524; 21102; 63525; 29398; 29400; 729; 63526; 29405; 13079; 63527; 29406; 63528; 63529; 63530; 63531; 29407; 17340; 17341; 26743; 26744; 63532; 63533; 63534; 63535; 63536; 63537; 29420; 63538; 29421; 63539; 29422; 29423; 29424; 29425; 63540.

The following SEQ ID NOs correspond to the polynucleotides encoding thymus-specific proteins as described in Table 69A identified using SBS: 24316; 65194; 65195.

The following SEQ ID NOs correspond to the amino acid sequences of thymus-specific proteins as described in Table 69A identified using SBS: 24446; 65196; 65197.

The following SEQ ID NOs correspond to the polynucleotides encoding trachea-specific proteins as described in Table 70A identified using SBS: 31349; 65203; 65204; 65205; 65206; 65207; 65208; 53071; 3642; 65209; 31849; 65210; 65211; 65212; 65213; 27579; 65214; 65215; 3673; 31854; 65216; 65217; 65218; 65219; 65220; 65221; 11974; 61672; 65222; 17596; 31858; 31859; 65223; 65224; 65225; 19082; 65226; 31861; 1946; 31868; 31869; 31870; 65227; 65228; 65229; 65230; 65231; 65232; 65233; 31871; 31872; 65234; 65235; 65236; 65237; 65238; 65239; 65240; 65241; 65242; 65243; 65244; 65245; 65246; 65247; 31875; 31876; 1970; 65248; 27350; 32043; 20237; 65249; 16114; 16115; 31878; 21792; 21793; 21794; 21795; 21796; 65250; 24402; 65251; 59764; 31879; 31880; 24419; 31882; 65252; 65253; 31884; 65254; 31477; 65255; 65256; 24893; 65257; 9312; 31887; 65258; 65259; 31492; 65260; 65261; 65262; 22004; 22005; 28404.

The following SEQ ID NOs correspond to the amino acid sequences of trachea-specific proteins as described in Table 70A identified using SBS: 31511; 65263; 65264; 65265; 65266; 65267; 65268; 53476; 4191; 65269; 31891; 65270; 65271; 65272; 65273; 28581; 65274; 65275; 4222; 31896; 65276; 65277; 65278; 65279; 65280; 65281; 12230; 62701; 65282; 18065; 31900; 31901; 65283; 65284; 65285; 19486; 65286; 31903; 2245; 31910; 31911; 31912; 65287; 65288; 65289; 65290; 65291; 65292; 65293; 31913; 31914; 65294; 65295; 65296; 65297; 65298; 65299; 65300; 65301; 65302; 65303; 65304; 65305; 65306; 65307; 31917; 31918; 2269; 65308; 27380; 32106; 20378; 65309; 16511; 16512; 31920; 22379; 22380; 22381; 22382; 22383; 65310; 24532; 65311; 59977; 31921; 31922; 24549; 31924; 65312; 65313; 31926; 65314; 31639; 65315; 65316; 25096; 65317; 10640; 31929; 65318; 65319; 31654; 65320; 65321; 65322; 22591; 22592; 29406.

The following SEQ ID NOs correspond to the polynucleotides encoding uterus-specific proteins as described in Table 71A identified using SBS: 27431; 32017; 65466; 32033; 65467; 65468; 65469; 65470; 65471; 65472; 65473; 65474; 65475; 65476; 28302; 28304; 28307; 28308; 65477; 65478; 65479; 32062; 65480.

The following SEQ ID NOs correspond to the amino acid sequences of uterus-specific proteins as described in Table 71A identified using SBS: 28433; 32080; 65481; 32096; 65482; 65483; 65484; 65485; 65486; 65487; 65488; 65489; 65490; 65491; 29304; 29306; 29309; 29310; 65492; 65493; 65494; 32125; 65495.

The following SEQ ID NOs correspond to the polynucleotides encoding male organ prostate-specific proteins as described in Table 72A identified using SBS: 13270; 21443; 3588; 21444; 21445; 17027; 21460; 16; 59267; 3616; 3618; 8196; 15403; 59268; 21492; 21493; 21494; 21495; 21496; 59269; 59270; 53089; 1068; 1847; 1848; 59271; 59272; 59273; 20170; 8343; 59274; 21557; 21558; 21559; 21560; 21561; 20617; 17601; 65511; 65512; 65513; 65514; 65515; 59275; 23359; 59276; 21618; 16037; 59277; 59278; 59279; 21636; 59280; 65516; 20661; 65517; 14189; 65518; 65519; 65520; 65521; 65522; 59281; 3780; 21644; 21645; 59282; 59283; 8668; 59284; 8669; 55235; 55236; 55237; 59285; 21665; 21666; 21667; 21668; 21669; 21670; 21672; 59286; 1159; 1160; 5391; 17103; 5392; 59287; 59288; 59289; 59290; 59291; 59292; 59293; 20702; 59294; 24389; 59295; 59296; 59297; 65523; 65524; 59298; 59299; 65525; 65526; 59300; 21715; 65527; 21717; 59301; 59302; 59303; 21723; 65528; 21724; 21725; 65529; 65530; 65531; 65532; 65533; 65534; 65535; 65536; 65537; 65538; 65539; 65540; 65541; 65542; 65543; 65544; 65545; 65546; 65547; 65548; 65549; 65550; 65551; 65552; 65553; 65554; 65555; 65556; 21726; 21727; 21728; 21729; 21730; 21731; 21732; 21733; 21734; 21735; 21736; 21737; 59304; 59305; 59306; 59307; 21742; 59308; 59309; 59310; 14256; 21786; 21787; 59311; 59312; 59313; 21800; 21801; 21802; 21803; 59314; 59315; 21821; 59316; 21829; 20751; 21838; 59317; 59318; 59319; 59320; 59321; 59322; 21853; 21854; 21855; 21856; 21857; 21858; 21859; 32804; 267; 32325; 32326; 59323; 59324; 59325; 32216; 59326; 59327; 32455; 30675; 59328; 65557; 65558; 21912; 21913; 4028; 59329; 59330; 59331; 59332; 12121; 59333; 21932; 9273; 21939; 57623; 57624; 21960; 59334; 21961; 21972; 59335; 21980; 59336; 32063; 59337; 59338; 59339; 22001; 59340.

The following SEQ ID NOs correspond to the amino acid sequences of male organ prostate-specific proteins as described in Table 72A identified using SBS: 13537; 22030; 4137; 22031; 22032; 17187; 22047; 384; 59341; 4165; 4167; 9524; 15579; 59342; 22079; 22080; 22082; 22081; 22083; 59343; 59344; 53494; 1351; 2147; 2146; 59345; 59346; 59347; 20311; 9671; 59348; 22144; 22145; 22146; 22147; 22148; 20884; 18070; 65559; 65560; 65561; 65562; 65563; 59349; 23690; 59350; 22205; 16434; 59351; 59352; 59353; 22223; 59354; 65564; 20928; 65565; 14604; 65566; 65567; 65568; 65569; 65570; 59355; 4329; 22231; 22232; 59356; 59357; 9996; 59358; 9997; 55371; 55372; 55373; 59359; 22252; 22253; 22254; 22255; 22256; 22257; 22259; 59360; 1442; 1443; 6225; 17263; 6226; 59361; 59362; 59363; 59364; 59365; 59366; 59367; 20969; 59368; 24519; 59369; 59370; 59371; 65571; 65572; 59372; 59373; 65573; 65574; 59374; 22302; 65575; 22304; 59375; 59376; 59377; 22310; 65576; 22311; 22312; 65577; 65578; 65579; 65580; 65581; 65582; 65583; 65584; 65585; 65586; 65587; 65588; 65589; 65590; 65591; 65592; 65593; 65594; 65595; 65596; 65597; 65598; 65599; 65600; 65601; 65602; 65603; 65604; 22313; 22314; 22316; 22315; 22317; 22318; 22319; 22320; 22322; 22321; 22323; 22324; 59378; 59379; 59380; 59381; 22329; 59382; 59383; 59384; 14670; 22373; 22374; 59385; 59386; 59387; 22387; 22388; 22389; 22390; 59388; 59389; 22408; 59390; 22416; 21018; 22425; 59391; 59392; 59393; 59394; 59395; 59396; 22440; 22441; 22442; 22443; 22444; 22445; 22446; 32860; 635; 32343; 32344; 59397; 59398; 59399; 32230; 59400; 59401; 32562; 30938; 59402; 65605; 65606; 22499; 22500; 4577; 59403; 59404; 59405; 59406; 12377; 59407; 22519; 10601; 22526; 57741; 57742; 22547; 59408; 22548; 22559; 59409; 22567; 59410; 32126; 59411; 59412; 59413; 22588; 59414.

The following SEQ ID NOs correspond to the polynucleotides encoding male sex organ testes-specific proteins as described in Table 73A identified using SBS: 61484; 61485; 61486; 61487; 61488; 61489; 61490; 27425; 61491; 8122; 8123; 8124; 8125; 8126; 8127; 8128; 8129; 8130; 27426; 61492; 61493; 27427; 61494; 61495; 27428; 27429; 61496; 27430; 61497; 20136; 20137; 5088; 5090; 17502; 61498; 61499; 61500; 61501; 61502; 27435; 27436; 27437; 65623; 65624; 65625; 27438; 27439; 65626; 61503; 61504; 25824; 27441; 27442; 53048; 61505; 61506; 27447; 27448; 8167; 61507; 27449; 27450; 61508; 61509; 61510; 61511; 27452; 1813; 27453; 30470; 61512; 21469; 2638; 2639; 27455; 61513; 61514; 61515; 27456; 27457; 61516; 27458; 27460; 65627; 61517; 12678; 2645; 27462; 27463; 12680; 12681; 5118; 61518; 61519; 27468; 27469; 27470; 27472; 27473; 27474; 27475; 27476; 13277; 13278; 27477; 5126; 61520; 8218; 27481; 27482; 61521; 61522; 61523; 18967; 27483; 27484; 24735; 27485; 27486; 27487; 27490; 27489; 33; 61524; 61525; 61526; 61527; 61528; 61529; 61530; 61531; 27492; 27493; 61532; 61533; 61534; 61535; 24739; 61536; 61537; 61538; 27497; 27498; 61539; 61540; 61541; 61542; 27499; 61543; 61544; 61545; 21488; 21489; 27501; 27502; 61546; 61547; 27503; 61548; 61549; 61550; 61551; 27505; 61552; 8243; 61553; 27507; 27508; 61554; 61555; 5131; 27509; 61556; 61557; 27510; 27511; 61558; 27513; 61559; 61560; 61561; 61562; 61563; 61564; 61565; 61566; 61567; 27516; 61568; 61569; 27517; 12688; 61570; 61571; 65628; 65629; 2662; 27518; 61572; 27519; 61573; 61574; 17531; 8246; 27521; 61575; 27523; 27524; 61576; 61577; 13304; 61578; 27525; 61579; 61580; 61581; 27527; 61582; 27528; 61583; 61584; 61585; 65630; 65631; 65632; 65633; 27530; 27531; 27533; 61586; 65634; 5135; 61587; 27535; 61588; 61589; 61590; 27537; 27538; 27539; 61591; 27540; 27541; 27542; 27544; 61592; 61593; 61594; 61595; 61596; 61597; 61598; 61599; 61600; 61601; 61602; 61603; 61604; 61605; 27546; 3657; 27548; 27549; 27550; 27551; 27552; 27553; 27554; 61606; 24744; 61607; 24745; 61608; 61609; 27559; 65635; 61610; 27560; 61611; 61612; 61613; 61614; 61615; 27561; 20591; 27562; 27563; 27564; 27565; 27566; 27567; 27568; 27569; 27570; 61616; 61617; 27574; 27575; 27576; 61618; 5162; 20160; 65636; 61619; 61620; 2677; 27579; 61621; 27581; 27582; 27583; 27584; 27585; 27586; 27587; 27588; 27589; 27590; 61622; 27591; 27592; 61623; 8278; 53095; 27595; 61624; 27597; 20602; 1075; 15986; 27602; 27604; 27605; 3681; 21523; 21524; 21525; 61625; 27607; 61626; 61627; 27609; 27610; 27611; 61628; 61629; 61630; 61631; 61632; 61633; 61634; 61635; 61636; 61637; 61638; 61639; 61640; 61641; 15991; 14104; 21535; 61642; 23323; 23324; 61643; 27617; 61644; 8317; 17579; 17580; 61645; 27618; 8323; 61646; 57536; 61647; 61648; 57537; 57538; 57539; 57540; 61649; 61650; 61651; 61652; 61653; 61654; 61655; 57541; 57542; 57543; 57544; 61656; 27620; 61657; 61658; 27622; 27623; 27624; 27625; 61659; 27629; 8336; 30499; 61660; 61661; 61662; 61663; 61664; 61665; 61666; 27632; 21546; 27636; 27637; 8353; 65637; 8356; 27641; 13333; 19052; 61667; 61668; 61669; 61670; 61671; 61672;

61673; 31377; 31378; 31379; 61674; 27646; 61675; 61676; 61677; 11981; 21556; 27647; 27648; 61678; 61679; 27649; 27650; 27651; 27653; 61680; 21558; 61681; 31381; 61682; 61683; 27655; 27656; 61684; 27658; 3708; 61685; 61686; 65638; 61687; 61688; 61689; 61690; 27661; 27663; 59629; 61691; 61692; 61693; 27670; 27671; 61694; 27672; 27673; 27674; 8418; 8419; 27675; 61695; 27677; 27676; 61696; 21578; 8426; 27678; 61697; 61698; 5237; 27681; 27682; 1105; 1106; 1890; 61699; 17611; 27684; 20183; 20184; 61700; 61701; 61702; 61703; 27690; 61704; 61705; 3731; 3732; 3733; 7300; 27692; 27693; 27694; 61706; 61707; 61708; 27695; 14146; 1893; 61709; 61710; 61711; 13347; 61712; 61713; 27696; 61714; 61715; 61716; 27698; 61717; 13350; 61718; 61719; 27699; 61720; 61721; 61722; 8500; 61723; 27708; 27709; 61724; 27712; 61725; 27713; 27715; 61726; 27717; 61727; 27718; 27720; 8507; 27722; 27723; 65639; 65640; 65641; 25382; 61728; 61729; 61730; 27727; 61731; 61732; 25383; 27728; 27729; 57174; 27731; 61733; 61734; 27733; 27734; 61735; 61736; 61737; 61738; 27735; 21613; 17625; 17624; 17623; 27737; 27738; 27739; 61739; 27740; 27741; 61740; 27742; 61741; 61742; 61743; 61744; 61745; 27745; 27746; 27747; 61746; 27748; 2721; 27751; 27753; 19080; 61747; 27754; 27755; 27756; 61748; 27757; 27758; 25947; 25948; 27759; 61749; 27763; 27764; 8533; 8535; 8534; 13354; 61750; 61751; 61752; 61753; 61754; 61755; 61756; 27768; 61757; 27770; 61758; 61759; 61760; 61761; 61762; 27771; 5263; 21620; 27773; 61763; 27775; 61764; 61765; 61766; 61767; 61768; 61769; 61770; 61771; 61772; 27777; 27778; 61773; 19091; 61774; 61775; 61776; 27781; 27782; 61777; 61778; 27783; 61779; 61780; 27789; 27790; 27791; 61781; 61782; 27793; 61783; 61784; 61785; 61786; 61787; 61788; 27797; 61789; 61790; 27802; 27803; 27804; 5292; 20662; 61791; 61792; 27805; 27806; 61793; 61794; 27807; 2743; 27810; 61795; 27811; 27812; 61796; 61797; 27814; 61798; 12009; 12010; 61799; 27815; 61800; 16051; 32422; 32423; 27818; 27819; 61801; 61802; 61803; 27820; 8650; 61804; 61805; 61806; 65642; 27821; 61807; 61808; 27822; 27823; 27824; 27825; 27826; 27827; 27828; 27829; 15458; 61809; 61810; 8657; 8658; 27832; 23402; 23403; 8672; 23404; 167; 27836; 27837; 7357; 61811; 61812; 24810; 2779; 2780; 2781; 61813; 14213; 27847; 8693; 8694; 5359; 26000; 21657; 27849; 61814; 27850; 27854; 8715; 8717; 13385; 27855; 27856; 5379; 5380; 5381; 5382; 5383; 5384; 5385; 5386; 5387; 5388; 5389; 61815; 61816; 61817; 61818; 27859; 61819; 55846; 27860; 27861; 27862; 27863; 27864; 23411; 61820; 61821; 27867; 27868; 61822; 61823; 61824; 27870; 61825; 2792; 61826; 61827; 27872; 61828; 27874; 27875; 27878; 61829; 27880; 27881; 27883; 27882; 61830; 61831; 27884; 27885; 27886; 27887; 61832; 27888; 61833; 5404; 61834; 27889; 61835; 61836; 61837; 27890; 61838; 32265; 61839; 61840; 61841; 61842; 61843; 61844; 61845; 61846; 27896; 27895; 61847; 27897; 27898; 61848; 27899; 61849; 27900; 61850; 2801; 2802; 61851; 61852; 61853; 27901; 27902; 61854; 61855; 27905; 27906; 27903; 27904; 14232; 61856; 61857; 54818; 54819; 27907; 61858; 61859; 61860; 27908; 61861; 61862; 27911; 12031; 61863; 27912; 61864; 61865; 27914; 27913; 61866; 61867; 27915; 27916; 27917; 61868; 61869; 61870; 61871; 61872; 61873; 61874; 61875; 27918; 27919; 27920; 27921; 27922; 27924; 61876; 61877; 61878; 61879; 23419; 61880; 61881; 61882; 8752; 61883; 61884; 61885; 61886; 1948; 61887; 61888; 21697; 61889; 27932; 27933; 61890; 61891; 61892; 61893; 61894; 61895; 61896; 61897; 61898; 61899; 26016; 61900; 27938; 27958; 61901; 27942; 27943; 27946; 27947; 27944; 27945; 61902; 27948; 61903; 61904; 65643; 65644; 61905; 27950; 61906; 27953; 27954; 61907; 27955; 27956; 27941; 61908; 61909; 61910; 61911; 27964; 61912; 61913; 61914; 61915; 27965; 61916; 61917; 61918; 61919; 61920; 61921; 61922; 61923; 61924; 61925; 61926; 61927; 61928; 61929; 61930; 61931; 61932; 61933; 27969; 61934; 61935; 61936; 61937; 61938; 61939; 61940; 61941; 61942; 61943; 61944; 61945; 61946; 61947; 8774; 61948; 21706; 61949; 61950; 61951; 61952; 61953; 61954; 61955; 61956; 61957; 61958; 61959; 61960; 61961; 61962; 61963; 61964; 61965; 61966; 61967; 61968; 28016; 61969; 61970; 27983; 27984; 27985; 27986; 61971; 27987; 61972; 8809; 61973; 61974; 61975; 3877; 61976; 65645; 61977; 61978; 61979; 27988; 27989; 61980; 27990; 61981; 12036; 61982; 61983; 61984; 61985; 61986; 61987; 61988; 61989; 61990; 61991; 61992; 61993; 61994; 61995; 61996; 61997; 61998; 61999; 62000; 3880; 62001; 62002; 62003; 62004; 62005; 27994; 62006; 62007; 62008; 62009; 27995; 28020; 62010; 61282; 61283; 62011; 27998; 62012; 62013; 62014; 62015; 14237; 62016; 62017; 62018; 62019; 62020; 62021; 62022; 62023; 62024; 62025; 62026; 28024; 62027; 62028; 62029; 62030; 62031; 62032; 62033; 62034; 62035; 62036; 62037; 62038; 62039; 62040; 62041; 62042; 62043; 62044; 62045; 62046; 62047; 62048; 62049; 62050; 62051; 62052; 62053; 62054; 62055; 62056; 62057; 62058; 62059; 28001; 62060; 62061; 62062; 62063; 62064; 62065; 62066; 62067; 28002; 65646; 62068; 62069; 59300; 62070; 62071; 7376; 62072; 62073; 62074; 28004; 62075; 62076; 62077; 62078; 62079; 62080; 62081; 62082; 28005; 28006; 62083; 62084; 62085; 32266; 32267; 62086; 62087; 62088; 8782; 62089; 62090; 62091; 62092; 62093; 62094; 28009; 62095; 62096; 28012; 62097; 62098; 62099; 62100; 62101; 28014; 28015; 62102; 62103; 27982; 62104; 62105; 62106; 28017; 62107; 62108; 62109; 62110; 28018; 62111; 28019; 62112; 62113; 65647; 62114; 62115; 27996; 62116; 23444; 62117; 62118; 28022; 62119; 62120; 62121; 62122; 62123; 62124; 62125; 62126; 62127; 62128; 8806; 62129; 62130; 62131; 65648; 62132; 62133; 62134; 62135; 27999; 62136; 62137; 62138; 62139; 62140; 62141; 62142; 62143; 62144; 65649; 7383; 28027; 28028; 62145; 62146; 28029; 28030; 8780; 28031; 28032; 62147; 62148; 62149; 62150; 62151; 62152; 62153; 62154; 28033; 62155; 62156; 62157; 62158; 62159; 62160; 62161; 62162; 62163; 28036; 28037; 28038; 28039; 28040; 28041; 28042; 62164; 62165; 62166; 62167; 62168; 62169; 62170; 62171; 62172; 28043; 28044; 28045; 62173; 62174; 8812; 28046; 28047; 57212; 62175; 62176; 62177; 62178; 62179; 62180; 62181; 62182; 62183; 62184; 62185; 62186; 62187; 62188; 62189; 28048; 28049; 28050; 28051; 28052; 62190; 62191; 62192; 62193; 62194; 62195; 62196; 62197; 62198; 62199; 62200; 62201; 62202; 62203; 62204; 62205; 62206; 62207; 62208; 62209; 62210; 62211; 62212; 62213; 28063; 62214; 62215; 62216; 62217; 62218; 62219; 62220; 62221; 62222; 62223; 62224; 62225; 28068; 62226; 62227; 62228; 62229; 62230; 62231; 28066; 28067; 28065; 62232; 62233; 32268; 32269; 62234; 65650; 62235; 1164; 62236; 62237; 62238; 31425; 19154; 8840; 20720; 62239; 32782; 53265; 28075; 26057; 28076; 62240; 62241; 28077; 28078; 62242; 62243; 62244; 62245; 62246; 62247; 62248; 28079; 28080; 28081; 62249; 62250; 62251; 62252; 28082; 28083; 62253; 62254; 23457; 23458; 23459; 62255; 62256; 62257; 30628; 62258; 65651; 15482; 28090; 62259; 62260; 32041; 62261; 62262; 62263; 28095; 62264; 62265; 28097; 28098; 28099; 28100; 62266; 62267; 28101; 8887; 62268; 62269; 28103; 62270; 62271; 62272; 62273; 28104; 26068; 28105; 62274; 62275; 62276; 65652; 28106; 8894; 62277; 28107; 62278; 62279; 28109; 62280; 62281; 28115; 17117; 14272; 28118; 62282; 62283; 28119; 28120; 62284; 62285; 28121; 8913; 12056; 12057; 12058; 12059; 12060; 5554; 5555; 217; 218; 219; 13428; 13429; 28122; 62286; 2846; 2847; 20239; 3926; 8922; 8923; 8924; 8925; 62287; 62288; 62289; 8929; 62290;

62291; 62292; 62293; 5635; 5638; 231; 232; 8957; 8958; 28125; 28126; 1991; 1993; 62294; 62295; 62296; 62297; 62298; 28131; 62299; 28132; 28133; 12810; 62300; 3937; 62301; 62302; 28134; 28135; 28136; 62303; 62304; 62305; 62306; 28140; 236; 62307; 20749; 28144; 62308; 28145; 28148; 28149; 62309; 28150; 62310; 62311; 62312; 3948; 28154; 28155; 28156; 28157; 28158; 28159; 62313; 65653; 1202; 9000; 62314; 28179; 23490; 62315; 62316; 53337; 62317; 9007; 62318; 28183; 62319; 62320; 9010; 9011; 9012; 62321; 250; 251; 28189; 28191; 28192; 62322; 62323; 28193; 16147; 62324; 62325; 62326; 13443; 28198; 28199; 28200; 28201; 28202; 26135; 62327; 53343; 16151; 16152; 16153; 7437; 62328; 62329; 62330; 62331; 65654; 65655; 28207; 28209; 28210; 28211; 28212; 28213; 62332; 28215; 28216; 28217; 28218; 62333; 62334; 28221; 28222; 55937; 62335; 62336; 7445; 62337; 62338; 62339; 265; 266; 28223; 28224; 28225; 14343; 14344; 14345; 28226; 62340; 62341; 9098; 62342; 21887; 23511; 23512; 23513; 23514; 23515; 14349; 271; 62343; 1228; 274; 17877; 17878; 17879; 17880; 17881; 62344; 62345; 9115; 9116; 2894; 62346; 62347; 28235; 28236; 62348; 62349; 62350; 4008; 28238; 4010; 62351; 28241; 28242; 28243; 62352; 62353; 62354; 284; 28244; 62355; 28246; 62356; 28248; 26161; 26162; 28249; 28250; 28251; 28252; 28253; 28254; 62357; 62356; 62358; 28257; 62359; 65656; 65657; 62360; 62361; 62362; 62363; 28258; 28259; 62364; 62365; 62366; 28260; 28261; 28262; 62367; 17888; 62368; 62369; 28265; 62370; 28266; 62371; 28268; 62372; 62373; 62374; 1241; 5749; 1242; 1243; 9177; 28275; 62375; 24887; 62376; 52875; 17902; 62377; 62378; 62379; 25450; 28281; 62380; 21920; 62381; 62382; 28285; 28286; 28287; 21922; 21923; 62383; 62384; 55311; 28290; 28292; 53396; 28294; 62385; 28295; 62386; 24898; 21930; 62387; 62388; 62389; 305; 306; 307; 2058; 2059; 28301; 62390; 62391; 62392; 62393; 28309; 62394; 62395; 65658; 65659; 308; 309; 62396; 28310; 62397; 62398; 62399; 28311; 28312; 62400; 28313; 62401; 62402; 62403; 7486; 62404; 28314; 62405; 62406; 62407; 28315; 28316; 12129; 28317; 28318; 28319; 28320; 62408; 62409; 62410; 2920; 2921; 26202; 62411; 62412; 24900; 62413; 62414; 62415; 62416; 62417; 62418; 28323; 62419; 28324; 28325; 14394; 4061; 28327; 28328; 28329; 62420; 62421; 28330; 5790; 1275; 62422; 4072; 4073; 62423; 28333; 62424; 62425; 62426; 28335; 28336; 62427; 62428; 62429; 17923; 28337; 62430; 62431; 62432; 28338; 28339; 62433; 4076; 62434; 62435; 20818; 28340; 28341; 28343; 62436; 28344; 12848; 28345; 62437; 28346; 62438; 28348; 28350; 62439; 9327; 28351; 28352; 62440; 62441; 62442; 62443; 28355; 28356; 28357; 28358; 28359; 28360; 62444; 62445; 62446; 62447; 62448; 62449; 62450; 62451; 62452; 28362; 62453; 12857; 62454; 62455; 62456; 62457; 62458; 17174; 28365; 65660; 62459; 28367; 28368; 5820; 62460; 62461; 28369; 62462; 28370; 28371; 62463; 62464; 62465; 62466; 28372; 62467; 345; 28374; 62468; 28375; 28378; 28379; 4100; 28384; 28385; 62469; 65661; 62470; 62471; 62472; 62473; 62474; 62475; 62476; 62477; 62478; 5825; 2958; 5826; 2959; 5827; 28386; 28387; 62479; 28389; 24912; 28390; 62480; 4106; 62481; 62482; 28391; 62483; 62484; 62485; 12151; 62486; 12152; 62487; 62488; 62489; 62490; 62491; 25473; 62492; 62493; 62494; 62495; 62496; 20835; 62497; 28396; 28398; 361; 62498; 4112; 28403; 12871; 62499; 28404; 62500; 62501; 62502; 62503; 28405; 17180; 17181; 26273; 26274; 62504; 62505; 62506; 62507; 62508; 65662; 62509; 22021; 28418; 62510; 28419; 62511; 28420; 28421; 28422; 28423; 62512.

The following SEQ ID NOs correspond to the amino acid sequences of male sex organ testes-specific proteins as described in Table 73A identified using SBS: 62513; 62514; 62515; 62516; 62517; 62518; 62519; 28427; 62520; 9450; 9451; 9452; 9453; 9454; 9455; 9456; 9457; 9458; 28428; 62521; 62522; 28429; 62523; 62524; 28430; 28431; 62525; 28432; 62526; 20277; 20278; 5922; 5924; 17971; 62527; 62528; 62529; 62530; 62531; 28437; 28438; 28439; 65663; 65664; 65665; 28440; 28441; 65666; 62532; 62533; 26294; 28443; 28444; 53453; 62534; 62535; 28450; 28449; 9495; 62536; 28451; 28452; 62537; 62538; 62539; 62540; 28454; 2112; 28455; 30733; 62541; 22056; 2994; 2995; 28457; 62542; 62543; 62544; 28458; 28459; 62545; 28460; 28462; 65667; 62546; 12886; 3001; 28464; 28465; 12888; 12889; 5952; 62547; 62548; 28470; 28471; 28472; 28475; 28474; 28476; 28477; 28478; 13544; 13545; 28479; 5960; 62549; 9546; 28483; 28484; 62550; 62551; 62552; 19371; 28486; 28485; 24938; 28488; 28487; 28489; 28492; 28491; 401; 62553; 62554; 62555; 62556; 62557; 62558; 62559; 62560; 28494; 28495; 62561; 62562; 62563; 62564; 24942; 62565; 62566; 62567; 28499; 28500; 62568; 62569; 62570; 62571; 28501; 62572; 62573; 62574; 22076; 22075; 28503; 28504; 62575; 62576; 28505; 62577; 62578; 62579; 62580; 28507; 62581; 9571; 62582; 28509; 28510; 62583; 62584; 5965; 28511; 62585; 62586; 28512; 28513; 62587; 28515; 62588; 62589; 62590; 62591; 62592; 62593; 62594; 62595; 62596; 28518; 62597; 62598; 28519; 12896; 62599; 62600; 65668; 65669; 3018; 28520; 62601; 28521; 62602; 62603; 18000; 9574; 28523; 62604; 28525; 28526; 62605; 62606; 13571; 62607; 28527; 62608; 62609; 62610; 28529; 62611; 28530; 62612; 62613; 62614; 65670; 65671; 65672; 65673; 28532; 28533; 28535; 62615; 65674; 5969; 62616; 28537; 62617; 62618; 62619; 28539; 28540; 28541; 62620; 28542; 28543; 28544; 28546; 62621; 62622; 62623; 62624; 62625; 62626; 62627; 62628; 62629; 62630; 62631; 62632; 62633; 62634; 28548; 4206; 28550; 28551; 28552; 28553; 28554; 28555; 28556; 62635; 24948; 62636; 24947; 62637; 62638; 28561; 65675; 62639; 28562; 62640; 62641; 62642; 62643; 62644; 28563; 20858; 28564; 28565; 28568; 28567; 28566; 28569; 28570; 28571; 28572; 62645; 62646; 28576; 28577; 28578; 62647; 5996; 20301; 65676; 62648; 62649; 3033; 28581; 62650; 28583; 28584; 28585; 28586; 28587; 28588; 28589; 28590; 28591; 28592; 62651; 28593; 28594; 62652; 9606; 53500; 28597; 62653; 28599; 20869; 1358; 16383; 28604; 28606; 28607; 4230; 22110; 22111; 22112; 62654; 28609; 62655; 62656; 28611; 28612; 28613; 62657; 62658; 62659; 62660; 62661; 62662; 62663; 62664; 62665; 62666; 62667; 62668; 62669; 62670; 16388; 14518; 22122; 62671; 23654; 23655; 62672; 28619; 62673; 9645; 18048; 18049; 62674; 62620; 9651; 62675; 57654; 62676; 62677; 57655; 57656; 57657; 57658; 62678; 62679; 62680; 62681; 62682; 62683; 62684; 57659; 57660; 57661; 57662; 62685; 28622; 62686; 62687; 28624; 28625; 28627; 29262; 62688; 28631; 9664; 30762; 62689; 62690; 62691; 62692; 62693; 62694; 62695; 28634; 22133; 28638; 28639; 9681; 65677; 9684; 28643; 13600; 19456; 62696; 62697; 62698; 62699; 62700; 62701; 62702; 31539; 31540; 31541; 62703; 28648; 62704; 62705; 62706; 12237; 22143; 28649; 28650; 62707; 62708; 28651; 28652; 28653; 28655; 62709; 22145; 62710; 31543; 62711; 62712; 28657; 28658; 62713; 28660; 4257; 62714; 62715; 65678; 62716; 62717; 62718; 62719; 28663; 28665; 59842; 62720; 62721; 62722; 28672; 28673; 62723; 28674; 28675; 28676; 9746; 9747; 28677; 62724; 28679; 28678; 62725; 22165; 9754; 28680; 62726; 62727; 6071; 28683; 28684; 1388; 1389; 2189; 62728; 18080; 28686; 20324; 20325; 62729; 62730; 62731; 62732; 28692; 62733; 62734; 4281; 4280; 4282; 7630; 28694; 28695; 28696; 62735; 62736; 62737; 28697; 14560; 2192; 62738; 62739; 62740; 13614; 62741; 62742; 28698; 62743; 62744; 62745; 28700; 62746; 13617; 62747; 62748; 28701; 62749; 62750; 62751; 9828;

62752; 28710; 28711; 62753; 28714; 62754; 28715; 28722; 62755; 28719; 62756; 28720; 28717; 9835; 28724; 28725; 65679; 65680; 65681; 25522; 62757; 62758; 62759; 28729; 62760; 62761; 25523; 28730; 28731; 57238; 28733; 62762; 62763; 28735; 28736; 62764; 62765; 62766; 62767; 28737; 22200; 18094; 18092; 18093; 28739; 29047; 29048; 62768; 28743; 28742; 62769; 28744; 62770; 62771; 62772; 62773; 62774; 28747; 28748; 28749; 62775; 28750; 3077; 28753; 28755; 19484; 62776; 28756; 28757; 28758; 62777; 28759; 28760; 26417; 26418; 28761; 62778; 28765; 62779; 9861; 9863; 9862; 13621; 62780; 62781; 62782; 62783; 62784; 62785; 62786; 28770; 62787; 28772; 62788; 62789; 62790; 62791; 62792; 28773; 6097; 22207; 28775; 62793; 28777; 62794; 62795; 62796; 62797; 62798; 62799; 62800; 62801; 62802; 28779; 28780; 62803; 19495; 62804; 62805; 62806; 28783; 28784; 62807; 62808; 28785; 62809; 62810; 28791; 28792; 28793; 62811; 62812; 28795; 62813; 62814; 62815; 62816; 62817; 62818; 28799; 62819; 62820; 28804; 28805; 28806; 6126; 20929; 62821; 62822; 28807; 28808; 62823; 62824; 28809; 3099; 28812; 62825; 28813; 28814; 28815; 62826; 28816; 62827; 12265; 12266; 62828; 28817; 62829; 16448; 32529; 32530; 28820; 28821; 62830; 62831; 62832; 28822; 9978; 62833; 62834; 62835; 65682; 28823; 62836; 62837; 28824; 28825; 26826; 28830; 28828; 28829; 62827; 28831; 15634; 62838; 62839; 9985; 9986; 28834; 23733; 23734; 10000; 23735; 535; 28838; 28839; 7687; 62840; 62841; 25013; 3135; 3136; 3137; 62842; 14627; 28849; 10021; 10022; 6207; 62843; 22244; 28851; 62844; 28852; 28856; 10043; 10045; 13652; 28857; 28858; 6213; 6214; 6215; 6216; 6221; 6218; 6219; 6220; 6217; 6222; 6223; 62845; 62846; 62847; 62848; 28861; 62849; 56168; 28862; 28863; 28864; 28865; 28866; 23742; 62850; 62851; 28869; 28870; 62852; 62853; 62854; 28872; 62855; 3148; 62856; 62857; 28874; 62858; 28876; 28877; 28880; 62859; 28882; 28883; 28885; 28884; 62860; 62861; 28886; 28888; 28887; 28889; 62862; 28890; 62863; 6238; 62864; 28891; 62865; 62866; 62867; 28892; 62868; 32279; 62869; 62870; 62871; 62872; 62873; 62874; 62875; 62876; 28898; 28897; 62877; 28900; 28899; 62878; 28901; 62879; 28902; 62880; 3150; 3158; 62881; 62882; 62883; 28904; 28903; 62884; 62885; 28907; 28908; 28905; 28906; 14646; 62886; 62887; 54833; 54834; 28909; 62888; 62889; 62890; 28910; 62891; 62892; 28913; 12287; 62893; 62894; 28914; 62895; 28915; 28916; 62896; 62897; 28918; 28919; 28917; 62898; 62899; 62900; 62901; 62902; 62903; 62904; 62905; 28920; 28921; 28922; 28923; 28924; 28926; 62906; 62907; 62908; 62909; 23750; 10080; 62910; 62911; 62912; 62913; 62914; 62915; 62916; 2247; 62917; 62918; 22284; 62919; 28934; 28935; 62920; 62921; 62922; 62923; 62924; 62925; 62926; 62927; 62928; 62929; 26486; 62930; 28940; 28959; 62931; 28944; 62932; 28948; 28946; 62933; 28947; 62934; 28950; 62935; 62936; 65683; 65684; 62937; 28952; 62938; 28956; 28955; 62939; 28957; 28958; 28961; 62940; 62941; 62942; 62943; 28966; 62944; 62945; 62946; 62947; 28967; 62948; 62949; 62950; 62951; 62952; 62953; 62954; 62955; 62956; 62957; 62958; 62959; 62960; 62961; 62962; 62963; 62964; 62965; 28971; 62966; 62967; 62968; 62969; 62970; 62971; 62972; 62973; 62974; 62975; 62976; 62977; 62978; 62979; 10102; 62980; 22293; 62981; 62982; 62983; 62984; 62985; 62986; 62987; 62988; 62989; 62990; 62991; 62992; 62993; 62994; 62995; 62996; 62997; 62998; 62999; 63000; 28984; 63001; 63002; 28985; 29049; 28987; 28740; 63003; 29019; 63004; 10108; 63005; 63006; 63007; 4429; 63008; 65685; 63009; 63010; 63011; 28991; 28990; 63012; 29035; 63013; 12292; 63014; 63015; 63016; 63017; 63018; 63019; 63020; 63021; 63022; 63023; 63024; 63025; 63026; 63027; 63028; 63029; 63030; 63031; 63032; 4426; 63033; 63034; 63035; 63036; 63037; 28996; 63038; 63039; 63040; 63041; 28997; 28998; 63042; 61340; 61341; 63043; 29000; 63044; 63045; 63046; 63047; 14651; 63048; 63049; 63050; 63051; 63052; 63053; 63054; 63055; 63056; 63057; 63058; 29026; 63059; 63060; 63061; 63062; 63063; 63064; 63065; 63066; 63067; 63068; 63069; 63070; 63071; 63072; 63073; 63074; 63075; 63076; 63077; 63078; 63079; 63080; 63081; 63082; 63083; 63084; 63085; 63086; 63087; 63088; 63089; 63090; 63091; 29003; 63092; 63093; 63094; 63095; 63096; 63097; 63098; 63099; 29011; 65686; 63100; 63101; 59374; 63102; 63103; 7706; 63104; 63105; 63106; 29006; 63107; 63108; 63109; 63110; 63111; 63112; 63113; 63114; 29007; 29016; 63115; 63116; 63117; 32280; 32281; 63118; 63119; 63120; 10110; 63121; 63122; 63123; 63124; 63125; 28766; 29004; 63126; 63127; 29014; 63128; 63129; 63130; 63131; 63132; 29008; 29017; 63133; 63134; 29018; 63135; 63136; 63137; 28989; 63138; 63139; 63140; 63141; 29020; 63142; 29021; 63143; 63144; 65687; 63145; 63146; 29022; 63147; 23775; 63148; 63149; 29024; 63150; 63151; 63152; 63153; 63154; 63155; 63156; 63157; 63158; 63159; 10134; 63160; 63161; 63162; 65688; 63163; 63164; 63165; 63166; 29001; 63167; 26470; 63168; 63169; 63170; 63171; 63172; 63173; 63174; 65689; 7713; 29029; 29030; 63175; 63176; 29031; 29032; 10137; 29033; 29034; 63177; 63178; 63179; 63180; 63181; 63182; 63183; 63184; 28992; 63185; 63186; 63187; 63188; 63189; 63190; 63191; 63192; 63193; 29038; 29039; 29040; 29041; 29042; 29043; 29044; 63194; 63195; 63196; 63197; 63198; 63199; 63200; 63201; 63202; 29045; 29046; 28986; 19552; 19550; 10140; 28741; 28988; 57276; 63203; 63204; 63205; 63206; 63207; 63208; 63209; 63210; 63211; 63212; 63213; 63214; 63215; 63216; 63217; 29050; 29051; 29052; 29053; 29054; 63218; 63219; 63220; 63221; 63222; 63223; 63224; 63225; 63226; 63227; 63228; 63229; 63230; 63231; 63232; 63233; 63234; 63235; 63236; 63237; 63238; 63239; 63240; 63241; 29065; 63242; 63243; 63244; 63245; 63246; 63247; 63248; 63249; 63250; 63251; 63252; 63253; 29070; 63254; 63255; 63256; 63257; 63258; 63259; 29068; 29069; 29067; 63260; 63261; 32282; 32283; 63262; 65690; 63263; 1447; 63264; 63265; 63266; 31587; 19558; 10168; 20987; 63267; 32838; 53670; 29077; 26527; 29078; 63268; 63269; 29079; 29080; 63270; 63271; 63272; 63273; 63274; 63275; 63276; 29083; 29082; 29081; 63277; 63278; 63279; 63280; 29084; 29085; 63281; 63282; 23788; 23789; 23790; 63283; 63284; 63285; 30891; 63286; 65691; 15658; 29092; 63287; 63288; 32104; 63289; 63290; 63291; 29097; 63292; 63293; 29099; 29100; 29101; 29102; 63294; 63295; 29103; 10215; 63296; 63297; 29105; 63298; 63299; 63300; 63301; 29106; 26538; 29107; 63302; 63303; 63304; 65692; 29108; 10222; 63305; 29109; 63306; 63307; 29111; 63308; 63309; 29117; 17277; 14686; 29120; 63310; 63311; 29121; 29122; 63312; 63313; 29123; 10241; 12312; 12313; 12314; 12315; 12316; 6389; 6321; 586; 587; 585; 13695; 13696; 29124; 63314; 3202; 3203; 20380; 4475; 10250; 10251; 10252; 10253; 63315; 63316; 63317; 10257; 63318; 63319; 63320; 63321; 6469; 6472; 599; 600; 10285; 10286; 29127; 29128; 2290; 2292; 63322; 63323; 63324; 63325; 63326; 29133; 63327; 29134; 29135; 13018; 63328; 4486; 63329; 63330; 29136; 29137; 29138; 63331; 63332; 63333; 63334; 29142; 604; 63335; 21016; 29146; 63336; 29147; 29150; 29151; 63337; 29152; 63338; 63339; 63340; 4497; 29156; 29157; 29158; 29159; 29160; 29161; 63341; 65693; 1485; 10328; 63342; 29181; 23821; 63343; 63344; 53742; 63345; 10335; 63346; 29185; 63347; 63348; 10338; 10339; 10340; 63349; 618; 619; 29191; 29193; 29194; 63350; 63351; 29195; 16544; 63352; 63353; 63354; 13710; 29200; 29201; 29202; 29203; 29204; 26605; 53748; 16548; 16549; 16550; 7767; 63356; 63357; 63358; 63359; 65694; 65695; 29209; 29213; 29214; 29211; 29212; 29215;

63360; 29217; 29218; 29219; 29220; 63361; 63362; 29223; 29224; 56259; 63363; 63364; 7775; 63365; 63366; 63367; 633; 634; 29225; 29226; 29227; 14757; 14758; 14759; 29228; 63368; 63369; 10426; 63370; 22474; 23842; 23843; 23844; 23845; 23846; 14763; 639; 63371; 1511; 642; 18346; 18347; 18348; 18349; 18350; 63372; 63373; 10443; 10444; 3250; 63374; 63375; 29237; 29238; 63376; 63377; 63378; 4557; 29240; 4559; 63379; 29243; 29244; 29245; 63380; 63381; 63382; 652; 29246; 63383; 29248; 63384; 29250; 26631; 26632; 29251; 29254; 29253; 29252; 29255; 29256; 63385; 29258; 63386; 29259; 63387; 65696; 65697; 63388; 63389; 63390; 63391; 29260; 29261; 63392; 63393; 63394; 28626; 29263; 29264; 63395; 18357; 63396; 63397; 29267; 63398; 29268; 63399; 29270; 63400; 63401; 63402; 1524; 6583; 1525; 1526; 10505; 29277; 63403; 25090; 63404; 52890; 18371; 63405; 63406; 63407; 25590; 29283; 63408; 22507; 63409; 63410; 29287; 29288; 29289; 22509; 22510; 63411; 63412; 55447; 29292; 29294; 53801; 29296; 63413; 29297; 63414; 25101; 22517; 63415; 63416; 63417; 673; 674; 675; 2357; 2358; 29303; 63418; 63419; 63420; 63421; 29311; 63422; 63423; 65698; 65699; 676; 677; 63424; 29312; 63425; 63426; 63427; 29313; 29314; 63428; 29315; 63429; 63430; 63431; 7816; 63432; 29316; 63433; 63434; 63435; 29317; 29318; 12385; 29319; 29320; 29321; 29322; 63436; 63437; 63438; 3276; 3277; 26672; 63439; 63440; 25103; 63441; 63442; 63443; 63444; 63445; 63446; 29325; 63447; 29326; 29327; 14808; 4610; 29329; 29330; 29331; 63448; 63449; 29332; 6624; 1558; 63450; 4621; 4622; 63451; 29335; 63452; 63453; 63454; 29337; 29338; 63455; 63456; 63457; 18392; 29339; 63458; 63459; 63460; 29340; 29341; 63461; 4625; 63462; 63463; 21085; 29342; 29343; 29345; 63464; 29346; 13056; 29347; 63465; 29348; 63466; 29350; 29352; 63467; 10655; 29353; 29354; 63468; 63469; 63470; 63471; 29357; 29358; 29359; 29360; 29361; 29362; 63472; 63473; 63474; 63475; 63476; 63477; 63478; 63479; 63480; 29364; 63481; 13065; 63482; 63483; 63484; 63485; 63486; 17334; 29367; 65700; 63487; 29369; 29370; 6654; 63488; 63489; 29371; 63490; 29372; 29373; 63491; 63492; 63493; 63494; 29374; 63495; 713; 29376; 63496; 29377; 29380; 29381; 4649; 29386; 29387; 63497; 65701; 63498; 63499; 63500; 63501; 63502; 63503; 63504; 63505; 63506; 6659; 3314; 6661; 3315; 6660; 29388; 29389; 63507; 29391; 25115; 29392; 63508; 4655; 63509; 63510; 29393; 63511; 63512; 63513; 12407; 63514; 12408; 63515; 63516; 63517; 63518; 63519; 25613; 63520; 63521; 63522; 63523; 63524; 21102; 63525; 29398; 29400; 729; 63526; 4661; 29405; 13079; 63527; 29406; 63528; 63529; 63530; 63531; 29407; 17340; 17341; 26743; 26744; 63532; 63533; 63534; 63535; 63536; 65702; 63537; 22608; 29420; 63538; 29421; 63539; 29422; 29423; 29424; 29425; 63540.

The following SEQ ID NOs correspond to the polynucleotides encoding female sex organ, breast-specific proteins as described in Table 74A identified using SBS: 17025; 65771; 14099; 8321; 54808; 54809; 17063; 17064; 17080; 54810; 54811; 54812; 54813; 54814; 54815; 54816; 54817; 54818; 54819; 32266; 32267; 54820; 54821; 9008; 17132; 65654; 65655; 54822; 17152; 17153; 24429; 17171; 17172.

The following SEQ ID NOs correspond to the amino acid sequences of female sex organ, breast-specific proteins as described in Table 74A identified using SBS: 17185; 65772; 14513; 9649; 54823; 54824; 17223; 17224; 17240; 54825; 54826; 54827; 54828; 54829; 54830; 54831; 54832; 54833; 54834; 32280; 32281; 54835; 54836; 10336; 17292; 65694; 65695; 54837; 17312; 17313; 24559; 17331; 17332.

The following SEQ ID NOs correspond to the polynucleotides encoding female sex organ, cervix-specific proteins as described in Table 75A identified using SBS: 14134; 32022; 54868; 21644; 65777; 65778; 65779; 65780; 65781; 65782; 14256; 54869; 54870; 54871; 65783; 54872; 54873; 54874.

The following SEQ ID NOs correspond to the amino acid sequences of female sex organ, cervix-specific proteins as described in Table 75A identified using SBS: 14548; 32085; 54875; 22231; 65784; 65785; 65786; 65787; 65788; 65789; 14670; 54876; 54877; 54878; 65790; 54879; 54880; 54881.

The following SEQ ID NOs correspond to the polynucleotides encoding female sex organ, ovary-specific proteins as described in Table 76A identified using SBS: 65793; 58733; 58734; 58735; 58736; 14166; 58737; 65642; 27821; 58738; 58739; 65646; 58740; 58741; 65649; 58742; 32270; 28222; 58743; 58744; 58745; 58746.

The following SEQ ID NOs correspond to the amino acid sequences of female sex organ, ovary-specific proteins as described in Table 76A identified using SBS: 65794; 58747; 58748; 58749; 58750; 14580; 58751; 65682; 28823; 58752; 58753; 65686; 58754; 58755; 65689; 58756; 32284; 29224; 58757; 58758; 58759; 58760.

The following SEQ ID NOs correspond to the polynucleotides encoding female sex organ, uterus-specific proteins as described in Table 77A identified using SBS: 27431; 65630; 65631; 65632; 65633; 32017; 65797; 65466; 32033; 65467; 65468; 65469; 65470; 65471; 65472; 65473; 65474; 65475; 65476; 28302; 28304; 28307; 28308; 65477; 65478; 65479; 32062; 65480; 65798.

The following SEQ ID NOs correspond to the amino acid sequences of female sex organ, uterus-specific proteins as described in Table 77A identified using SBS: 28433; 65670; 65671; 65672; 65673; 32080; 65799; 65481; 32096; 65482; 65483; 65484; 65485; 65486; 65487; 65488; 65489; 65490; 65491; 29304; 29306; 29309; 29310; 65492; 65493; 65494; 32125; 65495; 65800.

The following SEQ ID NOs correspond to the amino acid sequences of adrenal gland-specific proteins identified using SBS that have also been identified by mass spectrometry as described in Table 78A: 52880; 388; 449; 459; 479; 480; 541; 52888; 574; 649; 648; 52890; 52891.

The following SEQ ID NOs correspond to the amino acid sequences of bladder-specific proteins identified using SBS that have also been identified by mass spectrometry as described in Table 78A: 53001; 22128; 1470; 1471; 4654.

The following SEQ ID NOs correspond to the amino acid sequences of brain-specific proteins identified using SBS that have also been identified by mass spectrometry as described in Table 78A: 2095; 2096; 2097; 53446; 53449; 53456; 12175; 12176; 53461; 23617; 16313; 53464; 9519; 5946; 3003; 9529; 53469; 3007; 53470; 53481; 3023; 53488; 4208; 5987; 5988; 5989; 53491; 4211; 4213; 4215; 53493; 22102; 53499; 7605; 32081; 53508; 9640; 25504; 53511; 53512; 53513; 9662; 53514; 9665; 53518; 9682; 53520; 20319; 53523; 53524; 53525; 53526; 6057; 6060; 6061; 6064; 53533; 1390; 9809; 53542; 9864; 9868; 9877; 53560; 4304; 53561; 53562; 7662; 7668; 3093; 9908; 9909; 9910; 9911; 53571; 9914; 53574; 53575; 9915; 9916; 53580; 53582; 4336; 53583; 53584; 28820; 28821; 53586; 53590; 9999; 19523; 10019; 10020; 53604; 53605; 53608; 53611; 3141; 53665; 53666; 53667; 29074; 53674; 53675; 13004; 13005; 53676; 53677; 53678; 53679; 53680; 53686; 53687; 53688; 53692; 53693; 53695; 10213; 53700; 10240; 4466; 12317; 53708; 53710; 53712; 1482; 53718; 53719; 13014; 13015; 6470; 25566; 12324; 10277; 53722; 53723; 10278; 4487; 23814; 23815; 53730; 53731; 53733; 17288; 612; 613; 20386; 4503; 53744; 3234; 23837; 53773; 12363; 53777; 53780; 53790; 53791; 29286; 668; 53796; 53798; 13047; 53801; 53802; 3270; 29302; 53808; 25594; 53810; 4608;

4609; 53815; 53816; 3283; 53828; 19710; 3297; 4630; 3307; 53835; 1577; 4641; 53838; 22575; 53839; 3314; 3315.

The following SEQ ID NOs correspond to the amino acid sequences of breast-specific proteins identified using SBS that have also been identified by mass spectrometry as described in Table 78A: 17185; 54829; 54831; 54832; 17292; 17312; 17313; 17332.

The following SEQ ID NOs correspond to the amino acid sequences of cervix-specific proteins identified using SBS that have also been identified by mass spectrometry as described in Table 78A: 14670; 54876; 54877; 54878; 54880.

The following SEQ ID NOs correspond to the amino acid sequences of heart-specific proteins identified using SBS that have also been identified by mass spectrometry as described in Table 78A: 1313; 14454; 9460; 54932; 4211; 4213; 4215; 14512; 14517; 28771; 14668; 14691; 14702; 14707; 14709; 14710; 54946; 54947; 54948; 54949; 14777; 14787; 20404; 1568; 1569; 1570; 1571; 1572; 1574; 3308; 3309; 3311; 3312.

The following SEQ ID NOs correspond to the amino acid sequences of kidney-specific proteins identified using SBS that have also been identified by mass spectrometry as described in Table 78A: 12879; 12880; 55325; 55330; 26339; 23641; 14508; 55340; 55342; 55343; 55345; 55346; 55347; 55351; 55356; 55358; 55362; 55363; 2242; 55364; 55366; 55367; 55368; 55369; 55370; 55371; 55372; 55373; 32834; 32835; 28859; 17261; 17259; 17258; 25018; 20962; 55379; 55380; 55381; 55423; 32543; 55429; 15674; 15675; 15676; 15677; 15678; 31612; 31613; 31614; 31615; 31616; 23817; 15683; 16580; 16581; 55440; 55441; 55448; 3292; 55452; 21083; 2372; 55457; 55458.

The following SEQ ID NOs correspond to the amino acid sequences of liver-specific proteins identified using SBS that have also been identified by mass spectrometry as described in Table 78A: 55998; 56000; 56001; 56002; 56003; 56004; 12162; 56006; 56011; 5922; 1319; 56015; 56016; 56017; 56018; 20280; 17976; 17977; 56019; 9485; 56020; 56022; 15569; 20852; 56023; 56024; 56025; 4147; 386; 56026; 9500; 56027; 56028; 56029; 2113; 56031; 56032; 56033; 56034; 56036; 56037; 56038; 56039; 5976; 56042; 56043; 56044; 56045; 56046; 56047; 56048; 56049; 56050; 56051; 56052; 56053; 31530; 31529; 56059; 19418; 56060; 423; 56061; 56062; 56063; 23646; 23647; 56066; 56067; 56068; 56069; 56070; 56071; 56072; 56074; 56078; 56079; 56087; 24978; 24979; 24980; 2177; 56093; 56096; 20887; 2185; 56099; 13611; 56100; 56102; 56103; 25520; 23688; 56104; 13612; 56106; 56108; 56109; 56110; 56111; 56113; 56114; 56122; 56123; 56128; 56136; 56141; 19509; 56142; 56146; 14612; 56150; 56151; 15629; 56152; 56162; 56163; 56164; 56165; 56167; 15645; 56169; 56209; 56210; 56211; 56212; 56213; 56214; 56220; 56222; 56223; 56224; 56225; 56226; 14669; 56227; 56228; 56229; 56230; 7726; 2274; 56232; 13014; 13015; 56239; 56240; 26578; 56246; 56247; 56248; 56249; 56251; 56252; 56253; 56254; 56255; 56256; 15692; 56258; 56260; 56262; 56263; 56265; 56266; 56267; 56268; 17312; 17313; 56273; 13743; 13744; 13742; 56276; 56277; 56278; 56280; 56281; 56282; 56283; 56284; 56285; 10517; 56289; 56290; 56295; 56298; 14791; 56299; 56300; 687; 7844; 13071; 56310; 56311; 15721; 27388; 13793.

The following SEQ ID NOs correspond to the amino acid sequences of lung-specific proteins identified using SBS that have also been identified by mass spectrometry as described in Table 78A: 57229; 57232; 57233; 13591; 16384; 16385; 16412; 16413; 57242; 57243; 22218; 16451; 16459; 57275; 57284; 26647; 57286; 57288; 3284; 3285; 57290.

The following SEQ ID NOs correspond to the amino acid sequences of lymph node-specific proteins identified using SBS that have also been identified by mass spectrometry as described in Table 78A: 26363; 26364; 57462; 57463; 57464; 2250; 26503; 2256; 2258; 26504; 2260; 26505; 57467; 57468; 57469; 2262; 2266; 2267; 57474.

The following SEQ ID NOs correspond to the amino acid sequences of lymphocyte-specific proteins identified using SBS that have also been identified by mass spectrometry as described in Table 78A: 9528; 30736; 30737; 57636; 32496; 12212; 57645; 57646; 57650; 26351; 57651; 57652; 57653; 57669; 57671; 57676; 57681; 26448; 57686; 9984; 57687; 57696; 57697; 57699; 28867; 57703; 57723; 57724; 19601; 57733; 6541; 6542; 6544; 6545; 57738; 57739; 57740; 3297; 57745; 57747.

The following SEQ ID NOs correspond to the amino acid sequences of monocyte-specific proteins identified using SBS that have also been identified by mass spectrometry as described in Table 78A: 19373; 19374; 19375; 19376; 19377; 57651; 26356; 1369; 14621; 19535; 57949; 18175; 57951; 57952; 2271; 10294; 16541; 19608; 7756; 7757; 2306; 19612; 20394; 10559; 19720; 57979.

The following SEQ ID NOs correspond to the amino acid sequences of muscle-specific proteins identified using SBS that have also been identified by mass spectrometry as described in Table 78A: 2095; 2096; 2097; 1313; 9460; 58201; 58202; 58203; 58204; 58205; 58206; 14458; 14459; 14460; 14461; 58208; 9520; 9521; 9522; 9523; 22101; 58218; 58219; 58220; 14511; 14516; 14517; 58230; 1388; 1389; 14556; 14555; 58235; 58239; 58242; 14644; 58270; 58278; 58279; 14673; 14671; 14672; 10199; 22387; 22388; 22389; 22390; 31598; 10238; 31599; 31601; 31602; 14693; 3200; 14709; 14710; 58291; 58292; 58293; 58294; 58295; 58296; 58297; 14735; 58299; 2317; 14772; 58310; 3263; 58314; 58315; 58316; 10606; 58320; 58328; 1575; 1576; 18403; 14835; 3308; 3309; 3310; 3311; 3312; 1590.

The following SEQ ID NOs correspond to the amino acid sequences of ovary-specific proteins identified using SBS that have also been identified by mass spectrometry as described in Table 78A: 58747; 58748; 58749; 58751; 58753; 58755; 32284.

The following SEQ ID NOs correspond to the amino acid sequences of pancreas-specific proteins identified using SBS that have also been identified by mass spectrometry as described in Table 78A: 18875; 18874; 18876; 18873; 17978; 58866; 58868; 58869; 6011; 58871; 18881; 58880; 58881; 58882; 58883; 13654; 58907; 25068; 58917; 20386; 13717; 18895; 58922; 58923; 25081; 25080; 20395; 58925; 18901; 58928; 1540; 58932; 58933; 58935.

The following SEQ ID NOs correspond to the amino acid sequences of prostate-specific proteins identified using SBS that have also been identified by mass spectrometry as described in Table 78A: 13537; 22031; 22032; 17187; 22047; 4165; 15579; 59342; 59343; 59344; 59345; 59346; 59347; 20311; 22144; 22146; 22147; 59357; 55371; 55372; 55373; 22252; 22253; 22254; 22255; 22257; 22259; 1442; 1443; 6225; 17263; 6226; 59361; 59362; 59363; 59364; 59365; 59366; 59367; 20969; 24519; 22313; 22318; 22319; 22320; 22324; 22329; 22373; 22387; 22388; 22389; 22390; 30938; 22499; 22500; 59403; 59404; 59405; 59406; 59407; 22519; 22547; 22559; 59410.

The following SEQ ID NOs correspond to the amino acid sequences of skin-specific proteins identified using SBS that have also been identified by mass spectrometry as described in Table 78A: 59814; 59815; 59820; 32491; 32490; 59825; 24448; 24450; 30746; 59826; 59827; 59828; 59346; 59347; 59831; 59832; 59833; 59838; 59839; 59840; 59841; 59842; 59843; 466; 3055; 3056; 3057; 3058; 59845; 59847; 59851; 59852; 59856; 59357; 59870; 59871; 59872; 59873; 59874;

59875; 59878; 59881; 59882; 59886; 59887; 17262; 59888; 59889; 59890; 59891; 59892; 59893; 59894; 59895; 6225; 17263; 6226; 59896; 59897; 59900; 59912; 30817; 59914; 20963; 59362; 59363; 59364; 59365; 59924; 59925; 59951; 59958; 59965; 59967; 59968; 59969; 59973; 59974; 59977; 24540; 59978; 59979; 59981; 24545; 59984; 21042; 59987; 59988; 30938; 59989; 59991; 59992; 59403; 59405; 59997; 30960; 25597; 25598; 60005; 60007; 60012; 60013; 60014; 23916; 60016; 60017; 60018; 60025; 60026.

The following SEQ ID NOs correspond to the amino acid sequences of small intestine-specific proteins identified using SBS that have also been identified by mass spectrometry as described in Table 78A: 12878; 60534; 20843; 60536; 60539; 24920; 20280; 15568; 60544; 60545; 4147; 60546; 24963; 60571; 60572; 60573; 60574; 60576; 60578; 60579; 25526; 25527; 60590; 60596; 13655; 60606; 60608; 2257; 57467; 2268; 56209; 56210; 60621; 60622; 60623; 60624; 13679; 60627; 15659; 60637; 60638; 60639; 25064; 60643; 60644; 25068; 24539; 13709; 60650; 25076; 25092; 13750; 60668; 12376; 60669; 16621; 13779; 60682; 7847; 13792; 27388; 13793.

The following SEQ ID NOs correspond to the amino acid sequences of spleen-specific proteins identified using SBS that have also been identified by mass spectrometry as described in Table 78A: 2136; 26350; 61144; 2177; 56093; 61145; 2227; 2228; 61149; 61150; 2252; 2253; 61157; 2259; 2261; 56213; 18267; 61163; 12323; 61167; 26673.

The following SEQ ID NOs correspond to the amino acid sequences of stomach-specific proteins identified using SBS that have also been identified by mass spectrometry as described in Table 78A: 61304; 61311; 61312; 16384; 16385; 61323; 61333; 61351; 61352; 61357; 27382.

The following SEQ ID NOs correspond to the amino acid sequences of testes-specific proteins identified using SBS that have also been identified by mass spectrometry as described in Table 78A: 62513; 28427; 62520; 9450; 9451; 9452; 9453; 9454; 9455; 9456; 9457; 9458; 62524; 5922; 5924; 62527; 28437; 28438; 28439; 62534; 9495; 28452; 62539; 2112; 62541; 22056; 28459; 3001; 28465; 13544; 13545; 9546; 28483; 28484; 62550; 62551; 62552; 19371; 62553; 62554; 28495; 24942; 62566; 28501; 28504; 62575; 62578; 62583; 28513; 62594; 62597; 62598; 12896; 28520; 9574; 62606; 28541; 28542; 28548; 4206; 62635; 62643; 62644; 20858; 28564; 28568; 28566; 28569; 28570; 28576; 28577; 62647; 3033; 28581; 20869; 1358; 16383; 23654; 62674; 28622; 28625; 28627; 29262; 30762; 62689; 62691; 28634; 62696; 62697; 62698; 62699; 62706; 28651; 28660; 62719; 59842; 62723; 28675; 28676; 62725; 9754; 62727; 6071; 1388; 1389; 62730; 4281; 4280; 4282; 62737; 2192; 62738; 9828; 28710; 28729; 62762; 62763; 18094; 18092; 18093; 28748; 28755; 28756; 28757; 28759; 28777; 62803; 19495; 28784; 62807; 62818; 62819; 6126; 62823; 62824; 3099; 28816; 62827; 62828; 28817; 16448; 32529; 32530; 28820; 28821; 15634; 62838; 9985; 14627; 22244; 28856; 28858; 62850; 28870; 62852; 62853; 62855; 3148; 62856; 62858; 28876; 62886; 62887; 28921; 28934; 28940; 28959; 28961; 62944; 62945; 22293; 63004; 63097; 63107; 63123; 63131; 63213; 63215; 63216; 63217; 63237; 29065; 32283; 63263; 1447; 29077; 26527; 29078; 63268; 63279; 29085; 15658; 29092; 63287; 63292; 29101; 63298; 26538; 63304; 29109; 63308; 29121; 63312; 63313; 13695; 13696; 3202; 3203; 4475; 63317; 6472; 10285; 10286; 29128; 2290; 2292; 63324; 63325; 63335; 63336; 29159; 1485; 63345; 29185; 10338; 63350; 63351; 29195; 63353; 16548; 16549; 7767; 29217; 63364; 29225; 29226; 29227; 14757; 14758; 10426; 22474; 639; 642; 10444; 4559; 63382; 29258; 63386; 63390; 29261; 28626; 29263; 63401; 63402; 1526; 63403; 25090; 52890; 18371; 22507; 22509; 22510; 673; 674; 675; 2357; 2358; 63419; 676; 63424; 29314; 63435; 29319; 3276; 3277; 6624; 63452; 63453; 63454; 18392; 63460; 29354; 63468; 29364; 13065; 63483; 63484; 63489; 713; 29376; 63496; 4649; 29387; 63497; 3314; 3315; 29388; 29391; 4655; 63518; 63520; 63521; 63529; 63531; 29423; 29424; 29425.

The following SEQ ID NOs correspond to the amino acid sequences of trachea-specific proteins identified using SBS that have also been identified by mass spectrometry as described in Table 78A: 31511; 65263; 65265; 31891; 28581; 65276; 12230; 18065; 2245; 65305; 2269; 16511; 16512; 31920; 65310; 59977; 31926; 65314; 25096; 10640; 31654; 22592.

The following SEQ ID NOs correspond to the amino acid sequences of uterus-specific proteins identified using SBS that have also been identified by mass spectrometry as described in Table 78A: 28433; 65481; 32096.

The following SEQ ID NOs correspond to the amino acid sequences of sex organ, prostate-specific proteins identified using SBS that have also been identified by mass spectrometry as described in Table 79A: 384; 1351; 59346; 59347; 65564; 65565; 14604; 65566; 65567; 65568; 65569; 65570; 4329; 59357; 6225; 17263; 6226; 59362; 59363; 59364; 59365; 65577; 65578; 65585; 65587; 65588; 65589; 14670; 30938; 65605; 65606; 4577; 59403; 59405; 22526.

The following SEQ ID NOs correspond to the amino acid sequences of sex organ, testes-specific proteins identified using SBS that have also been identified by mass spectrometry as described in Table 79A: 65663; 65664; 65665; 28458; 65667; 401; 65670; 65671; 65672; 65673; 28581; 9651; 65678; 9746; 9747; 12315; 12316; 65694; 65695; 1511; 53801.

The following SEQ ID NOs correspond to the amino acid sequences of sex organ, breast-specific proteins identified using SBS that have also been identified by mass spectrometry as described in Table 79A: 10336; 65694; 65695; 17312; 17313.

The following SEQ ID NO correspond to the amino acid sequences of sex organ, cervix-specific proteins identified using SBS that have also been identified by mass spectrometry as described in Table 79A: 14670.

The following SEQ ID NOs correspond to the amino acid sequences of sex organ, uterus-specific proteins identified using SBS that have also been identified by mass spectrometry as described in Table 79A: 65670; 65671; 65672; 65673; 65799.

SEQ ID NOs:32935-52639 correspond to amino acid sequences of peptides previously identified by mass spectrometry that map to the organ-specific proteins as described in Table 43B.

SEQ ID NOs:52640-52699 correspond to amino acid sequences of peptides previously identified by mass spectrometry that map to the organ-specific proteins as described in Table 44B.

SEQ ID NOs:52700-52864 correspond to amino acid sequences of peptides previously identified by mass spectrometry that map to the organ-specific proteins as described in Table 45B.

SEQ ID NOs:65803-72641 correspond to amino acid sequences of peptides previously identified by mass spectrometry that map to the organ-specific proteins as described in Table 78B.

SEQ ID NOs:72642-72688 correspond to amino acid sequences of peptides previously identified by mass spectrometry that map to the organ-specific proteins as described in Table 79B.

DETAILED DESCRIPTION OF THE INVENTION

The present invention relates generally to organ-specific proteins and polynucleotides that encode them. In particular the invention relates to diagnostic panels comprising reagents to detect organ-specific proteins or polynucleotides and methods of identifying and using the same.

Because the blood bathes all of the organs of the body, the blood contains, as noted above, proteins that are secreted, leaked, excreted or shed from the cells of all the organs in the body. These proteins can provide information about the organs and serve as reporter groups or markers that accurately reflect the health or disease state of each organ or groups of organs. This is because under ordinary conditions the levels of these organ-specific proteins secreted or shed into the blood may attain normal levels, whereas under disease conditions the levels of the proteins may change, reflecting the altered behavior (e.g., control of protein expression) of the disease-perturbed networks in the disease organ. Thus the levels or organ-specific proteins in the blood will be altered with health and disease and, indeed, may be specifically altered for each type of disease for a particular organ and each stage of progression for each disease. Highly sensitive blood-protein diagnostics of organ-specific fingerprints could be used to detect the early stages of disease and monitor treatment when therapeutic intervention is most effective. Specific proteins in blood may be used as markers to diagnose disease at the earliest stages. Expression array studies have shown that such proteins, or protein panels, exist in cells and can serve as markers of disease progression or disease prognosis (E. E. Schadt et al., *Nat Genet* (2005) 37: 710, H. Dai et al., *Cancer Res* (2005) 65: 4059). However, specifically identifying such proteins has proved difficult. Particularly, when attempting to detect those proteins that are tissue or organ specific as well as secreted.

A systems view of disease is predicated upon a very simple idea—that disease arises from biological networks that have been disease perturbed either by gene mutations or pathogenic environmental signals (e.g., infections). These perturbed networks alter the expression levels of proteins they encode and these lead to the pathological symptoms of disease. Furthermore, a fraction of these proteins are expressed only by the organ of interest (are organ-specific) and it is postulated are secreted (or shed or deposited after cell destruction, etc) into the blood with distinct levels that correlate with health and each type of disease occurring in the organ. Thus each human organ or tissue type has a unique molecular fingerprint in the blood comprising distinct levels of organ-specific proteins. Blood, itself, may be considered an organ that circulates throughout the body and is in contact with all other organs and the protein concentrations or the organ-specific fingerprints serve as a diagnostic vehicle to measure the state of health or disease of a subject. Although, blood is a medium to measure the state of health and disease, significant limitations exist with current diagnostic assays that delay or prevent early diagnosis when it would be most effective.

Early diagnosis of disease by measuring changes in proteins in the blood would lead to earlier treatment and therefore healthier outcomes for patients. The determination of predetermined normal ranges of low abundance proteins in healthy organs gives diagnosticians a crucial advantage in health care: the potential to define disease at the earliest stages and initiate treatment when it may be most effective. If the organ-specific proteins that are normally found within a healthy organ could be identified and measured, the diagnostician would have the distinct advantage of comparing a patient sample to a set of expected normal values of blood proteins that are typically found in a state of health in an organ.

This invention pre-defines normal organ-specific protein sets specifically identified and quantified for each of multiple healthy human organs and major tissue types. These organ-specific proteins identified from healthy human organs may, in whole or in part, be used as markers or identifiers for health and disease. The levels of these organ-specific proteins in blood from diseased individuals may be distinguished from the levels of these organ-specific proteins in the blood of healthy individuals. By identifying organ-specific protein markers and measuring the level of these proteins in normal blood, the status of health or disease may be monitored through the correlation of the levels of proteins in this organ-specific fingerprint at the earliest stages of disease and lead to early diagnosis and treatment.

Thus, the present invention provides organ-specific proteins that serve as markers to measure changes in the status of an organ or organs to measure health and diagnose disease. The inventive markers, obtained from normal, healthy organ tissue (see Tables 1-32, 36-45 and 47-79) are used as a library of biological indicators to identify organ-specific blood proteins that are secreted, leaked, excreted or shed into blood in a human or mammal. Such markers can be used individually or collectively. For example a single marker for an organ or tissue could be used to monitor that organ or tissue. However, adding additional markers from that tissue to the assay will improve the diagnostic power as well as the sensitivity of the assay. Further, one of skill in the art can readily appreciate that probes to such markers, be they nucleic acid probes, nanoparticles, or polypeptides (e.g., antibodies) can comprise a kit, lateral flow test kit or an array and can include a few probes to proteins from several organs or several probes to proteins from one organ or tissue. For example, in one kit or assay device a whole body health assay may be used wherein several markers are tracked for every organ and when one or more organ or tissue demonstrates a deviation from normal a more rigorous test is performed with many more markers for that organ or tissue. Likewise, entire organ set assays may be devised. In such an example a cardiovascular assay may be employed wherein tissue/organ-specific markers from heart and lung are the basis of the assay kit.

One of skill in the art can readily appreciate that the application of these marker sets that are tissue and organ-specific are virtually limitless. From using as diagositic and prognostic indicators, to use in following drug treatment or in drug discovery to determine what proteins and genes are affected. Further, such markers can easily be used in combination with antibodies for other ligands for drug targeting or imaging via MRI or PET or by other means. In such examples, a marker specific for prostate could form the basis for targeted cancer therapy or possible imaging/therapy of metastatic cancer derived from prostate. The comparison of the normal levels of organ-specific proteins to the levels of these proteins found in a sample of patient blood or bodily fluid or other biological sample, such as a biopsy can be used to define normal health, detect the early stages of disease, monitor treatment, prognosticate disease, measure drug responses, titrate administered drug doses, evaluate efficacy, stratify patients according to disease type (e.g., prostate cancer may well have four or more major types) and define therapeutic targets when therapeutic intervention is most effective. This invention provides pre-defined normal organ-specific proteins and protein sets that have been specifically identified and quantified for each of 32 or more healthy, human organs examined. These organ-specific proteins identified from healthy, human organs may be used as markers or identifiers for health and disease and/or may be distinguished from constitutive proteins in the blood, fluid, or tissue. By using the approach of comparing the proteins found in a sample of blood with the organ-specific protein markers that have been identified as specific to a healthy organ, the status of health or disease may be monitored at the earliest stage and lead to early diagnosis and treatment.

When there is a change in health status that affects an organ, the blood fingerprint that is measured is reflective of the particular target organ. Proteins that comprise the organ-specific blood fingerprint will either increase or decrease in level in response to the changes brought by the stimulus of the disease. The increase or decrease in the amount in blood (or components specific for a cell, tissue or organ) of the components of the organ-specific blood fingerprint may be quantified by antibodies (or other specific protein-capture agents) specific for the proteins, by proteomic techniques (e.g., mass spectrometry) or by measurement with microfluidic and/or nanotechnology sensors and compared to the normal level of the organ-specific proteins. The disease-perturbed networks may alter the expression patterns of virtually any different type of proteins—those involved in signal transduction pathways, those involved in the execution of cellular differentiation, those involved in the response to physiological stimuli, those involved in the normal cellular functions such as the cell cycle, etc, and those involved in mediating whom cells will interact with or where they will migrate. When disease strikes an organ, the physical response may, for example, involve changes in the proteins that connect together in biological signal transduction networks to send information to other protein effector proteins also altering their levels of expression. These signal transduction pathways communicate changes in the body in response to a stimulus or disease. These signal transduction pathways also serve as a response network to a stimulus or disease. An example of a response network to a disease is the inflammatory pathway mediated by Phospholipase A2 (PLA2). PLA2 is modulated and may be used as a marker in the diagnosis of cardiovascular disease (Sudhir, K., *J Clin Endocrinol Metab* (2005) 90:3100-5), arteriosclerosis (Smitzko, et al., *Circulation* (2003), 108: 2041-2048; Sunara et al., *Cell Mol Life Sci* (2005) 62:2487-2494)), neurodegenerative disease (Farooqui et al., *Neurchem Res*, (2004), 11:1961-1977), allergic disease (Triggiani et al., *Journal of Allergy and Clinical Immunology*, (2005) 116: 1000-1006). Another example of effector protein changes that may be measured by blood fingerprints is the regulation of map kinase in response to cardiovascular disease or in certain cancers or tumors, including prostate cancer (Kopper at al., *Pathology of Oncology Research* (2005), 11:197203). Changes in signaling proteins serve as biological markers or blood fingerprints that may be used to diagnose or monitor disease.

As one of skill in the art can readily appreciate, certain aspects of the present invention refer to known protein and nucleic acid sequences. Wherein such sequences are included in a diagnostic or prognostic panel and have previously been described as indicative of disease or perturbation of that organ the inventive panel should comprise at least one additional organ-specific marker (nucleic acid or polypeptide sequence or detection reagent thereto). Accordingly, wherein a known sequence, either nucleic acid or polypeptide sequence, is included in a panel or mixture and wherein said sequence has been demonstrated by the art to be previously associated with the particular organ and/or indicative of perturbation such sequences should also be associated with at least one sequence not previously specifically associated with the organ and/or disease/perturbation.

Prior to setting forth the invention in further detail, it may be helpful to an understanding thereof to set forth definitions of certain terms that will be used hereinafter.

The term "blood" refers to whole blood, plasma or serum obtained from a mammal.

In the practice of the invention, an "individual" or "subject" refers to vertebrates, particularly members of a mammalian species, and includes, but is not limited to, primates, including human and non-human primates, domestic animals, and sports animals.

"Component" or "member" of a set refers to an individual constituent protein, peptide, nucleotide or polynucleotide of an organ-specific set.

As used herein an "organ-specific protein set" is made up of the set of organ-specific proteins identified from an organ sample obtained from a normal, healthy individual using the methods described herein (see, e.g., Example 1 and Example 9). Illustrative organ-specific protein sets are provided in Tables 1-32, 36-45 and 47-79 and were identified using analysis of MPSS transcripts as described further herein and using sequencing by synthesis (SBS) analysis as described further herein. Individual proteins that make up the set are referred to herein as components or members of the set. In the examples and recitation below, blood is used as the prototypic example, however, it should be understood that any biological fluid or sample may be exchanged for the terms blood, serum, or plasma. Accordingly, normal organ-specific blood fingerprint can be exchanged with "organ-specific saliva/urine/tissue, etc. fingerprint".

As used herein, a "normal serum organ-specific protein set" comprises the subset of proteins from an organ-specific protein set that are detected in normal serum. Individual proteins that make up the set are referred to herein as components or members of the set.

As used herein, a "normal organ-specific blood fingerprint" is a data set comprising the determined levels in blood from normal, healthy individuals of one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, sixty, seventy, eighty, ninety, one-hundred or more components of a serum organ-specific protein set of one organ, but could comprise multiples thereof if more than one organ is analyzed. The normal levels in the blood for each component included in a fingerprint are determined by measuring the level of protein in the blood using any of a variety of techniques known in the art and described herein, in a sufficient number of blood samples from normal, healthy individuals to determine the standard deviation (SD) with statistically meaningful accuracy. Thus, as would be recognized by one of skill in the art, a determined normal level is defined by averaging the level of protein measured in a statistically large number of blood samples from normal, healthy individuals and thereby defining a statistical range of normal. A normal organ-specific blood fingerprint comprises the determined levels in normal, healthy blood of N members of a serum organ-specific protein set wherein N is 1, 2, 3, 4, 5, 6, 7, 8, 9, 10, 11, 12, 13, 14, 15, or more members up to the total number of members in a given serum organ-specific protein set per organ being profiled. In certain embodiments, a normal organ-specific blood fingerprint comprises the determined levels in normal, healthy blood of at least two components of a serum organ-specific protein set. In other embodiments, a normal organ-specific blood fingerprint comprises the determined levels in normal, healthy blood of at least 3, 4, 5, 6, 7, 8, 9, 10, 11, 12, 13, 14, 15, 16, 17, 18, 19, or 20 components of a serum organ-specific protein set. In yet further embodiments, a normal organ-specific blood fingerprint comprises the presence or absence of organ, cell or tissue-specific proteins or transcripts and may or may not rely on absolute levels of said components per se. In specific embodiments, merely a change over a baseline measurement for a particular individual may be used. In such an embodiment, levels or mere presence or absence of proteins or transcripts from blood, body fluid or tissue may be measured at one time point and then compared to a subsequent measurement, hours, days, months or years later. Accordingly, normal changes per individual can be zeroed out and only those proteins or transcripts that change over time are focused on.

As used herein, a "predetermined normal level" is an average of the levels of a given component measured in a statistically large number of blood samples from normal, healthy individuals. Thus, a predetermined normal level is a statistical range of normal and is also referred to herein as "predetermined normal range". The normal levels or range of levels in the blood for each component are determined by measuring the level of protein in the blood using any of a variety of techniques known in the art and described herein in a sufficient number of blood samples from normal, healthy individuals to determine the standard deviation (SD) with statistically meaningful accuracy. In one embodiment it may be useful to determine average levels for individual falling into different age groups (e.g. 1-2, 3-5, 6-8, 9-12 and so forth if, indeed, these levels change with age). In another embodiment, one may also want to determine the levels at certain times of the day, at certain times from having eaten a meal, etc. One may also determine how common physiological stimuli affect the organ-specific blood fingerprints.

As used herein a "disease-associated organ-specific blood fingerprint" is a data set comprising the determined level in a blood sample from an individual afflicted with a disease of one or more components of a normal serum organ-specific protein set that demonstrates a statistically significant change as compared to the determined normal level (e.g., wherein the level in the disease sample is above or below a predetermined normal range). The data set is compiled from samples from individuals who are determined to have a particular disease using established medical diagnostics for the particular disease. The blood (serum) level of each protein member of a normal serum organ-specific protein set as measured in the blood of the diseased sample is compared to the corresponding determined normal level. A statistically significant variation from the determined normal level for one or more members of the normal serum organ-specific protein set provides diagnostically useful information (disease-associated fingerprint) for that disease. Thus, note that it may be determined for a particular disease or disease state that the level of only a few members of the normal serum organ-specific protein set change relative to the normal levels. Thus, a disease-associated organ-specific blood fingerprint may comprise the determined levels in the blood of only a subset of the components of a normal serum organ-specific protein set for a given organ and a particular disease. Thus, a disease-associated organ-specific blood fingerprint comprises the determined levels in blood (or as noted herein any bodily fluid or tissue sample, however in most embodiments samples from blood are compared with a normal from blood and so on) of N members of a serum organ-specific protein set wherein N is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or more or any integer value therebetween, or more members up to the total number of members in a given serum organ-specific protein set. In this regard, in certain embodiments, a disease-associated organ-specific blood fingerprint comprises the determined levels of one or more components of a normal serum organ-specific protein set. In one embodiment, a disease-associated organ-specific blood fingerprint comprises the determined levels of at least two components of a normal serum organ-specific protein set. In other embodiments, a disease-associated organ-specific blood fingerprint comprises the determined levels of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or more or any integer value therebetween components of a normal serum organ-specific protein set.

The term "test compound" refers in general to a compound to which a test cell is exposed, about which one desires to collect data. Typical test compounds will be small organic molecules, typically prospective pharmaceutical lead compounds, but can include proteins (e.g., antibodies), peptides, polynucleotides, heterologous genes (in expression systems), plasmids, polynucleotide analogs, peptide analogs, lipids, carbohydrates, viruses, phage, parasites, and the like.

The term "biological activity" as used herein refers to the ability of a test compound to alter the expression of one or more genes or proteins.

The term "test cell" refers to a biological system or a model of a biological system capable of reacting to the presence of a test compound, typically a eukaryotic cell or tissue sample, or a prokaryotic organism.

The term "gene expression profile" refers to a representation of the expression level of a plurality of genes in response to a selected expression condition (for example, incubation in the presence of a standard compound or test compound). Gene expression profiles can be expressed in terms of an absolute quantity of mRNA transcribed for each gene, as a ratio of mRNA transcribed in a test cell as compared with a control cell, and the like or the mere presence or absence of a protein an RNA transcript or more generally gene expression. As used herein, a "standard" gene expression profile refers to a profile already present in the primary database (for example, a profile obtained by incubation of a test cell with a standard compound, such as a drug of known activity), while a "test" gene expression profile refers to a profile generated under the conditions being investigated. The term "modulated" refers to an alteration in the expression level (induction or repression) to a measurable or detectable degree, as compared to a pre-established standard (for example, the expression level of a selected tissue or cell type at a selected phase under selected conditions).

"Similar", as used herein, refers to a degree of difference between two quantities that is within a preselected threshold. The similarity of two profiles can be defined in a number of different ways, for example in terms of the number of identical genes affected, the degree to which each gene is affected, and the like. Several different measures of similarity, or methods of scoring similarity, can be made available to the user: for example, one measure of similarity considers each gene that is induced (or repressed) past a threshold level, and increases the score for each gene in which both profiles indicate induction (or repression) of that gene.

As used herein, the term "target specific" is intended to mean an agent that binds to a target analyte selectively. This agent will bind with preferential affinity toward the target while showing little to no detectable cross-reactivity toward other molecules. For example, when the target is a nucleic acid, a target specific sequence is one that is complementary to the sequence of the target and able to hybridize to the target sequence with little to no detectable cross-reactivity with other nucleic acid molecules. A nucleic acid target could also be bound in a target specific manner by a protein, for example by the DNA binding domain of a transcription factor. If the target is a protein or peptide it can be bound specifically by a nucleic acid aptamer, or another protein or peptide, or by an antibody or antibody fragment which are sub-classes of proteins.

As used herein, the term "genedigit" is intended to mean a region of pre-determined nucleotide or amino acid sequence that serves as an attachment point for a label. The genedigit can have any structure including, for example, a single unique sequence or a sequence containing repeated core elements. Each genedigit has a unique sequence which differentiates it from other genedigits. An "anti-genedigit" is a nucleotide or amino acid sequence or structure that binds specifically to the gene digit. For example, if the genedigit is a nucleic acid, the anti-genedigit can be a nucleic acid sequence that is complementary to the genedigit sequence. If the genedigit is a nucleic acid that contains repeated core elements then the anti-genedigit can be a series of repeat sequences that are complementary to the repeat sequences in the genedigit. An anti-genedigit can contain the same number, or a lesser number, of repeat sequences compared to the genedigit as long as the anti-genedigit is able to specifically bind to the genedigit.

As used herein, the term "specifier" is intended to mean the linkage of one or more genedigits to a target specific sequence. The genedigits can be directly linked or can be attached using an intervening or adapting sequence. A specifier can contain a target specific sequence which will allow it to bind to a target analyte. An "anti-specifier" has a complementary sequence to all or part of the specifier such that it specifically binds to the specifier.

As used herein, the term "label" is intended to mean a molecule or molecules that render an analyte detectable by an analytical method. An appropriate label depends on the particular assay format and are well known by those skilled in the art. For example, a label specific for a nucleic acid molecule can be a complementary nucleic acid molecule attached to a label monomer or measurable moiety, such as a radioisotope, fluorochrome, dye, enzyme, nanoparticle, chemiluminescent marker, biotin, or other moiety known in the art that is measurable by analytical methods. In addition, a label can include any combination of label monomers.

As used herein, "unique" when used in reference to label is intended to mean a label that has a detectable signal that distinguishes it from other labels in the same mixture. Therefore, a unique label is a relative term since it is dependent upon the other labels that are present in the mixture and the sensitivity of the detection equipment that is used. In the case of a fluorescent label, a unique label is a label that has spectral properties that significantly differentiate it from other fluorescent labels in the same mixture. For example, a fluorescein label can be a unique label if it is included in a mixture that contains a rhodamine label since these fluorescent labels emit light at distinct, essentially non-overlapping wavelengths. However, if another fluorescent label was added to the mixture that emitted light at the same or very similar wavelength to fluorescein, for example the Oregon Green fluorophore, then the fluorescein would no longer be a unique label since Oregon Green and fluorescein could not be distinguished from each other. A unique label is also relative to the sensitivity of the detection equipment used. For example, a FACS machine can be used to detect the emission peaks from different fluorophore-containing labels. If a particular set of labels have emission peaks that are separated by, for example, 2 nm these labels would not be unique if detected on a FACS machine that can distinguish peaks that are separated by 10 nm or greater, but these labels would be unique if detected on a FACS machine that can distinguish peaks separated by 1 nm or greater.

As used herein, the term "signal" is intended to mean a detectable, physical quantity or impulse by which information on the presence of an analyte can be determined. Therefore, a signal is the read-out or measurable component of detection. A signal includes, for example, fluorescence, luminescence, calorimetric, density, image, sound, voltage, current, magnetic field and mass. Therefore, the term "unit signal" as used herein is intended to mean a specified quantity of a signal in terms of which the magnitudes of other quantities of signals of the same kind can be stated. Detection equipment can count signals of the same type and display the amount of signal in terms of a common unit. For example, a nucleic acid can be radioactively labeled at one nucleotide position and another nucleic acid can be radioactively labeled at three nucleotide positions. The radioactive particles emitted by each nucleic acid can be detected and quantified, for example in a scintillation counter, and displayed as the number of counts per minute (cpm). The nucleic acid labeled at three positions will emit about three times the number of radioactive particles as the nucleic acid labeled at one position and hence about three times the number of cpms will be recorded.

Because the disease-perturbed networks in the organ may initiate the expression of one or more proteins whose synthesis it does not ordinarily control, it should be noted that, in certain embodiments, a disease-associated organ-specific blood fingerprint will comprise the determined level of one or more components of a normal organ-specific protein set that are NOT components of the corresponding normal serum organ-specific protein set. Thus, in this regard, a disease-associated organ-specific blood fingerprint may comprise the determined level of one or more components of a normal organ-specific protein set or may comprise a protein or set of proteins not detected in a normal organ-specific protein set. Further, in certain embodiments, a disease-associated "organ-specific" blood fingerprint comprises the determined levels of one or more components of one, two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween or more normal serum organ-specific protein sets. Further, in additional embodiments, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or more or any integer value therebetween components of multiple sets could be combined for analysis of multiple organs, tissues, systems, or cells. Thus, in this regard, a disease-associated organ-specific blood fingerprint may comprise the determined levels of one or more components from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween components or more normal serum organ-specific protein sets.

The term "polynucleotide" refers to a polymeric form of nucleotides of any length, including deoxyribonucleotides or ribonucleotides, which can comprise analogs thereof.

As used herein, "purified" refers to a specific protein, polypeptide, or peptide composition that has been subjected to fractionation to remove various other proteins, polypeptides, or peptides, and which composition substantially retains its activity, as may be assessed, for example, by any of a variety of protein assays known to the skilled artisan for the specific or desired protein, polypeptide or peptide.

The terms "polypeptide", "peptide" and "protein" are used interchangeably herein to refer to polymers of amino acids of any length. The terms also encompass an amino acid polymer that has been modified; for example, by disulfide bond formation, glycosylation, lipidation, or conjugation with a labeling component.

The terms "glycopeptide" or "glycoprotein" refers to a peptide that contains covalently bound carbohydrate. The carbohydrate can be a monosaccharide, oligosaccharide or polysaccharide.

Organ-Specific Protein Sets

The invention provides organ-specific protein sets. An organ-specific protein set is made up of the set of organ-specific proteins (as defined further herein) identified from a normal, healthy sample of a particular organ using the methods described herein (see, e.g., Example 1 and Example 9). Illustrative organ-specific protein sets include those provided in Tables 1-32, 36-45 and 47-79. Amino acid and polynucleotide sequences for illustrative organ-specific proteins are set forth in SEQ ID NOs:1-72,689.

As used herein, the term "organ" is defined as would be understood in the art. Thus, the term, "organ-specific" as used herein generally refers to proteins (or transcripts) that are primarily expressed in a single organ. In addition, in a complex organ such as the brain, there will be distinct functional subregions (e.g. the cortex, the cerebellum, the thalamus, etc) that will be equivalent to different organs as defined above. It should be noted that the skilled artisan would readily appreciate upon reading the instant specification that cell-specific transcripts and proteins and tissue-specific transcripts and proteins are also contemplated in the present invention. Further, as those of skill in the art would appreciate the transcriptomes (e.g. quantitative collection of the full complement of mRNAs, or transcripts in a particular tissue or organ at a particular time) of organs that are specific for males or females should not be included when assessing organ-specific transcripts (or proteins) of the opposite sex (in this regard exemplary tables and analysis are set forth in Tables 36-42, 44, 45, 72-77 and 79). As such, and as discussed further herein, in certain embodiments, organ-specific protein is defined as a protein encoded by a transcript that is expressed at a level of at least 3 copies/million (as measured, for example, by massively parallel signature sequencing (MPSS) or sequencing by synthesis (SBS)) in the cell/tissue/organ of interest but is expressed at less than 3 copies/million in other cells/tissues/organs. In a further embodiment, an organ-specific protein is one that is encoded by a transcript that is expressed 95% in one organ and the remaining 5% in one or more other organs. (In this context, total expression across all organs examined is taken as 100%). In certain embodiments, an organ-specific protein is one that is encoded by a transcript that is expressed at about 50%, 55%, 60%, 65%, 70%, 75%, 80% to about 90% in one organ and wherein the remaining 10%-50% is expressed in one or more other organs.

In one embodiment, organ-specific transcripts and proteins encoded thereby are identified as follows:

Assume the expression (in tpm) and the associated SD of a MPSS sequence tag in a tissue is $\{(X_i, \sigma_i)\}$, where i=1, 2, ..., 32 represents individual tissues. Assume the tag has the highest expression levels in tissue m where the expression and the SD are $(X_m, \sigma_m)$. Three rules are then applied to determine whether the tag is specific to tissue m as follows:

i) The expression of the tag in tissue m is above a minimal, estimated noise levels, i.e., $$X_m \geq 5. \tag{1}$$

ii) The expression of the tag in tissue m is well above the expression of the tag in all other tissues. More specifically, the mean expression of the tag is first calculated in the other tissues being examined (e.g., all tissues except tissue m) as $$\overline{X} = \frac{1}{N} \sum_{i \neq m} X_i, \tag{2}$$

the associated standard error as $$\sigma_{\overline{X}} = \frac{1}{N} \sqrt{\sum_{i \neq m} \sigma_i^2}, \tag{3}$$

and the corresponding SD as $$s = \sqrt{\frac{1}{N-1} \sum_{i \neq m} (X_i - \overline{X})^2 + \frac{1}{N} \sum_{i \neq m} \sigma_i^2}, \tag{4}$$

where N=31.

The significance that the expression of the tag in tissue m is above the expression of the tag in other tissues is then evaluated as $$p_{dis} = \frac{1}{2} \text{erfc}\left(\frac{X_m - \overline{X}}{\sqrt{2(s^2 + \sigma_m^2 + \sigma_{\overline{X}}^2)}}\right). \tag{5}$$

For the tag to be specific to tissue m, in this embodiment, it is required that $$p_{dis} \leq 10^{-3}. \tag{6}$$

iii) The specificity f of the tag in tissue m has to be well above a pre-selected cutoff value $f_0$. More precisely, the specificity of the tag in tissue m is defined as $$f = \frac{X_m}{\sum_i X_i}, \tag{7}$$

and the associated SD is evaluated as $$\sigma_f = \frac{f}{X_m} \sqrt{(1-f)^2 \sigma_m^2 + f^2 \sum_{i \neq m} \sigma_i^2}. \tag{8}$$

The significance that f was above $f_0$ is then given by $$p_{spc} = \frac{1}{2}\text{erfc}\left(\frac{f - f_0}{\sqrt{2}\,\sigma_f}\right). \quad (9)$$

In this embodiment, nine different values of $f_0$ and $p_{spc}$ can be applied in determining organ-specific MPSS tags, ranging from the most stringent condition ($f_0=1$ and $p_{spc} \leq 10^{-3}$) to the least stringent condition ($f_0=0.5$ and $p_{spc} \leq 0.1$). In one particular embodiment, it is required that $$p_{spc} \leq 10^{-3}. \quad (10)$$

The number of organ-specific tags varies with the selected values of $f_0$ and $p_{spc}$.

As would be readily recognized by the skilled artisan upon reading the present disclosure, in certain embodiments, an organ-specific blood fingerprint can readily be discerned even if some expression of an "organ-specific" protein from a particular organ is detected at some level in another organ, or even more than one organ. For example, the organ-specific blood fingerprint from prostate can conclusively identify a particular prostate disease (and stage of disease) despite expression of one or more protein members of the fingerprint in one or more other organs. Thus, an organ-specific protein as described herein may be predominantly or differentially expressed in an organ of interest rather than uniquely or specifically expressed in the organ. In this regard, in certain embodiments, differentially expressed means at least 1.5 fold expression in the organ of interest as compared to other organs. In another embodiment, differentially expressed means at least 2 fold expression in the organ of interest as compared to expression in other organs. In yet a further embodiment, differentially expressed means at least 2.5, 3, 3.5, 4, 4.5, 5 fold or higher expression in the organ of interest as compared to expression of the protein in other organs. As described elsewhere herein, "protein" expression can be determined by analysis of transcript expression using a variety of methods.

In one embodiment, the organ-specific proteins are identified by preparing RNA and/or a cDNA library from an organ, tissue or biological fluid (e.g., whole blood, serum, etc.) of interest. Any organ of a mammalian body is contemplated herein. Illustrative organs include, but are not limited to, heart, kidney, ureter, bladder, urethra, liver, prostate, heart, blood vessels, bone marrow, skeletal muscle, smooth muscle, brain (amygdala, caudate nucleus, cerebellum, corpus callosum, fetal, hypothalamus, thalamus), spinal cord, peripheral nerves, retina, nose, trachea, lungs, mouth, salivary gland, esophagus, stomach, small intestines, large intestines, hypothalamus, pituitary, thyroid, pancreas, adrenal glands, ovaries, oviducts, uterus, placenta, vagina, mammary glands, testes, seminal vesicles, penis, lymph nodes, PBMC, thymus, and spleen. As noted above, upon reading the present disclosure, the skilled artisan would recognize that cell-specific and tissue-specific proteins are contemplated herein and thus, proteins specifically expressed in cells or tissues that make up such organs are also contemplated herein. In certain embodiments, in each of these organs, transcriptomes are obtained for the cell types in which the disease of interest arises. For example, in the prostate there are two dominant types of cells—epithelial cells and stromal cells. About 98% of prostate cancers arise in epithelial cells. Similarly, in the breast, 90% of cancers arise in epithelial cells. As such, in certain embodiments, transcriptomes are isolated from these particular cell types from an organ of interest (e.g., prostate epithelial cells; breast epithelial cells). In this regard, any cell type that makes up any of the organs described herein is contemplated herein. Illustrative cell types include, but are not limited to, epithelial cells, stromal cells, cortical cells, endothelial cells, endodermal cells, ectodermal cells, mesodermal cells, lymphocytes (e.g., B cells and T cells including CD4+ T helper 1 or T helper 2 type cells, CD8+ cytotoxic T cells), all of the major types of white blood cells present in the blood (e.g., eosinophils, megakaryocytes, granulocytes, macrophages, neutrophils, etc) erythrocytes, keratinocytes, and fibroblasts. In the case of the white blood cells, the organ-specific proteins can be obtain directly from the isolated cell types and will not have to be secreted into the blood for identification. Thus the organ-specific strategy will allow us to assess any diseases of the white blood cell types (e.g. neutrophils, basophils, eosinophils, macrophage, monocytes, and lymphocytes (including B and T-lymphocytes). Particular cell types within organs or tissues may be obtained by histological dissection, by the use of specific cell lines (e.g., prostate epithelial cell lines), by cell sorting or by a variety of other techniques known in the art. Not only are the above parameters useful in identifying organ-specific proteins or transcripts, but such analysis can be used in harvesting mRNA and cDNA from a fluid, tissue, organ of interest or blood for analysis.

In one embodiment, transcriptomes from a particular cell type of an organ of interest (such as prostate epithelial cells, breast epithelial cells, etc.) are isolated and analyzed using methods as described herein to determine which transcripts are organ-specific. The organ-specific transcripts identified from the particular cell type of the organ can then be compared to the organ-specific transcripts identified from whole organ samples (e.g., the organ-specific proteins provided in Tables 1-32, 36-45 and 47-79) to determine those transcripts that overlap or to identify additional organ-specific transcripts that may not have been detected from the whole tissue due to sensitivity issues. In this way, additional normal organ-specific protein members of a set can be identified. Further, in certain embodiments, a subset of normal organ-specific proteins can also be identified. For example, a normal prostate-epithelial cell-specific protein subset can be identified that is the set of proteins that are specifically expressed in prostate-epithelial cells. Thus, particular cell types from organs may include, but are not limited to, renal cortical epithelial cells, hepatocytes, mammary epithelial cells, prostate epithelial cells, renal proximal tubule epithelial cells, and epidermal keratinocytes. This list is only exemplary and not meant to be limiting.

As one of skill in the art can appreciate, technology in the area of detection techniques is rapidly evolving. In particular, techniques that only a few years ago required milligram quantities of sample can now be performed with pictogram quantities. Nanotechnology techniques can now be employed to assist in detection of nucleic acid and polypeptide targets of the present invention. Further, as this technology develops it will be feasible to achieve single cell-specific transcripts. These single-cell techniques are now available for abundant transcripts and can be adapted by the skilled artisan to permit the analyses of low abundance transcripts at the single cell level.

It should be noted that in certain embodiments, organ-specific blood fingerprints can be determined from "organ-specific" proteins from multiple organs, such as from organs that share a common function or make up a system (e.g., digestive system, circulatory system, respiratory system, cardiovascular system, the immune system (including the different cells of the immune system, such as, but not limited to, B cells, T cells including CD4+ T helper 1 or T helper 2 type cells, regulatory T cells, CD8+ cytotoxic T cells, NK cells, dendritic cells, macrophages, monocytes, neutrophils, granulocytes, mast cells, etc.), the sensory system, the skin, brain and the nervous system, and the like). Accordingly, panels of probes to the organ-specific components described herein can be fashioned in a way to analyze multiple organ combinations.

Nucleic Acid Analysis

As noted above, in addition to detection of polypeptides that are organ/tissue specific either in blood, tissue sample or biological fluid, nucleic acid detection techniques offer additional advantages due to sensitivity of detection. RNA can be collected and/or generated from blood, biological fluids, tissues, organs, cell lines, or other relevant sample using techniques known in the art, such as those described in Kingston. (2002 *Current Protocols in Molecular Biology*, Greene Publ. Assoc. Inc. & John Wiley & Sons, Inc., NY, N.Y. (see, e.g., as described by Nelson et al. *Proc Natl Acad Sci USA*, 99: 11890-11895, 2002) and elsewhere. Further, a variety of commercially available kits for constructing RNA are useful for making the RNA to be used in the present invention. RNA is constructed from organs/tissues/cells procured from normal healthy subjects; however, this invention contemplates construction of RNA from diseased subjects. This invention contemplates using any type of organ from any type of subject or animal. For test samples RNA may be procured from an individual (e.g., any animal, including mammals) with or without visible disease and from tissue samples, biological fluids (e.g., whole blood) or the like. In some embodiments amplification or construction of cDNA sequences may be helpful to increase detection capabilities. The present invention, as well as the art, provides the requisite level of detail to perform such tasks. In one aspect of the present invention, whole blood is used as the source of RNA and accordingly, RNA stabilizing regents are optionally used, such as PAX tubes, as described in Thach et al., *J. Immunol. Methods*. December 283(1-2):269-279, 2003 and Chai et al., *J. Clin. Lab Anal*. 19(5):182-188, 2005 (both of which are incorporated herein by reference in their entirety).

Complementary DNA (cDNA) libraries can be generated using techniques known in the art, such as those described in Ausubel et al. (2001 *Current Protocols in Molecular Biology*, Greene Publ. Assoc. Inc. & John Wiley & Sons, Inc., NY, N.Y.); Sambrook et al. (1989 *Molecular Cloning*, Second Ed., Cold Spring Harbor Laboratory, Plainview, N.Y.); Maniatis et al. (1982 *Molecular Cloning*, Cold Spring Harbor Laboratory, Plainview, N.Y.) and elsewhere. Further, a variety of commercially available kits for constructing cDNA libraries are useful for making the cDNA libraries of the present invention. Libraries are constructed from organs/tissues/cells procured from normal, healthy subjects.

Amplification or Nucleic Acid Amplification

By "amplification" or "nucleic acid amplification" is meant production of multiple copies of a target nucleic acid that contains at least a portion of the intended specific target nucleic acid sequence. The multiple copies may be referred to as amplicons or amplification products. In certain embodiments, the amplified target contains less than the complete target gene sequence (introns and exons) or an expressed target gene sequence (spliced transcript of exons and flanking untranslated sequences). For example, specific amplicons may be produced by amplifying a portion of the target polynucleotide by using amplification primers that hybridize to, and initiate polymerization from, internal positions of the target polynucleotide. Preferably, the amplified portion contains a detectable target sequence that may be detected using any of a variety of well-known methods.

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA. The ligase chain reaction (Weiss, R. 1991, Science 254: 1292), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product. Another method is strand displacement amplification (Walker, G. et al., 1992, Proc. Natl. Acad. Sci. USA 89:392-396; U.S. Pat. Nos. 5,270,184 and 5,455,166), commonly referred to as SDA, which uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315). Other amplification methods include: nucleic acid sequence based amplification (U.S. Pat. No. 5,130,238), commonly referred to as NASBA; one that uses an RNA replicase to amplify the probe molecule itself (Lizardi, P. et al., 1988, BioTechnol. 6: 1197-1202), commonly referred to as Qβ replicase; a transcription based amplification method (Kwoh, D. et al., 1989, Proc. Natl. Acad. Sci. USA 86:1173-1177); self-sustained sequence replication (Guatelli, J. et al., 1990, Proc. Natl. Acad. Sci. USA 87: 1874-1878); and, transcription mediated amplification (U.S. Pat. Nos. 5,480,784 and 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.).

Illustrative transcription-based amplification systems of the present invention include TMA, which employs an RNA polymerase to produce multiple RNA transcripts of a target region (U.S. Pat. Nos. 5,480,784 and 5,399,491). TMA uses a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In an illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce primer extension. From an unmodified promoter-primer, reverse transcriptase creates a cDNA copy of the target RNA, while RNase H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNase H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

"Selective amplification", as used herein, refers to the amplification of a target nucleic acid sequence according to the present invention wherein detectable amplification of the target sequence is substantially limited to amplification of target sequence contributed by a nucleic acid sample of interest that is being tested and is not contributed by target nucleic acid sequence contributed by some other sample source, e.g., contamination present in reagents used during amplification reactions or in the environment in which amplification reactions are performed.

By "amplification conditions" is meant conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention hybridize under stringent hybridization conditions. While the Examples section infra provides preferred amplification conditions for amplifying target nucleic acid sequences according to the present invention, other acceptable conditions to carry out nucleic acid amplifications according to the present invention could be easily ascertained by someone having ordinary skill in the art depending on the particular method of amplification employed.

Oligonucleotides & Primers for Amplification

As used herein, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof. The term oligonucleotide does not denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, and it may function to prevent hybridization or impede primer extension if appropriately situated and/or modified. Specific oligonucleotides of the present invention are described in more detail below, but are directed to binding the organ-specific transcript or the organ-specific transcript encoding the sequences listed in the attached Tables 1-32, 36-45 and 47-79 or the appended sequence listing. As used herein, an oligonucleotide can be virtually any length, limited only by its specific function in the amplification reaction or in detecting an amplification product of the amplification reaction.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl substitution to the ribofuranosyl moiety. See Becker et al., U.S. Pat. No. 6,130,038. Other sugar modifications include, but are not limited to 2'-amino, 2'-fluoro, (L)-alpha-threofuranosyl, and pentopuranosyl modifications. The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are commonly referred to as "peptide nucleic acids" or "PNA" and are disclosed by Nielsen et al., "Peptide Nucleic Acids," U.S. Pat. No. 5,539,082.) Other linkage modifications include, but are not limited to, morpholino bonds.

Non-limiting examples of oligonucleotides or oligomers contemplated by the present invention include nucleic acid analogs containing bicyclic and tricyclic nucleoside and nucleotide analogs (LNAs). See Imanishi et al., U.S. Pat. No.

6,268,490; and Wengel et al., U.S. Pat. No. 6,670,461.) Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions.

While design and sequence of oligonucleotides for the present invention depend on their function as described below, several variables must generally be taken into account. Among the most critical are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to screen large numbers of potential oligonucleotides for optimal ones.

The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer."

As used in this disclosure, the phrase "an oligonucleotide having a nucleic acid sequence 'comprising,' 'consisting of,' or 'consisting essentially of' a sequence selected from" a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

The phrase "an oligonucleotide substantially corresponding to a nucleic acid sequence" means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions.

One skilled in the art will understand that "substantially corresponding" oligonucleotides of the invention can vary from the referred to sequence and still hybridize to the same target nucleic acid sequence. This variation from the nucleic acid may be stated in terms of a percentage of identical bases within the sequence or the percentage of perfectly complementary bases between the probe or primer and its target sequence. Thus, an oligonucleotide of the present invention substantially corresponds to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. One skilled in the art will understand the various modifications to the hybridization conditions that might be required at various percentages of complementarity to allow hybridization to a specific target sequence without causing an unacceptable level of non-specific hybridization.

The skilled artisan will recognize that any of a wide variety of known and available amplification techniques may be employed in the methods of the present invention, even if not explicitly described herein. Illustrative non-limiting examples of such amplification techniques are described below.

One illustrative amplification technique useful in accordance with the methods herein is the polymerase chain reaction. As noted above, the polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

Another illustrative amplification method, the ligase chain reaction (Weiss, R. 1991, Science 254: 1292), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Another illustrative method is strand displacement amplification (Walker, G. et al., 1992, Proc. Natl. Acad. Sci. USA 89:392-396; U.S. Pat. Nos. 5,270,184 and 5,455,166), commonly referred to as SDA, which uses cycles of annealing pairs of primer sequences to opposite strands of a target sequence, primer extension in the presence of a dNTP☐S to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315).

Other amplification methods include, for example, nucleic acid sequence based amplification (U.S. Pat. No. 5,130,238), commonly referred to as NASBA; one that uses an RNA replicase to amplify the probe molecule itself (Lizardi, P. et al., 1988, BioTechnol. 6: 1197-1202), commonly referred to as Q☐ replicase; a transcription based amplification method (Kwoh, D. et al., 1989, Proc. Natl. Acad. Sci. USA 86:1173-1177); self-sustained sequence replication (Guatelli, J. et al., 1990, Proc. Natl. Acad. Sci. USA 87: 1874-1878); and, transcription mediated amplification (U.S. Pat. Nos. 5,480,784 and 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.).

In more particular embodiments, the amplification technique used in the methods of the present invention is a transcription-based amplification technique, such as TMA and NASBA.

All or substantially all of the unique transcripts of RNA or from a cDNA library, e.g., representing virtually or substantially all genes functioning in the organ of interest, can be identified and quantified using any of a variety of techniques known in the art. In this regard, in certain embodiments, substantially all refers to a sample representing at least 80% of all genes detectably expressed in the organ of interest. In a further embodiment, substantially all refers to a sample representing at least 65%, 70%, 80%, 85%, 90%, 95%, 96%, 97%, 98%, 99% or higher of all genes functioning in the organ of interest. In one embodiment, substantially all the transcripts from a cDNA library are amplified, sorted and signature sequences generated therefrom according to the methods described in U.S. Pat. Nos. 6,013,445; 6,172,218; 6,172,214; 6,140,489 and Brenner, P., et al., *Nat Biotechnol*, 18:630-634 2000. Briefly, polynucleotide templates from a cDNA library of interest are cloned into a vector system that contains a vast set of minimally cross-hybridizing oligonucleotide tags (see U.S. Pat. No. 5,863,722). The number of tags is usually at least 100 times greater than the number of cDNA templates (see e.g., U.S. Pat. No. 6,013,445 and Brenner, P., et al., supra). Thus, the set of tags is such that a 1% sample taken of template-tag conjugates ensures that essentially every template in the sample is conjugated to a unique tag and that at least one of each of the different template cDNAs is represented in the sample with >99% probability (U.S. Pat. No. 6,013,445 and Brenner, P., et al., supra). The conjugates are then amplified and hybridized under stringent conditions to microbeads each of which has attached thereto a unique complementary, minimally cross-hybridizing oligonucleotide tag. The transcripts are then directly sequenced simultaneously in a flow cell using a ligation-based sequencing method (see e.g., U.S. Pat. No. 6,013,445). A short signature sequence of about 16-20 base pairs (Brenner, P., et al., supra) is generated simultaneously from each of the hundreds of thousands of beads (or more) in the flow cell, each having attached thereto copies of a unique transcript from the sample. This technique is termed massively parallel signature sequencing (MPSS).

The resulting sequences, (e.g., MPSS signature sequences), are generally about 17-20 bases in length. However, in certain embodiments, the sequences can be about 8, 10, 15, 20, 25, 30, 35, 40, 45, 50, 55, 60, 65, 70, 75, 80, 85, 90, 95, or 100 or more bases in length. The sequences are annotated using annotated human genome sequence (such as human genome release hg16, released in November, 2003, or other public or private databases) and the human Unigene (Unigene build #184) using methods known in the art, such as the method described by Meyers, B. C., et al., Genome Res, 14: 1641-1653, 2004. Other databases useful in this regard include Genbank, EMBL, or other publicly available databases. In certain embodiments, transcripts are considered only for those with 100% matches between an MPSS or other type of signature and a genome signature. As would be readily appreciated by the skilled artisan upon reading the present disclosure, this is a stringent match criterion and in certain embodiments, it may be desirable to use less stringent match criteria. Indeed, polymorphisms could lead to variations in transcripts that would be missed if only exact matches were used. For example, it may be desirable to consider signature sequences that match a genome signature with 80%, 85%, 90%, 95%, 96%, 97%, 98%, or 99% identity. In one embodiment, signatures that are expressed at less than 3 transcripts per million in libraries of interest are disregarded, as they might not be reliably detected since this, in effect, represents less than one transcript per cell (see for example, Jongeneel, C. V., et al., *Proc Natl Acad Sci USA*, 2003). Alternatively, transcripts at this level may arise from cells that are present as only a fraction of the population (e.g., 1%)—hence the measurement could be real. cDNA signatures are classified by their positions relative to polyadenylation signals and poly (A) tails and by their orientation relative to the 5*3 orientation of source mRNA. Full-length sequences corresponding to the signature sequences can be thus identified.

In one embodiment, substantially all the transcripts from a cDNA library are identified using sequencing by synthesis (SBS) or similar technology, such as that developed by Solexa (now part of Illumina) (San Diego, Calif.). This technology may be used to identify signature sequences of the transcriptome of a particular organ/tissue/cell of interest. See for example, the methods described in Expert Rev Mol Diagn. 2007 January; 7(1):65-76; Rosenthal, A & Brenner, S. 1994-2000. U.S. Pat. No. 6,087,095 DNA sequencing method; Ronaghi, M., Uhlen, M., and Nyren, P. 1998. Science 281: 363. A sequencing method based on real-time pyrophosphate; Mitra, R D, Shendure, J, Olejnik, J, Olejnik, E K, and Church, G M 2003 Analyt. Biochem. 320:55-65 Fluorescent in situ Sequencing on Polymerase Colonies; Johnson D S, Mortazavi A, Myers R M, Wold B. (2007) Genome-wide mapping of in vivo protein-DNA interactions. Science 316 (5830):1441-2; A. Barski et al., 2007 Cell 129, 823-837; T. Mikkelsen et al., Nature. 2007 448(7153):553-60; G. Robertson et al., Nature Methods 2007 August; 4(8):651-7; R. F. Service 2006 Science 311, 1544-1546; and U.S. Pat. Nos. 7,232,656; 7,115,400; 7,057,026; 6,969,488; 6,897,023; 6,833,246.

In certain embodiments, other techniques may be used to evaluate RNA transcripts of the transcripts from a particular cDNA library, including microarray analysis (Han, M., et al., *Nat Biotechnol*, 19: 631-635, 2001; Bao, P., et al., *Anal Chem*, 74: 1792-1797, 2002; Schena et al., *Proc. Natl. Acad. Sci. USA* 93:10614-19, 1996; and Heller et al., *Proc. Natl. Acad. Sci. USA* 94:2150-55, 1997) and SAGE (serial analysis of gene expression). Like MPSS, SAGE is digital and can generate a large number of signature sequences. (see e.g., Velculescu, V. E., et al., *Trends Genet*, 16: 423-425., 2000; Tuteja R. and Tuteja N. *Bioessays*. 2004 August; 26(8):916-22), although orders of magnitude fewer than that are available from techniques such as MPSS.

As one of skill in the art could readily appreciate any number of methodologies can be employed to investigate the organ-specific nucleic acid and polypeptide sequences set forth by the present invention. In addition to protein or nucleic acid array or microarray analysis, other nanoscale analysis may be employed. Such methodologies include, but are not limited to microfluidic platforms, nanowire sensors (Bunimovich et al., Electrocheically Programmed, Spatially Selective Biofunctionalization of Silicon Wires, Langmuir 20, 10630-10638, 2004; Curreli et al., J. Am. Chem. Soc. 127, 6922-6923, 2005). Further, the use of high-affinity protein-capture agents is contemplated. Such capture agents may include DNA aptamers (U.S. Patent Application Pub. No. 20030219801, as well as the use of click chemistry for target-guided synthesis (Lewis et al., Angewandte Chemie-International Edition, 41, 1053-, 2002; Manetsch et al., J. Am. Chem. Soc. 126, 12809-12818, 2004; Ramstrom et al., Nature Rev. Drug Discov. 1, 26-36, 2002).

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry $^3$rd Ed., W.H. Freeman Pub., New York, N.Y. and Berg et al. (2002) Biochemistry, 5th Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098.

Nucleic acid arrays that are useful in the present invention include those known in the art and that can be manufactured using the cognate sequences to those organ-specific nucleic acid sequences and nucleic acid encoding sequence set forth in Tables 1-32, 36-45 and 47-79 and the attached sequence listing, as well as those that are commercially available from Affymetrix (Santa Clara, Calif.) under the brand name Gene-Chip™. Example arrays are shown on the website at affymetrix.com. Further exemplary methods of manufacturing and using arrays are provided in, for example, U.S. Pat. Nos. 7,028,629; 7,011,949; 7,011,945; 6,936,419; 6,927,032; 6,924,103; 6,921,642; and 6,818,394 to name a few.

The present invention as related to arrays and microarrays also contemplates many uses for polymers attached to solid substrates. These uses include gene expression monitoring, profiling, library screening, genotyping and diagnostics. Gene expression monitoring and profiling methods and methods useful for gene expression monitoring and profiling are shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,925,525, 6,268,141, 5,856,092, 6,267,152, 6,300,063, 6,525,185, 6,632,611, 5,858,659, 6,284,460, 6,361,947, 6,368,799, 6,673,579 and 6,333,179. Other methods of nucleic acid amplification, labeling and analysis that may be used in combination with the methods disclosed herein are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with analysis, the genomic sample may be amplified by a variety of mechanisms, some of which may employ PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. Modifications to PCR may also be used, for example, the inclusion of Betaine or trimethylglycine, which has been disclosed, for example, in Rees et al. Biochemistry 32:137-144 (1993), and in U.S. Pat. Nos. 6,270,962 and 5,545,539. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861, 245) nucleic acid based sequence amplification (NABSA), rolling circle amplification (RCA), multiple displacement amplification (MDA) (U.S. Pat. Nos. 6,124,120 and 6,323, 009) and circle-to-circle amplification (C2CA) (Dahl et al. Proc. Natl. Acad. Sci. 101:4548-4553 (2004). (See, U.S. Pat. Nos. 5,409,818, 5,554,517, and 6,063,603, each of which is incorporated herein by reference). Other amplification methods that may be used are described in, U.S. Pat. Nos. 5,242, 794, 5,494,810, 5,409,818, 4,988,617, 6,063,603 and 5,554, 517 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. Ser. Nos. 09/916,135, 09/920,491 (U.S. Patent Application Publication 20030096235), 09/910,292 (U.S. Patent Application Publication 20030082543), and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092; 5,902,723; 5,936,324; 5,981,956; 6,025,601; 6,090,555; 6,141,096; 6,185,030; 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

The whole genome sampling assay (WGSA) is described, for example in Kennedy et al., Nat. Biotech. 21, 1233-1237 (2003), Matsuzaki et al., Gen. Res. 14: 414-425, (2004), and Matsuzaki, et al. Nature Methods 1:109-111 (2004). Algorithms for use with mapping assays are described, for example, in Liu et al., Bioinformatics 19: 2397-2403 (2003) and Di et al. Bioinformatics 21:1958 (2005). Additional methods related to WGSA and arrays useful for WGSA and applications of WGSA are disclosed, for example, in U.S. Patent Application Nos. 60/676,058 filed Apr. 29, 2005, 60/616,273 filed Oct. 5, 2004, 10/912,445, 11/044,831, 10/442,021, 10/650,332 and 10/463,991. Genome wide association studies using mapping assays are described in, for example, Hu et al., Cancer Res.; 65(7):2542-6 (2005), Mitra et al., Cancer Res., 64(211:8116-25. (2004), Butcher et al., Hum Mol. Genet., 14(10):1315-25 (2005), and Klein et al., Science, 308(5720):385-9 (2005). Each of these references is incorporated herein by reference in its entirety for all purposes.

Additionally, the present invention may have preferred embodiments that include methods for providing genetic information over networks such as the Internet as shown in U.S. Ser. Nos. 10/197,621, 10/063,559 (United States Publication Number 20020183936), 10/065,856, 10/065,868, 10/328,818, 10/328,872, 10/423,403, and 60/482,389.

The term "array" as used herein refers to an intentionally created collection of molecules that can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "mRNA" or sometimes refer by "mRNAtranscripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

When referring to arrays and microarrays the term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Also contemplated by the present invention are polypeptide/protein arrays and microarrays. In certain embodiments, such arrays comprise probes such as antibodies, aptamers, other cognate binding ligands and the like specific to a component of the sets disclosed herein. For example, such probes are specific to the nucleic acid or polypeptide sequence set forth in Tables 1-32, 36-45 and 47-79 or the attached sequence listing. Such arrays and methods of constructing the same are well known in the art, for example, U.S. Pat. Publ. Nos. 20060035277; 20060166227; 20050260653; 20040199945; 20030044320; 20020102605; and U.S. Pat. Nos. 6,777,239; 6,696,620; 6,689,568; 6,448,387; and 5,081,584.

One class of protein microarray useful in the context of the present invention uses an immobilized "capture antibody." The polypeptides are bound to a solid substrate, such as glass with a treated surface, such as aminosilane or via a biotin-streptavidin conjugation. The arrays are then incubated with a solution-containing probe that will bind to the capture antibodies in a manner dependent upon time, buffer components, and recognition specificity. The probes may then be visualized directly if they have been previously labeled, or may be allowed to bind to a secondary labeled reagent, frequently another antibody. The means of visualizing the amount of probe bound to the capture antibody is dependent upon the labeling method utilized, but is often by a CCD imager or laser scanner using filter sets that are appropriate to excite and detect the emissions of the label. The imager converts the amount of detected photons into an electronic signal (often an 8-bit or 16-bit scale) which can then be analyzed using software packages.

In another embodiment, the present invention also provides a protein-coated substrate comprising a plurality of patches arranged in discrete, known regions on a substrate, where each of the patches comprises an immobilized protein with a different, known sequence and where each of the patches is separated from the neighboring patches by from about 50 nm to about 500 µm. In a preferred embodiment, the protein-coated substrate comprises 9 or more patches.

Arrays of proteins are also provided by the present invention. In one embodiment, the protein arrays comprise micrometer-scale, two-dimensional patterns of proteins immobilized on arrays of functionalized surface patches.

In one embodiment, the array of proteins comprises a plurality of patches, preferably 9 or more, arranged in discrete known regions on a substrate, wherein each of the patches comprises an immobilized protein with a different, known sequence and wherein each of the patches is separated from neighboring patches by from about 50 nm to about 500 µm. In a preferred embodiment, the patches are separated from neighboring patches from about 200 nm to about 500 µm.

In some versions of the array, the diameter of each of the patches is proportional to the distance separating the patches. Therefore, the area of each patch may be from about 100 nm$^2$ to about 40,000 µm$^2$. Each patch preferably has an area from about 1 µm$^2$ to about 10,000 µm$^2$.

In one embodiment of the array, the array comprises 9 or more patches within a total area of 1 cm$^2$. In preferred embodiments of the array, the array comprises 100 or more patches within a total area of 1 cm$^2$. In another embodiment, the array comprises or more patches within a total area of 1 cm$^2$.

In one embodiment of the array, the protein immobilized on one patch differs from the protein immobilized on a second patch of the same array.

In an alternative embodiment of the invention array, the proteins on different patches are identical.

The substrate of the array may be either organic or inorganic, biological or non-biological or any combination of these materials. In one embodiment, the substrate is transparent or translucent. The portion of the surface of the substrate on which the patches reside is preferably flat and firm or semi-firm. Numerous materials are suitable for use as a substrate in the array embodiment of the invention. For instance, the substrate of the invention array can comprise a material selected from a group consisting of silicon, silica, quartz, glass, controlled pore glass, carbon, alumina, titanium dioxide, germanium, silicon nitride, zeolites, and gallium arsenide. Many metals such as gold, platinum, aluminum, copper, titanium, and their alloys are also options for substrates of the array. In addition, many ceramics and polymers may also be used as substrates. Polymers which may be used as substrates include, but are not limited to, the following: polystyrene; poly(tetra)fluoroethylene; (poly)vinylidenedifluoride;

polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polyhydroxyethylmethacrylate; polydimethylsiloxane; polyacrylamide; polyimide; co-block-polymers; and Eupergit®. Photoresists, polymerized Langmuir-Blodgett films, and LICA structures may also serve as substrates in the present invention. The preferred substrates for the array comprise silicon, silica, glass, or a polymer.

In one embodiment of the invention array, the patches further comprise a monolayer on the surface of the substrate and the proteins of the patches are unmobilized on the monolayer. The monolayer is preferably a self-assembling monolayer. This monolayer may optionally comprise molecules of the formula X—R—Y, wherein R is a spacer, X is a functional group that binds R to the surface, and Y is a functional group for binding proteins onto the monolayer.

A variety of chemical moieties may function as monolayers in the array of the present invention. However, three major classes of monolayer formation are preferably used to expose high densities of bioreactive omega-functionalities on the patches of the arrays (i) alkylsiloxane monolayers ("silanes") on hydroxylated surfaces (as taught in, for example, U.S. Pat. No. 5,405,766, PCT Publication WO 96/38.726, U.S. Pat. No. 5,412,087, and U.S. Pat. No. 5,688,642); (ii) allyl-thiol/dialkyldisulfide monolayers on noble metals (preferably Au(111)) (as, for example, described in Allara et al., U.S. Pat. No. 4,690,715; Bamdad et al., U.S. Pat. No. 5,620,850, Wagner et al., Biophysical Journal, 1996, 70:2052-2066); and (iii) alkyl monolayer formation on oxide-free passivated silicon (as taught in, for example, Linford et al., J. Am. Chem. Soc., 1995, 117:3145-3155, Wagner et al., Journal of structural Biology, 1997, 119:189-201, U.S. Pat. No. 5,429,708). One of ordinary skill in the art, however, will recognize that many possible moieties may be substituted for X, R, and/or Y, dependent primarily upon the choice of substrate, coating, and affinity tag. Many examples of monolayers are described in Ulman, An Introduction to Ultrathin Organic Films: From Langmuir-Blodgett to Self Assembly, Academic press (1991).

An array of the present invention may optionally further comprise a coating between the substrate and the monolayer of its patches. This coating may either be formed on the substrate or applied to the substrate. The substrate can be modified with a coating by using thin-film technology based on either physical vapor deposition (PVD) or plasma-enhanced chemical vapor deposition (PECVD). Alternatively, plasma exposure can be used to directly activate the substrate. For instance, plasma etch procedures can be used to oxidize a polymeric surface (i.e. polystyrene or polyethylene to expose polar functionalities such as hydroxyls, carboxylic acids, aldehydes and the like).

The coating may comprise a metal film. Possible metal films include aluminum, chromium, titanium, nickel stainless steel zinc, lead, iron, magnesium, manganese, cadmium, tungsten, cobalt, and alloys or oxides thereof. In a preferred embodiment, the metal film is a noble metal film. Noble metals that may be used for a coating include, but are not limited to, gold, platinum, silver, copper, and palladium. In another embodiment, the coating comprises gold or a gold alloy. Electron-beam evaporation may be used to provide a thin coating of gold on the surface. In yet a further embodiment, the metal film is from about 50 nm to about 500 nm in thickness.

In alternative embodiments, the coating comprises a composition selected from the group consisting of silicon, silicon oxide, silicon nitride, silicon hydride, indium tin oxide, magnesium oxide, alumina, glass, hydroxylated surfaces, and a polymer.

An array of the present invention is typically comprised of a collection of addressable elements. Such elements can be spacially addressable, such as arrays contained within microtiter plates or printed on planar surfaces where each element is present at distinct X and Y coordinates. Alternatively, elements can be addressable based on tags, beads, nanoparticles, or physical properties. The microarrays can be prepared according to the methods known to the ordinarily skilled artisan (See for example, U.S. Pat. No. 5,807,522; Robinson et al. (2002) Nature Medicine 8:295-301; Robinson et al. (2002) 46:885-93). Arrays as used herein refers to any biologic assay with multiple addressable elements. In one embodiment the addressable elements are polypeptides (e.g., antibodies or fragments thereof) or nucleic acid probes. As used herein, elements refer to any probe (polypeptide or nucleic acid based) that can be bound by an organ-specific polypeptide, polypeptide fragment or transcript encoding such polypeptides, as set forth in the appended sequence listing and Tables 1-32, 36-45 and 47-79. Molecules can be, but are not limited to, proteins, polypeptides, peptides, RNA, DNA, lipids, glycosylated molecules, carbohydrates, polypeptides with phosphorylation modifications, and polypeptides with citrulline modifications, aptamers, oxidated molecules, other molecules, and other molecules.

For the elements described herein, addressibility refers to the location, position, tags, cleavable tags or markers, identifiers, spectral properties, electrophoretic properties, or other physical properties that enable identification of the element. One example of addressability, also known as coding, is spatial addressability, where the position of the molecule is fixed, and that position is correlated with the identity. This type of spatial array is generally synthesized or spotted onto a planar substrate, producing, for example, microarrays, where a large number of different molecules are densely laid out in a small area, e.g. comprising at least about 400 different sequences per $cm^2$, and may be 1000 sequences per $cm^2$, or as many as 5000 sequences per $cm^2$, or more. Less dense arrays, such as may be found in ELISA or RIA plates where wells in a plate each contain a distinct probe, may comprise from about 96 sequences per plate, up to about 100 sequences per $cm^2$, up to the density of a microarray. Other spatial arrays utilize fiber optics, where distinct probes are bound to fibers, which can then be formed into a bundle for binding and analysis. Methods for the manufacture and use of spatial arrays of polypeptides are known in the art. Recent articles include Joos et al. (2000) Electrophoresis 21(13):2641-50 describing a microarray-based immunoassay containing serial dilutions of probes; Roda et al. (2000) Biotechniques 28(3):492-6 describing a system obtained by adapting a commercial ink-jet printer and used to produce mono- and bidimensional arrays of spots containing protein on cellulose paper; and Ge (2000) Nucleic Acids Res 28(2):e3 describing a universal protein array system for quantitative detection of protein-protein, protein-DNA, protein-RNA and protein-ligand interactions. See also, Mendoza et al. (1999) "High-throughput microarray-based enzyme-linked immunosorbent assay (ELISA)" Biotechniques 27:778-780; and Lueking et al. (1999) "Protein microarrays for gene expression and antibody screening" Anal. Biochem. 270:103-111.

An alternative to this type of spatial coding array is the use of molecular "tags," where the target probes are attached to a detectable label, or tag, which provides coded information about the sequence of the probe. In certain cases these tags can be cleaved from the element, and subsequently detected to identity the element. In another embodiment, a set of probes may be synthesized or attached to a set of coded beads, where each bead is linked to a distinct probe, and where the beads are themselves coded in a manner that allows identification of the attached probe. The use of a multiplexed microsphere set for analysis of clinical samples by flow cytometry is described in International Patent application no. 97/14028; and Fulton et al. (1997) Clinical Chemistry 43:1749-1756). It is also possible to use other addressable particles or tags (reviewed in Robinson et al. (2002) Arthritis Rheumatism 46:885-93).

In this type of "tag array," where the probe is bound to beads or microspheres, one may utilize flow cytometry for detection of binding. For example, microspheres having fluorescence coding have been described in the art, where the color and level of fluorescence uniquely identifies a particular microsphere. The probe is thus covalently attached to a "color coded" object. A labeled target polypeptide can be detected by flow cytometry, and the coding on the microsphere used to identify the bound probe (e.g., immunoglobulin, antigen binding fragments of immunoglobulins, or ligands).

One embodiment of an array is an immunoglobulin (e.g., antibody or antigen-binding fragment thereof) array. An immunoglobulin array as used herein, refers to a spatially separated set of discrete molecular entities capable of binding to target polypeptides which are arranged in a manner that allows identification of the polypeptides contained within the sample. In other embodiments, the array may comprise one or more of proteins, polypeptides, peptides, RNA, DNA, lipid, glycosylated molecules, polypeptides with phosphorylation modifications, and polypeptides with citrulline modifications, aptamers, other molecules, and other molecules, where different classes of molecules may be combined in an array.

Other detection techniques using click chemistry reagents (Svenson et al., Adv. Drug. Deliv. Rev. 57(15):2106-2129, 2005; Kolb et al., Drug Discov. Today 8(24):1128-1137, 2003) or fluorophore related technologies such as that utilized by Nanostring Technologies and described in US Patent Application Publication No. 20030013091, incorporated herein by reference. In short, this aspect is directed at the use of a diverse population of unique labels for the detection, identification, and direct quantification of a wide variety of target analytes. In one embodiment, the invention is directed to detecting nucleic acid analytes in a complex mixture by first contacting the mixture under conditions sufficient for hybridization with a plurality of target specific nucleic acid probes. These target specific nucleic acid probes, called specifiers, contain a target specific region and a region containing one or more unique "genedigit" sequences. The genedigits consist of repeated core element sequences that can be specifically bound by a complementary anti-genedigit sequence which can contain a unique label. The mixture containing the nucleic acid analytes and the specifiers is then contacted with a corresponding plurality of labeled anti-genedigits having a diversity sufficient to uniquely hybridize to genedigits within the specifiers. This allows the unique detection of a hybridized complex between analytes in the mixture and specifiers with unique labels.

The present invention also provides utilizing the organ-specific sequences disclosed herein to detect and quantify analytes in a mixture by generating a diverse population of uniquely labeled probes, contacting a mixture with these probes, and detecting the complexes that result from hybridization of probes to analytes in the mixture. This technology may be applied in a variety of ways, including identifying and quantifying the expression of genes in normal and diseased cells, as well as aiding in the discovery of new drug and diagnostic targets.

The first step in this process involves producing a diverse population of uniquely labeled nucleic acid probes. This includes synthesizing a diverse population of target specific nucleic acid probes each having a different specifier; synthesizing a population of anti-genedigits capable of specifically binding to the gene digit of the probe and each having a unique label; and hybridizing the target nucleic acid probes to the anti-genedigits, thereby producing a population of uniquely labeled probes. Since a specifier may contain one or several genedigits the methods herein may use multiple unique labels may be available to bind analytes in a mixture. Thus, a large population of specifiers can be synthesized that contain several combinations of genedigits in order to label multiple analytes in a mixture. Conversely, in order to label one or a few analytes in a mixture, a specifier may be synthesized that contains one or a few genedigits.

Accordingly, using such genedigits, one can detect an analyte such as a nucleic acid analyte (such as polypeptides or transcripts encoding the same from a tissue sample or a sample from a biological sample such as whole blood) by contacting a mixture of analytes with a population of uniquely labeled probes, under conditions sufficient for hybridization. Following this hybridization, the signals are measured that result from one or more target specific probes bound to an analyte; wherein the signal uniquely identifies the analyte.

The present invention provides a diverse population of uniquely labeled probes in which a target specific nucleic acid contains a nucleic acid bound to a unique label. In addition, the invention provides a diverse population of uniquely labeled probes containing two attached populations of nucleic acids, one population of nucleic acids containing thirty or more target specific nucleic acid probes, and a second population of nucleic acids containing a nucleic acid bound by a unique label.

A target specific probe is intended to mean an agent that binds to the target analyte selectively. This agent will bind with preferential affinity toward the target while showing little to no detectable cross-reactivity toward other molecules.

The target analyte can be any type of macromolecule, including a nucleic acid, a protein or even a small molecule drug. For example, a target can be a nucleic acid that is recognized and bound specifically by a complementary nucleic acid including for example, an oligonucleotide or a PCR product, or a non-natural nucleic acid such as a locked nucleic acid (LNA) or a peptide nucleic acid (PNA). In addition, a target can be a peptide that is bound by a nucleic acid. For example, a DNA binding domain of a transcription factor can bind specifically to a particular nucleic acid sequence. Another example of a peptide that can be bound by a nucleic acid is a peptide that can be bound by an aptamer. Aptamers are nucleic acid sequences that have three dimensional structures capable of binding small molecular targets including metal ions, organic dyes, drugs, amino acids, co-factors, aminoglycosides, antibiotics, nucleotide base analogs, nucleotides and peptides (Jayasena, S. D., Clinical Chemistry 45:9, 1628-1650, (1999)) incorporated herein by reference. Further, a target can be a peptide that is bound by another peptide or an antibody or antibody fragment. The binding peptide or antibody can be linked to a nucleic acid, for example, by the use of known chemistries including chemical and UV cross-linking agents. In addition, a peptide can be linked to a nucleic acid through the use of an aptamer that specifically binds the peptide. Other nucleic acids can be directly attached to the aptamer or attached through the use of hybridization. A target molecule can even be a small molecule that can be bound by an aptamer or a peptide ligand binding domain.

The invention further provides a method for detecting a nucleic acid analyte, by contacting a mixture of nucleic acid analytes with a population of target specific probes each attached to a unique label under conditions sufficient for hybridization of the probes to the target and measuring the resulting signal from one or more of the target specific probes hybridized to an analyte where the signal uniquely identifies the analyte.

The nucleic acid analyte can contain any type of nucleic acid, including for example, an RNA population or a population of cDNA copies. The invention provides for at least one target specific probe for each analyte in a mixture. The invention also provides for a target specific probe that contains a nucleic acid bound to a unique label. Furthermore, the invention provides two attached populations of nucleic acids, one population of nucleic acids containing a plurality of target specific nucleic acid probes, and a second population of nucleic acids containing a nucleic acid bound by a unique label. When the target specific probes are attached to unique labels, this allows for the unique identification of the target analytes.

Identification of Unknown Transcripts

In order to identify organ-specific transcripts, the resulting annotated transcripts are compared against public and/or private sequence databases, such as a variety of annotated human genome sequence databases (e.g., HUPO, Genebank, the EMBL and Japanese databases and databases generated and compiled from other normal tissues), to identify those transcripts that are expressed primarily in the organ of interest but are not expressed in other organs. As noted elsewhere herein, some expression in organs other than the organ of interest does not necessarily preclude the use of a particular transcript in an organ-specific protein set or diagnostic panel of the present invention.

In certain embodiments, a particular transcript is considered to be organ-specific when the number of transcripts/ million as determined by MPSS is 3 copies/million or greater in the organ of interest but is less than 3 copies/million in all other organs examined, where, preferably 5, 10, 15, 20 or 25 organs are examined. In another embodiment, a transcript is considered organ-specific if it is expressed in the organ of interest at a detectable levels using a standard measurement (e.g., microarray analysis, quantitative real-time RT-PCR, MPSS, SBS) in the organ of interest but is not detectably expressed in other organs, using appropriate negative and positive controls as would be familiar to the skilled artisan. In a further embodiment, an organ-specific transcript is one that is expressed 99% in one organ and the remaining 1% in one or more other organs examined. (In this context, total expression across all organs examined is taken as 100%). In certain embodiments, an organ-specific transcript is expressed at about 50%, 60%, 70%, 80%, 90%, 95% to about 99% in one organ and wherein the remaining 1%-50% is expressed in one or more other organs examined. As would be readily recognized by the skilled artisan upon reading the present disclosure, in certain embodiments, an organ-specific blood fingerprint can readily be discerned even if some expression of an organ-specific protein from a particular organ is detected at some levels in another organ, or even more than one organ. This is because the fingerprint (e.g., the combination of the levels of multiple proteins; the pattern of the expression levels of multiple markers) itself is unique despite that the expression levels of one or more individual members of the fingerprint may not be unique to a particular organ. Thus the present invention relates to determining the presence or absence of a disease or condition or stage of disease based on a single marker or a pattern (e.g., fingerprint) of markers measured concurrently using any one or more of a variety of methods described herein (e.g., antibody binding, mass spectrometry, and the like).

In certain embodiments, the organ-specificity of a transcript is determined using the algorithms as outlined in Example 1 or Example 9.

In further embodiments, organ-specificity can be confirmed at the protein level using immunohistochemistry (IHC) and/or other protein measurement techniques known in the art (e.g., isotope-coded affinity tags and mass spectrometry, such as described by Han, D. K., et al., *Nat Biotechnol*, 19: 946-951, 2001). The Z-test (Man, M. Z., et al., *Bioinformatics*, 16: 953-959, 2000) or other appropriate statistical tests can be used to calculate P values for comparison of gene and protein expression levels between libraries from organs of interest.

Any of a variety of statistical methods known in the art and described herein, can be used to evaluate organ-specificity and, as discussed further herein, define statistical changes in the level of a particular protein measured between a normal control sample of blood and a blood sample that is changed from normal. Exemplary statistical methods include, for example, discriminant analysis, classification analysis, cluster analysis, analysis of variance (ANOVA), regression analysis, regression trees, decision trees, nearest neighbor algorithms, principal components, factor analysis, multidimensional scaling and other methods of dimensionality reduction, likelihood models, hypothesis testing, kernel density estimation and other smoothing techniques, cross-validation and other methods to guard against overfitting of the data, the bootstrap and other statistical resampling techniques, artificial intelligence, including artificial neural networks, machine learning, data mining, and boosting algorithms, and Bayesian analysis using prior probability distributions (see e.g., U.S. Patent Application No. 20020095259).

Comparisons of the transcripts between databases can be made using a variety of computer analysis algorithms known in the art. As such, alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. As would be understood by the skilled artisan, many algorithms are available and are continually being developed. Appropriate algorithms can be chosen based on the specific needs for the comparisons being made (See also, e.g., J. A. Cuff, et al., *Bioinformatics*, 16(2):111-116, 2000; S. F Altschul and B. W. Erickson. *Bulletin of Mathematical Biology*, 48(5/6):603-616, 1986; S. F. Altschul and B. W. Erickson. *Bulletin of Mathematical Biology*, 48(516):633-660, 1986; S. F. Altschul, et al., *J. Mol. Bio.*, 215:403-410, 1990; K. Bucka-Lassen, et al., *BIOINFORMATICS*, 15(2):122-130, 1999; K.-M. Chao, et al., *Bulletin of Mathematical Biology*, 55(3): 503-524, 1993; W. M. Fitch and T. F. Smith. *Proceedings of the National Academy of Sciences*, 80:1382-1386, 1983; A. D. Gordon. *Biometrika*, 60:197-200, 1973; 0. Gotoh. *J Mol Biol*, 162:705-708, 1982; O. Gotoh. *Bulletin of Mathematical Biology*, 52(3):359-373, 1990; X. Huang, et al., *CABIOS*, 6:373-381, 1990; X. Huang and W. Miller. *Advances in Applied Mathematics,* 12:337-357, 1991; J. D. Thompson, et al., *Nucleic Acids Research,* 27(13):2682-2690, 1999).

The organ-specific protein sets may be further characterized using computational methods to predict localization. In one embodiment, protein sequences in the RefSeq database are used to predict protein localization. One of the programs is TMHMM (server 2.0, http colon double slash www dot cbs dot dtu dot dk/services/TMHMM/), which applies hidden Markov model to predict protein transmembrane domains and is considered as one of the best such programs. Another program that can be used in this context is SignalP (server 3.0, http colon double slash www dot cbs dot dtu dot dk/services/SignalP/), which applies both artificial neural network and hidden Markov model to predict the presence and the location of signal peptide cleavage sites for classical (N-terminus lead) proteins. The outputs of the two programs can be combined into protein localization prediction, such as is outlined in Table 33.

Illustrative computational analyses that can be used for predicting proteins with signal peptides (classical secretory proteins) include, but are not limited to the criteria described by Chen at al., *Mamm Genome,* 14: 859-865, 2003. In certain embodiments, such analyses are carried out using prediction servers, for example SignalP 3.0 server developed by The Center for Biological Sequence Analysis, Lyngby, Denmark (http colon double slash www dot cbs dot dtu dot dk/services/SignalP-3.0; see also, J. D. Bendtsen, et al., *J. Mol. Biol.,* 340:783-795, 2004.) and the TMHMM2.0 server (see for example A. Krogh, et al., *Journal of Molecular Biology,* 305 (3):567-580, January 2001; E. L. L. Sonnhammer, at al., In J. Glasgow, T. Littlejohn, F. Major, R. Lathrop, D. Sankoff, and C. Sensen, editors, *Proceedings of the Sixth International Conference on Intelligent Systems for Molecular Biology,* pages 175-182, Menlo Park, Calif., 1998. AAAI Press). Other prediction methods that can be used in the context of the present invention include those described for example, in S. Moller, M. D. R. et al., *Bioinformatics,* 17(7):646-653, July 2001. Nonclassical secretory secreted proteins (without signal peptides) can be predicted using, for example, the SecretomeP 1.0 server with an odds ratio score >3.0. Other methods known in the art are also contemplated herein and Sigfind.

As would be recognized by the skilled artisan, while the organ-specific proteins, the levels of which make up a given normal or disease-associated fingerprint, need not be isolated, in certain embodiments, it may be desirable to isolate such proteins (e.g., for antibody production or for developing other detection reagents as described herein). As such, the present invention provides for isolated organ-specific proteins or fragments or portions thereof and polynucleotides that encode such proteins. As used herein, the terms protein and polypeptide are used interchangeably. Illustrative organ-specific proteins include those provided in the amino acid sequences set forth in the appended sequence listing. The terms polypeptide and protein encompass amino acid chains of any length, including full-length endogenous (i.e., native) proteins and variants of endogenous polypeptides described herein. Variants are polypeptides that differ in sequence from the polypeptides of the present invention only in substitutions, deletions and/or other modifications, such that either the variants disease-specific expression patterns are not significantly altered or the polypeptides remain useful for diagnostics/detection of organ-specific proteins as described herein. For example, modifications to the polypeptides of the present invention may be made in the laboratory to facilitate expression and/or purification and/or to improve immunogenicity for the generation of appropriate antibodies and other detection agents. Modified variants (e.g., chemically modified) of organ-specific proteins may be useful herein, (e.g., as standards in mass spectrometry analyses of the corresponding proteins in the blood, and the like). As such, in certain embodiments, the biological function of a variant protein is not relevant for utility in the methods for detection and/or diagnostics described herein. Polypeptide variants generally encompassed by the present invention will typically exhibit at least about 70%, 75%, 80%, 85%, 86%, 87%, 88%, 89%, 90%, 91%, 92%, 93%, 94%, 95%, 96%, 97%, 98%, or 99% or more identity along its length, to a polypeptide sequence set forth herein. Within a polypeptide variant, amino acid substitutions are usually made at no more than 50% of the amino acid residues in the native polypeptide, and in certain embodiments, at no more than 25% of the amino acid residues. In certain embodiments, such substitutions are conservative. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Thus, a variant may comprise only a portion of a native polypeptide sequence as provided herein. In addition, or alternatively, variants may contain additional amino acid sequences (such as, for example, linkers, tags and/or ligands), usually at the amino and/or carboxy termini. Such sequences may be used, for example, to facilitate purification, detection or cellular uptake of the polypeptide.

When comparing polypeptide sequences, two sequences are said to be identical if the sequence of amino acids in the two sequences is the same when aligned for maximum correspondence, as described below. Comparisons between two sequences are typically performed by comparing the sequences over a comparison window to identify and compare local regions of sequence similarity. A comparison window as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins Matrices for detecting distant relationships. In Dayhoff, M. O. (ed.) *Atlas of Protein Sequence and Structure,* National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Saitou, N. Nei, M. (1987) *Mol. Biol. Evol.* 4:406-425; Sneath, P. H. A. and Sokal, R. R. (1973) *Numerical Taxonomy the Principles and Practice of Numerical Taxonomy,* Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Illustrative examples of algorithms that are suitable for determining percent sequence identity and sequence similarity include the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example, to determine percent sequence identity for the polynucleotides and polypeptides of the invention. Software for performing BLAST analyses is publicly available through the National Center for Biotechnology Information.

An isolated polypeptide is one that is removed from its original environment. For example, a naturally occurring protein or polypeptide is isolated if it is separated from some or all of the coexisting materials in the natural system. In certain embodiments, such polypeptides are also purified, e.g., are at least about 90% pure by weight of protein in the preparation, in some embodiments, at least about 95% pure by weight of protein in the preparation and in further embodiments, at least about 99% pure by weight of protein in the preparation.

In one embodiment of the present invention, a polypeptide comprises a fusion protein comprising an organ-specific polypeptide. The present invention further provides fusion proteins that comprise at least one polypeptide as described herein, as well as polynucleotides encoding such fusion proteins. The fusion proteins may comprise multiple polypeptides or portions/variants thereof, as described herein, and may further comprise one or more polypeptide segments for facilitating the expression, purification, detection, and/or activity of the polypeptide(s).

In certain embodiments, the proteins and/or polynucleotides, and/or fusion proteins are provided in the form of compositions, e.g., pharmaceutical compositions, vaccine compositions, compositions comprising a physiologically acceptable carrier or excipient. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

In certain embodiments, wash buffer refers to a solution that may be used to wash and remove unbound material from an adsorbent surface. Wash buffers typically include salts that may or may not buffer pH within a specified range, detergents and optionally may include other ingredients useful in removing adventitiously associated material from a surface or complex.

In certain embodiments, elution buffer refers to a solution capable of dissociating a binding moiety and an associated analyte. In some circumstances, an elution buffer is capable of disrupting the interaction between subunits when the subunits are associated in a complex. As with wash buffers, elution buffers may include detergents, salt, organic solvents and may be used separately or as mixtures. Typically, these latter reagents are present at higher concentrations in an elution buffer than in a wash buffer making the elution buffer more disruptive to molecular interactions. This ability to disrupt molecular interactions is termed "stringency," with elution buffers having greater stringency that wash buffers.

In general, organ-specific polypeptides and polynucleotides encoding such polypeptides as described herein, may be prepared using any of a variety of techniques that are well known in the art. For example, a polynucleotide encoding an organ-specific protein may be prepared by amplification from a suitable cDNA or genomic library using, for example, polymerase chain reaction (PCR) or hybridization techniques. Libraries may generally be prepared and screened using methods well known to those of ordinary skill in the art, such as those described in Sambrook et al., *Molecular Cloning: A Laboratory Manual*, Cold Spring Harbor Laboratories, Cold Spring Harbor, N.Y., 1989. cDNA libraries may be prepared from any of a variety of organs, tissues, cells, as described herein. Other libraries that may be employed will be apparent to those of ordinary skill in the art upon reading the present disclosure. Primers for use in amplification may be readily designed based on the polynucleotide sequences encoding organ-specific polypeptides as provided herein, for example, using programs such as the PRIMER3 program (see website: http colon double slash www dash genome dot wi dot mit dot edu slash cgi dash bin slash primer slash primer3 www dot cgi).

Polynucleotides encoding the organ-specific polypeptides as described herein are also provided by the present invention. Polynucleotides of the present invention may comprise a native sequence (i.e., an endogenous polynucleotide, for instance, a native or non-artificially engineered or naturally occurring gene as provided herein) encoding an organ-specific protein, an alternate form of such a sequence, or a portion or splice variant thereof or may comprise a variant of such a sequence. Polynucleotide variants may contain one or more substitutions, additions, deletions and/or insertions such that the polynucleotide encodes a polypeptide useful in the methods described herein, such as for the detection of organ-specific proteins (e.g., wherein said polynucleotide variants encode polypeptides that can be used to generate detection reagents as described herein that specifically bind to an organ-specific protein). In certain embodiments, variants exhibit at least about 70% identity, and in other embodiments, exhibit at least about 80%, 85%, 86%, 87%, 88%, 89%, identity and in yet further embodiments, at least about 90%, 91%, 92%, 93%, 94%, 95%, 96%, 97%, 98%, or 99% identity to a polynucleotide sequence that encodes a native organ-specific polypeptide or an alternate form or a portion thereof. Illustrative polynucleotides of the present invention comprise the polynucleotides of set forth in the sequence listing attached hereto. The percent identity may be readily determined by comparing sequences using computer algorithms well known to those having ordinary skill in the art and described herein.

A polynucleotide as used herein may be single-stranded (coding or antisense) or double-stranded, and may be DNA (genomic, cDNA or synthetic) or RNA molecules. Thus, within the context of the present invention, a polynucleotide encoding a polypeptide may also be a gene. A gene is a segment of DNA involved in producing a polypeptide chain; it includes regions preceding and following the coding region (leader and trailer) as well as intervening sequences (introns) between individual coding segments (exons). Additional coding or non-coding sequences may, but need not, be present within a polynucleotide of the present invention, and a polynucleotide may, but need not, be linked to other molecules and/or support materials. An isolated polynucleotide, as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment using recombinant techniques known to the skilled artisan. Polynucleotides that are complementary to the polynucleotides described herein, or that have substantial identity to a sequence complementary to a polynucleotide as described herein are also within the scope of the present invention. Substantial identity, as used herein refers to polynucleotides that exhibit at least about 70% identity, and in certain embodiments, at least about 80%, 85%, 86%, 87%, 88%, 89%, 90%, 91%, 92%, 93%, 94%, 95%, 96%, 97%, 98%, or 99% identity to a polynucleotide sequence that encodes a native organ-specific polypeptide as described herein. Substantial identity can also refer to polynucleotides that are capable of hybridizing under stringent conditions to a polynucleotide complementary to a polynucleotide encoding an organ-specific protein. Suitable hybridization conditions include prewashing in a solution of 5×SSC, 0.5% SDS, 1.0 mM EDTA (pH 8.0); hybridizing at 50-65° C., 5×SSC, overnight; followed by washing twice at 65° C. for 20 minutes with each of 2×, 0.5× and 0.2×SSC containing 0.1% SDS. Nucleotide sequences that, because of code degeneracy, encode a polypeptide encoded by any of the above sequences are also encompassed by the present invention. Lastly, it should be understood by the skilled artisan that RNA as well as cDNA derived therefrom as well as the coding and non-coding strands may also be utilized in the methods or as panels described herein in the place of proteins or antibodies thereto.

Normal Serum Organ-Specific Protein Sets

A normal serum organ-specific protein set comprises the subset of proteins from an organ-specific protein set that are detected in normal serum. Identification of organ-specific proteins from a given organ-specific protein set that are found in normal serum can be carried out using a variety of methods known in the art. For example, antibodies specific for the proteins can be used to measure the presence of the protein in blood/serum/plasma or tissue sample/biopsy by a variety of immunoaffinity based techniques (e.g., immunoblot, Western analysis, immunoprecipitation, ELISA). Antibodies specific for the proteins described herein may be commercially available through any of a number of sources known to the skilled artisan or may be generated using techniques known in the art and described herein (See, e.g., Harlow and Lane, *Antibodies: A Laboratory Manual*, Cold Spring Harbor Laboratory, 1988).

As an alternative, aptamers (short DNA or RNA fragments with binding complementarily to the proteins of interest) may be used in assays similar to those described for antibodies (see for example, *Biotechniques*. 2001 February; 30(2):290-2, 294-5; *Clinical Chemistry.* 1999; 45:1628-1650). In this regard, an aptamer may be selected for specific binding properties and may be used in a similar manner to an antibody in a variety of appropriate binding assays known to the skilled artisan and described herein In addition, antibodies or aptamers may be used in connection with nanowires to create highly sensitive detections systems (see e.g., J. Heath et al., Science. 2004 Dec. 17; 306(5704):2055-6). In further embodiments, mass spectrometry-based methods can be used to confirm the presence of a particular protein in the blood.

A variety of mass spectrometry systems can be employed in the methods of the invention for identifying and/or quantifying organ-specific proteins in blood. Mass analyzers with high mass accuracy, high sensitivity and high resolution include, but are not limited to, ion trap, triple quadrupole, and time-of-flight, quadrupole time-of-flight mass spectrometers and Fourier transform ion cyclotron mass analyzers (FT-ICR-MS). Mass spectrometers are typically equipped with matrix-assisted laser desorption (MALDI) and electrospray ionization (ESI) ion sources, although other methods of peptide ionization can also be used. In ion trap MS, analytes are ionized by ESI or MALDI and then put into an ion trap. Trapped ions can then be separately analyzed by MS upon selective release from the ion trap. Organ-specific proteins can be analyzed, for example, by single stage mass spectrometry with a MALDI-TOF or ESI-TOF system. Methods of mass spectrometry analysis are well known to those skilled in the art (see, for example, Yates, *J. Mass Spect.* (1998) 33:1-19; Kinter and Sherman, Protein Sequencing and Identification Using Tandem Mass Spectrometry, John Wiley & Sons, New York (2000); Aebersold and Goodlett, *Chem. Rev.* (2001) 101:269-295; Banez et al, *Curr Opin Urol* (2005) 15:151-156). For high resolution protein separation, liquid chromatography ESI-MS/MS or automated LC-MS/MS, which utilizes capillary reverse phase chromatography as the separation method, can be used (Yates et al., *Methods Mol. Biol.* (1999) 112:553-569).

In another embodiment, organ-specific proteins may be detected and analyzed by immunoaffinity based assays such as ELISAs, Western blots, and radioimmunoassays. Other methods useful in this context include isotope-coded affinity tag (ICAT) followed by multidimensional chromatography and MS/MS. The procedures described herein for analysis of blood can be modified and adapted to make use of microfluidics and nanotechnology in order to miniaturize, parallelize, integrate and automate diagnostic procedures (see e.g., L. Hood, et al., *Science* (2004) 306:640-643; R. H. Carlson, et al., *Phys. Rev. Lett.* (1997) 79:2149; A. Y. Fu, at al., *Anal. Chem.* (2002) 74:2451; J. W. Hong, at al., *Nature Biotechnol.* (2004) 22:435; A. G. Hadd, et al., *Anal. Chem.* (1997) 69:3407; I. Karube, at al., *Ann. N.Y. Acad. Sci.* (1995) 750:101; L. C. Waters et al., *Anal. Chem.* (1998) 70:158; J. Fritz et al., *Science* (2000) 288, 316).

The levels of organ-specific proteins in blood can also be measured using any one or more methods such as nucleic acid based or polypeptide/peptide based microarrays.

Methods for measuring organ-specific protein levels from blood/serum/plasma include, but are not limited to, immunoaffinity based assays such as ELISAs, Western blots, and radioimmunoassays, fluorescence activated cell sorting (FACS) and mass spectrometry based methods (matrix-assisted laser desorption ionization (MALDI), MALDI-Time-of-Flight (TOF), Tandem MS (MS/MS), electrospray ionization (ESI), Surface Enhanced Laser Desorption Ionization (SELDI)-TOF MS (Xiao, at al., *Mol and Cell Endocrinology* 230:95-106 (2005), liquid chromatography (LC)-MS/MS,). Other methods useful in proteomic analysis include 2-D Difference Gel Electrophoresis (DIGE), and protein arrays (see e.g., Unlu et al., *Electrophoresis* 18:2071 (1997); Tonge et al, *Proteomics* 1:377 (2001); Macbeath et al., *Science* 289:1760 (2000); Walter at al., Trends in Molecular Medicine 8:250 (2002).

In one embodiment, the organ-specific proteins that are being measured are glycosylated. Thus, in certain embodiments, the invention contemplates the use of protein glycocapture methods for preparing proteins for analysis. Protein glycosylation is a very common post-translational modification. In particular, N-linked glycosylation is common in proteins that move to extracellular environments. These include proteins on the extracellular side of the plasma membrane, secreted proteins and proteins contained in body fluids. Body fluids include, but are not limited to, cerebrospinal fluid, blood serum, urine, breast milk, saliva, pancreatic juice, peritoneal, lacrimal, reproductive, intraocular, digestive, respiratory, pleural, pericardial, lymphatic, urine, intracellular and extracellular fluids, and neural fluids. This list is for illustrative purposes and it is not meant to be limiting. (Zhang et al., *Nat Biotechnol* 6:660, (2003)). Glycoproteins are isolated from any of a variety of tissue samples or plasma using methods as described in US Patent Application No. 20040023306. After isolating glycopolypeptides from a sample and cleaving the glycopolypeptide into fragments, the glycopeptide fragments released from the solid support and the released glycopeptide fragments are identified and/or quantified. A particularly useful method for analysis of the released glycopeptide fragments is mass spectrometry. For high resolution polypeptide fragment separation, liquid chromatography ESI-MS/MS or automated LC-MS/MS, which utilizes capillary reverse phase chromatography as the separation method, can be used (Yates et al., Methods Mol. Biol. 112:553-569 (1999)). Data dependent collision-induced dissociation (CID) with dynamic exclusion can also be used as the mass spectrometric method (Goodlett, et al., Anal. Chem. 72:1112-1118 (2000)). Once a peptide is analyzed by MS/MS, the resulting CID spectrum can be compared to databases for the determination of the identity of the isolated glycopeptide. Methods for protein identification using single peptides has been described previously (Aebersold and Goodlett, Chem. Rev. 101:269-295 (2001); Yates, J. Mass Spec. 33:1-19 (1998).

In one embodiment, normal, healthy blood samples are collected from healthy subjects, proteins present in the blood are identified using, for example, mass spectrometry, and the proteins identified in this manner are compared to the organ-specific proteins provided in Tables 1-32, 36-45 and 47-79 using any of a variety of computational methods readily known in the art.

Normal serum organ-specific proteins are generally identified from a sample of blood collected from a subject using accepted techniques. In one embodiment, blood samples are collected in evacuated serum separator tubes. In another embodiment, blood may be collected in blood collection tubes that contain any anti-coagulant. Illustrative anticoagulants include ethylenediaminetetraacetic acid (EDTA) and lithium heparin. However, any method of blood sample or other bodily fluid or biological/tissue sample collection and storage is contemplated herein. In particular blood may be collected by any portal including the finger, foot, intravenous lines, and portable catheter lines. In one embodiment, blood is centrifuged and the serum layer that separates from the red cells is collected for analysis. In another embodiment, whole blood or plasma is used for analysis.

In certain embodiments a normal blood sample is obtained from human serum recovered from whole blood donations from an FDA-approved clinical source. In this embodiment, the normal, healthy donor hematocrit is between the range of 38% and 55%, the donor weight is over 110 pounds, the donor age is between 18 and 65 years old, the donor blood pressure is in the range of 90-180 mmHg (systolic) and 50-100 mmHg (diastolic), the arms and general appearance of the donor are free of needle marks and any mark signifying risky behavior. The donor pulse should be between 50 bpm-100 bpm, the temperature of the donor should be between 97 and 99.5 degrees. The donor does not have diseases including, but not limited to chest pain, heart disease or lung disease including tuberculosis, cancer, skin disease, any blood disease, or bleeding problems, yellow jaundice, liver disease, hepatitis or a positive test for hepatitis. The donor has not had close contact with hepatitis in the past 12 months nor has the donor ever received pituitary growth hormones.

In certain embodiments, disease free blood is as follows: the donor has not made a donation of blood within the previous 8 weeks, the donor has not had a fever with headache within one week from the date of donation, the donor has not donated a double unit of red cells using an aphaeresis machine within the previous 16 weeks, the donor is not ill with Severe Acute Respiratory Syndrome (SARS), nor has the donor had close contact with someone with SARS, nor has the donor visited (SARS) affected areas. The donor has had no sexual contact with anyone who has HIV/AIDS or has had a positive test for the HIV/AIDS virus, and does not have syphilis or gonorrhea. From 1977 to present, the donor never received money, drugs, or other payment for sex, male donors have never had sexual contact with another male, donors have not had a positive test for the HIV/AIDS virus, donors have not used needles to take drugs, steroids, or anything not prescribed by a physician, donors have not used clotting factor concentrates, donors have not had sexual contact with anyone who was born in or lived in Africa, or traveled to Africa.

Thus, the present invention provides the normal serum level of components that make up a normal serum organ-specific protein set. This level is an average of the levels of a given component measured in a statistically large number of blood samples from normal, healthy individuals. Thus, a "predetermined normal level" is a statistical range of normal and is also referred to herein as "predetermined normal range". The normal levels or range of levels in the blood for each component are determined by measuring the level of protein in the blood using any of a variety of techniques known in the art and described herein in a sufficient number of blood samples from normal, healthy individuals to determine the standard deviation (SD) with statistically meaningful accuracy.

As would be recognized by the skilled artisan upon reading the present disclosure, in determining the normal serum level of a particular component of an organ-specific protein set, general biological data is considered and compared, including, for example, gender, time of day of blood sampling, fasting or after food intake, age, race, environment and/or polymorphisms. Biological data may also include data concerning the height, growth rate, cardiovascular status, reproductive status (pre-pubertal, pubertal, post-pubertal, pre-menopausal, menopausal, post-menopausal, fertile, infertile), body fat percentage, and body fat distribution. This list of individual differences that can be measured is exemplary and additional biological data is contemplated.

Thus, the levels of the components that make up a normal serum organ-specific protein set are determined. Normal organ-specific blood fingerprints comprise a data set comprising determined levels in blood from normal, healthy individuals of one, two, three, four, five, six, seven, eight, nine, ten, or more components of a normal serum organ-specific protein set. The normal levels in the blood for each component included in a fingerprint are determined by measuring the level of protein in the blood using any of a variety of techniques known in the art and described herein, in a sufficient number of blood samples from normal, healthy individuals to determine the standard deviation (SD) with statistically meaningful accuracy. Thus, as would be recognized by one of skill in the art, a determined normal level is defined by averaging the level of protein measured in a statistically large number of blood samples from normal, healthy individuals and thereby defining a statistical range of normal. A normal organ-specific blood fingerprint comprises the determined levels in normal, healthy blood of N members of a normal serum organ-specific protein set wherein N is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more members up to the total number of members in a given normal serum organ-specific protein set. In certain embodiments, a normal organ-specific blood fingerprint comprises the determined levels in normal, healthy blood of at least two components of a normal serum organ-specific protein set. In other embodiments, a normal organ-specific blood fingerprint comprises the determined levels in normal, healthy blood of at least 3, 4, 5, 6, 7, 8, 9, 10, 11, 12, 13, 14, 15, 16, 17, 18, 19, or 20 components of a normal serum organ-specific protein set. In yet further embodiments, a normal control would be run at the time of the assay such that only the presence of a normal sample and the test sample would be necessary and the specific differences between the test sample and the normal sample would then be delineated based upon the panels provided herein.

As would be understood by the skilled artisan upon reading the present disclosure, the subset of proteins from the organ-specific protein set that are found in blood may comprise proteins that are predicted to be secreted, anchored, transmembrane, or other/intracellular proteins. In this regard a variety of methods as described herein can be used for predicting and defining protein localization. As would be recognized by the skilled artisan, anchored, transmembrane and intracellular proteins may be detected in the blood for a variety of reasons. For example, the attachment linkages of anchored proteins may be cleaved by enzymes or by proteases and thereby be identified in the blood or biological fluids as an anchored protein. Anchored and transmembrane organ-specific proteins may also be shed into the blood. Further, organ-specific proteins that are predicted to be localized intracellularly may be leaked or excreted into the blood. In specific embodiments of the present invention, panels and detection methods may comprise components from or that detect only organ-specific secreted proteins or transcripts thereof or components that are leaked, excreted or shed, but not normally secreted by use of a secretion signal or by means of an alternative secretion method such as leaderless proteins (e.g., FGF-1, FGF-2, IL-1α, IL-1β, aldose reductase, PD-ECGF, CNTF, prothymosin α, parathymosin, galectin-1, Factor XIIIa, ATL-derived factor, annexin-1, transglutaminase, mammary-derived growth inhibitor, macrophage migration inhibitory factor (MIF), HIV tat, ATP synthase, aminoacyl-tRNA synthetase, EMAP, rhodanase, thioredoxin-like protein, and others.

In certain embodiments, the ability to detect an organ-specific protein in blood may be hampered due to sensitivity or other issues. As such, the present invention contemplates detection of organ-specific proteins from any of a variety of tissue sources and bodily fluids. Thus, organ-specific proteins can be measured from biopsy samples from normal or diseased organ or any bodily fluid, such as, but not limited to, cerebrospinal fluid, blood serum, urine, breast milk, saliva, pancreatic juice, peritoneal, lacrimal, reproductive, intraocular, digestive, respiratory, pleural, pericardial, lymphatic, urine, intracellular and extracellular fluids, and neural fluids. The present invention also contemplates detection of organ-specific proteins at the transcript level from any of these tissue sources using polynucleotide-based detection methods known in the art and described herein.

Diagnostic/Prognostic Panels

The normal serum organ-specific protein sets defined herein and the predetermined normal levels of the components that make up the organ-specific protein sets (e.g., the database of predetermined normal serum levels of organ-specific proteins) can be used as a baseline against which one can determine any perturbation of the normal state. Perturbation of the normal biological state is identified by measuring levels of organ-specific proteins from a patient and comparing the measured levels against the predetermined normal levels. Any level that is statistically significantly altered from the normal level (i.e., any level from the disease sample that is outside (either above or below) the predetermined normal range) indicates a perturbation of normal and thus, the presence of disease (or effect of a drug or environmental agent, etc.). In this way, the predetermined normal levels of normal serum organ-specific proteins are also used to identify and define disease-associated blood fingerprints. Such sets or panels typically comprise proteins or nucleic acid molecules that are organ-specific, but that may be found in a bodily fluid or tissue sample. In certain embodiments the present methods, panels, and sets are directed to either collective sets or individual sets of organ-specific proteins that can be detected in a bodily fluid and are secreted, leaked, excreted or shed. In certain specific embodiments, the present invention is directed to sets of proteins (including antibodies and fragments that bind thereto) that are secreted or the nucleic acid molecules that encode the same or nucleic acid probes that bind thereto. As used herein, a panel may comprise less than the entire set of sequences defined in the tables attached hereto for a given organ. For example, as can be readily appreciated by the skilled artisan, 1 transcript or protein of each organ may be enough to generally monitor the health of an organ. However, increasing the number of probes targeting the component (nucleic acid or polypeptide), while not necessary will add specificity and sensitivity to the assay. Accordingly, in certain aspects at least 5 probes per organ set for organ-specific components will be present in the panel, in other aspects at least 10 probes per organ set will be present, yet in others there may be 20, 30, 40, 50 or more probes present per organ set. In certain embodiments, probes per set may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween.

Thus, the present invention provides panels for detecting and measuring the level of organ-specific proteins in blood that can be used in a variety of diagnostic settings. As used herein and discussed further below, "diagnostic panel or prognostic panel" is meant to encompass panels, arrays, mixtures, and kits that may comprise detection reagents or probes specific to an organ specific component or a control (control nucleic acid or polypeptide sequences may or may not be a component of an organ specific set) and any of a variety of associated buffers, solutions, appropriate negative and positive controls, instruction sets, and the like. A "detection reagent" as used herein is meant to refer to any agent that that associates or binds directly or indirectly to a molecule in the test sample. In certain embodiments, a detection reagent may comprise antibodies (or fragments thereof) either with a secondary detection reagent attached thereto or without, nucleic acid probes, aptamers, click reagents, etc. Further, a "panel" may comprise panels, arrays, mixtures, kits, or other arrangements of proteins, antibodies or fragments thereof to organ-specific proteins, nucleic acid molecules encoding organ-specific proteins, nucleic acid probes to that hybridize to organ-specific nucleic acid sequences. Moreover, a panel may be derived from only one organ or two or more organs. In certain embodiments, organs that comprise a certain system such as the cardiovascular or central nervous system may be grouped together.

The present invention provides panels for detecting the organ-specific blood proteins at any given time in a subject. Examples of subjects include humans, monkeys, apes, dogs, cats, mice, rats, fish, zebra fish, birds, horses, pigs, cows, sheep, goats, chickens, ducks, donkeys, turkeys, peacocks, chinchillas, ferrets, gerbils, rabbits, guinea pigs, hamsters and transgenic species thereof. Further subjects contemplated herein include, but are not limited to, reptiles and amphibians, e.g., lizards, snakes, turtles, frogs, toads, salamanders, and newts and transgenic species thereof.

The panels are comprised of a plurality (e.g., at least two) of detection reagents that each specifically detects a protein (or transcript), in most embodiments substantially all are organ-specific but may also comprise non-organic specific reagents for use as controls or other purposes. In certain aspects the panels comprise detection reagents that each specifically detects a protein (or transcript) an organ-specific protein, wherein the levels of organ-specific proteins taken together form a unique pattern that defines a fingerprint. In certain embodiments, detection reagents can be bispecific such that the panel is comprised of a plurality of bispecific detection reagents that may specifically detect more than one organ-specific protein. The term specifically is a term of art that would be readily understood by the skilled artisan to mean, in this context, that the protein of interest is detected by the particular detection reagent but other proteins are not substantially detected. Specificity can be determined using appropriate positive and negative controls and by routinely optimizing conditions.

The diagnostic panels of the present invention comprise detection reagents wherein each detection reagent is specific for one protein or transcript of an organ or tissue, but as noted above, may also comprise controls that are not or may not be specific to a particular organ/tissue-specific protein or transcript. In certain embodiments, the detection reagents of a panel can each be specific for organ-specific proteins from one organ-specific protein set or from more than one organ-specific protein set. For example, a particular diagnostic panel may comprise detection reagents that detect one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, sixty, seventy, eighty, ninety, one-hundred or more prostate-specific proteins, such as those provided in Table 21, or a diagnostic panel may comprise detection reagents that detect one or more bladder-specific proteins and one or more kidney-specific proteins.

In specific embodiments, and as noted above, diagnostic or prognostic panels may include panels having reagents (e.g., probes) that bind organ-specific proteins or transcripts from one or more organs. To this end, it is envisioned that a panel such as an microarray can have placed thereon multiple protein or nucleic acid probes which specifically bind the organ-specific protein or transcript identified by the methods herein and/or expressly recited in the tables and sequence listing provided herewith. Further, such an array may have placed thereon probes specific for one, two, three, four, five, six, seven, eight, nine, ten, eleven, twelve, thirteen, fourteen, fifteen, sixteen, seventeen, eighteen, nineteen, twenty or more organs. Further, each organ could be represented with one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, sixty, seventy, eighty, ninety, one-hundred or more probes. Moreover, a single array may comprise organs associated with a particular bodily system, such as, the reproductive system (ovaries, uterus, etc.), cardiovascular system (heart, lungs, etc.), respiratory system, nervous system, endocrine system, skeletal system, etc. Lastly, it is contemplated that one could utilize a general health panel that screens one or more organ/tissue specific proteins or transcripts from nearly every organ and if an anomaly is noted a follow-up screen with a more detailed panel comprising additional probes for the anomalous organ.

In certain embodiments, the diagnostic panels comprise one or more detection reagents. In another embodiment, a diagnostic panel of the invention may comprise two or more detection reagents. Thus, the diagnostic panels of the invention may comprise a plurality of detection reagents. As would be recognized by the skilled artisan, the number of detection reagents on a given panel would be determined from the number of organ-specific proteins to be measured. In this regard, the plurality of detection reagents may be anywhere from 2 to 10, 20, 30, 40, 50, 60, 70, 80, 90, 100, 150, 160, 170, 180, 190, 200 or more detection reagents each specific for an organ-specific protein. In specific embodiments, the panel may comprise for example, 10-50 probes per organ/tissue/cell type and probe 30-50 organs/tissues or more. Accordingly, such arrays/panels may comprise 2500 or more probes. In one embodiment, the panels of the invention comprises at least 3, 4, 5, 6, 7, 8, 9, or 10 detection reagents each specific for one of the plurality of organ-specific proteins that make up a given fingerprint. In another embodiment, the panel comprises at least 11, 12, 13, 14, 15, 16, 17, 18, 19, or 20 detection reagents each specific for one of the plurality of organ-specific proteins that make up a given fingerprint. In a further embodiment, the panel comprises at least 21, 22, 23, 24, 25, 26, 27, 28, 29, or 30 detection reagents each specific for one of the plurality of organ-specific proteins that make up a given fingerprint. In an additional embodiment, the panel comprises at least 31, 32, 33, 34, 35, 36, 37, 38, 39, or 40 detection reagents each specific for one of the plurality of organ-specific proteins that make up a given fingerprint. In yet a further embodiment, the panel comprises at least 41, 42, 43, 44, 45, 46, 47, 48, 49, or 50 detection reagents each specific for one of the plurality of organ-specific proteins that make up a given fingerprint. In an additional embodiment, the panel comprises at least 51, 52, 53, 54, 55, 56, 57, 58, 59, or 60 detection reagents each specific for one of the plurality of organ-specific proteins that make up a given fingerprint. In one embodiment, the panel comprises at least 61, 62, 63, 64, 65, 66, 67, 68, 69, or 70 detection reagents each specific for one of the plurality of organ-specific proteins that make up a given fingerprint. In one embodiment, the panel comprises at least 75, 80, 85, 90, 100, 150, 160, 170, 180, 190, 200, or more, detection reagents each specific for one of the plurality of organ-specific proteins that make up a given fingerprint.

In one aspect, the detection reagents specific for the organ/tissue specific transcripts may be utilized in a multiparameter analysis method such as a method of classifying a population by drug responsiveness, comprising: (a) determining a multidimensional coordinate point representative of the expression levels of a sample of molecules in a specimen from individuals in a population of individuals administered a drug; and (b) determining a drug response-associated reference expression region of a group of individuals in said population using said multidimensional coordinate points, thereby classifying said group of individuals into a drug response reference population. Accordingly, the method provides a means of determining a comparative expression profile in an individual by comparing the expression levels of a sample of molecules in a population of molecules in a specimen from the individual with a health-associated reference expression region of the sample of molecules, wherein expression levels within the health-associated reference expression region indicate a reference expression profile and wherein expression levels outside the health-associated reference expression region indicate a perturbed expression profile. In addition, the method can be used for diagnosing a disease or a health state in an individual by comparing the expression level of a sample of molecules in a specimen from the individual with a health-associated reference expression region of the sample of molecules. Additionally, the reagent probes may be used in a method of classifying a population by drug responsiveness such methods are described in greater detail in U.S. Patent Application Publication No. 20020095259.

Panels of the invention comprise N detection reagents wherein N is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more detection reagents up to the total number of members in a given organ-specific protein set that are to be detected. As noted above, in certain embodiments, it may be desirable to detect proteins from two or more organ-specific protein sets. Accordingly, the diagnostic panels of the invention may comprise N detection reagents wherein N is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more detection reagents up to the total number of members in one or more organ-specific protein sets that are to be detected. Detection reagents of a given diagnostic panel may detect proteins from 1, 2, 3, 4, 5, 6, 7, 8, 9, 10, 11, 12, 13, 14, 15, 16, 17, 18, 19, 20, or more organ-specific protein sets, such as those provided in Tables 1-32, 36-45 and 47-79, or normal serum organ-specific protein sets thereof.

Organ-specific proteins can be detected and measured using any of a variety of detection reagents in the context of a variety of methods for measuring protein levels. Any detection reagent that can specifically bind to or otherwise detect an organ-specific protein as described herein is contemplated as a suitable detection reagent. Illustrative detection reagents include, but are not limited to antibodies, or antigen-binding fragments thereof, yeast ScFv, DNA or RNA aptamers, isotope labeled peptides, receptors, ligands, click reagents, molecular beacons, quantum dots, microfluidic/nanotechnology measurement devices and the like.

In one illustrative embodiment, a detection reagent is an antibody or an antigen-binding fragment thereof. Methods of producing polyclonal antibodies are well known to those skilled in the art. Exemplary protocols which may be used are described for example in Coligan et al., "Current Protocols In Immunology", (John Wiley & Sons, Inc, 1991 and subsequent updates). Monoclonal antibodies may be produced using the standard method as described, for example, by Köhler and Milstein (1975, *Nature* 256, 495-497), or by more recent modifications thereof as described, for example, in Coligan et al., (1991, supra) by immortalizing spleen or other antibody-producing cells derived from a production species which has been inoculated with an organ-specific protein of the invention. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, chicken, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, usually according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

In one embodiment, multiple target proteins or peptides are used in a single immune response to generate multiple useful detection reagents simultaneously. In one embodiment, the individual specificities are later separated out.

In certain embodiments, antibody can be generated by phage display methods (such as described by Vaughan, T. J., et al., *Nat Biotechnol*, 14: 309-314, 1996; and Knappik, A., et al., *Mol Biol*, 296: 57-86, 2000); ribosomal display (such as described in Hanes, J., et al., *Nat Biotechnol*, 18: 1287-1292, 2000), or periplasmic expression in *E. coli* (see e.g., Chen, G., et al., *Nat Biotechnol*, 19: 537-542, 2001.). In further embodiments, antibodies can be isolated using a yeast surface display library. See e.g., nonimmune library of $10^9$ human antibody scFv fragments as constructed by Feldhaus, M. J., et al., *Nat Biotechnol*, 21: 163-170, 2003. There are several advantages of this yeast surface display compared to more traditional large nonimmune human antibody repertoires such as phage display, ribosomal display, and periplasmic expression in *E. coli* 1). The yeast library can be amplified $10^{10}$-fold without measurable loss of clonal diversity and repertoire bias as the expression is under control of the tightly GAL1/10 promoter and expansion can be done under non induction conditions; 2) nanomolar-affinity scFvs can be routinely obtained by magnetic bead screening and flow-cytometric sorting, thus greatly simplified the protocol and capacity of antibody screening; 3) with equilibrium screening, a minimal affinity threshold of the antibodies desired can be set; 4) the binding properties of the antibodies can be quantified directly on the yeast surface; 5) multiplex library screening against multiple antigens simultaneously is possible; and 6) for applications demanding picomolar affinity (e.g. in early diagnosis), subsequent rapid affinity maturation (Kieke, M. C., et al., *J Mol Biol*, 307: 1305-1315, 2001.) can be carried out directly on yeast clones without further re-cloning and manipulations.

Monoclonal antibodies specific for an organ-specific polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, in certain embodiments, one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. An illustrative selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of diagnostically useful molecules are known in the art which comprise antigen-binding sites that are capable of exhibiting immunological binding properties of an antibody molecule. The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the $F(ab")_2$ fragment which comprises both antigen-binding sites. An Fv fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar at al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

A single chain Fv (sFv) polypeptide is a covalently linked $V_H::V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated but chemically separated light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term CDR set refers to the three hypervariable regions of a heavy or light chain V region. Proceeding from the N-terminus of a heavy or light chain, these regions are denoted as CDR1, CDR2, and CDR3 respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a molecular recognition unit. Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term FR set refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain canonical structures regardless of the precise CDR amino acid sequence. Further, certain FR residues are known to participate in non-covalent interdomain contacts which stabilize the interaction of the antibody heavy and light chains.

In certain embodiments the use of click chemistry (e.g., click reagents) to anchor on or more probes/reagents specific to an organ/tissue specific protein or transcript to a detection label or to an array or other surface (e.g., nanoparticle). While such chemistries are well known in the art, in short, the chemistries utilized allow bioconjugation by the formation of triazoles that readily associate with biological targets, through hydrogen bonding and dipole interactions. Chemistries such as this are detailed in the art that is incorporated herein by reference in its entirety and includes Kolb and Sharpless, DDT, Vol. 8 (24), 1128-1137, 2003; U.S. Patent Application Publication No. 20050222427.

The detection reagents of the present invention may comprise any of a variety of detectable labels or reporter groups. The invention contemplates the use of any type of detectable label, including, e.g., visually detectable labels, fluorophores, and radioactive labels. The detectable label may be incorporated within or attached, either covalently or non-covalently, to the detection reagent. Detectable labels or reporter groups may include radioactive groups, dyes, fluorophores, biotin, colorimetric substrates, enzymes, or colloidal compounds. Illustrative detectable labels or reporter groups include but are not limited to, fluorescein, tetramethyl rhodamine, Texas Red, coumarins, carbonic anhydrase, urease, horseradish peroxidase, dehydrogenases and/or colloidal gold or silver. For radioactive groups, scintillation counting or autoradiographic methods are generally appropriate for detection. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

The present invention also contemplates detecting polynucleotides that encode the organ-specific proteins of the present invention. Accordingly, detection reagents also include polynucleotides, oligonucleotide primers and probes that specifically detect polynucleotides encoding any of the organ-specific proteins as described herein from any of a variety of tissue sources. Thus, the present invention contemplates detection of expression levels by detection of polynucleotides encoding any of the organ-specific proteins described herein using any of a variety of known techniques including, for example, PCR, RT-PCR, quantitative PCR, real-time PCR, northern blot analysis, and the like. Oligonucleotide primers for amplification of the polynucleotides encoding organ-specific proteins are within the scope of the present invention where polynucleotide-based detection is desired to better detect organ-specific proteins in a diagnostic assay or kit. Oligonucleotide primers for amplification of the polynucleotides encoding organ-specific proteins are also within the scope of the present invention to amplify transcripts in a biological sample. Many amplification methods are known in the art such as PCR, RT-PCR, quantitative real-time PCR, and the like. The PCR conditions used can be optimized in terms of temperature, annealing times, extension times and number of cycles depending on the oligonucleotide and the polynucleotide to be amplified. Such techniques are well known in the art and are described in, for example, Mullis et al., *Cold Spring Harbor Symp. Quant. Biol.*, 51:263, 1987; Erlich ed., *PCR Technology, Stockton* Press, NY, 1989. Oligonucleotide primers can be anywhere from 8, 9, 10, 11, 12, 13, 14, 15, 16, 17, 18, 19, 20, 21, 22, 23, 24, 25, 26, 27, 28, 29, or 30 nucleotides in length. In certain embodiments, the oligonucleotide primers/probes of the present invention are typically 35, 40, 45, 50, 55, 60, or more nucleotides in length.

The panels of the present invention may be comprised of a solid phase surface having attached thereto a plurality of detection reagents each attached at a distinct location. Further in this regard, the solid phase surface may be of any material, including, but not limited to, plastic, polycarbonate, polystyrene, polypropylene, polyethlene, glass, nitrocellulose, dextran, nylon, metal, silicon and carbon nanowires, nanoparticles that can be made of a variety of materials and photolithographic materials. In certain embodiments, the solid phase surface is a chip. In another embodiment, the solid phase surface may comprise microtiter plates, beads, membranes, microparticles, the interior surface of a reaction vessel such as a test tube or other reaction vessel. In other embodiments the peptides will be fractionated by one or more one-dimensional columns using size separations, ion exchange or hydrophobicity properties and, for example, deposited in a MALDI 96 or 384 well plate and then injected into an appropriate mass spectrometer.

In one embodiment, the panel is an addressable array. As such, the addressable array may comprise a plurality of distinct detection reagents, such as antibodies, aptamers or oligonucleotides, attached to precise locations on a solid phase surface, such as a plastic chip. The position of each distinct detection reagent on the surface is known and therefore addressable. In one embodiment, the detection reagents are distinct antibodies that each has specific affinity for one of a plurality of organ-specific polypeptides.

In one embodiment, the detection reagents, such as antibodies, are covalently linked to the solid surface, such as a plastic chip, for example, through the Fc domains of antibodies. In another embodiment, antibodies are adsorbed onto the solid surface. In a further embodiment, the detection reagent, such as an antibody, is chemically conjugated to the solid surface. In a further embodiment, the detection reagents are attached to the solid surface via a linker.

Methods of constructing protein arrays, including antibody arrays, are known in the art (see, e.g., U.S. Pat. No. 5,489,678; U.S. Pat. No. 5,252,743; Blawas and Reichert, 1998, *Biomaterials* 19:595-609; Firestone et al., 1996, *J. Amer. Chem. Soc.* 18, 9033-9041; Mooney et al., 1996, *Proc. Natl. Acad. Sci.* 93, 12287-12291; Pirrung et al, 1996, *Bioconjugate Chem.* 7, 317-321; Gao et al, 1995, *Biosensors Bioelectron* 10, 317-328; Schena et al., 1995, *Science* 270, 467-470; Lom et al., 1993, *J. Neurosci. Methods,* 385-397; Pope et al., 1993, *Bioconjugate Chem.* 4, 116-171; Schramm et al., 1992, *Anal. Biochem.* 205, 47-56; Gombotz et al., 1991, *J. Biomed. Mater. Res.* 25, 1547-1562; Alarie et al., 1990, *Analy. Chim. Acta* 229, 169-176; Owaku et al, 1993, *Sensors Actuators B,* 13-14, 723-724; Bhatia et al., 1989, *Analy. Biochem.* 178, 408-413; Lin et al., 1988, *IEEE Trans. Biomed. Engng.*, 35(6), 466-471).

In one embodiment, the detection reagents, such as antibodies or aptamers, are arrayed on a chip comprised of electronically activated copolymers of a conductive polymer and the detection reagent. Such arrays are known in the art (see e.g., U.S. Pat. No. 5,837,859 issued Nov. 17, 1998; PCT publication WO 94/22889 dated Oct. 13, 1994). The arrayed pattern may be computer generated and stored. The chips may be prepared in advance and stored appropriately. The antibody array chips can be regenerated and used repeatedly.

In certain embodiments, detection with multiple specific detection reagents is carried out in solution.

The detection reagents of the present invention may be provided in a diagnostic kit. As such a diagnostic kit may comprise any of a variety of appropriate reagents or buffers, enzymes, dyes, colorimetric or other substrates, and appropriate containers to be used in any of a variety of detection assays as described herein. Kits may also comprise one or more positive controls, one or more negative controls, and a protocol for identification of the organ-specific proteins of interest using any one of the assays as described herein.

In certain embodiments, the detection reagents for a diagnostic panel are selected such that the level of at least one of the organ-specific proteins detected by the plurality of detection reagents in a blood sample from a subject afflicted with a disease affecting the organ or organs from which the organ-specific proteins are derived is above or below a predetermined normal range. In certain embodiments, the detection reagents for a diagnostic panel are selected such that the level of at least two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, sixty, seventy, eighty, ninety, one-hundred or more of the organ-specific proteins detected by the plurality of detection reagents in a biological sample (e.g., blood) from a subject afflicted with a disease affecting the organ or organs from which the organ-specific proteins are derived is above or below a predetermined normal range. Thus, the detection reagents for a diagnostic panel, kit, or array may be selected such that the level of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween, or more of the organ-specific proteins detected by the plurality of detection reagents in a blood sample from a subject afflicted with a disease affecting the organ or organs from which the organ-specific proteins are derived is above or below a predetermined normal range.

The levels and locations of organ-specific proteins may change as the result of disease. Thus, in certain embodiments, in vivo imaging techniques can be used to visualize the levels and locations of organ-specific proteins in bodily fluid. In this embodiment, exemplary in vivo imaging techniques include, but are not limited to PET, SPECT (Sharma et al; *Journal of Magnetic Resonance Imaging* (2002), 16: 336-351), MALDI (Stoeckli, et al. *Nature Medicine* (2001) 7: 493-496), and Fluorescence resonance energy transfer (FRET) (Seker et al, *The Journal of Cell Biology,* 160 5, (2003) 629-633).

Methods of Use

The present invention provides organ-specific protein and transcript sets and normal serum organ-specific protein and transcript sets, panels thereof, reagents and probes directed thereto and methods for use and identifying the same. The present invention further provides panels, arrays, mixtures, and kits comprising detection reagents or probes for detecting such organ-specific proteins or polynucleotides that encode them in blood, other bodily fluid, and tissue samples such as biopsy samples from diseased organs.

It should also be understood that the blood protein and transcript fingerprints constitute assays for the normal organ and all the diseases of the organ. Thus all different diseases affecting such organ either directly or indirectly may be detected or monitored because each different type of disease arises from distinct disease-perturbed networks that change the levels of different combinations of proteins whose synthesis they control. The present invention is not claiming disease-specific proteins, rather the fingerprints report the organ status for all different normal and disease organ conditions.

The present invention further provides methods of identifying new drug targets for a disease or indication by detecting specific up-regulation of a transcript or polypeptide in a diseased state. In addition, the present invention contemplates using such targets for imaging or drug targeting such that a probe to a disease specific protein or transcript may be utilized alone as a targeting agent or coupled to another therapeutic or diagnostic imaging agent.

The present invention also provides defined normal and disease-associated organ-specific blood fingerprints. As such, the present invention provides methods of detecting diseases or following disease progression. The invention further provides methods for stratifying disease types and for monitoring the progression of a disease. The present invention also provides for following responses to therapy, stratifying or qualifying patients for therapy or a clinical trial, in a variety of disease settings and methods for detecting the disease state in humans using the visualization of nanoparticles with appropriate reporter groups and organ-specific antibodies or aptamers.

The present invention can be used as a standard screening test. In this regard, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween or more of the detection reagents specific for the organ-specific proteins described herein can be used to measure the level of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween or more organ-specific proteins in a blood sample and any statistically significant deviation from a normal serum organ-specific blood fingerprint would indicate that disease-related perturbation was present. Thus, the present invention provides a normal organ-specific blood fingerprint for any given organ. In certain embodiments, a normal organ-specific blood fingerprint is determined by measuring the normal range of levels of the individual protein members of a fingerprint. Any deviation therefrom or perturbation of the normal fingerprint that is outside the standard deviation (normal range) has diagnostic utility (see also U.S. Patent Application No. 0020095259). As would be recognized by the skilled artisan, the significance of any deviation in the levels of (e.g., a significantly altered level of one or more of) the individual protein members of a fingerprint can be determined using statistical methods known in the art and described herein. As noted elsewhere herein, perturbation of the normal fingerprint can indicate primary disease of the organ being tested or secondary, indirect affects on that organ resulting from disease of another organ. Perturbation from normal may also include the presence of a protein in a sample of a patient being tested for a perturbed state not present in organ-specific panel (e.g., when analyzing a certain patient sample such as in the prostate a protein or transcript not found in the normal prostate panel may appear in a perturbed sample) may be an indicator of disease. Further, the absence of a protein or transcript found in the normal organ-specific panel may also be an indicator of a perturbed state.

In an additional embodiment, the present invention can be used to determine distinct normal organ-specific blood fingerprints, such as in different populations of people. In this regard, distinct normal patterns of organ-specific blood fingerprints may have differences in populations of patients that permit one to stratify patients into classes that would respond to a particular therapeutic regimen and those which would not.

In a further embodiment, the present invention can be used to determine the risk of developing a particular biological condition. A statistically significant alteration (e.g., increase or decrease) in the levels of one or more members of a particular blood fingerprint may signify a risk of developing a particular disease, such as a cancer, an autoimmune disease, or other biological condition.

To monitor the progression of a disease, or monitor responses to therapy, one or more organ-specific blood fingerprints are detected/measured as described herein using any of the methods as described herein at one time point and detected/measured again at subsequent time points, thereby monitoring disease progression or responses to therapy.

The normal organ-specific blood fingerprints of the present invention can be used as a baseline for detecting any of a variety of diseases (or the lack thereof). In certain embodiments, the organ-specific blood fingerprints of the present invention can be used to detect cancer. As such, the present invention can be used to detect, monitor progression of, or monitor therapeutic regimens for any cancer, including brain cancer, melanoma, non-Hodgkin's lymphoma, Hodgkin's disease, leukemias, plasmocytomas, sarcomas, adenomas, gliomas, thymomas, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers. In addition, for the white blood cell cancers, cell sorting can optionally take place so that only analysis of white blood cells is carried out and thus direct analysis of the organ-specific proteins or transcripts from the cells that have been specifically sorted will be accomplished. Moreover, it should be understood that any condition, such as a chronic disease, to cancer to infectious diseases may change the blood immune cells in specific ways that will be revealed by organ-specific (or cell-type specific) analyses.

In certain embodiments, the organ-specific blood fingerprints of the present invention can be used to detect, to monitor progression of, or monitor therapeutic regimens for diseases of the heart, kidney, ureter, bladder, urethra, liver, prostate, heart, blood vessels, bone marrow, skeletal muscle, smooth muscle, various specific regions of the brain (including, but not limited to the amygdala, caudate nucleus, cerebellum, corpus callosum, fetal, hypothalamus, thalamus), spinal cord, peripheral nerves, retina, nose, trachea, lungs, mouth, salivary gland, esophagus, stomach, small intestines, large intestines, hypothalamus, pituitary, thyroid, pancreas, adrenal glands, ovaries, oviducts, uterus, placenta, vagina, mammary glands, testes, seminal vesicles, penis, lymph nodes, thymus, and spleen. The present invention can be used to detect, to monitor progression of, or monitor therapeutic regimens for cardiovascular diseases, neurological diseases, metabolic diseases, respiratory diseases, autoimmune disease and lung diseases. As would be recognized by the skilled artisan, the present invention can be used to detect, monitor the progression of, or monitor treatment for, virtually any disease wherein the disease causes perturbation in organ-specific proteins.

In certain embodiments, the organ-specific blood fingerprints of the present invention can be used to detect autoimmune disease. As such, the present invention can be used to detect, monitor progression of, or monitor therapeutic regimens for autoimmune diseases such as, but not limited to, rheumatoid arthritis, multiple sclerosis, insulin dependent diabetes, Addisons disease, celiac disease, chronic fatigue syndrome, inflammatory bowel disease, ulcerative colitis, Crohn's disease, Fibromyalgia, systemic lupus erythematosus, psoriasis, Sjogren's syndrome, hyperthyroidism/Graves disease, hypothyroidism/Hashimoto's disease, Insulin-dependent diabetes (type 1), Myasthenia Gravis, endometriosis, scleroderma, pernicious anemia, Goodpasture syndrome, Wegener's disease, glomerulonephritis, aplastic anemia, paroxysmal nocturnal hemoglobinuria, myelodysplastic syndrome, idiopathic thrombocytopenic purpura, autoimmune hemolytic anemia, Evans syndrome, Factor VIII inhibitor syndrome, systemic vasculitis, dermatomyositis, polymyositis and rheumatic fever.

In certain embodiments, the organ-specific blood fingerprints of the present invention can be used to detect diseases associated with infections with any of a variety of infectious organisms, such as viruses, bacteria, parasites and fungi. Infectious organisms may comprise viruses, (e.g., RNA viruses, DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as *Plasmodia* species, *Leishmania* species, *Schistosoma* species, *Trypanosoma* species), bacteria (e.g., *Mycobacteria*, in particular, *M. tuberculosis, Salmonella, Streptococci, E. coli, Staphylococci*), fungi (e.g., *Candida* species, *Aspergillus* species), *Pneumocystis carinii*, and prions.

The diagnostic panels and generally, methods used for detecting normal serum organ-specific proteins, can be used to define/identify disease-associated organ-specific blood fingerprints. A disease-associated organ-specific blood fingerprint is a data set comprising the determined level in a blood sample from an individual afflicted with a disease of one or more components of a normal serum organ-specific protein set that demonstrates a statistically significant change as compared to the determined normal level (e.g., wherein the level in the disease sample is above or below a predetermined normal range). The data set is compiled from samples from individuals who are determined to have a particular disease using established medical diagnostics for the particular disease. The determined blood (serum) level of each protein member of a normal serum organ-specific protein set as measured in the blood of the diseased sample is compared to the corresponding predetermined normal level. A statistically significant variation from the predetermined normal level for one or more members of the normal serum organ-specific protein set provides diagnostically useful information (disease-associated fingerprint) for that disease. Note that it may be determined for a particular disease or disease state that the level of only a few members of the normal serum organ-specific protein set change relative to the normal levels. Thus, a disease-associated organ-specific blood fingerprint may comprise the determined levels in the blood of only a subset of the components of a normal serum organ-specific protein set for a given organ and a particular disease. Thus, a disease-associated organ-specific blood fingerprint comprises the determined levels in blood of N members of a serum organ-specific protein set wherein N is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween or more members up to the total number of members in a given serum organ-specific protein set. In this regard, in certain embodiments, a disease-associated organ-specific blood fingerprint comprises the determined levels of one or more components of a normal serum organ-specific protein set. In one embodiment, a disease-associated organ-specific blood fingerprint comprises the determined levels in a sample from an individual known to have a particular disease of at least two components of a normal serum organ-specific protein set. In other embodiments, a disease-associated organ-specific blood fingerprint comprises the determined levels in a sample from an individual known to have a particular disease of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween components of a normal serum organ-specific protein set.

In certain embodiments, a disease-associated organ-specific blood fingerprint comprises the determined level in the blood of components from multiple organs. As noted elsewhere, in certain embodiments, a disease can impact multiple organs with the result being a change in blood level of proteins from more than one organ-specific protein set. Therefore, in certain embodiments, a disease-associated organ-specific fingerprint comprises the determined level in the blood of components from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween or more organ-specific protein sets.

It should be noted that, in certain embodiments, a disease-associated organ-specific fingerprint will comprise the determined level of one or more components of a normal organ-specific protein set that are NOT components of the corresponding normal organ-specific protein set. Thus, in this regard, a disease-associated organ-specific blood fingerprint may comprise the determined level of one or more components of a normal organ-specific protein set. Further, in certain embodiments, a disease-associated "organ-specific" blood fingerprint comprises the determined levels of one or more components of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween or more normal serum organ-specific protein sets. Thus, in this regard, a disease-associated organ-specific blood fingerprint may comprise the determined levels of one or more components from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110 or any integer value therebetween or more normal serum organ-specific protein sets.

One of ordinary skill in the art could readily conclude that the present invention is useful in defining the normal parameters for any number of organs in the body. To that end, the present invention may also be used to define subclinical perturbations from normal during annual screenings that could be utilized to initiate therapy or more aggressive examinations at an earlier date. Further, defining normal for two, three, or more related organs can be accomplished by the present invention. Such groupings would be clear to those of skill in the art and could be any of a variety, include those related to cardiovascular health, including the heart, lungs, liver, etc. As well as looking at groupings of liver and blood for infectious and parasitic diseases such as malaria, HIV, etc.

Using the diagnostic panels and methods described herein, a vast array of disease-associated organ-specific blood fingerprints can be defined for any of a variety of diseases as described further herein. As such, the present invention further provides information databases comprising data that make up blood fingerprints as described herein. As such, the databases may comprise the defined differential expression levels as determined using any of a variety of methods such as those described herein, of each of the plurality of organ-specific proteins that make up a given fingerprint in any of a variety of settings (e.g., normal or disease fingerprints).

Targeting for Treatment or Imaging

In the present specification, the invention describes the identification of various polypeptides (and their encoding nucleic acids or fragments thereof) which are expressed as organ-specific transcripts and in particular embodiments secreted organ-specific proteins as compared to other organs.

Accordingly, in one embodiment of the present invention, the invention provides an isolated nucleic acid molecule having a nucleotide sequence that encodes an organ-specific target polypeptide or fragment thereof.

In certain aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule encoding a full-length organ-specific polypeptide having an amino acid sequence as disclosed herein, an organ-specific polypeptide amino acid sequence lacking the signal peptide as disclosed herein, an extracellular domain of a transmembrane organ-specific polypeptide, with or without the signal peptide, as disclosed herein or any other specifically defined fragment of a full-length organ-specific polypeptide amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule comprising the coding sequence of a full-length organ-specific polypeptide cDNA as disclosed herein, the coding sequence of an organ-specific polypeptide lacking the signal peptide as disclosed herein, the coding sequence of an extracellular domain of a transmembrane organ-specific polypeptide, with or without the signal peptide, as disclosed herein or the coding sequence of any other specifically defined fragment of the full-length organ-specific polypeptide amino acid sequence as disclosed herein, or (b) the complement of the DNA molecule of (a).

In further aspects, the invention concerns an isolated nucleic acid molecule comprising a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule that encodes the same mature polypeptide encoded by the full-length coding region of any of the human protein cDNAs as disclosed herein, or (b) the complement of the DNA molecule of (a).

In other aspects, the present invention is directed to isolated nucleic acid molecules which hybridize to (a) a nucleotide sequence encoding an organ-specific polypeptide having a full-length amino acid sequence as disclosed herein or any other specifically defined fragment of a full-length organ-specific polypeptide amino acid sequence as disclosed herein, or (b) the complement of the nucleotide sequence of (a). In this regard, an embodiment of the present invention is directed to fragments of a full-length organ-specific polypeptide coding sequence, or the complement thereof, as disclosed herein, that may find use as, for example, hybridization probes useful as, for example, diagnostic probes, antisense oligonucleotide probes, or for encoding fragments of a full-length organ-specific polypeptide that may optionally encode a polypeptide comprising a binding site for an anti-organ-specific polypeptide antibody, an organ-specific binding oligopeptide or other small organic molecule that binds to an organ-specific polypeptide. Such nucleic acid fragments are usually at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length. It is noted that novel fragments of an organ-specific polypeptide-encoding nucleotide sequence may be determined in a routine manner by aligning the organ-specific polypeptide-encoding nucleotide sequence with other known nucleotide sequences using any of a number of well known sequence alignment programs and determining which organ-specific polypeptide-encoding nucleotide sequence fragment(s) are novel. All of such novel fragments of organ-specific polypeptide-encoding nucleotide sequences are contemplated herein. Also contemplated are the organ-specific polypeptide fragments encoded by these nucleotide molecule fragments, preferably those organ-specific polypeptide fragments that comprise a binding site for an anti-organ-specific antibody, an organ-specific binding oligopeptide or other small organic molecule that binds to an organ-specific polypeptide.

In another embodiment, the invention provides isolated organ-specific polypeptides encoded by any of the isolated nucleic acid sequences hereinabove identified.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an anti-organ-specific polypeptide antibody to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies of the present invention may optionally be produced in CHO cells or bacterial cells and preferably induce death of a cell to which they bind. For diagnostic purposes, the antibodies of the present invention may be detectably labeled, attached to a solid support, or the like.

In other embodiments of the present invention, the invention provides vectors comprising DNA encoding any of the herein described antibodies. Host cell comprising any such vector are also provided. By way of example, the host cells may be CHO cells, *E. coli* cells, or yeast cells. A process for producing any of the herein described antibodies is further provided and comprises culturing host cells under conditions suitable for expression of the desired antibody and recovering the desired antibody from the cell culture.

In another embodiment, the invention provides oligopeptides ("organ-specific binding oligopeptides") which bind, preferably specifically, to any of the above or below described organ-specific polypeptides. Optionally, the organ-specific binding oligopeptides of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The organ-specific binding oligopeptides of the present invention may optionally be produced in CHO cells or bacterial cells and preferably induce death of a cell to which they bind. For diagnostic purposes, the organ-specific binding oligopeptides of the present invention may be detectably labeled, attached to a solid support, or the like.

In other embodiments of the present invention, the invention provides vectors comprising DNA encoding any of the herein described organ-specific binding oligopeptides. Host cell comprising any such vector are also provided. By way of example, the host cells may be CHO cells, *E. coli* cells, or yeast cells. A process for producing any of the herein described organ-specific binding oligopeptides is further provided and comprises culturing host cells under conditions suitable for expression of the desired oligopeptide and recovering the desired oligopeptide from the cell culture.

In another embodiment, the invention provides small organic molecules ("organ-specific binding organic molecules") which bind, preferably specifically, to any of the above or below described organ-specific polypeptides. Optionally, the organ-specific binding organic molecules of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The organ-specific binding organic molecules of the present invention preferably induce death of a cell to which they bind. For diagnostic purposes, the organ-specific binding organic molecules of the present invention may be detectably labeled, attached to a solid support, or the like.

In a still further embodiment, the invention concerns a composition of matter comprising an organ-specific polypeptide as described herein, a chimeric organ-specific polypeptide as described herein, an anti-organ-specific antibody as described herein, an organ-specific binding oligopeptide as described herein, or an organ-specific binding organic molecule as described herein, in combination with a carrier. Optionally, the carrier is a pharmaceutically acceptable carrier.

In yet another embodiment, the invention concerns an article of manufacture comprising a container and a composition of matter contained within the container, wherein the composition of matter may comprise an organ-specific polypeptide as described herein, a chimeric organ-specific polypeptide as described herein, an anti-organ-specific antibody as described herein, an organ-specific binding oligopeptide as described herein, or an organ-specific binding organic molecule as described herein. The article may further optionally comprise a label affixed to the container, or a package insert included with the container, that refers to the use of the composition of matter for the therapeutic treatment or diagnostic detection of a tumor.

Another embodiment of the present invention is directed to the use of an organ-specific polypeptide as described herein, a chimeric organ-specific polypeptide as described herein, an anti-organ-specific polypeptide antibody as described herein, an organ-specific binding oligopeptide as described herein, or an organ-specific binding organic molecule as described herein, for the preparation of a medicament useful in the treatment of a condition which is responsive to the organ-specific polypeptide, chimeric organ-specific polypeptide, anti-organ-specific polypeptide antibody, organ-specific binding oligopeptide, or organ-specific binding organic molecule.

Another embodiment of the present invention is directed to a method for inhibiting the growth of a cell that expresses an organ-specific polypeptide, wherein the method comprises contacting the cell with an antibody, an oligopeptide or a small organic molecule that binds to the organ-specific polypeptide, and wherein the binding of the antibody, oligopeptide or organic molecule to the organ-specific polypeptide causes inhibition of the growth of the cell expressing the organ-specific polypeptide. In preferred embodiments, the cell is a cancer cell or disease harboring cell and binding of the antibody, oligopeptide or organic molecule to the organ-specific polypeptide causes death of the cell expressing the organ-specific polypeptide. Optionally, the antibody is a monoclonal antibody, antibody fragment, chimeric antibody, humanized antibody, or single-chain antibody. Antibodies, organ-specific binding oligopeptides and organ-specific binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and organ-specific binding oligopeptides employed in the methods of the present invention may optionally be produced in CHO cells or bacterial cells.

Yet another embodiment of the present invention is directed to a method of therapeutically treating a mammal having a cancerous cells or disease containing cells or tissues comprising cells that express an organ-specific polypeptide, wherein the method comprises administering to the mammal a therapeutically effective amount of an antibody, an oligopeptide or a small organic molecule that binds to the organ-specific polypeptide, thereby resulting in the effective therapeutic treatment of the tumor. Optionally, the antibody is a monoclonal antibody, antibody fragment, chimeric antibody, humanized antibody, or single-chain antibody. Antibodies, organ-specific binding oligopeptides and organ-specific binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

Yet another embodiment of the present invention is directed to a method of determining the presence of an organ-specific polypeptide in a sample suspected of containing the organ-specific polypeptide, wherein the method comprises exposing the sample to an antibody, oligopeptide or small organic molecule that binds to the organ-specific polypeptide and determining binding of the antibody, oligopeptide or organic molecule to the organ-specific polypeptide in the sample, wherein the presence of such binding is indicative of the presence of the organ-specific polypeptide in the sample. Optionally, the sample may contain cells (which may be cancer cells) suspected of expressing the organ-specific polypeptide. The antibody, organ-specific binding oligopeptide or organ-specific binding organic molecule employed in the method may optionally be detectably labeled, attached to a solid support, or the like.

A further embodiment of the present invention is directed to a method of diagnosing the presence of a tumor in a mammal, wherein the method comprises detecting the level of expression of a gene encoding an organ-specific polypeptide (a) in a test sample of tissue cells obtained from said mammal, and (b) in a control sample of known normal non-cancerous cells of the same tissue origin or type, wherein a higher level of expression of the organ-specific polypeptide in the test sample, as compared to the control sample, is indicative of the presence of tumor in the mammal from which the test sample was obtained.

Another embodiment of the present invention is directed to a method of diagnosing the presence of a tumor in a mammal, wherein the method comprises (a) contacting a test sample comprising tissue cells obtained from the mammal with an antibody, oligopeptide or small organic molecule that binds to an organ-specific polypeptide and (b) detecting the formation of a complex between the antibody, oligopeptide or small organic molecule and the organ-specific polypeptide in the test sample, wherein the formation of a complex is indicative of the presence of a tumor in the mammal. Optionally, the antibody, organ-specific binding, oligopeptide or organ-specific binding organic molecule employed is detectably labeled, attached to a solid support, or the like, and/or the test sample of tissue cells is obtained from an individual suspected of having a cancerous tumor.

Yet another embodiment of the present invention is directed to a method for treating or preventing a cell proliferative disorder associated with altered, preferably increased, expression or activity of an organ-specific polypeptide, the method comprising administering to a subject in need of such treatment an effective amount of an antagonist of an organ-specific polypeptide. Preferably, the cell proliferative disorder is cancer and the antagonist of the organ-specific polypeptide is an anti-organ-specific polypeptide antibody, organ-specific binding oligopeptide, organ-specific binding organic molecule or antisense oligonucleotide. Effective treatment or prevention of the cell proliferative disorder may be a result of direct killing or growth inhibition of cells that express an organ-specific polypeptide or by antagonizing the cell growth potentiating activity of an organ-specific polypeptide.

Yet another embodiment of the present invention is directed to a method of binding an antibody, oligopeptide or small organic molecule to a cell that expresses an organ-specific polypeptide, wherein the method comprises contacting a cell that expresses an organ-specific polypeptide with said antibody, oligopeptide or small organic molecule under conditions which are suitable for binding of the antibody, oligopeptide or small organic molecule to said organ-specific polypeptide and allowing binding therebetween.

Other embodiments of the present invention are directed to the use of (a) an organ-specific polypeptide, (b) a nucleic acid encoding an organ-specific polypeptide or a vector or host cell comprising that nucleic acid, (c) an anti-organ-specific polypeptide antibody, (d) an organ-specific-binding oligopeptide, or (e) an organ-specific-binding small organic molecule in the preparation of a medicament useful for (i) the therapeutic treatment or diagnostic detection of a cancer or tumor, or (ii) the therapeutic treatment or prevention of a cell proliferative disorder.

Another embodiment of the present invention is directed to a method for inhibiting the growth of a cancer cell, wherein the growth of said cancer cell is at least in part dependent upon the growth potentiating effect(s) of an organ-specific polypeptide (wherein the organ-specific polypeptide may be expressed either by the cancer cell itself or a cell that produces polypeptide(s) that have a growth potentiating effect on cancer cells), wherein the method comprises contacting the organ-specific polypeptide with an antibody, an oligopeptide or a small organic molecule that binds to the organ-specific polypeptide, thereby antagonizing the growth-potentiating activity of the organ-specific polypeptide and, in turn, inhibiting the growth of the cancer cell. Preferably the growth of the cancer cell is completely inhibited. Even more preferably, binding of the antibody, oligopeptide or small organic molecule to the organ-specific polypeptide induces the death of the cancer cell. Optionally, the antibody is a monoclonal antibody, antibody fragment, chimeric antibody, humanized antibody, or single-chain antibody. Antibodies, organ-specific binding oligopeptides and organ-specific binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and organ-specific binding oligopeptides employed in the methods of the present invention may optionally be produced in CHO cells or bacterial cells.

Yet another embodiment of the present invention is directed to a method of therapeutically treating a tumor in a mammal, wherein the growth of said tumor is at least in part dependent upon the growth potentiating effect(s) of an organ-specific polypeptide, wherein the method comprises administering to the mammal a therapeutically effective amount of an antibody, an oligopeptide or a small organic molecule that binds to the organ-specific polypeptide, thereby antagonizing the growth potentiating activity of said organ-specific polypeptide and resulting in the effective therapeutic treatment of the tumor. Optionally, the antibody is a monoclonal antibody, antibody fragment, chimeric antibody, humanized antibody, or single-chain antibody. Antibodies, organ-specific binding oligopeptides and organ-specific binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

Anti-Organ-Specific Polypeptide Antibodies

In one embodiment, the present invention provides anti-organ-specific antibodies which may find use herein as therapeutic, diagnostic, and/or imaging agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myelomacells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs. 130: 151-188 (1992).

In a further embodiment, monoclonal antibodies or antibody fragments can be isolated from antibody phage libraries generated using the techniques described in McCafferty et al., Nature, 348:552-554 (1990). Ctackson et al., Nature, 352: 624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (C.sub.H and C.sub.L) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-organ-specific antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al. Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-organ-specific antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (J.sub.H) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., Nature 348:552-553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of probes (including self-antigens) can be isolated essentially following the techniques described by Marks et al., J. Mol. Biol. 222: 581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869, 046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641, 870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of an organ-specific protein as described herein. Other such antibodies may combine an organ-specific binding site with a binding site for another protein. Alternatively, an anti-organ-specific arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the organ-specific-expressing cell. Bispecific antibodies may also be used for diagnostic purposes, attaching imaging agents or localizing cytotoxic agents to cells which express organ-specific transcripts and/or polypeptides. These antibodies possess an organ-specific-binding arm and an arm which binds the cytotoxic agent (e.g., saporin, anti-interferon-.alpha., vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fc.alpha. antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the C.sub.H3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med. 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a V$_H$ connected to a V$_L$ by a linker which is too short to allow pairing between the two domains on the same chain. Accordingly, the V$_H$ and V$_L$ domains of one fragment are forced to pair with the complementary V$_L$ and V$_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1).sub.n-VD2-(X2).sub.n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-

2922 (1992). Homodimeric antibodies with enhanced antitumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG.sub.1$, $IgG_2$, $IgG.sub.3$, or $IgG.sub.4$) that is responsible for increasing the in vivo serum half-life of the IgG molecule.

9. Immunoconjugate

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

10. Immunoliposomes

The anti-organ-specific antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl. Acad. Sci. 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19): 1484 (1989).

B. Organ-Specific Binding Oligopeptides

Organ-specific binding oligopeptides of the present invention are oligopeptides that bind, preferably specifically, to an organ-specific polypeptide as described herein. organ-specific binding oligopeptides may be chemically synthesized using known oligopeptide synthesis methodology or may be prepared and purified using recombinanttechnology. organ-specific binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to an organ-specific polypeptide as described herein. organ-specific binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708, 871, 4,833,092, 5,223,409, 5,403,484, 5,571,689, 5,663,143; PCT Publication Nos. WO 84/03506 and WO084/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al.

(1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO95/34683; U.S. Pat. No. 5,627,024), T4 phagedisplay systems (Ren, Z-J. et al. (1998) Gene 215:439; Zhu, Z. (1997) CAN 33:534; Jiang, J. et al. (1997) can 128:44380; Ren, Z-J. et al. (1997) CAN 127:215644; Ren, Z-J. (1996) Protein Sci. 5:1833; Efimov, V. P. et al. (1995) Virus Genes 10:173) and T7 phage display systems (Smith, G. P. and Scott, J. K. (1993) Methods in Enzymology, 217, 228-257; U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol. Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. Organ-Specific Binding Organic Molecules

Organ-specific binding organic molecules are organic molecules other than oligopeptides or antibodies as defined herein that bind, preferably specifically, to an organ-specific polypeptide as described herein. organ-specific binding organic molecules may be identified and chemically synthesized using known methodology (see, e.g., PCT Publication Nos. WO00/00823 and WO00/39585). organ-specific binding organic molecules are usually less than about 2000 daltons in size, alternatively less than about 1500, 750, 500, 250 or 200 daltons in size, wherein such organic molecules that are capable of binding, preferably specifically, to an organ-specific polypeptide as described herein may be identified without undue experimentation using well known techniques.

In this regard, it is noted that techniques for screening organic molecule libraries for molecules that are capable of binding to a polypeptide target are well known in the art (see, e.g., PCT Publication Nos. WO00/00823 and WO00/39585). organ-specific binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Anti-Organ-Specific Antibodies, Organ-Specific Binding Oligopeptides and Organ-Specific Binding Organic Molecules with the Desired Properties Techniques for generating antibodies, oligopeptides and organic molecules that bind to organ-specific polypeptides have been described above. One may further select antibodies, oligopeptides or other organic molecules with certain biological characteristics, as desired.

The growth inhibitory effects of an anti-organ-specific antibody, oligopeptide or other organic molecule of the invention may be assessed by methods known in the art, e.g., using cells which express an organ-specific polypeptide either endogenously or following transfection with the organ-specific gene. For example, appropriate tumor cell lines and organ-specific-transfected cells may treated with an anti-organ-specific monoclonal antibody, oligopeptide or other organic molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-organ-specific antibody, organ-specific binding oligopeptide or organ-specific binding organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that overexpresses an organ-specific polypeptide. Preferably, the anti-organ-specific antibody, organ-specific binding oligopeptide or organ-specific binding organic molecule will inhibit cell proliferation of an organ-specific-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-organ-specific antibody at about 1 µg/kg to about 100 mg/kg body weight results in reduction in tumor size or reduction of tumor cell proliferation within about 5 days to 3 months from the first administration of the antibody, preferably within about 5 to 30 days.

To select for an anti-organ-specific antibody, organ-specific binding oligopeptide or organ-specific binding organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. organ-specific polypeptide-expressing tumor cells are incubated with medium alone or medium containing the appropriate anti-organ-specific antibody (e.g., at about 10 µg/ml), organ-specific binding oligopeptide or organ-specific binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (1 µg/ml). Samples may be analyzed using a FACSCAN®. flow cytometer and FACSCONVERT®. CellQuest software (Becton Dickinson). Those anti-organ-specific antibodies, organ-specific binding oligopeptides or organ-specific binding organic molecules that induce statistically significant levels of cell death as determined by PI uptake may be selected as cell death-inducing anti-organ-specific antibodies, organ-specific binding oligopeptides or organ-specific binding organic molecules.

To screen for antibodies, oligopeptides or other organic molecules which bind to an epitope on an organ-specific polypeptide bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody, oligopeptide or other organic molecule binds the same site or epitope as a known anti-organ-specific antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of an organ-specific polypeptide can be used in competition assays with the test antibodies or with a test antibody and an antibody with a characterized or known epitope.

Other methods of using the present panels, sets and individual members of the panels noted herein includes the use for evaluation of test compounds in a biological system to monitor changes related thereto. As one of skill in the art could readily appreciate, when observing a disease related profile, a test compound that changes said profile to be more similar to the normal profile is of significant interest as a drug lead. Accordingly, the present invention also provides a method for optimizing drug/test compound leads by treating an animal, cell, or tissue with said compound and observing whether the organ, cell, or tissue-specific profile changes to deviate from the diseased profile toward a more normal profile.

One aspect of the invention is a method for evaluating a test compound for biological activity, comprising: providing a database comprising a plurality of reference/normal organ-specific protein and/or gene expression profiles, each profile comprising a representation of the expression level of a plurality of genes or proteins in a test cell exposed to a reference compound and a representation of the reference compound; providing a test expression profile, comprising a representation of the expression level of a plurality of genes and/or proteins in a test cell exposed to said test compound; comparing said test expression profile with said first expression profiles; identifying at least one first expression profile that is similar to said test expression profile; displaying said selected expression profile.

Another aspect of the invention is a system for performing the method of the invention.

Another aspect of the invention is a computer-readable medium having encoded thereon a set of instructions enabling a computer system to perform the method of the invention.

An additional aspect of the present invention provides a system comprising a correlative database that permits one to study relationships between different genes or polypeptides encoded thereby, between genes or the polypeptides and a variety of compounds, to investigate structure-function relationships between different compounds. The database contains a plurality of standard gene expression or protein expression profiles of organ-specific components or under a plurality of specified conditions. The conditions specified can include expression within a particular cell type (for example, fibroblast, lymphocyte, neuron, oocyte, hepatocyte, and the like), expression at a particular point in the cell cycle (e.g., G1), expression in a specified disease state, the presence of environmental factors (for example, temperature, pressure, $CO_2$ partial pressure, osmotic pressure, shear stress, confluency, adherence, and the like), the presence of pathogenic organisms (for example, viruses, bacterial, fungi, and extra- or intracellular parasites), expression in the presence of heterologous genes, expression in the presence of test compounds, and the like, and combinations thereof. The database preferably comprises expression profiles for at least 10 different genes from specific to a particular organ or tissue. The standard expression profiles are preferably annotated, for example, with information regarding the conditions under which the profile was obtained. Preferably, the database also contains annotations for one or more genes, more preferably for each gene represented in the database. The annotations can include any available information about the gene, such as, for example, the gene's or protein's names and synonyms, the sequence, any known biological activity or function, any genes or proteins of similar sequence, any metabolic or protein interaction pathways to which it is known to belong, and the like.

The database contains interpretive gene expression profiles and bioassay profiles for a plurality of different compounds that comprise a representation of a compound's mode of action and/or toxicity ("drug signatures"), and can include experimental compounds and/or "standard" compounds. Drug signatures provide a unique picture of a compound's comprehensive activity in vivo, including both its effect on gene transcription and its interaction with proteins. Standard compounds are preferably well-characterized, and preferably exhibit a known biological effect on host cells and/or organisms. Standard compounds can advantageously be selected from the class of available drug compounds, natural toxins and venoms, known poisons, vitamins and nutrients, metabolic byproducts, and the like. The standard compounds can be selected to provide, as a set, a wide range of different gene expression profiles. The records for the standard compounds are preferably annotated with information available regarding the compounds, such as, for example, the compound name, structure and chemical formula, molecular weight, aqueous solubility, pH, lipophilicity, known biological activity, source, proteins and/or genes it is known to interact with, assays for detecting and/or confirming activity of the compound or related compounds, and the like. Alternatively, one can employ a database constructed from random compounds, combinatorial libraries, and the like.

The database further contains bioassay data derived from experiments in which one or more compounds represented in the database are examined for activity against one or more proteins represented in the database. Bioassay data can be obtained from open literature and directly by experiment.

Further, the database preferably contains product data related to the compounds, genes, proteins, expression profiles, and/or bioassay data otherwise present in the database. The product data can be information regarding physical products, such as bioassay kits and reagents, compounds useful as positive and negative controls, compounds similar to the test compound useful for further study, DNA microarrays and the like, or can comprise information-based products, such as additional data regarding gene or protein function and/or relationships (for example, sequence data from other species, information regarding metabolic and/or signal pathways to which the gene or protein belong, and the like), algorithmic analysis of the compounds to determine critical features and likely cross-reactivity, and the like. The product information can take the form of data or information physically present in the database, hyperlinks to external information sources (such as a vendor's catalog, for example, supplied via the Internet or CD-ROM), and the like.

The database thus preferably contains five main types of data: gene information, compound information, bioassay information, product information, and profile information. Gene information comprises information specific to each included gene, and can include, for example, the identity and sequence of the gene, one or more unique identifiers linked to public and/or commercial databases, its location on a standard array plate, a list of genes having similar sequences, any known disease associations, any known compounds that modulate the encoded protein activity, conditions that modulate expression of the gene or modulate the protein activity, and the like. Product information comprises information specific to the available products, and varies depending on the exact nature of the product, and can include information such as price, manufacturer, contents, warranty information, availability, delivery time, distributor, and the like. Bioassay information comprises information specific to particular compounds (where available), and can include, for example, results from high-throughput screening assays, cellular assays, animal and/or human studies, biochemical assays (including binding assays and enzymatic assays) and the like. Compound information comprises information specific to each included compound, such as, for example, the chemical name(s) and structure of the compound, its molecular weight, solubility and other physical properties, proteins that it is known to interact with, the profiles in which it appears, the genes that are affected by its presence, and available assays for its activity. Profile information includes, for example, the conditions under which it was generated (including, for example, the cell type(s) used, the species used, temperature and culture conditions, compounds present, time elapsed, and the like), the genes modulated with reference to a standard, a list of similar profiles, and the like. The information is obtained by assimilation of and/or reference to currently-available databases, and by collecting experimental data. It should be noted that the gene database, although large, contains a finite number of records, limited by the number of genes in the organisms under study. The compound database is potentially unlimited, as new compounds are made and tested constantly. The profile database, however, is still larger, as it represents information regarding the interaction of a very large number of genes with a potentially infinite number of different compounds, under a variety of conditions.

Experimental data is preferably collected using a high-throughput assay format, capable of examining, for example, the effects of a plurality of compounds (preferably a large number of standard compounds, for example 10,000) when administered individually or as a mixture to a plurality of different cell types. Assay data collected using a uniform format are more readily comparable, and provide a more accurate indication of the differences between, for example, the activity of similar compounds, or the differences in sensitivity of similar genes.

The system provides several different ways to access the information contained within the database. An operator can enter a test gene expression profile into the system, cause the system to compare the test profile with stored standard gene expression profiles in the database, and obtain an output comprising one or more standard expression profiles that are similar to the test profile. The standard expression profiles are preferably accompanied by annotations, for example providing information to the operator as to the similarity of the test profile to standard profiles obtained from disease states and/or standard compounds. The test gene expression profile preferably includes an indication of the conditions under which the profile is obtained, for example a representation of a test compound used, and/or the culture conditions.

The output preferably further comprises a list of the organ-specific genes, proteins, or transcripts that are modulated (up-regulated or down-regulated) in the test profile, as compared with a pre-established expression value, a pre-selected standard expression profile, a second test expression profile, or another pre-set threshold value.

The output is preferably hyperlinked, so that the operator can easily switch from, for example, a listing of the similar standard expression profiles to a listing of the modulated genes in a selected standard expression profile, or from a gene listed in the test profile to a list of the standard expression profiles in which the gene is similarly modulated, or to a list of the standard compounds (and/or conditions) which appear to modulate the selected gene. The output can comprise correlation information that highlights features in common between different genes, targets, profiles, compounds, assays, and the like, to assist the user in drawing useful correlations. For example, the output can contain a list of genes that were modulated in the user's experiment with a selected compound: if a plurality of the genes are indicated as associated with liver toxicity, the system can prompt the user that the compound is associated with a toxic drug signature, and prompt the user to continue with the next compound. Conversely, the output could indicate previously unnoticed associations between different pathways, leading the user to explore a hitherto unknown connection. The output preferably includes hyperlinks to product information, encouraging the user to purchase or order one or more products from a selected vendor, where the product(s) relate specifically to the focus of the database inquiry and the correlation information that results, and is presented back to the user to facilitate hypothesis generation. For example, the output can provide links to products useful for confirming the apparent activity of a compound, for measuring biological activity directly, for assaying the compound for possible side effects, and the like, prompting the user to select products useful in the next stage of experimentation.

The system is preferably provided with an algorithm for assessing similarity of compounds. Suitable methods for comparing compounds and determining their morphological similarity include "3D-MI", as set forth in copending application U.S. Ser. No. 09/475,413, now U.S. Pat. No. 6,470,305, incorporated herein by reference in full, Tanimoto similarity (Daylight Software), and the like. Preferably, the system can be queried for any compounds that are similar to the test compound in structure and/or morphology. The output from this query preferably includes the corresponding standard expression profiles (or hyperlinks to the corresponding standard expression profiles), and preferably further includes a listing, description, or hyperlink to an assay capable of determining the biological activity of the standard and/or test compound.

Thus, for example, if the user inputs an experimental expression profile resulting from incubation of test cells with a particular experimental compound, the user can obtain an output comprising an estimate of the quality of the data, an identification of the genes affected by the compound, a listing of similar profiles and the conditions under which they were obtained (for example, the compounds used), and a list of compounds having a structural similarity. The output can be provided in a hyperlinked format that permits the user to then investigate and explore the data. For example, the user can examine which genes are modulated, and determine whether or not the genes have yet been characterized as to function or activity, and under what conditions each gene is modulated in a similar fashion. Alternatively, the user can compare the profile obtained with the profile of a desired outcome, for example comparing the profile obtained by incubation of diseased or infected tissue with a test compound against a profile obtained from healthy (unperturbed) tissue. Alternatively, the user can compare the profile with the profiles obtained using standard compounds, for example using a drug of known activity, mechanism of action, and specificity, thus determining whether the test compound operates by a different mechanism, or if by the same mechanism whether it is more or less active than the standard. Additionally, the user can compare the structure of the test compound with the structures of other compounds with similar profiles (to determine which structural features of the compounds are common, and thus likely to be important for activity), or can compare the compound's profile with the profiles obtained from structurally similar compounds in general.

The system can be configured as a single, integrated whole, or can be distributed over a variety of locations. For example, the system can be provided as a central database/server with remotely-located access units. The remote access units can be provided with sufficient system capability to accept and interpret test gene expression profiles, and to compare the test profiles with standard gene expression profiles. Remote units can further be provided with a copy of some or all of the database information. Optionally, the remote system can be used to upload test gene expression profiles to the central system to update the central database, or a "private" database supplementary to the main database can be stored in or near the remote unit.

The present invention also generally provides, as noted above, for the monitoring of the perturbation of the levels of organ-specific polypeptides and transcripts and is certain embodiments, secreted organ-specific polypeptides and their transcripts. Such monitoring can be performed by analysis of tissue samples, cell samples and biological fluid samples and the like. In specific embodiments, blood is utilized as for analysis. The monitoring perturbations in organ-specific protein and transcript levels can assist in monitoring, diagnosing, imaging, and treating neurological diseases, immune system related diseases, cardiovascular diseases, infectious diseases, cancers, and essentially any disease, state, or indication as the health of each organ or a collection of organs can be simultaneously monitored.

The present invention contemplates the use of blood to determine the quantitative expression of various organ-specific, tissue-specific, or cell-specific mRNAs that reflect the health/disease state of the subject through the use of RT-PCR analysis (or similar amplification techniques). This entire process takes about three hours or less. The single drop of blood may also be used for multiple RT-PCR analyses. It is believed that the present finding can potentially revolutionize the way that diseases are detected, diagnosed and monitored because it provides a non-invasive, simple, highly sensitive and quick screening for tissue-specific transcripts. The transcripts detected in whole blood have potential as prognostic or diagnostic markers of disease, as they reflect disturbances in homeostasis in the human body. Delineation of the sequences and/or quantitation of the expression levels of these marker genes by RT-PCR will allow for an immediate and accurate diagnostic/prognostic test for disease or to assess the efficacy and monitor a particular therapeutic.

In one embodiment of the present invention, there is provided a method for detecting expression of a organ-specific transcript or protein in blood from a subject, comprising the steps of: a) quantifying RNA or protein from a subject blood sample; and b) detecting expression of the protein or gene in the quantified RNA, wherein the expression of protein or the gene in quantified RNA indicates the expression of the protein or gene in the subject blood. An example of the quantifying method is by mass spectrometry.

In another embodiment of the present invention, there is provided a method for detecting expression of one or more genes in blood from a subject, comprising the steps of: a) obtaining a subject blood sample; b) extracting RNA from the blood sample; c) amplifying the RNA; d) generating expressed sequence tags (ESTs) from the amplified RNA product; and e) detecting expression of the genes in the ESTs, wherein the expression of the genes in the ESTs indicates the expression of the genes in the subject blood. Preferably, the subject is a fetus, an embryo, a child, an adult or a non-human animal. The genes are non-cancer-associated and tissue-specific genes. Still preferably, the amplification is performed by RT-PCR using random sequence primers or gene-specific primers.

In still another embodiment of the present invention, there is provided a method for detecting expression of one or more genes in blood from a subject, comprising the steps of: a) obtaining a subject blood sample; b) extracting DNA fragments from the blood sample; c) amplifying the DNA fragments; and d) detecting expression of the genes in the amplified DNA product, wherein the expression of the genes in the amplified DNA product indicates the expression of the genes in the subject blood.

In yet another embodiment of the present invention, there is provided a method for monitoring a course of a therapeutic treatment in an individual, comprising the steps of: a) obtaining a blood sample from the individual; b) extracting RNA from the blood sample; c) amplifying the RNA; d) generating expressed sequence tags (ESTs) from the amplified RNA product; e) detecting expression of genes in the ESTs, wherein the expression of the genes is associated with the effect of the therapeutic treatment; and f) repeating steps a)-e), wherein the course of the therapeutic treatment is monitored by detecting the change of expression of the genes in the ESTs. Such a method may also be used for monitoring the onset of overt symptoms of a disease, wherein the expression of the genes is associated with the onset of the symptoms. Preferably, the amplification is performed by RT-PCR, and the change of the expression of the genes in the ESTs is monitored by sequencing the ESTs and comparing the resulting sequences at various time points; or by performing single nucleotide polymorphism analysis and detecting the variation of a single nucleotide in the ESTs at various time points.

In still yet another embodiment of the present invention, there is provided a method for diagnosing a disease in a test subject, comprising the steps of: a) generating a cDNA library for the disease from a whole blood sample from a normal subject; b) generating expressed sequence tag (EST) profile from the normal subject cDNA library; c) generating a cDNA library for the disease from a whole blood sample from a test subject; d) generating EST profile from the test subject cDNA library; and e) comparing the test subject EST profile to the normal subject EST profile, wherein if the test subject EST profile differs from the normal subject EST profile, the test subject might be diagnosed with the disease.

In still yet another embodiment of the present invention, there is provided a kit for diagnosing, prognosing or predicting a disease, comprising: a) gene-specific primers; wherein the primers are designed in such a way that their sequences contain the opposing ends of two adjacent exons for the specific gene with the intron sequence excluded; and b) a carrier, wherein the carrier immobilizes the primer(s). Preferably, the gene-specific primers are selected from the group consisting of insulin-specific primers, atrial natriuretic factor-specific primers, zinc finger protein gene-specific primers, beta-myosin heavy chain gene-specific primers, amyloid precursor protein gene-specific primers, and adenomatous polyposis-coli protein gene-specific primers. Such a kit may be applied to a test subject whole blood sample to diagnose, prognose or predict a disease by detecting the quantitative expression levels of specific genes associated with the disease in the test subject and then comparing to the levels of same genes expressed in a normal subject. Such a kit may also be used for monitoring a course of therapeutic treatment or monitoring the onset of overt symptoms of a disease.

In yet another embodiment of the present invention, there is provided a kit for diagnosing, prognosing or predicting a disease, comprising: a) probes derived from a whole blood sample for a specific disease; and b) a carrier, wherein the carrier immobilizes the probes. Such a kit may be applied to a test subject whole blood sample to diagnose, prognose or predict a disease by detecting the quantitative expression levels of specific genes associated with the disease in the test subject and then comparing to the levels of same genes expressed in a normal subject. Such a kit may also be used for monitoring a course of therapeutic treatment or monitoring the onset of overt symptoms of a disease.

Furthermore, the present invention provides a cDNA library specific for a disease, wherein the cDNA library is generated from whole blood samples.

In one embodiment of the present invention, there is a method of identifying one or more genetic markers for a disease, wherein each of said one or more genetic markers corresponds to a gene transcript, comprising the steps of: a) determining the level of one or more gene transcripts expressed in blood obtained from one or more individuals having a disease, wherein each of said one or more transcripts is expressed by a gene that is a candidate marker for disease; and b) comparing the level of each of said one or more gene transcripts from said step a) with the level of each of said one or more genes transcripts in blood obtained from one or more individuals not having a disease, wherein those compared transcripts which display differing levels in the comparison of step b) are identified as being genetic markers for a disease.

In another embodiment of the present invention, there is a method of identifying one or more genetic markers for a disease, wherein each of said one or more genetic markers corresponds to a gene transcript, comprising the steps of: a) determining the level of one or more gene transcripts expressed in blood obtained from one or more individuals having a disease, wherein each of said one or more transcripts is expressed by a gene that is a candidate marker for a disease; and b) comparing the level of each of said one or more gene transcripts from said step a) with the level of each of said one or more genes transcripts in blood obtained from one or more individuals having a disease, wherein those compared transcripts which display the same levels in the comparison of step b) are identified as being genetic markers for a disease.

In another embodiment of the present invention, there is a method of identifying one or more genetic markers of a stage of a disease progression or regression, wherein each of said one or more genetic markers corresponds to a gene transcript, comprising the steps of: a) determining the level of one or more gene transcripts expressed in blood obtained from one or more individuals having a stage of a disease, wherein said one or more individuals are at the same progressive or regressive stage of a disease, and wherein each of said one or more transcripts is expressed by a gene that is a candidate marker for determining the stage of progression or regression of a disease, and; b) comparing the level of each of said one or more gene transcripts from said step a) with the level of each of said one or more genes transcripts in blood obtained from one or more individuals who are at a progressive or regressive stage of a disease distinct from that of said one or more individuals of step a), wherein those compared transcripts which display differing levels in the comparison of step b) are identified as being genetic markers for the stage of progression or regression of a disease.

In another embodiment of the present invention, there is a method of identifying one or more genetic markers of a stage of a disease progression or regression, wherein each of said one or more genetic markers corresponds to a gene transcript, comprising the steps of: a) determining the level of one or more gene transcripts expressed in blood obtained from one or more individuals having a stage of a disease, wherein said one or more individuals are at the same progressive or regressive stage of a disease, and wherein each of said one or more transcripts is expressed by a gene that is a candidate marker for determining the stage of progression or regression of a disease, and b) comparing the level of each of said one or more gene transcripts from said step a) with the level of each of said one or more genes transcripts in blood obtained from one or more individuals who are at a progressive or regressive stage of a disease identical to that of said one or more individuals of step a), wherein those compared transcripts which display the same levels in the comparison of step b) are identified as being genetic markers for the stage of progression or regression of a disease.

In another embodiment of the present invention, there is a method of diagnosing or prognosing a disease in an individual, comprising the steps of: a) determining the level of one or more gene transcripts in blood obtained from said individual suspected of having a disease, and b) comparing the level of each of said one or more gene transcripts in said blood according to step a) with the level of each of said one or more gene transcripts in blood from one or more individuals not having a disease, wherein detecting a difference in the levels of each of said one or more gene transcripts in the comparison of step b) is indicative of a disease in the individual of step a).

In another embodiment of the present invention, there is a method of diagnosing or prognosing a disease in an individual, comprising the steps of: a) determining the level of one or more organ-specific gene transcripts or organ-specific proteins in blood obtained from said individual suspected of having a disease, and b) comparing the level of each of said one or more transcripts or protein in said blood according to step a) with the level of each of said one or more transcripts or protein in blood from one or more individuals having a disease, wherein detecting the same levels of each of said one or more transcripts or proteins in the comparison of step b) is indicative of a disease in the individual of step a).

In another embodiment of the present invention, there is a method of determining a stage of disease progression or regression in an individual having a disease, comprising the steps of: a) determining the level of one or more organ-specific gene transcripts or organ-specific proteins in blood obtained from said individual having a disease, and b) comparing the level of each if said one or more organ-specific gene transcripts or organ-specific proteins in said blood according to step a) with the level of each of said one or more organ-specific gene transcripts or organ-specific proteins in blood obtained from one or more individuals who each have been diagnosed as being at the same progressive or regressive stage of a disease, wherein the comparison from step b) allows the determination of the stage of a disease progression or regression in an individual.

Further embodiments of the methods described herein include embodiments comprising a further step of isolating RNA from said blood samples, and embodiments comprising determining the level of each of said one or more gene transcripts comprising quantitative RT-PCR (QRT-PCR), wherein said one or more transcripts are from step a) and/or step b) of said methods. Further embodiments of these methods include embodiments wherein said QRT-PCR comprises primers which hybridize to one or more transcripts or the complement thereof, wherein said one or more transcripts are from step a) and/or step b) of said methods, embodiments wherein said primers are 15-25 nucleotides in length, and embodiments wherein said primers hybridize to one or more of the sequences of any one of Tables 1-32, 36-45 and 47-79, or the complement thereof. Further embodiments of the methods described in the previous eight paragraphs include embodiments wherein the step of determining the level of each of said one or more gene transcripts comprises hybridizing a first plurality of isolated nucleic acid molecules that correspond to said one or more transcripts to an array comprising a second plurality of isolated nucleic acid molecules, wherein in one embodiment said first plurality of isolated nucleic acid molecules comprises RNA, DNA, cDNA, PCR products or ESTs, wherein in one embodiment said array comprises a plurality of isolated nucleic acid molecules comprising RNA, DNA, cDNA, PCR products or ESTs, wherein in one embodiment said array comprises two or more of the genetic markers of said methods, wherein in one embodiment said array comprises a plurality of nucleic acid molecules that correspond to genes of the human genome.

In another embodiment of the present invention, kits or panels comprise a plurality of nucleic acid molecules or protein sequences that correspond to two or more sequences from each of any one of Tables 1-32, 36-45 and 47-79.

In another embodiment of the present invention, there is an array which comprises a plurality of nucleic acid molecules or protein-binding agents (such as immunoglobulins and fragments thereof) that correspond or specifically bind to two or more sequences from each of any one of Tables 1-32, 36-45 and 47-79.

In another embodiment of the present invention, there is a kit for monitoring a course of therapeutic treatment of a disease, comprising a) two gene-specific priming means designed to produce double stranded DNA complementary to a gene selected group consisting of any one of Tables 1-32, 36-45 and 47-79; wherein said first priming means contains a sequence which can hybridize to RNA, cDNA or an EST complementary to said gene to create an extension product and said second priming means capable of hybridizing to said extension product; b) an enzyme with reverse transcriptase activity c) an enzyme with thermostable DNA polymerase activity and d) a labeling means; wherein said primers are used to detect the quantitative expression levels of said gene in a test subject.

In another embodiment of the present invention, there is a kit for monitoring progression or regression of a disease, comprising: a) two gene-specific priming means designed to produce double stranded DNA complementary to a gene selected group consisting of any one of Tables 1-32, 36-45 and 47-79; wherein said first priming means contains a sequence which can hybridize to RNA, cDNA or an EST complementary to said gene to create an extension product and said second priming means capable of hybridizing to said extension product; b) an enzyme with reverse transcriptase activity c) an enzyme with thermostable DNA polymerase activity and d) a labeling means; wherein said primers are used to detect the quantitative expression levels of said gene in a test subject.

In another embodiment of the present invention, there is a plurality of nucleic acid molecules or polypeptide molecules that identify or correspond to two or more sequences from any one of Tables 1-32, 36-45 and 47-79.

It would be readily understood by review of the instant specification that while some methods are described as gene or nucleic acid based or polypeptide based, that all such methods would be readily interchangeable. Accordingly, where a method is described that could use a polypeptide for detection of another polypeptide in place of nucleic acid to nucleic acid detection and vice versa, such interchangeability is explicitly considered to be a part of the invention described herein. Likewise, wherein blood is described as the prototypic biological component for analysis, it should be understood that any cell sample, tissue sample, or biological fluid sample may be used interchangeably therewith.

As used herein, a disease of the invention includes, but is not limited to, blood disorders, blood lipid disease, autoimmune disease, arthritis (including osteoarthritis, rheumatoid arthritis, lupus, allergies, juvenile rheumatoid arthritis and the like), bone or joint disorder, a cardiovascular disorder (including heart failure, congenital heart disease; rheumatic fever, valvular heart disease; corpulmonale, cardiomyopathy, myocarditis, pericardial disease; vascular diseases such as atherosclerosis, acute myocardial infarction, ischemic heart disease and the like), obesity, respiratory disease (including asthma, pneumonitis, pneumonia, pulmonary infections, lung disease, bronchiectasis, tuberculosis, cystic fibrosis, interstitial lung disease, chronic bronchitis emphysema, pulmonary hypertension, pulmonary thromboembolism, acute respiratory distress syndrome and the like), hyperlipidemias, endocrine disorder, immune disorder, infectious disease, muscle wasting and whole body wasting disorder, neurological disorders (including migraines, seizures, epilepsy, cerebrovascular diseases, alzheimers, dementia, Parkinson's, ataxic disorders, motor neuron diseases, cranial nerve disorders, spinal cord disorders, meningitis and the like) including neurodegenerative and/or neuropsychiatric diseases and mood disorders (including schizophrenia, anxiety, bipolar disorder; manic depression and the like, skin disorder, kidney disease, scleroderma, stroke, hereditary hemorrhage telangiectasia, diabetes, disorders associated with diabetes (e.g., PVD), hypertension, Gaucher's disease, cystic fibrosis, sickle cell anemia, liver disease, pancreatic disease, eye, ear, nose and/or throat disease, diseases affecting the reproductive organs, gastrointestinal diseases (including diseases of the colon, diseases of the spleen, appendix, gall bladder, and others) and the like. For further discussion of human diseases, see Mendelian Inheritance in Man: A Catalog of Human Genes and Genetic Disorders by Victor A. McKusick (12th Edition (3 volume set) June 1998, Johns Hopkins University Press, ISBN: 0801857422) and Harrison's Principles of Internal Medicine by Braunwald, Fauci, Kasper, Hauser, Longo, & Jameson (15th Edition, 2001), the entirety of which is incorporated herein.

In another embodiment of the invention, a disease refers to an immune disorder, such as those associated with overexpression of a gene or expression of a mutant gene (e.g., autoimmune diseases, such as diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing; loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

In another embodiment, a disease of the invention is a cellular proliferative and/or differentiative disorder that includes, but is not limited to, cancer e.g., carcinoma, sarcoma or other metastatic disorders and the like. As used herein, the term "cancer" refers to cells having the capacity for autonomous growth, i.e., an abnormal state of condition characterized by rapidly proliferating cell growth. "Cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumour, in situ, Krebs 2, Merkel cell, mucinous, non-small cell lung, oat cell, papillary, scirrhous, bronchiolar, bronchogenic, squamous cell, and transitional cell), histiocytic disorders, leukaemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumour, adeno-carcinoma, adenoma, cholangioma, cholesteatoma, cylindroma, cystadenocarcinoma, cystadenoma, granulosa cell tumour, gynandroblastoma, hepatoma, hidradenoma, islet cell tumour, Leydig cell tumour, papilloma, Sertoli cell tumour, theca cell tumour, leiomyoma, leiomyosarcoma, myoblastoma, mymoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic respiratory tract, and urogenital), neurofibromatosis, and cervical dysplasia, and other conditions in which cells have become immortalized or transformed.

In another embodiment, a disease of the invention includes but is not limited to a condition wherein said condition is reflective of the state of a particular individual, whether said state is a physical, emotional or psychological state, said state resulting from the progression of time, treatment, environmental factors or genetic factors.

When comparing two or more samples for differences, results are reported as statistically significant when there is only a small probability that similar results would have been observed if the tested hypothesis (i.e., the genes are not expressed at different levels) were true. A small probability can be defined as the accepted threshold level at which the results being compared are considered significantly different. The accepted lower threshold is set at, but not limited to, 0.05 (i.e., there is a 5% likelihood that the results would be observed between two or more identical populations) such that any values determined by statistical means at or below this threshold are considered significant.

When comparing two or more samples for similarities, results are reported as statistically significant when there is only a small probability that similar results would have been observed if the tested hypothesis (i.e., the genes are not expressed at different levels) were true. A small probability can be defined as the accepted threshold level at which the results being compared are considered significantly different. The accepted lower threshold is set at, but not limited to, 0.05 (i.e., there is a 5% likelihood that the results would be observed between two or more identical populations) such that any values determined by statistical means above this threshold are not considered significantly different and thus similar.

Identification of genes differentially expressed in blood samples from patients with disease as compared to healthy patients or as compared to patients without said disease is determined by statistical analysis of the gene expression profiles from healthy patients or patients without disease compared to patients with disease using the Wilcox Mann Whitney rank sum test. Other statistical tests can also be used, see for example (Sokal and Rohlf (1987) Introduction to Biostatistics 2nd edition, WH Freeman, New York), which is incorporated herein in their entirety.

In order to facilitate ready access, e.g., for comparison, review, recovery and/or modification, the expression profiles of patients with disease and/or patients without disease or healthy patients can be recorded in a database, whether in a relational database accessible by a computational device or other format, or a manually accessible indexed file of profiles as photographs, analogue or digital imaging, readouts spreadsheets etc. Typically the database is compiled and maintained at a central facility, with access being available locally and/or remotely.

As would be understood by a person skilled in the art, comparison as between the expression profile of a test patient with expression profiles of patients with a disease, expression profiles of patients with a certain stage or degree of progression of said disease, without said disease, or a healthy patient so as to diagnose or prognose said test patient can occur via expression profiles generated concurrently or non concurrently. It would be understood that expression profiles can be stored in a database to allow said comparison.

As additional test samples from test patients are obtained, through clinical trials, further investigation, or the like, additional data can be determined in accordance with the methods disclosed herein and can likewise be added to a database to provide better reference data for comparison of healthy and/or non-disease patients and/or certain stage or degree of progression of a disease as compared with the test patient sample. These and other methods, including those described in the art (e.g., U.S. Patent Application Pub No. 20060134637) can be used in the context of the sequences disclosed.

Business Methods

A further embodiment of the present invention comprises business methods for manufacturing one or more of the detection reagents, panels, arrays as described herein as well as providing diagnostic services for analyzing and/or comparing organ-specific fingerprints or individual proteins (or nucleic acid molecules) from a subject with one, two or more organ-specific proteins or nucleic acid molecules described herein, identifying disease fingerprints or organ-specific proteins or nucleic acid molecules that vary or become present with disease, identifying fingerprints or proteins or nucleic acid molecule levels perturbed from normal, providing manufacturers of genomics devices the use of the detection reagents, panels, arrays, organ-specific fingerprints or specific organ-specific proteins or nucleic acid probes for nucleic acid molecules encoding the same described herein to develop diagnostic devices, where the genomics device includes any device that may be used to define differences in a sample between the normal and disturbed state resulting from one or more effects, providing manufacturers of proteomics devices the use of the detection reagents, panels, arrays, organ-specific proteins described herein to develop diagnostic devices, where the proteomics device includes any device that may be used to define differences in a sample between the normal and disturbed state resulting a disease, disorder or therapy, providing manufacturers of imaging devices detection reagents, panels, arrays, lateral flow devices, organ-specific proteins or nucleic acid molecules or probes thereto described herein to develop diagnostic devices, where the proteomics devices include any device that may be used to define differences in a blood sample between the normal and disturbed state resulting from disease, drug side-effects, or therapeutic interventions, providing manufacturers of molecular imaging devices the use of the detection reagents, panels, arrays, blood fingerprints or transcriptomes described herein to develop diagnostic devices, where the proteomics device includes any device that may be used to define differences in a blood sample between the normal and disturbed state and marketing to healthcare providers the benefits of using the detection reagents, panels, arrays, and diagnostic services of the present invention to enhance diagnostic capabilities and thus, to better treat patients.

Also provided is an aspect of the invention to utilize databases to store data and analysis of panels and organ/tissue-specific sets and individual components thereof for certain ethnic populations, genders, etc. and for analysis over a lifetime for individuals based upon the data from millions or more individuals. In addition, the present invention contemplates the storage an access to such information via an appropriate secured and private setting wherein HIPAA standards are followed.

Another aspect of the invention relates to a method for conducting a business, which includes: (a) manufacturing one or more of the detection reagents, panels, arrays, (b) providing services for analyzing organ-specific molecular blood fingerprints and (c) marketing to healthcare providers the benefits of using the detection reagents, panels, arrays, and services of the present invention to enhance capabilities to detect disease or disease progression and thus, to better treat patients.

Another aspect of the invention relates to a method for conducting a business, comprising: (a) providing a distribution network for selling the detection reagents, panels, arrays, diagnostic services, and access to organ-specific molecular blood fingerprint databases (b) providing instruction material to physicians or other skilled artisans for using the detection reagents, panels, arrays, and organ-specific molecular blood fingerprint databases to improve the ability to detect disease, analyze disease progression, or stratify patients.

For instance, the subject business methods can include an additional step of providing a sales group for marketing the database, or panels, or arrays, to healthcare providers.

Another aspect of the invention relates to a method for conducting a business, comprising: (a) preparing one or more normal organ-specific molecular blood fingerprints and (b) licensing, to a third party, the rights for further development and sale of panels, arrays, and information databases related to the organ-specific molecular blood fingerprints of (a).

The business methods of the present application relate to the commercial and other uses, of the methodologies, panels, arrays, organ-specific proteins (e.g., including secreted organ-specific proteins and panels thereof), organ-specific molecular blood fingerprints, and databases comprising identified fingerprints of the present invention. In one aspect, the business method includes the marketing, sale, or licensing of the present invention in the context of providing consumers, i.e., patients, medical practitioners, medical service providers, and pharmaceutical distributors and manufacturers, with all aspects of the invention described herein, (e.g., the methods for identifying organ-specific secreted proteins, detection reagents for such proteins, molecular blood fingerprints, etc., as provided by the present invention).

In a particular embodiment of the present invention, a business method or diagnostic method relating to providing information related to organ-specific proteins (nucleic acids encoding the same), a plurality thereof, or a fingerprint of a plurality (e.g., levels of the plurality of organ-specific secreted proteins that make up a given fingerprint), method for determining organ-specific protein (or transcripts encoding the same) or levels thereof or fingerprints of the same and sale of such panels. In a specific embodiment, that method may be implemented through the computer systems of the present invention. For example, a user (e.g. a health practitioner such as a physician or a diagnostic laboratory technician) may access the computer systems of the present invention via a computer terminal and through the Internet or other means. The connection between the user and the computer system is preferably secure.

In practice, the user may input, for example, information relating to a patient such as the patient's disease state and/or drugs that the patient is taking, e.g., levels determined for the organ-specific proteins of interest or that make up a given molecular blood fingerprint using a panel or array of the present invention. The computer system may then, through the use of the resident computer programs, provide a diagnosis, detect changes in disease states, stratify patients, or determination of drug side-effects that fits with the input information by matching the parameters of particular protein or panel thereof (e.g., levels of the proteins present in the blood as detected using a particular panel or array of the present invention) with a database of fingerprints.

A computer system in accordance with a preferred embodiment of the present invention may be, for example, an enhanced IBM AS/400 mid-range computer system. However, those skilled in the art will appreciate that the methods and apparatus of the present invention apply equally to any computer system, regardless of whether the computer system is a complicated multi-user computing apparatus or a single user device such as a personal computer or workstation. Computer systems suitably comprise a processor, main memory, a memory controller, an auxiliary storage interface, and a terminal interface, all of which are interconnected via a system bus. Note that various modifications, additions, or deletions may be made to the computer system within the scope of the present invention such as the addition of cache memory or other peripheral devices.

The processor performs computation and control functions of the computer system, and comprises a suitable central processing unit (CPU). The processor may comprise a single integrated circuit, such as a microprocessor, or may comprise any suitable number of integrated circuit devices and/or circuit boards working in cooperation to accomplish the functions of a processor.

In a preferred embodiment, the auxiliary storage interface allows the computer system to store and retrieve information from auxiliary storage devices, such as magnetic disk (e.g., hard disks or floppy diskettes) or optical storage devices (e.g., CD-ROM). One suitable storage device is a direct access storage device (DASD). A DASD may be a floppy disk drive that may read programs and data from a floppy disk. It is important to note that while the present invention has been (and will continue to be) described in the context of a fully functional computer system, those skilled in the art will appreciate that the mechanisms of the present invention are capable of being distributed as a program product in a variety of forms, and that the present invention applies equally regardless of the particular type of signal bearing media to actually carry out the distribution. Examples of signal bearing media include: recordable type media such as floppy disks and CD ROMS, and transmission type media such as digital and analog communication links, including wireless communication links.

The computer systems of the present invention may also comprise a memory controller, through use of a separate processor, which is responsible for moving requested information from the main memory and/or through the auxiliary storage interface to the main processor. While for the purposes of explanation, the memory controller is described as a separate entity, those skilled in the art understand that, in practice, portions of the function provided by the memory controller may actually reside in the circuitry associated with the main processor, main memory, and/or the auxiliary storage interface.

Furthermore, the computer systems of the present invention may comprise a terminal interface that allows system administrators and computer programmers to communicate with the computer system, normally through programmable workstations. It should be understood that the present invention applies equally to computer systems having multiple processors and multiple system buses. Similarly, although the system bus of the preferred embodiment is a typical hardwired, multidrop bus, any connection means that supports bidirectional communication in a computer-related environment could be used.

The main memory of the computer systems of the present invention suitably contains one or more computer programs relating to the organ-specific molecular blood fingerprints and an operating system. Computer program is used in its broadest sense, and includes any and all forms of computer programs, including source code, intermediate code, machine code, and any other representation of a computer program. The term "memory" as used herein refers to any storage location in the virtual memory space of the system. It should be understood that portions of the computer program and operating system may be loaded into an instruction cache for the main processor to execute, while other files may well be stored on magnetic or optical disk storage devices. In addition, it is to be understood that the main memory may comprise disparate memory locations.

As should be clear to the skilled artisan from the above, the present invention provides databases, readable media with executable code, and computer systems containing information comprising predetermined normal serum levels of organ-specific proteins that make up organ-specific protein sets. Further, the present invention provides databases of information comprising disease-associated organ-specific proteins, nucleic acid molecules encoding the same, as well as panels and in some embodiments, levels thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Moreover, all numerical ranges utilized herein explicitly include all integer values within the range and selection of specific numerical values within the range is contemplated depending on the particular use. Further, the following examples are offered by way of illustration, and not by way of limitation.

EXAMPLES

Example 1

Identification of Organ-Specific Proteins by Analysis of MPSS Data

This example shows the identification of organ-specific protein sets from 32 normal, healthy organs.

1. Normalized MPSS Dataset

The normalized MPSS data used in this study was previously described (Jongeneel, et al., *Genome* (2005), 15:1007-1014) but re-annotated by Solexa (Hayward, Calif., USA) to the new UniGene database. The data contained a total of 391,669 MPSS sequence tags, their gene annotation, their expression levels in 32 different tissues as specified by their transcription per million (tpm) and the associated standard deviation (SD), and information on the sequence tags such as significance, selected step, class, and global replication. This dataset was used to identify organ-specific proteins as described below.

Identification of Organ-Specific MPSS Tags

Assume the expression (in tpm) and the associated SD of a MPSS sequence tag in the 32 tissues were $\{(X_i, \sigma_i)\}$, where $i=1, 2, \ldots, 32$ represents individual tissues. Assume the tag had the highest expression levels in tissue m where the expression and the SD were $(X_m, \sigma_m)$. We then applied three rules to determine whether the tag was specific to tissue m as follows:

i) The expression of the tag in tissue m was above a minimal, estimated noise levels, i.e., $$X_m \geq 5. \quad (1)$$

ii) The expression of the tag in tissue in was well above the expression of the tag in all other tissues. More specifically, we first calculated the mean expression of the tag in the other 31 tissues (except tissue m) as $$\overline{X} = \frac{1}{N} \sum_{i \neq m} X_i, \quad (2)$$

the associated standard error as $$\sigma_{\overline{X}} = \frac{1}{N} \sqrt{\sum_{i \neq m} \sigma_i^2}, \quad (3)$$

and the corresponding SD as $$s = \sqrt{\frac{1}{N-1} \sum_{i \neq m} (X_i - \overline{X})^2 + \frac{1}{N} \sum_{i \neq m} \sigma_i^2}, \quad (4)$$

where N=31.

We then evaluated the significance that the expression of the tag in tissue m was above the expression of the tag in other tissues as $$p_{dis} = \frac{1}{2} \mathrm{erfc}\left(\frac{X_m - \overline{X}}{\sqrt{2(s^2 + \sigma_m^2 + \sigma_{\overline{X}}^2)}}\right). \quad (5)$$

For the tag to be specific to tissue m, we required that $$p_{dis} \leq 10^{-3}. \quad (6)$$

iii) The specificity f of the tag in tissue m had to be well above a pre-selected cutoff value $f_0$. More precisely, we defined the specificity of the tag in tissue m as $$f = \frac{X_m}{\sum_i X_i}, \quad (7)$$

and evaluated the associated SD as $$\sigma_f = \frac{f}{X_m} \sqrt{(1-f)^2 \sigma_m^2 + f^2 \sum_{i \neq m} \sigma_i^2}. \quad (8)$$

The significance that f was above $f_0$ is then given by $$p_{spc} = \frac{1}{2} \mathrm{erfc}\left(\frac{f - f_0}{\sqrt{2}\, \sigma_f}\right). \quad (9)$$

Nine different values of $f_0$ and $p_{spc}$ were applied in determining organ-specific MPSS tags, ranging from the most stringent condition ($f_0=1$ and $p_{spc} \leq 10^{-3}$) to the least stringent condition ($f_0=0.5$ and $p_{spc} \leq 0.1$): See Tables 1-32 and 36-45. However, in most cases, we required that $$p_{spc} \leq 10^{-3}. \quad (10)$$

The stringency for each organ-specific transcript is noted in Tables 1-32 and 36-45. (see column marked "Specificity")

When we applied rules i)-iii) (Eqs. (1), (6) and (10) with $f_0=0.8$) to the 391,669 MPSS sequence tags, we identified a total of 17,638 organ-specific tags. The number of organ-specific tags varies with the selected values of $f_0$ and $p_{spc}$: See Tables 1-32 and 36-45.

Mapping Organ-Specific MPSS Tags to Corresponding Proteins

MPSS tags were annotated to gene accession numbers in the UniGene database by Solexa. In cases where MPSS tags were mapped to multiple genes in the UniGene database, Solexa intentionally annotated the MPSS tags only to genes having the longest sequences. A script was developed to annotate the MPSS tags to all genes containing the MPSS tags. A separate script was then developed to map gene accession numbers in the UniGene database to the corresponding gene accessions, protein accessions and protein sequences in the RefSeq database (web address: ftp colon double slash ftp dot ncbi dot gov slash refseq slash H sapiens/). In this way, organ-specific tags were mapped to corresponding proteins. In some cases multiple MPSS tags may be mapped to the same proteins. In such cases only the MPSS tag having the most abundant expression was kept for each organ-specific protein. The organ-specific proteins identified are provided in Tables 1-32 and 36-45. Information on each protein includes gene name, gene accession number, protein accession number, summary description of the protein, predicted protein localization (as described further below), corresponding MPSS tag, the class of the MPSS tag, the expression of the tag in the particular tissue (count), the specificity of the tag in the particular tissue (as described above), and the number of peptides identified on the protein by HUPO (as described further below). The amino acid sequences corresponding to the organ-specific proteins and the polynucleotides encoding the proteins are provided in the sequence listing. Sequences corresponding to the MPSS tags as shown in Tables 1-32 and 36-45 are also provided, Sequences corresponding to peptides previously identified by mass spectrometry that map to organ-specific proteins described in Tables 43, 44 and 45 are shown in those Tables and are provided in the sequence listing.

Prediction of Protein Localization

Protein sequences in the RefSeq database were used to predict protein localization using TMHMM (server 2.0, http colon double slash www dot cbs dot dtu dot dk/services/

TMHMM/), which applies hidden Markov model to predict protein transmembrane domains SignalP (server 3.0, http colon double slash www dot cbs dot dtu dot dk/services/SignalP/), which applies both artificial neural network and hidden Markov model to predict the presence and the location of signal peptide cleavage sites for classical (N-terminus lead) secreted proteins. This was performed computationally using a combination of hidden Markov model (HMM) algorithms (Krogh et al., *J Mol Biol* (2001) 305:567) and transmembrane (TM) region predictions from a commercial version of the TMHMM algorithm. The subcellular localizations of proteins were categorized as follows: a) extracellular-proteins, (including secreted proteins) which contain predicted signal peptides and no predicted transmembrane segments; c) transmembrane-proteins, which contain predicted transmembrane segments; or d) other which includes intracellular-proteins, which contain neither predicted signal peptides nor predicted transmembrane regions was then used to combine the outputs of the two programs into protein localization prediction, which is outlined in Table 33. The localization prediction for all organ-specific proteins is summarized in Table 33.

TABLE 33

Rules used to combine outputs of TMHMM and SignalP for the prediction of protein localization

| TM domains (TMHMM) | Secretion (SignalP) | Cleavage (SignalP) | Localization prediction |
|---|---|---|---|
| >1 | | | Transmembrane |
| 1 | N | | Transmembrane |
| 1 (not cleaved) | Y | Y | Transmembrane |
| 1 (cleaved) | Y | Y | Secreted |
| 0, 1 | Y | N | Anchored |
| 0 | Y | Y | Secreted |
| 0 | N | | Other |

Overlap with Identified Human Plasma Proteins

The Plasma Proteome Project of the Human Proteome Organization (HUPO) released a list of human plasma proteins including the number of identified peptides on each protein (Omenn, et al. *Proteomics*. (2005):3226-45). These proteins were specified by protein IDs in the International Protein Index (IPI) database (web address: ftp colon double slash ftp dot ebi dot ac dot uk slash pub/databases/IPI/current/ipi dot HUMAN dot fasta dot gz). A list for mapping protein IPI IDs to protein RefSeq accession numbers was also provided. Overlap between the organ-specific proteins and the HUPO plasma proteins were analyzed. The identified overlap is shown in Tables 1-32. Further classification by class and ranks were used to formulate statistical tests to determine significant genes (Stolovitzky et al, PNAS (2005) 1402-1407).

Example 2

Identification of Organ-Specific Proteins in Human Serum Using Mass Spectrometry This experiment demonstrates the process of identifying organ-specific proteins in a normal sample of blood serum from a healthy, human volunteer. For normal control serum, venous blood samples were drawn from a fasted, human volunteer. Samples were collected with minimal stasis in evacuated serum separator tubes. After at least 30 min, but within 2 hours, the tubes were centrifuged at 23° C. for 15 minutes at 1,200 g and serum was stored in plastic vials at −80° C. To reduce sample complexity, plasma was passed over a column containing antibodies to the most abundant proteins. In this example, an affinity column was used to remove albumin, IgG, IgA, anti-trypsin, transferrin, and haptoglobin; however, affinity columns with an expanded repertoire could also be used. Since most proteins found on the cell surface or secreted from cells are glycoproteins, and can be isolated via the glycopeptide capture method, proteins were further enriched and identified by specifically capturing N-linked glycopeptides from plasma.

A recently developed mass spectrometry-based screening technology provided specific targets—glycoproteins in a plasma sample for identification and quantification. The glycopeptides isolated from plasma and tissues were analyzed by MALDI-TOF/TOF (ABI 4800 Proteomics Analyzer, Applied Biosystems) after front-end separation of peptides using strong cation exchange fractionation followed by reversed phase chromatography. The advantage of this platform is its high mass accuracy, resolution, sensitivity, and the ability to do targeted MS/MS analysis on peptides of interest. Since the separation is performed off-line, more time is available for deeper interrogation of the observed tryptic peptides. Multiple plates can also be spotted and analyzed by MALDI-TOF/TOF to increase the depth of proteomic coverage. This platform will also be used in the direct follow up analysis of potential peptides during the comparison of cancer and control sera using heavy isotope labeled synthetic peptide standards.

HPLC and Maldi Plate Spotting

Up to 20 µg total peptide was loaded onto a 150 mm×0.3 mm poly sulfoethyl A column, and peptides were eluted using five to ten steps of increasing salt concentration. Up to 2 µg total peptide that was bumped from the strong cation exchange column was trapped onto a 250 micron×3 cm trap column self-packed with 5 micron particle Vydac C8 (#208MS54). The Eksigent HPLC and autosampler (Model: NanoLC-2D, Dublin, Calif.) uses a 10 ul sample loop. After capturing the strong cation exchange eluate, the trap column was brought in-line with a 100 micron ID×20 cm resolving column that was self-packed with 5 micron particle Vydac C18 (#218MS54) at a flow rate of 500 nanoliters per minute using 0.1% TFA and 2% acetonitrile as solvent A, and 0.08% TFA and 80% acetonitrile as solvent B. Peptides were eluted using a 90 min gradient up to 75% solvent B. The effluent of the HPLC column enters a mixing tee, where it combines with matrix solution flowing at 0.75 ul/min prior to spotting to a MALDI plate at the rate of 25 seconds per spot. The matrix solution was 4 mg/ml alpha-cyano-4-hydroxycinnamic acid (Aldrich) in 70% acetonitrile 0.1% TFA containing 5 mM ammonium dihydrogen phosphate. The spots were placed in a 25×40 array, where each HPLC gradient has 200 spots; thus, each Maldi plate can hold 5 reversed phase HPLC gradients.

MALDI Tof Tof

The spotted plates contain 8 locations around the perimeter of the plate where an external calibrant was placed. The external calibrant was the "4700 mix" (Applied Biosystems) prepared as directed. Upon insertion into the mass spectrometer, the laser was aligned with the crosshairs of the sample viewer, and the plate was aligned to the four corners of the 25×40 spot sample array. The mass spectrometer was tuned for sensitivity and resolution using the calibration spots, and then an external calibration was obtained in MS and MSMS mode. Each HPLC gradient (200 spots) was analyzed by acquiring an MS spectrum at each spot using 100 laser shots randomly located at 10 positions within each sample spot. Upon completion of the 200 MS spectra for each of the sample spots, the data system determines the top 20 precursor ions per sample spot (user selected variable) precursor ions for subsequent acquisition of MS/MS spectra. Alternatively, specific precursor masses can be acquired regardless of their presence or absence in the MS spectra. Each MS/MS spectra was obtained from 2000 laser shots from 20 random positions within each sample spot without using collision gas. Upon completion, the MS/MS spectra can be exported to the supplied database search engine (Mascot) for peptide/protein identification. Analysis of the collected spectra led to the identification of approximately 150 unique proteins from plasma. When compared to the organ-specific proteins summarized in Tables 1-32, it was shown that this dataset includes seven glycosylated, tissue-specific proteins. These seven proteins are listed in Table 34A and 34B.

TABLE 34A

ORGAN-SPECIFIC GLYCOSYLATED PROTEINS IDENTIFIED FROM A SAMPLE OF NORMAL HUMAN SERUM

| Gene | Accession | Description | Type | Signature | Class | Count | Specificity |
|---|---|---|---|---|---|---|---|
| CLU | NM_203339; SEQ ID NO: 25362; NP_976084; SEQ ID NO: 25502 | Homo sapiens clusterin (complement lysis inhibitor, SP-40, 40, sulfated glycoprotein 2, testosterone-repressed prostate message 2, apolipoprotein J) (CLU), transcript variant 2, mRNA [Homo sapiens] | secr | GATCCACCAGGCCT CAG; SEQ ID NO: 25654 | 4 | 80 | 0.64 |
| C3 | NM_000064; SEQ ID NO: 5142; NP_000055; SEQ ID NO: 5976 | Homo sapiens complement component 3 (C3), mRNA [Homo sapiens] | secr | GATCTTGGGCCTTA GCA; SEQ ID NO: 6789 | 14 | 49 | 0.803 |
| IGJ | NM_144646; SEQ ID NO: 8639; NP_653247; SEQ ID NO: 9967 | Homo sapiens immunoglobulin J polypeptide, linker protein for immunoglobulin alpha and mu polypeptides (IGJ), mRNA [Homo sapiens] | secr | GATCACAGTTTGTTT AC; SEQ ID NO: 11123 | 15 | 14 | 0.778 |
| HRG | NM_000412; SEQ ID NO: 15453; NP_000403; SEQ ID NO: 15629 | Homo sapiens histidine-rich glycoprotein (HRG), mRNA [Homo sapiens] | secr | GATCAAATGGAAAG GAG; SEQ ID NO: 15808 | 1 | 69 | 0.697 |
| APOD | NM_001647; SEQ ID NO: 15915; NP_001638; SEQ ID NO: 16312 | Homo sapiens apolipoprotein D (APOD), mRNA [Homo sapiens] | secr | GATCCAAGCAAAATC CA; SEQ ID NO: 16713 | 14 | 42 | 1 |
| SERPIN G1 | NM_000062; SEQ ID NO: 23547; NP_000053; SEQ ID NO: 23878 | Homo sapiens serpin peptidase inhibitor, clade G (C1 inhibitor), member 1, (angioedema, hereditary) (SERPING1), transcript variant 1, mRNA [Homo sapiens] | secr | GATCAGGTTAGGGC GAT; SEQ ID NO: 27220 | 1 | 118 | 0.881 |
| SERPIN G1 | NM_00103229 5; SEQ ID NO: 23548; NP_00102746 6; SEQ ID NO: 23879 | Homo sapiens serpin peptidase inhibitor, clade G (C1 inhibitor), member 1, (angioedema, hereditary) (SERPING1), transcript variant 2, mRNA [Homo sapiens] | secr | GATCAGGTTAGGGC GAT; SEQ ID NO: 27220 | 1 | 118 | 0.881 |
| THBS1 | NM_003246; SEQ ID NO: 17925; NP_003237; SEQ ID NO: 18394 | Homo sapiens thrombospondin 1 (THBS1), mRNA [Homo sapiens] | secr | GATCACTTCTCCTTG GC; SEQ ID NO: 18807 | 3 | 1002 | 0.809 |

TABLE 34B

ORGAN-SPECIFIC GLYCOSYLATED PROTEINS IDENTIFIED FROM A SAMPLE OF NORMAL HUMAN SERUM

| Gene | Accession | Tissue | peptide NXS/Tlength | expectation score | peptide score | protein score | peptides | Peptide Sequence (SEQ ID NO:) |
|---|---|---|---|---|---|---|---|---|
| CLU | NM_203339; SEQ ID NO: 25362; NP_976084; SEQ ID NO: 25502 | Spinal Cord | Yes 14 | 4.60E-08 | 93 | 108 | 2 | LANLTQGEDQYYLR + Deamidation (N) (SEQ ID NO: 50184) |
| C3 | NM_000064; SEQ ID NO: 5142; NP_000055; SEQ ID NO: 5976 | Brain Cerebellum | Yes 28 | 8.90E-07 | 78 | 174 | 3 | LVLSSEKTVLTPATNHMGNVTFTI PANR (+ Deamidation (N); Oxidation (M) (SEQ ID NO: 37801) |
| IGJ | NM_144646; SEQ ID NO: 8639; NP_653247; SEQ ID NO: 9967 | Brain Fetal | Yes 19 | 5.0E-06 | 68 | 68 | 1 | IIVPLNNRENISDPTSPLR + Deamidation (N) (SEQ ID NO: 41099) |
| HRG | NM_000412; SEQ ID NO: 15453; NP_000403; SEQ ID NO: 15629 | Kidney | Yes 19 | 1.40E-08 | 99 | 98 | 1 | VIDFNCTTSSVSSALANTK + Deamidation (N) (SEQ ID NO: 44534) |
| APOD | NM_001647; SEQ ID NO: 15915; NP_001638; SEQ ID NO: 16312 | Lung | Yes 26 | 3.10E-05 | 62 | 74 | 2 | ADGTVNQIEGEATPVNLTEPAKLE VK + Deamidation (N) (SEQ ID NO: 45400) |
| SERPING1 | NM_000062; SEQ ID NO: 23547; NP_000053; SEQ ID NO: 23878 | Spleen | Yes 21 | 1.20E-05 | 67 | 67 | 1 | VLSNNSDANLELINTWVAK (SEQ ID NO: 49773) |
| SERPING1 | NM_001032295; SEQ ID NO: 23548; NP_001027466; SEQ ID NO: 23879 | Spleen | Yes 21 | 1.20E-05 | 67 | 67 | 1 | VLSNNSDANLELINTWVAK (SEQ ID NO: 49773) |
| THBS1 | NM_003246; SEQ ID NO: 17925; NP_003237; SEQ ID NO: 18394 | Monocyte | Yes 13 | 3.60E-05 | 65 | 65 | 1 | WNSTTGPGEHLR + Deamidation (N) (SEQ ID NO: 72689) |

Thus, this example identifies numerous normal serum organ specific proteins (Table 34A and 34B). These proteins are diagnostically useful in a variety of settings as described herein, for example, for defining a biological state of a subject and for the diagnosis of specific diseases.

Example 3

Verification and Quantification of Serum Proteins Using Enzyme-Linked Immunosorbant Assay (ELISA)

Blood serum tests to detect and monitor proteins were developed using an enzyme-linked immunosorbent assay (ELISA). The assay system utilized two antibodies directed against different antigenic regions of the candidate protein. A monoclonal antibody directed against a distinct antigenic determinant on the intact candidate protein was used for solid phase immobilization on the microtiter wells. A detection antibody conjugated to horseradish peroxidase (HRP) or fluorescence tag recognized the candidate protein within different region of the same protein. The candidate protein reacted simultaneously with the two antibodies, resulting in the protein being sandwiched between the solid phase and detection antibody. The detection antibody was visualized by colorimetric fluorescence analysis.

In the case of peptides detected in blood, the specific peptide was further enriched from peptide mixture isolated from plasma using the physico-chemical properties of the peptide or affinity reagents developed for the peptide. Protein concentrations were estimated by an ELISA employing specific antibodies to capture and detect the protein of interest in serum. Wells of 96-well microtiter plates ("Maxisorp," Nunc, Roskilde, Denmark) were coated with protein-specific antibodies and incubated overnight at 2-8° C. Well surfaces were saturated with a solution of irrelevant protein to prevent non-specific binding of subsequent reactants and washed with Phosphate Buffered Saline (PBS), pH 7.2 with 0.05% Tween-20 (PBST) prior to use. Samples and reagents were dispensed into the wells in the following sequence, each separated by an incubation period and wash step: (1) serum samples and protein concentration standards, (2) detection antibodies, (3) horseradish peroxidase conjugate, and (4) peroxidase substrate. The substrate reaction was stopped after a final incubation period with the addition of acid to the wells, and the O.D.s were determined with a microplate spectrophotometer. Sample concentrations were then extrapolated from the dose-response curve.

Example 4

Identification of STEAP2 Protein Expression in Human Blood Serum

A Comparison of Proteins in Normal Controls, Early Prostate Disease and Late Stage Prostate Disease Current methods for prostate cancer screening include cancer screening with Prostate Specific Antigen (PSA). The PSA test is not always predictive of prostate cancer due to individual patient risk factors including ethnicity, family history, as well as the patient's individual status and individual risk aversion to complications from prostate cancer. Since the PSA test is not entirely predictive, future prostate cancer screening will need to incorporate new biomarkers to predict the risk of disease (Thompson, et al., *Surg Oncol Clin N Am.* (2005) 14:747-60).

This example describes a multiparameter diagnostic fingerprint using STEAP2, a multiple transmembrane protein of the prostate as a biological marker. STEAP2 is the gene encoding a Human, six transmembrane epithelial antigen of the prostate (STEAP2). STEAP2 was previously shown to have prostate-specific expression (Porkka, K P et al *Lab Invest.* (2002) 82:1573-1582; Kormaz, K S, *J. Biol. Chem.* (2002) 27:36689-96). Further, as outlined in Example 1 and shown in Table 21, STEAP2 was shown to be a prostate-specific protein using the methods outlined herein.

Commercially available antibodies specific for numerous proteins encoded by prostate-specific genes (see Table 21) were used to determine which proteins would be useful in a multiparameter diagnostic assay for prostate cancer. The antibody available for STEAP2 (anti-STEAP2; Cat #A23080; Genway Biotech Inc.) was shown to bind specifically to a fragment of STEAP2 from human serum. In this example, TGM4 was used as a control. TGM4 is the gene encoding Human prostate-specific transglutaminase (hTGP). hTGP has prostate-specific expression (Dubbink, et al *GENOMICS* (1998) 51:434-444). The antibody available for TGM4 (anti-TGM4; Cat #G23082; Genway Biotech Inc.) was shown to specifically bind to TGM4 from human serum.

Western blot analysis was used to measure serum protein expression as follows: Serum was diluted (1:25) with sample buffer (50 mM Tris-HCl (pH 6.8), 100 mM dithiothreitol, 2% sodium dodecylsulphate, 0.1% bromophenol blue, 10% glycerol). Serum proteins in 4 µA of 4% serum solution were analyzed with SDS-PAGE and transferred to a PVDF membrane (Hybond-P, Millipore, Billerica, Mass.). The membrane was blocked with 1% non-fat dry milk in TBS-T (25 mM Tris, pH 7.4, 125 mM NaCl, 0.1% Tween-20) for 1 hour at room temperature, followed by incubation with primary antibodies against STEAP2 (1:5000) or TGM4 (1:5000) for 1 h at room temperature (23° C.). The membranes were washed 3 times with TBS-T, and then incubated with horseradish peroxidase conjugated anti-chicken antibodies (1:10,000) for 0.5 h. The immunoblot was then washed five times with TBS-T and developed using enhanced chemoluminescence following the manufacturer's recommendation (Pierce) (see FIG. 2). The densities of the single bands corresponding to STEAP2 and TGM4 were quantified using ImageJ software (available at http colon double slash rsb dot info dot nih dot gov/ij/). The results are summarized in Table 35. PSA scores for each of the tested sera were obtained using a commercially available ELISA kit. For these prostate cancer patients, the majority of samples showed PSA levels above what is considered the normal range (0-4 ng/mL). STEAP2 levels also appeared elevated in many prostate cancer sera relative to sera from normal patients. However, the combination of PSA and STEAP2 proved to be a better predictor of prostate cancer than PSA levels alone, identifying cancer in three samples with normal PSA levels (samples 7, 9, 10) and in one sample with only slightly elevated PSA levels (sample 3).

TABLE 35

Relative density of STEAP2 and TGM4 determined using ImageJ software.

| Sample ID | Prostate Cancer Stage | Prostate Cancer Progression | PSA (ng/mL) | STEAP2 AU | TGM4 AU |
|---|---|---|---|---|---|
| 1 | Normal | Normal | 1.6 | 0.09 | 8.4974 |
| 2 | Normal | Normal | 1.8 | 1.95 | 9.5073 |
| 3 | T1N0M0 | Early PCa | 5.56 | 11.95 | 8.8023 |
| 4 | T2aN0MX | Early PCa | 4.06 | 6.68 | 9.3466 |
| 5 | T1NXM0 | Early PCa | 6.37 | 4.39 | 5.7375 |
| 6 | T2aN0M0 | Early PCa | 12 | 12.23 | 1.3447 |
| 7 | T2aN0M0 | Early PCa | 2.24 | 8.1 | 6.4363 |
| 8 | Normal | Normal | 1.1 | 7.99 | 9.4223 |
| 9 | T3N0Mx | Late PCa | 1.58 | 15.82 | 5.5885 |
| 10 | T3aNXM0 | Late PCa | 2.84 | 9.5 | 7.3708 |
| 11 | T3aNXM0 | Late PCa | 4.6 | 7.49 | 7.6887 |
| 12 | T3bN0MX | Late PCa | 6.12 | 9.69 | 9.6478 |
| 13 | Normal | Normal | 2.1 | 4.12 | 10.6099 |

In summary, the STEAP2 prostate-specific protein further improved prostate cancer detection when used in combination with PSA (see FIG. 2 and Table 35). Thus, using the methods described herein, a multiparameter diagnostic panel was developed comprising the STEAP2 prostate-specific protein and PSA.

Example 5

RNA Extraction from Organs Prior to Transcript Analysis

In further experiments, normal, healthy organ samples were obtained. For each organ total RNA was isolated from each tissue as follows: Tissue (0.1-0.2 mgs) from a specific organ was excised from frozen tissue and placed in 4 mL of TRIZOL Reagent (Invitrogen), (U.S. Pat. No. 5,346,994; Chomczynski at al., *Analytical Biochemistry*, (1987) 162: 156). Each sample was quickly homogenized for up to 90 seconds at room temperature. The homogenate of tissue and TRIZOL Reagent was incubated for 5 min at room temperature. Chloroform (800 uL) was added to each sample and incubated for 5 min at room temperature. Each sample was centrifuged at 12,000×g for 10 min at 4° C. The aqueous layer containing nucleic acids was collected and transferred to fresh tubes. Nucleic acids were precipitated by the addition of 2 mL of 2-propanol and incubated at room temperature for 10 minutes. The precipitate was centrifuged at 12,000×g for 10 minutes and nucleic acid pellets were collected. The supernatants were decanted and pellets washed with 2 mL of 70% ethanol and air dried. Pellets were suspended in 50-100 uL of RNase free water. The nucleic acid concentration was calculated using spectroscopy at wavelength (260 nm) and purity was determined by calculating the ratio of absorbance at 260 nm and 280 nm in each sample. Total RNA was analyzed by microcapillary electrophoresis using a Bioanalyzer following the manufacturer's procedures (Agilent 2100). Briefly, 1 uL of each RNA sample was diluted to 250 ng/uL in water was loaded onto a nano-CHIP and RNA profiles were visualized using a standard protocol provided by the manufacturer. The quality of the RNA was determined by examining the electrophoresis peaks and by determining the relative ratio of the 28X and 18S ribosomal RNA. This ratio was used as a metric to estimate the overall integrity of all other RNA species in the sample. Samples where the electrophoresis peaks and the 28S:18S ratio was greater than 1.5 were deemed acceptable for further transcript analyses.

Example 6

Identification of Male and Female Organ-Specific Proteins

This example shows a further refinement and the identification of organ-specific protein sets for prostate and testes in the male and mammary gland and uterus in the female.

The normalized MPSS dataset described in Example 1 was further refined to elicit nucleotide and protein sequences which were specific to various male or female organs. To that end the data from the thirty-two tissues described therein were delineated further to identify sequences specific to male prostate (Table 36) and testes (Table 37) and female mammary gland (Table 38) and uterus (Table 39).

Refinement procedure to identify the organ-specific MPSS sequences required examining the tissue-specific sequences of the thirty-two tissues and subtracting the tissues specific for females (in this case mammary gland and uterus) in order to fully examine those sequences specific to male organs listed (particularly testes and prostate). Similarly in order to examine organ-specific sequences which relate specifically to female organs, subtraction of the prostate and testes sequences from the thirty-two tissues was performed.

Briefly, to identify nucleotide and protein sequences that were specific to male organs (prostate and testis), MPSS data of mammary gland and uterus were first removed from MPSS dataset of the thirty-two tissues. MPSS data of the remaining thirty tissues were then used to identify organ-specific MPSS sequences, using the procedure described in Example 1. MPSS sequences that were specific to prostate and testis were further annotated to their corresponding nucleotide and protein sequences, as described in Example 1. The obtained prostate-specific nucleotide and protein sequences were summarized in Table 36 and the obtained testis-specific nucleotide and protein sequences were summarized in Table 37.

Similarly, to identify nucleotide and protein sequences that were specific to female organs (mammary gland and uterus), MPSS data of prostate and testis were first removed from MPSS dataset of the thirty-two tissues that were described in Example 1. MPSS data of the remaining thirty tissues were then used to identify organ-specific MPSS sequences, as described in Example 1. MPSS sequences that were specific to mammary gland and uterus were further annotated to their corresponding nucleotide and protein sequences, following the procedure described in Example 1. The obtained mammary gland-specific nucleotide and protein sequences were summarized in Table 38 and the obtained uterus-specific proteins were summarized in Table 39.

Example 7

Identification of Potential Biomarkers for Prostate Cancer

This example shows the identification of protein sets that are potential biomarkers for prostate cancer.

LNCaP cell line is a cellular model for early-stage prostate cancer and CL1 cell line is a cellular model for late-stage prostate cancer. Normalized MPSS dataset of LNCaP cells and CL1 cells were obtained for the purpose of identifying potential biomarkers for prostate cancer. The new data were combined with the normalized MPSS dataset of the thirty-two tissues that were described in Example 1. Normal prostate-, LNCaP- and CL1-specific nucleotide and protein sequences were identified from the combined dataset and were potential biomarkers for prostate cancer.

More specifically, MPSS data of female organs (mammary gland and uterus) were first removed from MPSS dataset of the thirty-two tissues described in Example 1. MPSS data of the remaining thirty tissues were then combined with normalized MPSS dataset of LNCaP cells and CL1 cells. Following the procedure described in Example 1, the combined MPSS dataset of the thirty-two samples (the thirty two tissues described in Example 1, minus mammary gland and uterus, and plus LNCaP and CL1 cells) was used to identify nucleotide and protein sequences that were specific to CL1 cells (Table 40), LNCaP cells (Table 41) and normal prostate (Table 42). While normal prostate-specific nucleotide and protein sequences are potential biomarkers for the lack of prostate cancer, LNCaP-specific nucleotide and protein sequences are potential biomarkers for early-stage prostate cancer and CL1-specific nucleotide and protein sequences are potential biomarkers for late-stage prostate cancer. The obtained CL1-specific nucleotide and protein sequences were summarized in Table 40, the obtained LNCaP-specific nucleotide and protein sequences were summarized in Table 41, and the obtained normal prostate-specific nucleotide and protein sequences were summarized in Table 42.

Example 8

Collection of Organ-Specific Proteins that were Identified in Body Fluids by Mass Spectrometry Large amounts of mass spectrometry data on protein identifications are accumulated very rapidly in the proteomics field. Such data provide insightful information on the presence of proteins in various biological specimens. This example shows the collection of organ-specific proteins that have been identified by mass spectrometry in body fluids such as serum, plasma and seminal plasma.

Hundreds to thousands of proteins were identified in body fluids such as serum, plasma and seminal plasma in several proteomics studies and are stored in several proteomics databases. The available mass spectrometry datasets on protein identifications include: 1) human plasma proteins that were identified and managed by the Human Proteome Organization (HUPO, Omenn, et al., *Proteomics*. (2005):3226-45), 2) peptides that were identified from human plasma (PeptideAtlas, Deutsch et al., *Proteomics* (2005):3497-500), 3) human plasma N-glycoproteins (Liu et al., *J Proteome Res* (2005): 2070-80), 4) human seminal plasma proteins (Pilch B. and Mann M., *Genome Biol* (2006): R40), 5) N-glycopeptides that were identified from various human specimens, and 6) proprietary human serum protein databases. Proteins in the original datasets were specified by their accession numbers in either different protein sequence databases or different versions of the databases. Thus proteins were not consistently annotated, which made it impossible to directly combine proteins in different datasets. To solve this problem, peptides that were directly identified from mass spectrometry data were downloaded from datasets 1)-6). These peptides were then assembled to proteins in RefSeq database (ftp://ftp.ncbi.nih.gov/refseq/H_sapiens), following a procedure described in the ProteinProphet algorithm (Nesvizhskii et al., *Anal Chem* (2003): 4646-58). Hence we obtained a list of proteins, and their belonging peptides, that were identified in body fluids by mass spectrometry.

Proteins that were identified in body fluids by mass spectrometry were then compared with organ-specific proteins identified in Examples 1, 6, and 7. The overlap between proteins identified in body fluids and organ-specific proteins listed in Tables 1-32 was summarized in Table 43. The overlap between proteins identified in body fluids and proteins specific to sex organs (prostate, testis, mammary gland and uterus) that were listed in Tables 36-39 was summarized in Table 44. The overlap between proteins identified in body fluids and potential protein biomarkers for prostate cancer that were listed in Tables 40-42 was summarized in Table 45.

Example 9

Identification of Tissue Specific Genes and Proteins Using Sequencing-by-Synthesis Analysis This example shows the identification of organ-specific protein sets from normal, healthy organs using sequencing-by-synthesis (SBS).

SBS Dataset of Human Tissues

A total of 53 samples of human normal tissues and epithelial cells were collected from different patients (see Table 46 for details). These samples were different from the samples used to generate the MPSS dataset described in Example 1. RNA molecules were extracted from each sample using standard procedures (see e.g., Example 5). Collected RNA samples were then sent to Solexa (Hayward, Calif., USA, now part of Illumine, San Diego, Calif., USA) to measure the abundance of RNA molecules in each sample, using their sequencing-by-synthesis (SBS) RNA analysis platform (see e.g., Johnson D S, et al. (2007) Science 316(5830):1441-2; A. Barski et al., 2007 Cell 129, 823-837; T. Mikkelsen at al., Nature. 2007 448(7153):553-60; G. Robertson at al., Nature Methods 2007 August; 4(8):651-7). Some samples were analyzed in duplicate (for example, the two breast samples). As a result, a total of 64 SBS datasets were received from Solexa (See Table 46).

Similar to MPSS data, each SBS dataset contains all identified SBS tags, each tag comprised of a DNA sequence 20 bases in length, their raw counts that qualify the abundance of the tags in the sample, their annotations to the UniGene database, their classification classes based on annotation quality, and descriptions of the corresponding UniGene entries to which the tags are annotated. This SBS dataset was then used to identify organ-specific proteins as described below.

Assignment of Individual SBS Datasets to Organs

Some SBS datasets (such as HCC01_A and HCC01_B) were generated from the same tissue. Some (such as HCC18 and HCC51) were generated from tissues of the same organ but from different patients. In addition, some samples were closely related to each other (for example, hepatocytes and liver). To identify organ-specific proteins, all SBS datasets were assigned to one of the 25 organs listed in Table 46.

TABLE 46

List of all SBS datasets, the samples that generated the datasets, and the organs to which the datasets were assigned.

| Organ | Sample | Sex | Patient ID | SBS Dataset |
|---|---|---|---|---|
| Adrenal Gland | Adrenal Gland | M | 23209 | HCC38 |
| Artery | Artery | M | 23060 | HCC39 |
| Bladder | Bladder | F | THB196 | HCC11_A |
| Bladder | Bladder | F | THB196 | HCC11_B |
| Bladder | Bladder | M | 23060 | HCC10 |
| Bladder | Bladder | M | 21538 | HCC42 |
| Brain | Brain (Amygdala) | F | BR4-8L | HCC26 |
| Brain | Brain (Nucleus Caudate) | F | BR4-10L | HCC27 |
| Breast | Breast | F | 108046 | HCC01_A |
| Breast | Breast | F | 108046 | HCC01_B |
| Breast | Breast | F | 108046 | HCC17_A |
| Breast | Breast | F | 108046 | HCC17_B |
| Breast | Breast | F | 108034 | HCC19 |
| Breast | Breast | F | 108034 | HCC02_A |
| Breast | Breast | F | 108034 | HCC02_B |
| Cervix | Cervix | F | 1-21 | HCC05 |
| Heart | Heart | F | 19941 | HCC51 |
| Heart | Heart | M | 23060 | HCC18 |
| Kidney | Kidney | F | 301002 | HCC53 |
| Kidney | Kidney | M | 301028 | HCC52 |
| Kidney | Renal Cortical Epithelial Cells | | | HCCHuECReCo |
| Kidney | Renal Epithelial Cells | | | HCCHuECRena |
| Kidney | Renal Proximal Tubule Epithelial Cells | | | HCCHuECRPT |
| Liver | Liver | M | 53891 | HCC54 |
| Liver | Liver | M | 56310 | HCC08 |
| Liver | Hepatocytes | F | | HCCHuHep |
| Lung | Lung | F | 301008 | HCC56_A |
| Lung | Lung | F | 301008 | HCC56_B |
| Lung | Lung | F | 301008 | HCC56_C |
| Lung | Lung | M | AST6161 | HCC55 |
| Lymph Node | Lymph Node | F | 20951 | HCC46 |
| Lymph Node | Lymph Node | F | 19941 | HCC57_A |
| Lymph Node | Lymph Node | F | 19941 | HCC57_B |
| Lymph Node | Lymph Node | M | THB196 | HCC25 |
| Lymphocytes | Lymphocytes (B) | F | NF11 + NF4 | HCC14 |
| Lymphocytes | Lymphocytes (B) | M | NMS10 | HCC21 |
| Lymphocytes | Lymphocytes (T) | F | NF11 | HCC15 |
| Monocytes | Monocytes | F | NF11 | HCC16 |
| Monocytes | Monocytes | M | NMS5 | HCC20 |
| Muscle | Muscle (Skeletal) | M | 54509 | HCC58 |
| Muscle | Muscle (Smooth) | F | 20951 | HCC36 |
| Ovary | Ovary | F | 23011 | HCC06 |
| Pancreas | Pancreas | F | 301002 | HCC60 |
| Pancreas | Pancreas | M | 301001 | HCC59 |
| Pancreas | Pancreatic Islet Cells | F | Islets | HCC40b |
| Prostate | Prostate | M | 23060 | HCC03_A |
| Prostate | Prostate | M | 23060 | HCC03_B |
| Prostate | Prostate | M | 21538 | HCC04 |
| Prostate | Prostate Epithelial Cells | M | | HCCHuECPros |

TABLE 46-continued

List of all SBS datasets, the samples that generated the datasets, and the organs to which the datasets were assigned.

| Organ | Sample | Sex | Patient ID | SBS Dataset |
|---|---|---|---|---|
| Skin | Skin | F | 20951 | HCC30 |
| Skin | Epidermal Keratinocytes | F | | HCCHuEK |
| Small Intestine | Small Intestine | F | 301003 | HCC62 |
| Small Intestine | Small Intestine | M | 21538 | HCC31 |
| Spleen | Spleen | F | 20951 | HCC23 |
| Spleen | Spleen | F | 19941 | HCC64 |
| Spleen | Spleen | M | 21538 | HCC50 |
| Stomach | Stomach | F | 19941 | HCC65 |
| Stomach | Stomach | M | 23060 | HCC24 |
| Stomach | Stomach | M | 56310 | HCC50A |
| Testes | Testes | M | 23060 | HCC09 |
| Thymus | Thymus | F | 20951 | HCC34 |
| Thymus | Thymus | M | 23060 | HCC33 |
| Trachea | Trachea | F | 20951 | HCC29 |
| Uterus | Uterus | F | 23011 | HCC07 |

Identification of Organ-Specific SBS Tags

The methods for identifying organ-specific SBS tags were similar to those for identifying organ-specific MPSS tags, as described in Example 1. There were a few modifications to accommodate difference in the two datasets. In particular, as outlined further below, changes were made to account for having multiple SBS datasets for some organs (see e.g., Table 46, multiple samples for breast, spleen, lymph node, etc.).

One of the modifications was first to normalize raw counts of SBS tags to transcription per million (tpm). In comparison, MPSS data were already normalized to tpm. The methods for identifying organ-specific SBS tags were as follows.

Assume the expression (in tpm) of a SBS sequence tag in the 64 SBS datasets was $\{X_{ij}\}$, where i=1, 2, . . . , 25 represents individual organs and j=1, 2, . . . , $k_i$ represents individual datasets of the same organ. Apparently $k_i$=1 if organ i had only one dataset. For each organ, we first evaluated the following three quantities:

(a) The highest expression of the tag in the organ, i.e., $$X_i^m = \max\{X_{i1}, X_{i2}, \ldots, X_{ik_i}\}; \quad (1)$$

(b) the averaged expression of the tag in the organ, i.e., $$\overline{X_i} = \frac{1}{k_i} \sum_{j=1}^{k_i} X_{ij}; \quad (2)$$

and (c) the corresponding standard deviation (SD) for $k_i$>1, i.e., $$s_i = \sqrt{\frac{1}{k_i - 1} \sum_{j=1}^{k_i} (X_{ij} - \overline{X_i})^2}. \quad (3)$$

If $k_i$=1, one has $X_i^m = \overline{X_i} = X_{i1}$ and $s_i$=0.

Assume organ m had the highest value of $\{X_i^m\}$ among all organs. We then applied three rules to determine whether the tag was specific to organ m as follows:

i) The highest expression of the tag in organ m was above a minimal, estimated noise level, i.e., $$X_m^m \geq 5. \quad (4)$$

ii) The highest expression of the tag in organ m was well above the averaged expression of the tag in all other tissues. More specifically, we first calculated the mean averaged expression of the tag in the other 24 organs (except organ m) as $$\overline{X} = \frac{1}{N} \sum_{i \neq m} \overline{X_i}, \quad (5)$$

the associated standard error as $$\sigma_{\overline{X}} = \frac{1}{N} \sqrt{\sum_{i \neq m} s_i^2}, \quad (6)$$

and the corresponding SD as $$s = \sqrt{\frac{1}{N-1} \sum_{i \neq m} (\overline{X_i} - \overline{X})^2 + \frac{1}{N} \sum_{i \neq m} s_i^2}, \quad (7)$$

where N=24.

We then evaluated the significance that the expression of the tag in organ m was above the expression of the tag in other organs as $$p_{dis} = \frac{1}{2} \text{erfc}\left(\frac{X_m^m - \overline{X}}{\sqrt{2(s^2 + \sigma_{\overline{X}}^2)}}\right). \quad (8)$$

For the tag to be specific to organ m, we required that $$p_{dis} \leq 10^{-3}. \quad (9)$$

iii) The specificity f of the tag in organ m had to be well above a pre-selected cutoff value $f_0$. More precisely, we defined the specificity of the tag in tissue m as $$f = \frac{X_m^m}{X_m^m + \sum_{i \neq m} \overline{X_i}}, \quad (10)$$

and evaluated the associated SD as $$\sigma_f = \frac{f^2}{X_m^m} \sqrt{\sum_{i \neq m} s_i^2}. \quad (11)$$

The significance that f was above $f_0$ is then given by $$p_{spc} = \frac{1}{2} \text{erfc}\left(\frac{f - f_0}{\sqrt{2}\, \sigma_f}\right). \quad (12)$$

For the tag to be specific to organ m, we selected $$f_0 = 0.5 \quad (13)$$

and required that $$p_{spc} \leq 0.1. \quad (14)$$

A tag was identified as specific to organ m if its expression satisfied the three conditions in Eqs. (4), (9) and (14).

Lists of Organ-Specific Proteins

The mapping of organ-specific SBS tags to organ-specific proteins was the same as that for the MPSS data as described in Example 1.

All organ-specific proteins identified from the SBS data were listed in Tables 47-71.

All proteins discovered from SBS data as specific to male or female sex organs were listed in Tables 72-77. The methods for this analysis are as described in Example 6.

All organ-specific proteins discovered from SBS data and previously identified by mass spectrometry were listed in Table 78. The methods for this analysis are as described in Example 8.

All proteins discovered from SBS data as specific to male or female sex organs and previously identified by mass spectrometry were listed in Table 79. The methods for this analysis are as described in Example 8.

Information on each protein listed in Tables 47-79 includes gene name, gene accession number, protein accession number, summary description of the protein, predicted protein localization (as described in Example 1), corresponding MPSS tag, the class of the MPSS tag, the expression of the tag in the particular tissue (count), the specificity of the tag in the particular tissue (as described above), and the number of peptides identified on the protein by HUPO (as described further below). Those proteins identified by MPSS and by SBS are noted by "&". The amino acid sequences corresponding to the organ-specific proteins and the polynucleotides encoding the proteins are provided in the sequence listing. Sequences corresponding to the MPSS tags as shown in Tables 47-79 are also provided. Sequences corresponding to peptides previously identified by mass spectrometry that map to organ-specific proteins described in Tables 78 and 79 are shown in those Tables and are provided in the sequence listing.

In summary, the experiments described in this Example identified organ-specific protein sets as set forth in Tables 47-79. These proteins are diagnostically and therapeutically useful in a variety of settings as described herein, for example, for defining a biological state of a subject and for the diagnosis of specific diseases. These proteins and detection reagents thereto can be used in accurate assays, panels, arrays and methods to measure health, detect disease and to monitor treatment.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08586006B2). An electronic copy of the "Sequence Listing" will also be available from the USPTO upon request and payment of the fee set forth in 37 CFR 1.19(b)(3).

What is claimed is:

1. A method for detecting an abnormal prostate state in a subject comprising,
a) contacting a blood sample from the subject with a panel of at least four detection reagents wherein each detection reagent is specific for one prostate-specific protein; wherein the prostate-specific proteins are selected from the prostate-specific protein set as follows;

| Gene | Protein ID | SEQ ID NO | Description |
|---|---|---|---|
| ANXA8*& | NP_001621 | 384 | annexin A8 |
| CAV1& | NP_001744 | 1351 | caveolin 1 |
| CLCA2* | NP_006527 | 59346 | calcium activated chloride channel 2 |
| COL17A1* | NP_000485 | 59347 | alpha 1 type XVII collagen |
| H2BFS | NP_059141 | 65564 | H2B histone family, member S |
| HIST1H2BC | NP_003517 | 65565 | H2B histone family, member L |
| HIST1H2BD& | NP_066407 | 14604 | H2B histone family, member B |
| HIST1H2BE | NP_003514 | 65566 | H2B histone family, member H |
| HIST1H2BJ | NP_066402 | 65567 | H2B histone family, member R |
| HIST1H2BM | NP_003512 | 65568 | H2B histone family, member E |
| HIST1H2BN | NP_003511 | 65569 | H2B histone family, member D |
| HIST1H2BO | NP_003518 | 65570 | histone H2B |
| HNT*& | NP_057606 | 4329 | neurotrimin |
| IL1A* | NP_000566 | 59357 | interleukin 1, alpha proprotein |
| KRT6A*& | NP_005545 | 6225 | keratin 6A |
| KRT6B*& | NP_005546 | 17263 | keratin 6B |
| KRT6C*& | NP_490596 | 6226 | keratin 6C |
| LAMA3* | NP_000218 | 59362 | laminin alpha 3 subunit isoform 2 |
| LAMA3* | NP_937762 | 59363 | laminin alpha 3 subunit isoform 1 |
| LAMB3* | NP_000219 | 59364 | laminin subunit beta 3 precursor |
| LAMB3* | NP_001017402 | 59365 | laminin subunit beta 3 precursor |
| LOC653107* | XP_931601 | 65577 | PREDICTED: similar to Annexin A8 (Annexin VIII) (Vascular anticoagulant-beta) (VAC-beta) isoform 1 |
| LOC653107* | XP_936422 | 65578 | PREDICTED: similar to Annexin A8 (Annexin VIII) (Vascular anticoagulant-beta) (VAC-beta) isoform 2 |
| LOC653107* | XP_936471 | 65585 | PREDICTED: similar to Annexin A8 (Annexin VIII) (Vascular anticoagulant-beta) (VAC-beta) isoform 10 |
| LOC653107* | XP_936481 | 65587 | PREDICTED: similar to Annexin A8 (Annexin VIII) (Vascular anticoagulant-beta) (VAC-beta) isoform 12 |

-continued

| Gene | Protein ID | SEQ ID NO | Description |
|---|---|---|---|
| LOC653107* | XP_936484 | 65588 | PREDICTED: similar to Annexin A8 (Annexin VIII) (Vascular anticoagulant-beta) (VAC-beta) isoform 13 |
| LOC653107* | XP_936492 | 65589 | PREDICTED: similar to Annexin A8 (Annexin VIII) (Vascular anticoagulant-beta) (VAC-beta) isoform 14 |
| MASP1*& | NP_624302 | 14670 | mannan-binding lectin serine protease 1 isoform 2 precursor |
| S100A2& | NP_005969 | 30938 | S100 calcium binding protein A2 |
| SCRN3* | NP_078859 | 65605 | secernin 3 |
| SEMA3C* | NP_006370 | 65606 | semaphorin 3C |
| SEPT11*& | NP_060713 | 4577 | septin 11 |
| SERPINB5* | NP_002630 | 59403 | serine (or cysteine) proteinase inhibitor, clade B (ovalbumin), member 5 |
| SFN* | NP_006133 | 59405 | stratifin | b) measuring the amount of prostate-specific protein detected in the blood sample by each detection reagent; and c) comparing the amount of prostate-specific protein detected in the blood sample by each detection reagent to a predetermined normal control amount for each respective prostate-specific protein;

wherein a statistically significant altered level in said prostate-specific proteins indicates a perturbation in the normal biological state.

2. The method of claim 1 wherein the amounts of at least five prostate-specific proteins are measured and compared to normal control amounts.

3. The method of claim 1 wherein the amounts of at least ten prostate-specific proteins are measured and compared to normal control amounts.

4. A panel of reagents for use in a method to detect abnormal prostate state in a subject comprising at least four detection reagents wherein each detection reagent is specific for one prostate-specific protein; wherein the prostate-specific proteins are selected from the prostate-specific protein set of claim 1.

5. The panel of claim 4 comprising at least five prostate-specific protein reagents.

6. The panel of claim 4 comprising at least ten prostate-specific protein reagents.

* * * * *

UNITED STATES PATENT AND TRADEMARK OFFICE
CERTIFICATE OF CORRECTION

| | |
|---|---|
| PATENT NO. | : 8,586,006 B2 |
| APPLICATION NO. | : 12/376951 |
| DATED | : November 19, 2013 |
| INVENTOR(S) | : Leroy Hood et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1111 days.

Signed and Sealed this
Thirtieth Day of June, 2015

Michelle K. Lee
*Director of the United States Patent and Trademark Office*